(12) United States Patent
Gray

(10) Patent No.: US 12,246,005 B2
(45) Date of Patent: Mar. 11, 2025

(54) 5-METHOXY-N,N-DIMETHYLTRYPTAMINE (5-MeO-DMT) FORMULATIONS

(71) Applicant: Beckley Psytech Limited, Oxford (GB)

(72) Inventor: Jason Gray, Oxford (GB)

(73) Assignee: Beckley Psytech Limited, Oxford (GB)

( * ) Notice: Subject to any disclaimer, the term of this patent is extended or adjusted under 35 U.S.C. 154(b) by 0 days.

(21) Appl. No.: 18/607,093

(22) Filed: Mar. 15, 2024

(65) Prior Publication Data

US 2024/0415811 A1 Dec. 19, 2024

Related U.S. Application Data

(63) Continuation-in-part of application No. 18/229,041, filed on Aug. 1, 2023, now Pat. No. 11,980,605.

(30) Foreign Application Priority Data

| Jun. 13, 2023 | (GB) | 2308830 |
| Sep. 29, 2023 | (GB) | 2314993 |
| Oct. 3, 2023 | (GB) | 2315176 |
| Nov. 3, 2023 | (GB) | 2316902 |
| Jan. 18, 2024 | (GB) | 2400703 |

(51) Int. Cl.
| *A61K 31/4045* | (2006.01) |
| *A61K 9/00* | (2006.01) |
| *A61K 9/16* | (2006.01) |
| *A61K 9/19* | (2006.01) |
| *A61M 15/08* | (2006.01) |

(52) U.S. Cl.
CPC ........ *A61K 31/4045* (2013.01); *A61K 9/0043* (2013.01); *A61K 9/1611* (2013.01); *A61K 9/1623* (2013.01); *A61K 9/1652* (2013.01); *A61K 9/19* (2013.01); *A61M 15/08* (2013.01)

(58) Field of Classification Search
CPC .............. A61K 31/4045; A61K 9/0043; A61K 9/1611; A61K 9/1623; A61K 9/1652; A61M 15/08
See application file for complete search history.

(56) References Cited

U.S. PATENT DOCUMENTS

| 2,774,763 A | 12/1956 | Garbrecht |
| 2,997,470 A | 8/1961 | Pioch |

(Continued)

FOREIGN PATENT DOCUMENTS

| CH | 578565 A5 | 8/1976 |
| CN | 103816150 A | 5/2014 |

(Continued)

OTHER PUBLICATIONS

Sherwood et al., Synthesis and Characterization of 5MeO-DMT Succinate for Clinical Use', ACS Omega, vol. 5, pp. 32068-32069. (Year: 2020).*

(Continued)

*Primary Examiner* — Carlos A Azpuru
(74) *Attorney, Agent, or Firm* — Clark & Elbing LLP

(57) ABSTRACT

The present invention provides a dry powder formulation of 5-MeO-DMT or a pharmaceutically acceptable salt thereof, and one or more pharmaceutically acceptable carriers or excipients. The formulations described herein may be used to treat a disease or condition, such as depression or alcohol use disorder in a subject in need thereof.

20 Claims, 57 Drawing Sheets

(56) References Cited

U.S. PATENT DOCUMENTS

| | | | |
|---|---|---|---|
| 3,078,214 | A | 2/1963 | Albert et al. |
| 3,224,945 | A | 12/1965 | Tyler, Jr. |
| 4,176,182 | A | 11/1979 | Ferrari et al. |
| 4,180,581 | A | 12/1979 | Stadler |
| 4,348,391 | A | 9/1982 | Stutz et al. |
| 5,811,436 | A | 9/1998 | Leonard et al. |
| 10,519,175 | B2 | 12/2019 | Londesbrough et al. |
| 11,518,742 | B2 | 12/2022 | Feilding-Mellen et al. |
| 11,518,743 | B2 | 12/2022 | Feilding-Mellen et al. |
| 11,773,063 | B1 | 10/2023 | Gray et al. |
| 11,980,605 | B1 * | 5/2024 | Gray .................. A61K 9/1694 |
| 2005/0019411 | A1 | 1/2005 | Colombo et al. |
| 2008/0293695 | A1 | 11/2008 | Bristol et al. |
| 2012/0108510 | A1 | 5/2012 | Young et al. |
| 2017/0348303 | A1 | 12/2017 | Bosse et al. |
| 2017/0360772 | A1 | 12/2017 | Bosse et al. |
| 2018/0021326 | A1 | 1/2018 | Stamets |
| 2018/0147142 | A1 | 5/2018 | Knight |
| 2020/0179349 | A1 | 6/2020 | Yun et al. |
| 2020/0187777 | A1 | 6/2020 | Luderer et al. |
| 2021/0058956 | A1 | 2/2021 | Chatterjee et al. |
| 2021/0069170 | A1 | 3/2021 | Stamets |
| 2021/0085671 | A1 | 3/2021 | Chadeayne |
| 2021/0322743 | A1 | 10/2021 | Rinti et al. |
| 2022/0062238 | A1 | 3/2022 | Layzell et al. |
| 2022/0362237 | A1 | 11/2022 | Barrow et al. |
| 2022/0396552 | A1 | 12/2022 | Feilding-Mellen et al. |
| 2023/0031944 | A1 | 2/2023 | Feilding-Mellen et al. |
| 2023/0348381 | A1 | 11/2023 | Feilding-Mellen et al. |

FOREIGN PATENT DOCUMENTS

| | | |
|---|---|---|
| CN | 113288883 A | 8/2021 |
| DE | 2617738 A1 | 11/1976 |
| EP | 0008802 A1 | 3/1980 |
| EP | 0026899 A1 | 4/1981 |
| EP | 0131301 A2 | 1/1985 |
| EP | 2067780 A1 | 6/2009 |
| EP | 3868364 A1 | 8/2021 |
| EP | 3941583 A1 | 1/2022 |
| EP | 4159192 A1 | 4/2023 |
| EP | 4159201 A1 | 4/2023 |
| GB | 912715 A | 12/1962 |
| GB | 981192 A | 1/1965 |
| GB | 1410349 A | 10/1975 |
| GB | 1584464 A | 2/1981 |
| GB | 2588505 A | 4/2021 |
| GB | 2596884 A | 1/2022 |
| WO | WO-01/15677 A2 | 3/2001 |
| WO | WO-01/15677 A3 | 3/2002 |
| WO | WO-02/38142 A2 | 5/2002 |
| WO | WO-2004/000849 A2 | 12/2003 |
| WO | WO-2008/003028 A2 | 1/2008 |
| WO | WO-2010/054202 A2 | 5/2010 |
| WO | WO-2012/173701 A1 | 12/2012 |
| WO | WO-2013/063492 A1 | 5/2013 |
| WO | WO-2013/191704 A1 | 12/2013 |
| WO | WO-2016/118541 A1 | 7/2016 |
| WO | WO-2016/145193 A1 | 9/2016 |
| WO | WO-2018/064465 A1 | 4/2018 |
| WO | WO-2018/195455 A1 | 10/2018 |
| WO | WO-2019/073379 A1 | 4/2019 |
| WO | WO-2019/081764 A1 | 5/2019 |
| WO | WO-2019/173797 A1 | 9/2019 |
| WO | WO-2019/246532 A1 | 12/2019 |
| WO | WO-2020/157569 A1 | 8/2020 |
| WO | WO-2020/169850 A1 | 8/2020 |
| WO | WO-2020/169851 A1 | 8/2020 |
| WO | WO-2020/176597 A1 | 9/2020 |
| WO | WO-2020/181194 A1 | 9/2020 |
| WO | WO-2020/212948 A1 | 10/2020 |
| WO | WO-2020/212951 A1 | 10/2020 |
| WO | WO-2021/003467 A1 | 1/2021 |
| WO | WO-2021/030571 A1 | 2/2021 |
| WO | WO-2021/041407 A1 | 3/2021 |
| WO | WO-2021/076572 A1 | 4/2021 |
| WO | WO-2021/089872 A1 | 5/2021 |
| WO | WO-2021/111098 A1 | 6/2021 |
| WO | WO-2021/155470 A1 | 8/2021 |
| WO | WO-2021/175816 A1 | 9/2021 |
| WO | WO-2021/179091 A1 | 9/2021 |
| WO | WO-2021/209815 A1 | 10/2021 |
| WO | WO-2021/222885 A1 | 11/2021 |
| WO | WO-2021/225796 A1 | 11/2021 |
| WO | WO-2021/250434 A1 | 12/2021 |
| WO | WO-2021/250435 A1 | 12/2021 |
| WO | WO-2021/253116 A1 | 12/2021 |
| WO | WO-2022/000091 A1 | 1/2022 |
| WO | WO-2022/008627 A2 | 1/2022 |
| WO | WO-2022/016289 A1 | 1/2022 |
| WO | WO-2022038299 A1 | 2/2022 |
| WO | WO-2022/094719 A1 | 5/2022 |
| WO | WO-2022/117359 A1 | 6/2022 |
| WO | WO-2022/125616 A1 | 6/2022 |
| WO | WO-2022/133314 A1 | 6/2022 |
| WO | WO-2022/153266 A1 | 7/2022 |
| WO | WO-2022/153268 A1 | 7/2022 |
| WO | WO-2022/175821 A1 | 8/2022 |
| WO | WO-2022/195489 A2 | 9/2022 |
| WO | WO-2022207746 A1 | 10/2022 |
| WO | WO-2022/246572 A1 | 12/2022 |
| WO | WO-2023/002005 A1 | 1/2023 |
| WO | WO-2023/028086 A1 | 3/2023 |
| WO | WO-2023/111544 A2 | 6/2023 |
| WO | WO-2023/186797 A1 | 10/2023 |
| WO | WO-2023/186798 A1 | 10/2023 |
| WO | WO-2023/186806 A1 | 10/2023 |
| WO | WO-2023/186808 A1 | 10/2023 |
| WO | WO-2023/186816 A1 | 10/2023 |
| WO | WO-2023/186820 A1 | 10/2023 |
| WO | WO-2023/186821 A1 | 10/2023 |
| WO | WO-2023/186823 A1 | 10/2023 |
| WO | WO-2023/186824 A1 | 10/2023 |
| WO | WO-2023/186826 A1 | 10/2023 |
| WO | WO-2023/186827 A1 | 10/2023 |
| WO | WO-2023/186828 A1 | 10/2023 |
| WO | WO-2023/186829 A1 | 10/2023 |
| WO | WO-2023/186830 A1 | 10/2023 |
| WO | WO-2023/186831 A1 | 10/2023 |
| WO | WO-2023/186832 A1 | 10/2023 |
| WO | WO-2023/186834 A1 | 10/2023 |
| WO | WO-2023/186835 A1 | 10/2023 |
| WO | WO-2023/186837 A1 | 10/2023 |
| WO | WO-2024/146917 A1 | 7/2024 |
| WO | WO-2024/160389 A1 | 8/2024 |
| WO | WO-2024/160390 A1 | 8/2024 |
| WO | WO-2024/160391 A1 | 8/2024 |
| WO | WO-2024/160392 A1 | 8/2024 |

OTHER PUBLICATIONS

Berge et al., "Pharmaceutical salts," J Pharm Sci. 66(1):1-19 (1977).

Registry No. 2761182-82-3, File REGISTRY on STN, entered STN: Mar. 3, 2022 (2 pages).

"Cancer," MedLine Plus, <http://www.nlm.nih.gov/medlineplus/cancer.html>, retrieved Jul. 6, 2007 (10 pages).

"Psychedelic Compounds Chemical and Physical Properties," DMT-Nexus Wiki, Feb. 10, 2023, <https://wiki.dmt-nexus.me/Psychedelic_Compounds_Chemical_and_Physical_Properties#DMT_Benzoate>, (18 pages).

Bastin et al., "Salt selection and optimisation procedures for pharmaceutical new chemical entities," Org Process Res Dev 4(5):427-35 (2000).

Benington et al., "Synthesis of O- and N-Methylated Derivatives of 5-Hydroxytryptamine," The Journal of Organic Chemistry 23:1977-9 (Dec. 1958).

Bergman et al., "Synthesis and Reactions of some 3-(2-Haloacyl)indoles," Pergamon Press. 29:971-976 (1973).

CAplus. Chemical Abstracts Service: Columbus. CAplus Accession No. 2017:1595854. Title: Preparation of tetrahydropyridoindolylcycloalkylacrylic acid derivatives and analogs for use as estrogen receptor modulators. Inventor: Huang, P.Q. et al. (4 pages).

(56) References Cited

OTHER PUBLICATIONS

Carhart-Harris et al., "Psilocybin with psychological support for treatment-resistant depression: six-month follow-up," Psychopharmacology (Berl). 235(2):399-408 (Feb. 2018).
CHEMCATS. Chemical Abstracts Service: Columbus, OH. Chemical Name: 1-methyl-1H-pyrrolo[2,3-b]pyridin-4-ol. CHEMCATS Accession No. 0002254898. Catalog Name: FCH Group Reagents for Synthesis. Order Number Catalog: FCH1635008. Cas Registry No. 1781876-60-5 (May 2021) (1 page).
CHEMCATS. Chemical Abstracts Service: Columbus, OH. Chemical Name: 1-methyl-1H-pyrrolo[2,3-b]pyridin-4-ol. CHEMCATS Accession No. 1545199867. Catalog Name: Azepine Product List. Order Number Catalog: AZ04819515. CAS Registry No. 1781876-60-5 (Mar. 2019) (1 page).
CHEMCATS. Chemical Abstracts Service: Columbus, OH. Chemical Name: 1-methylpyrrolo[2,3-b]pyridin-4-ol. CHEMCATS Accession No. 1442516433. Catalog Name: Aurora Building Blocks 2. Order Number Catalog: 115.267.167. CAS Registry No. 1781876-60-5 (Apr. 2021) (1 page).
CHEMCATS. Chemical Abstracts Service: Columbus, OH. Chemical Name: 1H-Pyrrolo[2,3-b]pyridin-4(7H)-one. CHEMCATS Accession No. 1621739382. Catalog Name: Ambeed, Inc. Product List. Order Number Catalog: A763560. Cas Registry No. 1076197-59-5 (May 2021) (1 page).
CHEMCATS. Chemical Abstracts Service: Columbus, OH. Chemical Name: 1H-Pyrrolo[2,3-B]Pyridin-4(7H)-One. CHEMCATS Accession No. 2022337458. Catalog Name: Chemieliva Pharmaceutical Product List. Order Number Catalog: CE0957308. Cas Registry No. 1076197-59- 5 (Jan. 2021) (1 page).
CHEMCATS. Chemical Abstracts Service: Columbus, OH. Chemical Name: 1H-pyrrolo[2,3-b]pyridin-4-ol hydrate. CHEMCATS Accession No. 0968477988. Catalog Name: ASW MedChem Product List. Order Number Catalog: TH-45275. Cas Registry No. 2031269-35-7 (Jun. 2020) (1 page).
CHEMCATS. Chemical Abstracts Service: Columbus, OH. Chemical Name: 1H-Pyrrolo[2,3- b]pyridin-4-ol hydrate. CHEMCATS Accession No. 1773869211. Catalog Name: Aurora Building Blocks 3. Order Number Catalog: 129.194.895. CAS Registry No. 2031269-35-7 (Apr. 2021) (1 page).
CHEMCATS. Chemical Abstracts Service: Columbus, OH. Chemical Name: 4H-Pyrrolo[2,3-b]pyridine-4-one, 1,7-dihydro-. CHEMCATS Accession No. 1756550559. Catalog Name: Sagechem Limited Product List. Order Number Catalog: S243355. Cas Registry No. 1076197-59-5 (May 2020) (1 page).
Cingolani et al., "In vitro investigation on the impact of airway mucus on drug dissolution and absorption at the air-epithelium interface in the lungs," Eur J. Pharm Biopharm. 141: 210-220 (2019).
Database Registry. Chemical Abstracts Service: Columbus, OH. Chemical Name: 1H-Indole-3-ethanamine, 5-methoxy-N,N dimethyl-, benzoate (1:1); RN 282103-25-7; ED Aug. 1, 2000 (1 page).
Davis et al., "5-methoxy-N,N-dimethyltryptamine (5-MeO-DMT) used in a naturalistic group setting is associated with unintended improvements in depression and anxiety," Am J Drug Alcohol Abuse. 45(2): (15 pages) (2019).
Dunlap et al., "Identification of Psychoplastogenic N,N-Dimethylaminoisotryptamine (isoDMT) Analogs Through Structure-Activity Relationship Studies," available in PMC Feb. 13, 2021, published in final edited form as: J Med Chem. 63(3): 1142-1155 (Jan. 2020) (36 pages).
Falkenberg et al., "The Crystal and Molecular Structure of 5-Methoxy-(N,N)-dimethyltryptamine Hydrochloride," Acta Cryst. 27:411-8 (1971).
Florence, "Polymorph screening in pharmaceutical development," European Pharmaceutical Review, Issue 4, dated Aug. 19, 2010, retrieved Nov. 30, 2023, at <https://www.europeanpharmaceuticalreview.com/article/3659/polymorph-screening-in- pharmaceutical-development> (19 pages).

Galeffi et al., "N,N-dimethyl-5-methoxytryptamine, a component of a dart poison of the yanoáma indians," Journal of Natural Products 46:586-7 (Jul.-Aug. 1983).
Glennon et al., "Serotonin receptor binding affinities of tryptamine analogues," J Med Chem. 22(4):428-32 (Apr. 1979).
Glässer, "Some pharmacological actions of D-lysergic acid methyl carbinolamide," Nature 189:313-4 (Jan. 28, 1961).
Golub et al., "Molecular classification of cancer: class discovery and class prediction by gene expression monitoring," Science. 286(5439):531-7 (1999) (8 pages).
Griffiths et al., "Psilocybin produces substantial and sustained decreases in depression and anxiety in patients with life-threatening cancer: A randomized double-blind trial," J Psychopharmacol. 30(12):1181-97 (Dec. 2016).
Gupta et al., "Salts of Therapeutic Agents: Chemical, Physicochemical, and Biological Considerations," Molecules. 23(7): (15 pages) (2018).
Gupta, "QSAR Studies on Drugs Acting at the Central Nervous System," Chem Rev. 89(8):1765-800 (1989).
Halberstadt et al., "Pharmacological characterization of the LSD analog N-ethyl-N-cyclopropyl lysergamide (ECPLA)," Psychopharmacology (Berl). 236(2):799-808 (Feb. 2019).
Huang et al., "Drug discrimination and receptor binding studies of N-isopropyl lysergamide derivatives," Pharmacol Biochem Behav. 47(3):667-73 (Mar. 1994).
Illum et al., "The effect of blood sampling site and physicochemical characteristics of drugs on bioavailability after nasal administration in the sheep model," Pharm Res. 20(9):1474-84 (Sep. 2003).
International Search Report and Written Opinion for International Application No. PCT/GB2023/052179, mailed Sep. 27, 2023 (19 pages).
International Search Report for International Application No. PCT/GB2022/053208, mailed Apr. 3, 2023 (6 pages).
International Search Report in International Application No. PCT/GB2021/051475, mailed Sep. 16, 2021 (3 pages).
International Search Report in International Application No. PCT/GB2021/051476, mailed Sep. 15, 2021 (5 pages).
Ishii et al., "Studies on Lysergic Acid Diethylamide and Related Compounds. IX. Microbial Transformation of Amides Related to Lysergic Acid Diethylamide by *Streptomyces roseochromogenes*," Chem Pharm Bull. 27(12):3029-38 (1979).
Ishii et al., "Studies on lysergic acid diethylamide and related compounds. Part 8. Structural identification of new metabolites of lysergic acid diethylamide obtained by microbial transformation using *Streptomyces roseochromogenes*," J Chem Soc Perkin 1. 4:902-5 (1980).
Johnson et al., "Emetic activity of reduced lysergamides," J Med Chem. 16(5):532-7 (May 1973).
Klein et al., "Investigation of the Structure-Activity Relationships of Psilocybin Analogues," ACS Pharmacol Transl Sci. 4(2):533-42 (Dec. 14, 2020).
Lala et al., "Role of nitric oxide in tumor progression: lessons from experimental tumors," Cancer Metastasis Rev. 17(1):91-106 (1998).
Liu et al., "Particle Size Distribution Analysis of OTC Aerosol or Powder Drug Products With Potential for Inadvertent Inhalation Exposure to Consumers," J Pharm Sci. 18(4):1506-1511 (2019).
Lyon et al., "Indolealkylamine analogs share 5-HT2 binding characteristics with phenylalkylamine hallucinogens," Eur J Pharmacol. 145(3):291-7 (Jan. 19, 1988).
McKenna et al., "Differential interactions of indolealkylamines with 5-hydroxytryptamine receptor subtypes, " Neuropharmacology 29(3):193-8 (Mar. 1990).
Monson et al., "MDMA-facilitated cognitive-behavioural conjoint therapy for posttraumatic stress disorder: an uncontrolled trial," Eur J Psychotraumatol. 11(1):1840123 (Dec. 7, 2020).
Monte et al., "Stereoselective LSD-like activity in a series of d-lysergic acid amides of (R)- and (S)-2-aminoalkanes," J Med Chem. 38(6):958-66 (Mar. 15, 1995).
Nakahara et al., "Studies on lysergic acid diethylamide and related compounds. III. Improvement of amidation of lysergic acid," Yakugaku Zasshi. 94(3):407-12 (Mar. 1974). English abstract included.

(56) References Cited

OTHER PUBLICATIONS

Ott, "Pharmepena-Psychonautics: Human intranasal, sublingual and oral pharmacology of 5-methoxy-N, N-dimethyl-tryptamine," J. Psychoactive Drugs. 33(4): 403-407 (2001).
PharmaTher Holdings Ltd. Dec. 14, 2021. PharmaTher Announces Positive Research Results for LSD Microneedle Patch. Press Release. <URL: https://psychedelicinvest.com/pharmather-announces-positive-research-results-for-lsd-microneedle-patch/> (6 pages).
Pubchem, Substance Record for CID 1832, Modify Date: Jul. 13, 2024. <https://pubchem.ncbi.nlm.nih.gov/compound/MeODMT> Retrieved on Jul. 19, 2024 (54 pages).
Roseman et al., "Increased amygdala responses to emotional faces after psilocybin for treatment-resistant depression," Neuropharmacology 142:263-9 (Nov. 2018).
Sard et al., "SAR of psilocybin analogs: discovery of a selective 5-HT 2C agonist," Bioorg Med Chem Lett. 15(20):4555-9 (Oct. 15, 2005).
Schneller et al., "Synthesis of 4-Amino-1H-pyrrolo[2,3-b]pyridine (1,7-Dideazaadenine) and 1H-Pyrrolo[2,3-b]pyridin-4-ol (1,7-Dideazahypoxantine)," J Org Chem. 45(20):4045-8 (1980).
Shen et al., "Psychedelic 5-methoxy-N,N-dimethyltryptamine: metabolism, pharmacokinetics, drug interactions, and pharmacological actions," Curr Drug Metab. 11(8):659-66 (18 pages) (Oct. 2010).
Sherwood et al., "Synthesis and Characterization of 5-MeO-DMT Succinate for Clinical Use," ACS Omega. 5(49):32067-32075 (2020).
Shulgin et al., TIHKAL: The Continuation. #38. 5-MeO-DMT. Tryptamine, 5-Methoxy-N,N-Dimethyl; Indole, 5-Methoxy-3-[2-(Dimethylamino)Ethyl]; 5-Methoxy-N,N-Dimethyltryptamine; 5-Methoxy-3-[2-Dimethylamino)Ethyl]Indole; N,N,O-Trimethylserotonin; N,N,O-TMS; Bufotenine Methyl Ether; O-Methylbufotenine; OMB. <URL: https://erowid.org/library/books_online/tihkal/tihkal38.shtml.> (3 pages).
Singh et al., "An ab Initio Study of the Effect of Substituents on the n àpi* Interactions between 7-Azaindole and 2,6-Difluorosubstituted Pyridines," J Phys Chem A. 120(31):6258-69 (Aug. 11, 2016).
Sohlberg et al., "The impact of the site of blood sampling on pharmacokinetic parameters following sublingual dosing to dogs," J Pharmacol Toxicol Methods. 67(1):1-4 (6 pages) (Jan.-Feb. 2013).
Stoll et al., "49. Amide der stereoisomeren Lysergsäuren und Dihydro-lysergsäuren," Helvetica Chimica Acta 38:421-33 (1955).
Szabo et al., "Psychedelic N, N-dimethyltryptamine and 5-methoxy-N,N-dimethyltryptamine modulate innate and adaptive inflammatory responses through the sigma-1 receptor of human monocyte-derived dendritic cells," PLoS One 9(8):e106533 (12 pages) (Aug. 29, 2014).
The Third Wave. The Ultimate Guide To 5-MeO-DMT. <https://web.archive.org/web/20200513112802/https://thethirdwave.co/psychedelics/5-meo-dmt/> Retrieved on Jul. 19, 2024 (24 pages).
U.S. Appl. No. 18/065,030, filed Dec. 13, 2022 (57 pages).
Uthaug et al., "Prospective examination of synthetic 5-methoxy-N,N-dimethyltryptamine inhalation: effects on salivary IL-6, cortisol levels, affect, and non-judgment," Psychopharmacology (Berl). 237(3):773-85 (Mar. 2020).
Vangveravong et al., "Synthesis and serotonin receptor affinities of a series of trans-2-(indol-3-yl) cyclopropylamine derivatives," J Med Chem. 41(25):4995-5001 (Dec. 3, 1998).
Wolfson et al., "MDMA-assisted psychotherapy for treatment of anxiety and other psychological distress related to life-threatening illnesses: a randomized pilot study," Sci Rep. 10(1):20442 (15 pages) (Nov. 24, 2020).
Written Opinion for International Application No. PCT/GB2022/053208, mailed Apr. 3, 2023 (9 pages).
Yazar-Klosinski et al., "Potential Psychiatric Uses for MDMA," Clin Pharmacol Ther. 101(2):194-6 (Feb. 2017).
Henriques et al., "Spray dried powders for nasal delivery: Process and formulation considerations," Eur J Pharm Biopharm. 176:1-20 (May 2022).
"Beckley Psytech and PsyPAN launch Participant Impact Report and Peer Support Pilot Program," Beckley Psytech Press Release Jun. 14, 2024 (7 pages).
"Beckley Psytech Announces Dosing of First Healthy Volunteers in Phase 1 Clinical Trial Assessing Safety and Pharmacokinetics of Second Innovative Formulation of 5-MeO-DMT," Apr. 5, 2022. https://www.businesswire.com/news/home/20220404005960/en/Beckley-Psytech-Announces-Dosing-of-First-Healthy-Volunteers-in-Phase-1-Clinical-Trial-Assessing-Safety-and-Pharmacokinetics-of-Second-Innovative-Formulation-of-5-MeO-DMT. (2 pages).
"Beckley Psytech Announces First Cohort Dosed in Phase 1 Clinical Trial Assessing Safety and Tolerability of Intranasal 5-MeO-DMT," Oct. 25, 2021. https://www.businesswire.com/news/home/20211024005026/en/Beckley-Psytech-Announces-First-Cohort-Dosed-in-Phase-1-Clinical-Trial-Assessing-Safety-and-Tolerability-of-Intranasal-5-MeO-DMT. (2 pages).
"Beckley Psytech Announces First Cohort of Psychotherapists Have Begun Training for Treatment Resistant Depression Phase 2 Trials," Jan. 24, 2022. https://www.businesswire.com/news/home/20220123005101/en/Beckley-Psytech-Announces-First-Cohort-of-Psychotherapists-Have-Begun-Training-for-Treatment-Resistant-Depression-Phase-2-Trials. (3 pages).
"Beckley Psytech Announces First Participant Dosed in Phase I Trial of ELE-101, A Novel Intravenous Formulation of Psilocin," Nov. 9, 2022. https://www.businesswire.com/news/home/20221108005986/en/Beckley-Psytech-Announces-First-Participant-Dosed-in-Phase-I-Trial-of-ELE-101-A-Novel-Intravenous-Formulation-of-Psilocin. (2 pages).
"Beckley Psytech announces first patient has received low-dose psilocybin in world-first clinical trial for rare headache disorder," Beckley Psytech Press Release Sep. 14, 2021 (5 pages).
"Beckley Psytech announces initial results from Phase I study and first patients dosed in Phase IIa study of ELE-101 (IV psilocin benzoate) for Major Depressive Disorder," Beckley Psytech Press Release Jun. 20, 2024 (7 pages).
"Beckley Psytech Announces Partnership With Empatica in Latest Step of Digital Strategy, Designed to Deliver Personalised Patient Care," May 19, 2022. https://www.businesswire.com/news/home/20220518006041/en/Beckley-Psytech-Announces-Partnership-With-Empatica-in-Latest-Step-of-Digital-Strategy-Designed-to-Deliver-Personalised-Patient-Care. (4 pages).
"Beckley Psytech Announces Partnership With Ksana Health, Building on Digital Strategy to Deliver Optimised Patient Outcomes," Jun. 14, 2022. https://www.businesswire.com/news/home/20220613005701/en/Beckley-Psytech-Announces-Partnership-With-Ksana-Health-Building-on-Digital-Strategy-to-Deliver-Optimised-Patient-Outcomes. (3 pages).
"Beckley Psytech announces positive initial data from Phase IIa study of novel 5-MeO-DMT formulation BPL-003 for Treatment Resistant Depression," Mar. 27, 2024. https://www.businesswire.com/news/home/20240326357401/en/Beckley-Psytech-announces-positive-initial-data-from-Phase-IIa-study-of-novel-5-MeO-DMT-formulation-BPL-003-for-Treatment-Resistant-Depression. (3 pages).
"Beckley Psytech announces strategic investment from atai Life Sciences to accelerate the clinical development of short-duration psychedelics," Beckley Psytech Press Release Jan. 4, 2024 (10 pages).
"Beckley Psytech announces £14m raise to conduct clinical trials on psychedelic medicine pipeline," Beckley Psytech Press Release Dec. 22, 2020 (5 pages).
"Beckley Psytech applies for B Corporation status as part of its commitment to have a positive impact on society," Beckley Psytech Press Release Dec. 21, 2021 (5 pages).
"Beckley Psytech appoints Dr Rob Hershberg to its Board of Directors," Beckley Psytech Press Release Jun. 24, 2024 (6 pages).
"Beckley Psytech Bolsters Pipeline of Next-Generation Psychedelic Medicines With Research Collaboration and Strengthening of Relationship With Lophora ApS," May 11, 2022. https://www.beckleypsytech.com/posts/beckley-psytech-bolsters-pipeline-of-next-generation-psychedelic-medicines-with-research-collaboration-and-strengthening-of-relationship-with-lophora-aps (6 pages).
"Beckley Psytech completes oversubscribed $80m (£58m) fundraise to develop portfolio of psychedelic medicine breakthroughs," Beckley Psytech Press Release Aug. 15, 2021 (3 pages).

(56) References Cited

OTHER PUBLICATIONS

"Beckley Psytech grows team with new Clinical Operations and Communications hires," Beckley Psytech Press Release Oct. 18, 2022 (4 pages).
"Beckley Psytech initiates Phase IIa study of 5-MeO-DMT candidate BPL-003 for Alcohol Use Disorder," Apr. 5, 2023. https://www.businesswire.com/news/home/20230405005132/en/Beckley-Psytech-initiates-Phase-IIa-study-of-5-MeO-DMT-candidate-BPL-003-for-Alcohol-Use-Disorder. (2 pages).
"Beckley Psytech Launches Phase IIa Study of Lead Candidate BPL-003, a Novel Benzoate Formulation of 5-MeO-DMT, for Treatment Resistant Depression," Dec. 21, 2022. https://www.businesswire.com/news/home/20221221005221/en/Beckley-Psytech-Launches-Phase-IIa-Study-of-Lead-Candidate-BPL-003-a-Novel-Benzoate-Formulation-of-5-MeO-DMT-for-Treatment-Resistant-Depression. (2 pages).
"Beckley Psytech publishes peer-reviewed paper on 5-MeO-DMT in Journal of Psychopharmacology, " Beckley Psytech Press Release Feb. 22, 2022 (4 pages).
"Beckley Psytech receives approval for clinical trial using psychedelic agent to treat severe headache condition, " Beckley Psytech Press Release Jan. 27, 2021 (4 pages).
"Beckley Psytech receives FDA Investigational New Drug (IND) approval for Phase IIb study of BPL-003, a novel synthetic formulation of 5-MeO-DMT (Mebufotenin)," Feb. 21, 2023. https://www.businesswire.com/news/home/20230221005523/en/Beckley-Psytech-receives-FDA-Investigational-New-Drug-IND-approval-for-Phase-IIb-study-of-BPL-003-a-novel-synthetic-formulation-of-5-MeO-DMT-Mebufotenin. (2 pages).
"Beckley Psytech Strengthens Pipeline and Development Team With Acquisition of Eleusis Therapeutics Limited," Oct. 24, 2022. https://www.businesswire.com/news/home/20221023005029/en/Beckley-Psytech-Strengthens-Pipeline-and-Development-Team-With-Acquisition-of-Eleusis-Therapeutics-Limited. (3 pages).
"Beckley Psytech Strengthens Senior Leadership Team With Appointment of Dr. Laura Trespidi as Chief Development Officer," May 24, 2022. https://www.businesswire.com/news/home/20220523005870/en/Beckley-Psytech-Strengthens-Senior-Leadership-Team-With-Appointment-of-Dr.-Laura-Trespidi-as-Chief-Development-Officer. (4 pages).
"Beckley Psytech Successfully Completes Phase I Clinical Study of Lead Candidate BPL-003, a Novel Benzoate Formulation Of 5-MeO-DMT," Nov. 15, 2022. https://www.businesswire.com/news/home/20221114005907/en/Beckley-Psytech-Successfully-Completes-Phase-I-Clinical-Study-of-Lead-Candidate-BPL-003-a-Novel-Benzoate-Formulation-Of-5-MeO-DMT. (2 pages).
"Beckley Psytech to attend 11th Annual LifeSci Partners Virtual Corporate Access Event," Dec. 8, 2021. https://www.businesswire.com/news/home/20211207006217/en/Beckley-Psytech-to-attend-11th-Annual-LifeSci-Partners-Virtual-Corporate-Access-Event. (2 pages).
"Beckley Psytech to Attend and Present at 8th Annual LSX World Congress 2022," Apr. 13, 2022. https://www.businesswire.com/news/home/20220412005773/en/Beckley-Psytech-to-Attend-and-Present-at-8th-Annual-LSX-World-Congress-2022. (2 pages).
"Beckley Psytech to Attend and Present at the Jefferies London Healthcare Conference—Nov. 15-17, 2022," Nov. 4, 2022. https://www.businesswire.com/news/home/20221104005095/en/Beckley-Psytech-to-Attend-and-Present-at-the-Jefferies-London-Healthcare-Conference-%E2%80%93-November-15-17-2022. (2 pages).
"Beckley Psytech to participate in Canaccord Genuity's Symposium on New Paradigms and Treatment Approaches in Mental Health—Dec. 13, 2022," Beckley Psytech Press Release Dec. 7, 2022 (4 pages).
"Beckley Psytech to Present at 32nd Annual Oppenheimer Healthcare Conference," Mar. 10, 2022. https://www.businesswire.com/news/home/20220309005837/en/Beckley-Psytech-to-Present-at-32nd-Annual-Oppenheimer-Healthcare-Conference. (2 pages).
"Beckley Psytech to present at H.C. Wainwright 2nd Annual Psychedelics Conference and Stifel 2nd Annual Conference "The Future of Healthcare"," Dec. 2, 2021. https://www.businesswire.com/news/home/20211201006018/en/Beckley-Psytech-to-present-at-H.C.-Wainwright-2nd-Annual-Psychedelics-Conference-and-Stifel-2nd-Annual-Conference-%E2%80%9CThe-Future-of-Healthcare%E2%80%9D. (2 pages).
"Beckley Psytech to present at Jefferies 2021 London Healthcare Conference," Nov. 2, 2021. https://www.businesswire.com/news/home/20211102005131/en/Beckley-Psytech-to-present-at-Jefferies-2021-London-Healthcare-Conference. (2 pages).
"Beckley Psytech to present data from Phase I study of BPL-003, a novel synthetic formulation of 5-MeO-DMT (Mebufotenin), at upcoming scientific conference," Beckley Psytech Press Release Apr. 24, 2023 (5 pages).
"Beckley Psytech's Phase I study results of novel 5-MeO-DMT formulation BPL-003 published in The Journal of Psychopharmacology," Beckley Psytech Press Release Apr. 17, 2024 (6 pages).
"Brunch with Sifted: Amanda Feilding and Cosmo Feilding-Mellen on the psychedelic renaissance," Beckley Psytech Press Release Nov. 24, 2021 (13 pages).
"Cimarec+ stirrers, hotplates, and stirring hotplates: Operating Manual and Parts List," Thermo Scientific (Feb. 2017) (31 pages).
"Clinical Practice Guideline: Intranasal Medication Administration," Emergency Nurses Association. (36 pages) (2016).
"Clomipramine," <https://www.drugs.com/monograph/clomipramine.html>, medically reviewed on May 22, 2024 (16 pages).
"Cosmo Feilding Mellen on Beckley Psytech's plans for 2021," Beckley Psytech Press Release Apr. 12, 2021 (6 pages).
"Dr Frank Wiegand, Experienced Neuroscience Leader Joins Beckley Psytech as Chief Medical Officer," Nov. 3, 2021. https://www.businesswire.com/news/home/20211103005056/en/Dr-Frank-Wiegand-Experienced-Neuroscience-Leader-Joins-Beckley-Psytech-as-Chief-Medical-Officer. (2 pages).
"Enhancing the accessibility of psychedelic healthcare," Beckley Psytech Press Release Nov. 23, 2021 (7 pages).
"European companies set to dominate psychedelics market," Beckley Psytech Press Release Mar. 1, 2021 (12 pages).
"First participant dosed in research study investigating the effects of BPL-003, a novel formulation of 5-MeO-DMT, on the human brain," Beckley Psytech Press Release Jun. 3, 2024 (6 pages).
"First patient dosed in Beckley Psytech's international Phase IIb study of BPL-003, a novel synthetic intranasal formulation of 5-MeO-DMT, for Treatment Resistant Depression (TRD)," Beckley Psytech Press Release Oct. 24, 2023 (6 pages).
"First Patient Dosed in Beckley Psytech's Phase IIa Study of BPL-003 for Treatment Resistant Depression," May 4, 2023. https://www.businesswire.com/news/home/20230504005020/en/First-Patient-Dosed-in-Beckley-Psytech%E2%80%99s-Phase-IIa-Study-of-BPL-003-for-Treatment-Resistant-Depression. (2 pages).
"First patient dosed in Beckley Psytech's Phase IIa study of BPL-003 in combination with SSRIs for Treatment Resistant Depression," Beckley Psytech Press Release Apr. 24, 2024 (6 pages).
"Former GW Pharmaceuticals CFO joins Beckley Psytech's Board," Beckley Psytech Press Release Apr. 13, 2021 (4 pages).
"Global Investors Back Psychedelic Medicine Start-Up With $3.8m Series A Round," Beckley Psytech Press Release Jun. 30, 2020 (9 pages).
"Investors think mind-bending drug DMT could rival psilocybin as a cost-effective psychedelic treatment for conditions like depression. 3 VCs explain why its fast-acting properties are appealing," Beckley Psytech Press Release May 30, 2021 (3 pages).
"Learning from 50 years of psychedelic progress," Psytech Press Release Oct. 19, 2020 (6 pages).
"Meet our new scientific advisors," Psytech Press Release Nov. 6, 2020 (4 pages).
"Meet our new Scientific Advisory Board!," Beckley Psytech Press Release Sep. 10, 2020 (6 pages).
"N-[2-(1-methyl-1H-indol-3-yl)ethyl]oxan-4-amine," Chemazone. Product No. 171.355.434, retrieved Oct. 24, 2024 (4 pages).
"N-[2-(1H-indol-3-yl)ethyl]oxan-4-amine," National Library of Medicine. PubChem CID: 43608479, retrieved Oct. 25, 2024 (2009) (7 pages).

(56) References Cited

OTHER PUBLICATIONS

"New psychedelic medicine COO looks to boost pharma and biotech collaborations," Beckley Psytech Press Release 2.22.21 (4 pages).

"Prescribe Software for Mental Health Treatment," Beckley Psytech Press Release Jun. 16, 2021 (6 pages).

"Psychedelic Compounds Chemical and Physical Properties," <https://wiki.dmt-nexus.me/Psychedelic_Compounds_Chemical_and_Physical_Properties>, last modified on May 19, 2023 (18 pages).

"Psychedelics breakthroughs—why now?," Beckley Psytech Press Release Sep. 10, 2020 (6 pages).

"Quiet! Seed Crystals Growing," Flinn Scientific Inc, <https://www.flinnsci.com/api/library/Download/fcd83e5a579b470f9c0acc678ac6564c>, (6 pages) (2017).

"Researchers In Europe, U.S. Team Up To Produce First Ever 5-MeO-DMT Psychedelic Training Program," Beckley Psytech Press Release Apr. 19, 2021 (8 pages).

"Seed crystal," <https://web.archive.org/web/20201209202659/https://en.wikipedia.org/wiki/Seed_crystal>, last modified Mar. 29, 2020 (2 pages).

"Spotlight on Beckley Psytech and psilocybin," Beckley Psytech Press Release Mar. 22, 2021 (5 pages).

"Spotlight on the psychedelic experience," Beckley Psytech Press Release Jun. 9, 2021 (5 pages).

"Spravato (esketamine) nasal spray, CIII." Janssen Pharmaceuticals, prescribing information. Jul. 2020 (15 pages).

"Thermal Applications Note: Purge Gas Recommendations for use in Modulated DSC," TA Instruments: Thermal Analysis & Rheology (3 pages).

"This psychedelic medicine company wants to treat psychiatric and neurological disorders," Psytech Press Release Dec. 21, 2020 (5 pages).

"Understanding 5-MeO-DMT: Historical use," Beckley Psytech Press Release Mar. 11, 2021 (5 pages).

"Vacuum for Laboratories: Vacuu-Lan Local Vacuum Networks," Vacuubrand (2019) (16 pages).

"Wearable technology can revolutionise our clinical research," Beckley Psytech Press Release Mar. 2, 2021 (5 pages).

"Woman who has suffered with a non-stop headache for eight years fulfils dream of becoming a mum," Beckley Psytech Press Release Mar. 2, 2021 (8 pages).

Akai et al., "Anxiolytic effects of lisuride and its agonistic action to central 5-HT1A receptors," Nihon Yakurigaku Zasshi. 97(4):209-20 (English Abstract Included) (Apr. 1991).

Family et al., "Safety, tolerability, pharmacokinetics, and pharmacodynamics of low dose lysergic acid diethylamide (LSD) in healthy older volunteers," Psychopharmacology. 237(3):841-853 (13 pages) (Dec. 2019).

Greenan et al., "Preparation and Characterization of Novel Crystalline Solvates and Polymorphs of Psilocybin and Identification of Solid Forms Suitable for Clinical Development," ResearchGate (Feb. 2020) (29 pages).

Haridy, Rich, "The start-up behind a magic mushroom nose spray for psychedelic microdosing," New Atlas. Dec. 5, 2019 (12 pages).

Kargbo et al., "Direct Phosphorylation of Psilocin Enables Optimized cGMP Kilogram-Scale Manufacture of Psilocybin," ACS Omega. 5(27): 16959-16966 (Jul. 2020).

Kargbo et al., "Psilocybin: Characterization of the Metastable Zone Width (MSZW), Control of Anhydrous Polymorphs, and Particle Size Distribution (PSD)," ACS Omega. 7(6): 5429-5436 (Feb. 2022) with supporting information.

Katzman, Martin A., "Aripiprazole: A clinical review of its use for the treatment of anxiety disorders and anxiety as a comorbidity in mental illness," Journal of Affective Disorders. 128S1:S11-20 (2011).

Kooijman et al., "Are psychedelics the answer to chronic pain: A review of current literature," Pain Pract. 23(4): 447-458 (Apr. 2023).

Lieberman et al., "Lisuride in Parkinson disease: efficacy of lisuride compared to levodopa," Neurology. 31(8):961-5. Abstract (Aug. 1981).

Malik et al., "Phase 1 Study Results on the Effects of 5-MeO-DMT Benzoate on Facial Emotion Processing in Psychedelic-Naïve Healthy Subjects," Neuroscience Applied 2. P.0097:45-46 (2 pages).

Malik et al., "Phase 1 study results on the effects of 5-MeO-DMT. benzoate (BPL-003) on facial emotion processing in psychedelic-naïve healthy subjects," Beckley Psytech. Poster No. P.0097. Presented: Sep. 30, 2023 (1 page).

Marek et al., "The selective 5-HT2A receptor antagonist M100907 enhances antidepressant-like behavioral effects of the SSRI fluoxetine," Neuropsychopharmacology. 30(12):2205-2015 (Dec. 2005).

Nakamura et al., "Effects in animal models of depression of lisuride alone and upon coadministration with antidepressants," Folia pharmacol japon. 94(1):81-9 (English language abstract) (1989).

Passie et al., "The pharmacology of lysergic acid diethylamide: a review," CNS Neurosci Ther. 14(4):295-314 (2008) (20 pages).

Reckweg et al., "A Phase 1, Dose-Ranging Study to Assess Safety and Psychoactive Effects of a Vaporized 5-Methoxy-N, N-Dimethyltryptamine Formulation (GH001) in Healthy Volunteers," Front Pharmacol. 12 (760671) (12 pages) (Nov. 2021).

Reckweg et al., "A phase 1/2 trial to assess safety and efficacy of a vaporized 5-methoxy-N,N-dimethyltryptamine formulation (GH001) in patients with treatment-resistant depression," Front Psychiatry. (8 pages) (Jun. 2023).

Roberts et al., "Intranasal 5-MeO-DMT (BPL-003) safety, pharmacokinetics and psychedelic effects in healthy volunteers," Beckley Psytech. Poster No. p. 0639. Presented: 6th ECNP Congress, Barcelona, Spain, Oct. 7-10, 2023 (1 page).

Roberts et al., "Intranasal 5-Methoxy-N, N-Dimethyltryptamine Safety, Pharmacokinetics and Psychedelic Effects in Healthy Volunteers," Neuroscience Applied 2. P.0639:6-7 (Oct. 2023) (2 pages).

Robertson, Dr. Donald L., "Supersaturated Solution," modified Oct. 18, 2010 (1 page).

Rucker et al., "Intranasal 5-MeO-DMT (BPL-003) Safety, PK, and effect on altered states of consciousness in healthy volunteers," Beckley Psytech. Poster No. T152. Presented: SOBP Annual Meeting, San Diego, California, Apr. 27-29, 2023 (1 page).

Rucker et al., "Phase 1, placebo-controlled, single ascending dose trial to evaluate the safety, pharmacokinetics and effect on altered states of consciousness of intranasal BPL-003 (5-methoxy- N,N-dimethyltryptamine benzoate) in healthy participants," J. Psychopharmacol. Clinical Trial 38(8): 712-723 (Aug. 2024).

Shen et al., "Nonlinear pharmacokinetics of 5-methoxy-N, N-dimethyltryptamine in mice," Drug Metab Dispos. 39(7): 1227-34 (Jul. 2011).

Sherwood et al., "Psilocybin: crystal structure solutions enable phase analysis of prior art and recently patented examples," Acta Crystallogr C Struct Chem. 78(Pt 1):36-55 (Jan. 2022).

Turton et al., "A qualitative report on the subjective experience of intravenous psilocybin administered in an FMRI environment," Curr Drug Abuse Rev. 7(2):117-127 (2014).

Tyles et al., "Psilocybin—summary of knowledge and new perspectives," Eur Neuropsychopharmacol. 24(3): 342-56 (Mar. 2014).

* cited by examiner

5-METHOXY-N,N-DIMETHYLTRYPTAMINE (5-MeO-DMT) FORMULATIONS

FIELD OF THE INVENTION

This invention relates to 5-methoxy-N,N-dimethyltryptamine (5-MeO-DMT) formulations, more particularly intranasal formulations of pharmaceutically acceptable salts of 5-MeO-DMT comprising silicon dioxide, nasal delivery devices comprising the same, and methods of administration and treatment.

BACKGROUND OF THE INVENTION 5-methoxy-N,N-dimethyltryptamine is a pharmacologically active compound of the tryptamine class and has the chemical formula:

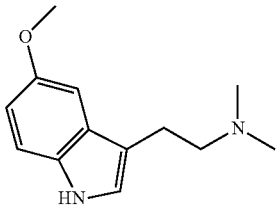 [SMILES: COc1ccc2[nH]cc(CCN(C)C)c2c1]

5-MeO-DMT is a psychoactive/psychedelic substance found in nature. Man-made salts of 5-MeO-DMT are also known in the art e.g. Sherwood, Alexander M., et al. "Synthesis and Characterization of 5-MeO-DMT succinate for clinical use." ACS omega 5.49 (2020): 32067-32075 discloses the hydrochloride salt of 5-MeO-DMT. However, 5-MeO-DMT, and salts thereof, are not well understood and methods of administration, in particular intranasal methods of administration of formulations of this compound, and the salts thereof, are difficult to develop and have not been well explored.

For example, it has been found that liquid intranasal formulations of the hydrochloride salt of 5-MeO-DMT experience issues relating to stability, discolouration and a reduction in desirable pharmacokinetic properties. For the sake of brevity, the term '5-MeO-DMT' used herein, may also be understood to be referring to the salts of 5-MeO-DMT.

5-MeO-DMT is not suitable for oral delivery and so other methods of administration have been considered. Other methods of administration are possible e.g. intravenous and inhalation by smoking. Intranasal administration, e.g. nasal spray formulation, is also another way of providing systemic drug delivery across the blood brain barrier, in particular when oral administration is not effective.

There remains a need in the art for improved formulations, in particular free-flowing dry powder intranasal formulations, comprising 5-MeO-DMT and the salts thereof, and methods of administration and treatment using the same to enable safe and non-invasive dosing that allows for greater accessibility for patients and greater patient compliance.

SUMMARY OF THE INVENTION

The nasal cavity is recognised as a promising systemic drug delivery route due to the highly vascularised capillary bed within the nasal mucosa. The inventors have surprisingly discovered a dry blended free-flowing dry powder formulation comprising 5-MeO-DMT, or a pharmaceutically acceptable salt thereof, and silicon dioxide (see, e.g., Example 32). Said formulation remained free-flowing following storage in a range of conditions, including 25° C./60% RH, and possesses the most desirable flow properties compared to a range of other excipients tested. Such formulations, and uses thereof, are described herein.

Furthermore, it was discovered that delivery of 5-MeO-DMT formulations by an active nasal delivery device surprisingly produced a desirable nasal deposition profile whilst delivery of 5-MeO-DMT formulations by a passive nasal delivery device produced an undesirable nasal deposition profile.

Herein disclosed, there is provided an active nasal delivery device comprising a pharmaceutical formulation of 5-MeO-DMT and one or more pharmaceutically acceptable carriers or excipients. In an embodiment, the pharmaceutical formulation of 5-MeO-DMT is a spray dried formulation. In an embodiment, the formulation comprises below about 5% moisture content by weight of the formulation.

In an embodiment, at least 95% (e.g., at least 96%, at least 97%, at least 98%, or at least 99%) of the particles of the formulation are larger than 10 microns in size. In an embodiment, the formulation comprises methyl cellulose, optionally a high viscosity methyl cellulose (e.g., a refined methylcellulose characterized by it's high viscosity properties in water). In an embodiment, the formulation comprises a low viscosity methyl cellulose, and a high viscosity methyl cellulose. In an embodiment, the formulation comprises a cellulose like/based excipient; optionally HPMC, further optionally a high viscosity HPMC (e.g., a refined HPMC characterized by it's high viscosity properties in water). In an embodiment, the formulation comprises a low viscosity HPMC (e.g., commonly used grades of LV HPMC are E3 LV, E5 LV, E6 LV, E15 LV, E50 LV, and K100 LV) and a high viscosity HPMC.

In an embodiment, the ratio of the low viscosity HPMC to high viscosity HPMC is in the ratio of 1:10 to 10:1 (e.g., 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1), optionally 1:4 to 4:1 (e.g., 1:4, 1:3, 1:2, 1:1, 2:1, 3:1, or 4:1) and further optionally 1:2 to 2:1 (e.g., 0.5±0.25, 0.75±0.25, 1±0.25, 1.25±0.25, 1.5±0.25, 1.75±0.25, or 2±0.25). In an embodiment, the ratio of the low viscosity HPMC to high viscosity HPMC is in the ratio of 50:50, 45:55, 40:60, 35:65, 30:70 or 25:75. In an embodiment, the high viscosity HPMC has a viscosity greater or equal to about 20, 30, 40, 50 or 60 megaPascals, optionally where the HPMC is a HPMC containing about 7.0-12.0% hydroxypropyl content, about 28.0-30.0% methoxy content, and a viscosity of about 50 mPas. In an embodiment, the low viscosity HPMC has a viscosity less than about 20, 15, 10, 5, 1 megaPascals, optionally where the HPMC is a HPMC containing about 7.0-12.0% (e.g., 7%±1%, 8%±1%, 9%±1%, 10%±1%, 11%±1%, or 12%±1%) hydroxypropyl content, about 28.0-30.0% (e.g., 28%±2%, 29%±2%, or 30%±2%) methoxy content, and a viscosity of about 4.8-7.2 (e.g., 4.8±0.5, 5.3±0.5, 5.7±0.5, 6.2±0.5, 6.7±0.5, 7±0.5, or 7.2±0.5) mPas.

In an embodiment, the formulation comprises a polyol. The polyol may be mannitol, xylitol, sorbitol, maltitol, erythritol, lactitol or isomalt, further optionally the polyol is sorbitol. In an embodiment, the formulation comprises about 1-10% (e.g., 1%±0.5%, 1.5%±0.5%, 2%±1%, 3%±1%, 4%±1%, 5%±1%, 6%±1%, 7%±1%, 8%±1%, 9%±1%, or 10%±1%), 2-5% (e.g., 1%±0.5%, 1.5%±0.5%, 2%±0.5%, 2.5%±0.5%, 3%±0.5%, 3.5%%±0.5%, 4%%±0.5%, 4.5%±0.5%, or 5%±0.5%) or 3% polyol by weight, optionally about 3% (e.g., 3%±1%) sorbitol or mannitol or isomalt by weight.

In an embodiment, the formulation comprises a 5-MeO-DMT salt. In an embodiment, the formulation comprises 5-MeO-DMT benzoate. In an embodiment, the formulation comprises 5-MeO-DMT hydrochloride. In an embodiment, the formulation comprises 5-MeO-DMT hydrobromide. In an embodiment, the 5-MeO-DMT salt is amorphous. In an embodiment, the 5-MeO-DMT salt is crystalline. In an embodiment, the crystalline 5-MeO-DMT salt is selected from: a crystalline form of 5-MeO-DMT benzoate, characterised by one or more peaks in an XRPD diffractogram at 17.5, 17.7 and 21.0°2θ±0.1°2θ as measured using an x-ray wavelength of 1.5406 Å; a crystalline form of 5-MeO-DMT hydrochloride, characterised by one or more peaks in an XRPD diffractogram at 9.2°±0.1°, 12.2°±0.1°, 14.1°±0.1°, 15.0°±0.1°, 18.5°±0.1°, and 19.5°±0.1°2θ as measured by x-ray powder diffraction using an x-ray wavelength of 1.5406 Å; or a crystalline form of 5-MeO-DMT hydrobromide, characterised by one or more peaks in an XRPD diffractogram at 14.6, 16.8, 20.8, 24.3, 24.9 and 27.5°2θ±0.1°2θ as measured by x-ray powder diffraction using an x-ray wavelength of 1.5406 Å.

In an embodiment, the active nasal delivery device comprises: a dispenser outlet; an air expeller for generating a flow of air while the device is being actuated; and at least one reservoir that contains a single dose of formulation.

In an embodiment, the active nasal delivery device comprises: a dispenser outlet; an air expeller for generating a flow of air while the device is being actuated, said air expeller including a piston that slides in an air chamber between a rest position and a dispensing position, said air chamber including a cylindrical body in which said piston slides in airtight manner; and at least one reservoir that contains a single dose of formulation, said reservoir including an air inlet that is connected to said air expeller, and a formulation outlet that is connected to said dispenser outlet, said air inlet including a formulation retainer member for retaining the formulation in the reservoir until the formulation is dispensed, and said formulation outlet being closed by a closure element that is force fitted in the formulation outlet of the reservoir; said device further including a mechanical opening system that co-operates with said closure element so as to expel said closure element mechanically from a closed position while the device is being actuated, said piston of said air expeller, when in the rest position, co-operating in non-airtight manner with said air chamber, in such a manner that said air chamber is in communication with the atmosphere in the rest position, wherein said piston includes an inner lip configured to cooperate with a cylindrical surface of a cylindrical member extending inside the cylindrical body, said cylindrical surface including fluting that co-operates in non-airtight manner with said inner lip of the piston in the rest position.

In an embodiment, the active nasal delivery device is for use in a method of treating a disease or condition. In an embodiment, the active nasal delivery device is for use in treating a mental health condition, optionally depression and/or alcohol use disorder.

Herein disclosed, there is provided a dry powder formulation, produced by spray drying, lyophilisation or hot melt extrusion, wherein the formulation comprises 5-MeO-DMT, or a pharmaceutically acceptable salt thereof, and one or more pharmaceutically acceptable carriers or excipients. Beneficially, spray drying, lyophilisation or hot melt extrusion provide an intimate mix of the 5-MeO-DMT salt with any of the carriers, excipients or any other additives.

In a first aspect, there is provided a state-stable amorphous dry powder formulation comprising 5-MeO-DMT HBr (the hydrobromide salt of 5-MeO-DMT) or 5-MeO-DMT HCl (the hydrochloride salt of 5-MeO-DMT) and one or more pharmaceutically acceptable carriers or excipients. Beneficially, the amorphous state does not revert to a crystalline form, and so the nature of the formulation is well understood.

In an embodiment, the formulation is a spray dried formulation. In an embodiment, no more than 80% of the 5-MeO-DMT is released from the formulation by 4 minutes in water at 37° C. In an embodiment, no more than 80% of the 5-MeO-DMT is released from the formulation by 5, 6, 7, 8, 9 or 10 minutes in water at 37° C. In an embodiment, no more than 80% of the 5-MeO-DMT is released from the formulation by 5, 6, 7, 8, 9 or 10 minutes in a simulated nasal fluid. Beneficially, the 5-MeO-DMT is not released immediately, and indeed released relatively slowly. Beneficially, the person being treated receives the active substance over a duration of time. On some occasions, receiving the active substance, a psychoactive substance, over a very short period of time can be quite intense.

In an embodiment, at least 95% (e.g., 95%, 96%, 97%, 98%, 99%, or 100%) of the particles of the formulation are larger than 10 microns in size. Beneficially, the formulation does not substantially contain respirable fines (undesirable particles that could enter the lungs).

In an embodiment, the 5-MeO-DMT HBr is non-hygroscopic. In an embodiment, the formulation comprises below about 5% (e.g., less that 5%, 4%, 3%, 2%, or 1%) moisture content by weight of the formulation. In an embodiment, the formulation is a free flowing formulation.

In an embodiment, greater than 70% (w/w) (e.g., 70% (w/w)±10% (w/w), 80% (w/w)±10% (w/w), 90% (w/w) ±10% (w/w)) of the 5-MeO-DMT HBr in the formulation is in an amorphous form. In an embodiment, the formulation comprises at least about 10%±5%, 15%±5%, 20%±10%, 30%±10%, 40%±10%, 50%±10%, 60%±10%, 70%±10%, 80%±10%, 90%±10%, 95% or 99% by weight 5-MeO-DMT HBr.

In an embodiment, greater than 70% (w/w) (e.g., 70% (w/w)±10% (w/w), 80% (w/w)±10% (w/w), 90% (w/w) ±10% (w/w)) of the 5-MeO-DMT HCl in the formulation is in an amorphous form. In an embodiment, the formulation comprises at least about 10%±5%, 15%±5%, 20%±10%, 30%±10%, 40%±10%, 50%±10%, 60%±10%, 70%±10%, 80%±10%, 90%±10%, 95% or 99% 95% or 99% by weight 5-MeO-DMT HCl In an embodiment, upon administration to a nasal cavity of a subject the formulation exhibits a residence time. In an embodiment, the length of time a substance is present in nasal cavity, for example along the nasal cilia and mucus layer, in the nasal cavity of at least 10, 15, 20, 25, 30, 35, 40, 45, 50, 55 or 60 minutes. Beneficially, the person being treated receives the active substance over a duration of time. On some occasions, receiving the active substance, a psychoactive substance, over a very short period of time can be quite intense.

In an embodiment, the formulation comprises a cellulose like/based excipient; optionally cellulose ethers, optionally HPMC, further optionally a high viscosity HPMC, still further optionally a high viscosity HPMC. In an embodiment, the formulation comprises a low viscosity HPMC and a high viscosity HPMC. In an embodiment, wherein the ratio of the low viscosity HPMC to high viscosity HPMC is in the ratio of 1:10 to 10:1 (e.g., 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1), optionally 1:4 to 4:1 (e.g., 1:4, 1:3, 1:2, 1:1, 2:1, 3:1, or 4:1) and further optionally 1:2 to 2:1 (e.g., 0.5±0.25, 0.75±0.25, 1±0.25, 1.25±0.25, 1.5±0.25, 1.75±0.25, or 2±0.25). In an embodiment, the ratio of the low viscosity HPMC to high viscosity HPMC is in the ratio of 50:50, 45:55, 40:60, 35:65, 30:70 or 25:75. In an embodiment, the high viscosity HPMC has a viscosity greater or equal to about 20, 30, 40, 50 or 60 megaPascals, optionally where the HPMC is a HPMC containing about 7.0-12.0% (e.g., 7%±1%, 8%±1%, 9%±1%, 10%±1%, 11%±1%, or 12%±1%) hydroxypropyl content, about 28.0-30.0% (e.g., 28%±2%, 29%±2%, or 30%±2%) methoxy content, and a viscosity of about 50 mPas. In an embodiment, the low viscosity HPMC has a viscosity less than about 20, 15, 10, 5, 1 megaPascals, optionally where the HPMC is a HPMC containing about 7.0-12.0% (e.g., 7%±1%, 8%±1%, 9%±1%, 10%±1%, 11%±1%, or 12%±1%) hydroxypropyl content, about 28.0-30.0% (e.g., 28%±2%, 29%±2%, or 30%±2%) methoxy content, and a viscosity of about 4.8-7.2 (e.g., 4.8±0.5, 5.3±0.5, 5.7±0.5, 6.2±0.5, 6.7±0.5, 7±0.5, or 7.2±0.5) mPas. In an embodiment, the formulation comprises a polyol, optionally the polyol is mannitol, xylitol, sorbitol, maltitol, erythritol, lactitol or isomalt, further optionally the polyol is sorbitol. In an embodiment, the formulation comprises about 1-10% (e.g., 1%±0.5%, 1.5%±0.5%, 2%±1%, 3%±1%, 4%±1%, 5%±1%, 6%±1%, 7%±1%, 8%±1%, 9%±1%, or 10%±1%), 2-5% (e.g., 1%±0.5%, 1.5%±0.5%, 2%±0.5%, 2.5%±0.5%, 3%±0.5%, 3.5%%±0.5%, 4%%±0.5%, 4.5%±0.5%, or 5%±0.5%) or 3% polyol by weight, optionally about 3% (e.g., 3%±1%) sorbitol by weight.

In an embodiment, the formulation comprises one or more of: chitosan, chitosan derivatives, β-cyclodextrin, *Clostridium perfringens* enterotoxin, zonula occludens toxin (ZOT), human neutrophil elastase inhibitor (ER143), sodium taurocholate, sodium deoxycholate sodium, sodium lauryl sulphate, glycodeoxycholat, palmitic acid, palmitoleic acid, stearic acid, oleyl acid, oleyl alcohol, capric acid sodium salt, DHA, EPA, dipalmitoyl phophatidyl choline, soybean lecithin, lysophosphatidylcholine, dodecyl maltoside, tetradecyl maltoside, EDTA, lactose, cellulose, and citric acid. In an embodiment, the formulation comprises one or more of: mucoadhesive enhancer, penetrating enhancer, cationic polymers, cyclodextrins, Tight Junction Modulators, enzyme inhibitors, surfactants, chelators, and polysaccharides.

In an embodiment, the formulation comprises one or more anti-caking agents. In an embodiment, the formulation comprises one or more of: calcium silicate, sodium aluminosilicate, sodium ferrocyanide, potassium ferrocyanide, calcium carbonate, magnesium carbonate, silicon dioxide, tricalcium phosphate, powdered cellulose, magnesium stearate, sodium bicarbonate, sodium ferrocyanide, potassium ferrocyanide, calcium ferrocyanide, microcrystalline cellulose, calcium phosphate, sodium silicate, silicon dioxide, calcium silicate, magnesium trisilicate, talcum powder, sodium aluminosilicate, potassium aluminium silicate, calcium aluminosilicate, bentonite, aluminium silicate, stearic acid, sodium stearyl fumarate, polydimethylsiloxane or leucine.

In an embodiment, there is provided a nasal delivery device comprising the formulation. In an embodiment, the proportion of the active substance (5-MeO-DMT), in the active substance salt is greater than about 65%, 70%, or 80% (e.g., 65%±5%, 70%±5%, 75%±5%, 80%±5%, 85%±5%, 90%±5%, or 95%±5%) (i.e. using a counter ion of smaller relative molecular mass). Beneficially, in a device with a small delivery chamber, a high proportion of active in the salt is desirable. Similarly, the higher the proportion of the salt in the particles is desirable.

In an embodiment, there is provided a method of treating depression and/or substance use disorders (for example recreational drugs and or alcohol) in a subject in need thereof, the method comprising intranasally administering to the subject the formulation in an amount sufficient to treat the depression and/or alcohol use disorder. In an embodiment, there is provided a method of making the formulation, the method comprising (i) mixing the components of the formulation with a liquid to form a mixture and spray drying the mixture to form a solid; and (ii) following following step (i), further drying the solid to form the formulation and optionally wherein the drying step is performed at between 45° C. and 15° C. (e.g., 15° C.±5° C., 20° C.±5° C., 25° C.±5° C., 30° C.±5° C., 35° C.±5° C., 40° C.±5° C., or 45° C.±5° C.) and between 85% to 65% (e.g., 65%±10%, 75%±10%, or 85%±10%) relative humidity (RH); between 35 and 20° C. (e.g., 20° C.±5° C., 25° C.±5° C., 30° C.±5° C., or 35° C.±5° C.) and between 80% to 70% (e.g., 71%, 72%, 73%, 74%, 75%, 76%, 77%, 78%, 79%, or 80%) RH; and further optionally at 25° C. and 75% RH.

In an embodiment, the formulation comprises about:
- 40-60% (e.g., 40%±5%, 45%±5%, 50%±5%, 55%±5%, or 60%±5%) by weight 5-MeO-DMT or pharmaceutically acceptable salt.
- 30-40% (e.g., 30%±2%, 32%±2%, 34%±2% 36%±2%, 38%±2%, or 40%±2%) by weight a HPMC containing about 7.0-12.0% (e.g., 7%±1%, 8%±1%, 9%±1%, 10%±1%, 11%±1%, or 12%±1%) hydroxypropyl content, about 28.0-30.0% (e.g., 28%±2%, 29%±2%, or 30%±2%) methoxy content, and a viscosity of about 4.8-7.2 (e.g., 4.8±0.5, 5.3±0.5, 5.7±0.5, 6.2±0.5, 6.7±0.5, 7±0.5, or 7.2±0.5) mPas;
- 7-15% (e.g., 7%±3%, 10%±3%, 12%±3%, or 15%±3%) by weight a HPMC containing about 7.0-12.0% (e.g., 4.8±0.5, 5.3±0.5, 5.7±0.5, 6.2±0.5, 6.7±0.5, 7±0.5, or 7.2±0.5) hydroxypropyl content, about 28.0-30.0% (e.g., 28%±2%, 29%±2%, or 30%±2%) methoxy content, and a viscosity of about 50 mPas; and
- 0-5% (e.g., 1%±1%, 2%±1%, 3%±1%, 4%±1%, or 5%±1%) by weight sorbitol.

In a further embodiment, the formulation comprises about:
- 40-60% (e.g., 40%±5%, 45%±5%, 50%±5%, 55%±5%, or 60%±5%) by weight 5-MeO-DMT HBr or 5-MeO-DMT HCl
- 30-40% (e.g., 30%±2%, 32%±2%, 34%±2% 36%±2%, 38%±2%, or 40%±2%) by weight a HPMC containing about 7.0-12.0% (e.g., 7%±1%, 8%±1%, 9%±1%, 10%±1%, 11%±1%, or 12%±1%) hydroxypropyl content, about 28.0-30.0% (e.g., 28%±2%, 29%±2%, or 30%±2%) methoxy content, and a viscosity of about 4.8-7.2 (e.g., 4.8±0.5, 5.3±0.5, 5.7±0.5, 6.2±0.5, 6.7±0.5, 7±0.5, or 7.2±0.5) mPas;
- 7-15% (e.g., 7%±3%, 10%±3%, 12%±3%, or 15%±3%) by weight a HPMC containing about 7.0-12.0% (e.g., 7%±1%, 8%±1%, 9%±1%, 10%±1%, 11%±1%, or 12%±1%) hydroxypropyl content, about 28.0-30.0% (e.g., 28%±2%, 29%±2%, or 30%±2%) methoxy content, and a viscosity of about 50 mPas; and
- 0-5% (e.g., 1%±1%, 2%±1%, 3%±1%, 4%±1%, or 5%±1%) by weight sorbitol.

In an embodiment, the 5-MeO-DMT, or a pharmaceutically acceptable salt thereof, is in an amorphous (non-crystalline) form. In an embodiment, the formulation is a stable free flowing formulation.

In an embodiment, the formulation is a state-stable free flowing formulation. In an embodiment, the formulation comprises at least about 10%, 20%, 30%, 40%, 50%, 60%, 70%, 80%, 90%, 95% or 99% by weight 5-MeO-DMT, or a pharmaceutically acceptable salt thereof. In an embodiment, the formulation exhibits an extended release profile, optionally having a residence time in the nasal cavity of at least 10, 15, 20, 25 or 30 minutes. In an embodiment, the formulation exhibits an extended release profile, wherein 80% of the 5-MeO-DMT active agent dissolves over a period of time of about 2 to 40, optionally 3 to 30, further optionally 4 to 15 minutes.

In an embodiment, the formulation comprises a cellulose like/based excipient; optionally cellulose ethers, optionally HPMC, further optionally a high viscosity HPMC, still further optionally a high viscosity HPMC. In an embodiment, the formulation exhibits an extended release profile. In an embodiment, the formulation comprises a cellulose like/based excipient; optionally HPMC, further optionally a high viscosity HPMC, still further optionally a high viscosity HPMC, and wherein the formulation exhibits an extended release profile. In an embodiment, the formulation exhibits an extended release profile when compared with a formulation without the cellulose like/based excipient. In an embodiment, the formulation comprises a low viscosity HPMC and a high viscosity HPMC. In an embodiment, the formulation exhibits an extended release profile.

In an embodiment, the formulation comprises a low viscosity HPMC and a high viscosity HPMC, and wherein the formulation exhibits an extended release profile. In an embodiment, the ratio of the low viscosity HPMC to high viscosity HPMC is in the ratio of 1:10 to 10:1 (e.g., 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1), optionally 1:4 to 4:1 (e.g., 1:4, 1:3, 1:2, 1:1, 2:1, 3:1, or 4:1) and further optionally 1:2 to 2:1 (e.g., 0.5±0.25, 0.75±0.25, 1±0.25, 1.25±0.25, 1.5±0.25, 1.75±0.25, or 2±0.25). In an embodiment, the ratio of the low viscosity HPMC to high viscosity HPMC is in the ratio of 50:50, 45:55, 40:60, 35:65, 30:70 or 25:75. In an embodiment, the ratio of the low viscosity HPMC to high viscosity HPMC is in the ratio of 50:50, 45:55, 40:60, 35:65, 30:70 or 25:75 and wherein the formulation exhibits an extended release profile. In an embodiment, wherein the high viscosity HPMC has a viscosity greater or equal to about 20, 30, 40, 50 or 60 megaPascals, optionally where the HPMC is metolose 60SH50.

In an embodiment, the low viscosity HPMC has a viscosity less than about 20, 15, 10, 5, 1 megaPascals, optionally where the HPMC is pharmacoat 606. In an embodiment, the formulation comprises a polyol, optionally the polyol is mannitol, xylitol, sorbitol, maltitol, erythritol, lactitol or isomalt, further optionally the polyol is sorbitol. In an embodiment, the formulation comprises about 1-10%, 2-5% or 3% polyol by weight, optionally about 3% sorbitol by weight.

In an embodiment, the formulation comprises 5-MeO-DMT hydrochloride, optionally the salt is in an amorphous form, further optionally a state-stable amorphous form. In an embodiment, the formulation comprises 5-MeO-DMT hydrobromide, optionally the salt is in an amorphous form, further optionally a state-stable amorphous form. In an embodiment, the formulation comprises 5-MeO-DMT benzoate, optionally the salt is in an amorphous form, further optionally a state-stable amorphous form. In an embodiment, the formulation comprises 5-MeO-DMT oxalate, optionally the salt is in an amorphous form, further optionally a state-stable amorphous form. In an embodiment, the formulation comprises 5-MeO-DMT phosphate, optionally the salt is in an amorphous form, further optionally a state-stable amorphous form. In an embodiment, the formulation comprises 5-MeO-DMT fumarate, optionally the salt is in an amorphous form, further optionally a state-stable amorphous form.

In an embodiment, the formulation comprises a 5-MeO-DMT salt, optionally the salt is in an amorphous form, further optionally a state-stable amorphous form. In a further aspect of the invention, there is provided a nasal delivery device comprising the formulations herein described, and/or in any aspect or embodiment of the invention. In an embodiment, the device is single use. In an embodiment, the device contains a single dose of the formulation. In an embodiment, the formulation or nasal delivery device is for use as a medicament.

In an embodiment, the formulation or nasal delivery device is for use in a method of treatment of depression and/or alcohol use disorder. In an embodiment, the formulation is produced by spray drying and wherein following the spray drying of the formulation, an additional conditioning step is performed to condition the formulation. In an embodiment, the drying step is performed at between 45 and 15° C. and between 85% to 65% relative humidity (RH); optionally between 35 and 20° C. and between 80% to 70% RH; and further optionally at 25° C. and 75% RH.

In an embodiment, there is provided a dry powder formulation, produced by a method of spray drying, wherein the formulation comprises about:
- 50% by weight 5-MeO-DMT, or a pharmaceutically acceptable salt thereof;
- 35% by weight HPMC 606;
- 12% by weight Metolose 60 SH 50; and
- 3% by weight sorbitol.

Liquid intranasal administration is one way of providing systemic drug delivery across the blood brain barrier. However, one of the challenges faced with these liquid formulations is the limited residence time in the nasal cavity. The mucociliary clearance mechanism is responsible for this limited residence time, the movement of the nasal cilia leads the upper gel-like mucus layer in the epithelia to move with a velocity of about 6 mm/min towards the nasopharynx and throat. As such, such liquid formulations are rapidly removed from the nasal cavity. In addition, some liquid intranasal formulations of 5-MeO-DMT, can have stability issues, e.g. discolouration and/or a reduction in desirable pharmacokinetic properties.

Some attempts have been made to develop dry powder formulations for intranasal administration which overcome the problems associated with liquid formulations. However, this has proved challenging. The first intranasal dry powder formulations were approved by the Food and Drug Administration in 2016 and 2019 for Onzentra (containing Sumatriptan) and Baqsimi (containing Glucagon) respectively. Onzentra uses a passive administration device and Baqsimi uses an active device; and so work was needed to find a formulation and device that in each case would work well in concert.

In addition, some 5-MeO-DMT salts have been found to be very soluble in water (e.g. some crystalline forms of the halide salts of 5-MeO-DMT have a solubility of >400 mg/ml in water) and have very rapid dissolution profiles. While these properties can be desirable in solid oral or intravenous dosage formulations, they are not necessarily beneficial for intranasal formulations of 5-MeO-DMT.

This is because 5-MeO-DMT can provide a very intense Mystical Experience in a subject. So, for a highly soluble intranasal formulation that rapidly crosses the blood brain barrier (e.g. 80% of the dose of the active agent in under about 4 minutes) the Mystical Experience generated may happen very quickly, and can be quite intense, cause irritation, and this may be unsettling for some users.

The applicant has beneficially found that dry powder formulations of 5-MeO-DMT (and the salts described herein), in particular amorphous dry powder formulations of the same, address and/or ameliorate the problems encountered in the prior art as discussed further herein below.

The applicant has beneficially found that the following factors (not necessary listed in the order of importance) provide beneficial properties when making dry powder formulations of 5-MeO-DMT: amorphous (non-crystalline) form/state; moderate/lower solubility forms; excipients/agents that slow/retard the dissolution of the active agent across the nasal blood brain barrier (e.g. in particular cellulose like/based excipients like HMPC and (methyl) cellulose). As such, the applicant has sought to increase the residency time of the active agent (5-MeO-DMT) in the nasal cavity. Other modifications have not proved effective and indeed in some case have lessened the residency time in the nasal cavity. Also, when matching the formulation to a dry powdered delivery device, the proportion of the active agent in the formulation should be relatively high (so a smaller formula weight counter ion can be beneficial, as is a low proportion of any excipient/additives), e.g. to maximize the proportion of the active agent in the delivery vehicle, which may need to fit within a relatively small delivery chamber in the delivery vehicle (e.g. holding a volume of less than about 0.05 ml). Also, beneficially, the—formulation should be state-stable e.g. it should not (re) crystalize, in particular upon storage. More beneficially, an amorphous (non-crystalline) form/state should be state-stable at or above room temperature e.g. it should not (re) crystalize when stored at about above 0, 5, 10, 15, 20, 25, 30 or 35° C. Also, the cellulose like/based excipients may have a viscosity to suit need, e.g. high, moderate or low viscosity or contain a mixture of these with different viscosities (e.g. a high and low viscosity). Without being bound by theory, it is possible that the 5-MeO-DMT is preferentially soluble in the cellulose like/based excipients, and this delays/retards the API (i.e. 5-MeO-DMT) travelling across the nasal blood brain barrier. Advantageously, the formulation should be free from respirable API fines (e.g. which may enter the lungs) and/or significant amounts of any aggregation. Respirable fines are particles which are 10 microns or less. In an embodiment, the formulation comprises particles which are larger than 10 microns. In an embodiment, the formulation is substantially free of respirable fines. In an embodiment, 75, 80, 90, 95, 98, 99, 99.5, 99.8 or 99.9% of the particles of the formulation are larger than 10 microns.

In an embodiment the formulation comprises particles having a median diameter of less than 2000 μm, 1000 μm, 500 μm, 250 μm, 100 μm, 50 μm, or 1 μm. In an embodiment, the particles have a median diameter of greater than 500 μm, 250 μm, 100 μm, 50 μm, 40 μm, 30 μm, 25 μm, 20 μm, 15 μm, 10 μm, 5 μm, 1 μm or 0.5 μm. In an embodiment formulation has a particle size distribution of d10=20-60 μm, and/or d50=80-120 μm, and/or d90=130-300 μm.

It is considered that a formulation could be prepared that contained a slow release element/portion and a standard release element/portion (e.g. a mixture of amorphous and partially crystalline 5-MeO-DMT (the API)), such that there is an initial release of the API (e.g. a lower amount), followed by a slower release of the API (e.g. a larger amount).

In an embodiment, the formulation comprises crystalline API dry blended with SDD comprising API/HPMC. Beneficially, this may provide for higher drug loadings within a single device.

Herein disclosed, the formulation is free from the one or more pharmaceutically acceptable carriers or excipients.

5-MeO-DMT is very likely to be treated as a controlled drug by Health Authorities. The Authorities would require the setting up of specific methodology for the prescribing and use of this drug in patients. When taken as prescribed by a licensed physician, controlled substances can effectively treat many conditions. However, over the past decade, in many countries, it can be seen that a drastic increase in controlled substance diversion, misuse, and abuse has occurred.

Most drugs of abuse directly or indirectly target the brain's reward system affecting the body's ability to regulate movement, emotion, motivation, and feelings of pleasure. When the system is overstimulated with certain controlled substances, it produces euphoric effects, which strongly reinforce the behaviour of substance use, thereby teaching the user to repeat the action. Although the leading route of administration is oral, some individuals alter the route of administration to intensify the effect or as they build a tolerance to the substance.

Alternative routes of administration, including intranasal (e.g. crushing and snorting) and intravenous (e.g. dissolving and injecting) methods, smoking inhalation, often provide faster drug delivery and onset, and intensified effects. Individuals who use altered routes of administration are at an increased risk for overdose and the development or exacerbation of substance use disorders. Abuse-deterrent formulations prevent inexperienced substance users from successfully ingesting substances via altered routes of administration, and thereby prevent associated overdoses and escalation of substance use, resulting in significant personal and public health benefits.

Abuse-deterrent formulations limit one or more forms of such abuse by reducing the attractiveness or drug-liking qualities of a controlled substance by: (1) Hindering the extraction of active ingredients; (2) Decreasing their bioavailability through product manipulation, thereby reducing the feeling of euphoria; (3) Preventing administration through alternative routes; (4) Making abuse of the manipulated product less attractive or rewarding.

In an embodiment the 5-MeO-DMT composition is formulated as an abuse-deterrent formulation to include one or more of the following types of abuse deterrent technology: (1) Physical barriers: to prevent chewing, crushing, cutting, grating or grinding; (2) Chemical barriers: to resist extraction of the opioid using common solvents, such as water, alcohol, or other organic solvents; (3) Agonist/antagonist combinations: to interfere with, reduce, or defeat the euphoria associated with abuse upon manipulation of the product; (4) Aversion: to combine substances in order to produce an unpleasant effect if the dosage form is manipulated prior to ingestion or a higher dosage than directed is used; (5) Delivery systems: certain drug release designs or methods of drug delivery that offer resistance to abuse, such as depot injectable formulations or implants; 6) Prodrugs: to lack activity until transformed in the gastrointestinal tract, thereby making intravenous injection or intranasal abuse less attractive; (7) Combination: products that combine two or more of the above-mentioned methods.

Particular 5-MeO-DMT compositions as described herein in the form of, for example, spray dried dispersions of 5-MeO-DMT in combination with one or more pharmaceutically acceptable excipients benefit not only from the herein described advantageous properties of said dispersions, but also from the fact that said dispersions provide a deterrent to abuse. The intimately mixed nature of the dispersions provides a barrier to the easy extraction of the active pharmaceutical ingredient.

In an embodiment, there is provided a 5-MeO-DMT composition or formulation as described herein wherein said composition or formulation comprises a polyol and wherein said composition or formulation shows a strong reduction of mucosal irritation upon the intranasal, buccal, sublabial or sublingual administration thereof, compared with a composition or formulation without a polyol.

In an embodiment, there is provided a method of reducing mucosal irritation in a subject upon intranasal, buccal, sublabial or sublingual administration of 5-MeO-DMT to the subject, wherein said method comprises providing the 5-MeO-DMT in a composition or formulation as described herein, wherein said composition or formulation comprises a polyol.

In an embodiment, there is provided a 5-MeO-DMT composition or formulation as described herein wherein said composition or formulation comprises 5-MeO-DMT as the saccharinate salt and wherein said composition or formulation shows a strong reduction of mucosal irritation upon the intranasal, buccal, sublabial or sublingual administration thereof, compared with a composition or formulation of 5-MeO-DMT freebase or an alternative salt form.

In an embodiment, there is provided a method of reducing mucosal irritation in a subject upon intranasal, buccal, sublabial or sublingual administration of 5-MeO-DMT to the subject, wherein said method comprises providing the 5-MeO-DMT in a composition or formulation as described herein, wherein said composition or formulation 5-MeO-DMT as the saccharinate salt.

In an embodiment, there is provided a composition or a formulation comprising 5-MeO-DMT, or a pharmaceutically acceptable salt thereof, wherein said composition or formulation is as described herein and/or is produced as described herein and has a residency time in the nasal cavity of greater than or equal to 5, 6, 7, 8, 9, 10, 11, 12, 13, 14, 15, 16, 17, 18, 19, 20, 25, 30, 35, 40, 45, 50, 55 or 60 minutes.

In an embodiment, the composition comprises a salt of 5-MeO-DMT. In an embodiment, the composition comprises a crystalline salt of 5-MeO-DMT. In an embodiment, there is provided a crystalline form of 5-MeO-DMT hydrobromide. In an embodiment, there is provided a crystalline form of 5-MeO-DMT hydrobromide, characterised by one or more peaks in an XRPD diffractogram at 14.6, 16.8, 20.8, 24.3, 24.9 and 27.5°2θ±0.1°2θ as measured by x-ray powder diffraction using an x-ray wavelength of 1.5406 Å.

In an embodiment, there is provided a crystalline form of 5-MeO-DMT phosphate, characterised by one or more peaks in an XRPD diffractogram at 12.9, 20.4 and 23.1°2θ±0.1°2θ as measured by x-ray powder diffraction using an x-ray wavelength of 1.5406 Å. In an embodiment, there is provided a crystalline form of 5-MeO-DMT fumarate, characterised by one or more peaks in an XRPD diffractogram at 13.0, 16.3 and 22.1°2θ±0.1°2θ as measured by x-ray powder diffraction using an x-ray wavelength of 1.5406 Å. In an embodiment, there is provided a crystalline form of 5-MeO-DMT oxalate, characterised by one or more peaks in an XRPD diffractogram at 13.0, 19.9 and 26.0°2θ±0.1°2θ as measured by x-ray powder diffraction using an x-ray wavelength of 1.5406 Å. In an embodiment, there is provided a crystalline form of 5-MeO-DMT tartrate, characterised by one or more peaks in an XRPD diffractogram at 18.3, 18.6, and 20.7°2θ±0.1°2θ as measured by x-ray powder diffraction using an x-ray wavelength of 1.5406 Å. In an embodiment, there is provided a crystalline form of 5-MeO-DMT benzenesulfonate, characterised by one or more peaks in an XRPD diffractogram at 9.5, 21.2, and 23.6°2θ±0.1°2θ as measured by x-ray powder diffraction using an x-ray wavelength of 1.5406 Å. In an embodiment, there is provided a crystalline form of 5-MeO-DMT tosylate, characterised by one or more peaks in an XRPD diffractogram at 19.3, 23.6 and 24.1°2θ±0.1°2θ as measured by x-ray powder diffraction using an x-ray wavelength of 1.5406 Å. In an embodiment, there is provided a crystalline form of 5-MeO-DMT glycolate, characterised by one or more peaks in an XRPD diffractogram at 20.2, 21.1 and 23.4°2θ±0.1°2θ as measured by x-ray powder diffraction using an x-ray wavelength of 1.5406 Å. In an embodiment, there is provided a crystalline form of 5-MeO-DMT ketoglutarate, characterised by one or more peaks in an XRPD diffractogram at 14.4, 18.2 and 20.9°2θ±0.1°2θ as measured by x-ray powder diffraction using an x-ray wavelength of 1.5406 Å. In an embodiment, there is provided a crystalline form of 5-MeO-DMT malate, characterised by one or more peaks in an XRPD diffractogram at 18.3, 18.7 and 18.9°2θ±0.1°2θ as measured by x-ray powder diffraction using an x-ray wavelength of 1.5406 Å. In an embodiment, there is provided a crystalline form of 5-MeO-DMT saccharinate, characterised by one or more peaks in an XRPD diffractogram at 8.7, 15.2 and 20.9°2θ±0.1°2θ as measured by x-ray powder diffraction using an x-ray wavelength of 1.5406 Å. In an embodiment, there is provided a crystalline form of 5-MeO-DMT hydrochloride, characterised by one or more peaks in an XRPD diffractogram at 9.2°±0.1°, 12.2°±0.1°, 14.1°±0.1°, 15.0°±0.1°, 18.5°±0.1°, and 19.5°±0.1°2θ as measured by x-ray powder diffraction using an x-ray wavelength of 1.5406 Å. In an embodiment, there is provided a crystalline form of 5-MeO-DMT benzoate, characterised by one or more peaks in an XRPD diffractogram at 17.5, 17.7 and 21.0°2θ±0.1°2θ as measured using an x-ray wavelength of 1.5406 Å.

DESCRIPTION OF THE INVENTION

In an embodiment, there is provided a dry powder formulation comprising 5-MeO-DMT, or a pharmaceutically acceptable salt thereof, and polyvinylpyrrolidone (PVP).

Herein disclosed, there is provided a method of production of a formulation of 5-MeO-DMT comprising the steps of:
a. Atomisation of a liquid mixture comprising 5-MeO-DMT to produce droplets;
b. Contact between a hot gas and the droplets to dry the droplets;
c. Optionally, the separation of the dried product from the drying medium; and
d. Conditioning of the dried product.

In an embodiment, the conditioning step comprises exposing the dried product to between 15 to 45° C. and between 65% to 85% relative humidity (RH); optionally between 2° and 35° C. and between 70 to 80% RH; and further optionally 25° C. and 75% RH.

In an embodiment, the conditioning step takes place for between 1 day and several weeks. In an embodiment, the conditioning step takes place for between 1 day and 1 week. In an embodiment, the conditioning step takes place for between 1 day and 3 days. In an embodiment, the conditioning step takes place for less than 1 day.

In an embodiment, there is provided a formulation as described previously or subsequently. In an embodiment, the formulation is produced by spray drying, lyophilisation and/or hot melt extrusion.

Unless otherwise stated herein all X-ray powder diffractograms (XRPD) were generated using an X-ray wavelength of 1.5406 Å; all modulated differential scanning calorimetry (DSC) thermograms were generated using a 2° C./min heating rate.

The applicant has beneficially found that in order to slow the dissolution rate, and therefore increase the residency time in the nasal cavity, the dry powder formulation should optionally include one or more suitable excipient.

Hydroxypropyl methylcellulose (HPMC) or hypromellose refers to soluble methylcellulose ethers and is approved as an inactive ingredient. Without being bound by theory, HPMC is believed to act as a viscosity enhancer, and delays/slows mucociliary clearance. HPMC polymers for fabricating hydrophilic matrix systems are available in various viscosity grades ranging from 4000-100,000 mPas. The polymer chain length, size and degree of branching determine the viscosity of the polymer in solution.

Different grades of HPMC (with lower viscosities than that above) are also available according to their particle size distribution, viscosity, molecular weights, and substitution of methoxy and hydroxypropyl groups.

The HPMC in compositions of the invention can be selected to function as a binder, film former, and/or hydrophilic matrix material. HPMC polymers for fabricating hydrophilic matrix systems are available in various viscosity grades. The viscosity of the HPMC may be measured at 20° C. in an aqueous solution of 2% (w/w). In certain instances, the viscosity of the HPMC may be measured at 2% (w/v) in an aqueous solution at 20° C. The solid dispersions of the invention can be tuned/controlled by selection of a suitable molecular weight of polymer.

In some embodiments, the solid dispersion comprises a polymer(s) having a low viscosity grade, e.g., a low molecular weight, such as a weight average molecular weight of less than or equal to 100,000 g/mol, less than or equal to 90,000 g/mol, less than or equal to 80,000 g/mol, less than or equal to 70,000 g/mol, less than or equal to 60,000 g/mol, less than or equal to 50,000 g/mol, less than or equal to 40,000 g/mol, less than or equal to 30,000 g/mol, less than or equal to 20,000 g/mol, less than or equal to 15,000 g/mol. Typically, the lower limit of weight average molecular weight for low viscosity grade polymers may be from 1,000 g/mol, from 2,000 g/mol, from 4,000 g/mol, from 6,000 g/mol, from 8,000 g/mol, from 10,000 g/mol, from 12,000 g/mol, from 14,000 g/mol. In some embodiments, the low molecular weight polymer is a low molecular weight HPMC polymer, having a molecular weight within the above recite range, alone or as a polymer blend. Examples of a low molecular weight HPMC polymers which can be used herein include, but are not limited to, AFFINISOL™ HPMC HME 15LV (water soluble; amorphous HPMC polymer with a molecular weight of less than 100 kDa; bulk density of 0.42 g/cc; D (0.5) of 104.49 pm), METHOCEL™ E3 LV (2910 substitution type: 28-30% methoxy substitution, 7-12% hydroxypropyl substitution; viscosity of 4.0-6.0 mPa-s as 2% solution in water at 20° C.), METHOCEL™ E6 premium LV (70,000-80,000 g/mol, 2910 substitution type: 28-30% methoxy substitution, 7-12% hydroxypropyl substitution; viscosity of 4.8-7.2 mPa-s as 2% solution in water at 20° C.), each available from DuPont, and PHARMACOAT® 606 (2910 substitution type: 28-30% methoxy substitution, 7-12% hydroxypropyl substitution; viscosity of 6.0 mPa-s as 2% solution in water at 20° C.), available from Shin-Etsu Chemical Co. Ltd. The selection of a low molecular weight polymer may provide solid dispersions adapted for immediate release or fast release of the 5-MeO-DMT. For example, immediate release may refer to dosage forms which release greater than 80 wt. % of the active ingredient within about 1 minute following administration, while the phrase fast release may refer to dosage forms in which the release of 80 wt. % of the active ingredient takes place in a range of about 1 minute to about 5 minutes following administration. While not limited to specific manufacturing techniques, solid dispersions comprising a low molecular weight polymer or polymer blend may be advantageously suited for freeze drying or spray drying preparation methods. For the purposes of this application a low viscosity HPMC would generally be considered to be one with a viscosity grade of less than 20 mPas.

In some embodiments, the solid dispersion comprises a polymer having a high viscosity grade, e.g., a high molecular weight, such as a weight average molecular weight of at least 150,000 g/mol, at least 200,000 g/mol, at least 250,000 g/mol, at least 300,000 g/mol, at least 350,000 g/mol, at least 400,000 g/mol, at least 450,000 g/mol, at least 500,000 g/mol, at least 550,000 g/mol, at least 600,000 g/mol, at least 650,000 g/mol, at least 700,000 g/mol, at least 750,000 g/mol, at least 800,000 g/mol, at least 850,000 g/mol, at least 900,000 g/mol, at least 950,000 g/mol, at least 1,000,000 g/mol. The upper limit of molecular weight for high viscosity grade polymers is not particularly limited, but is typically up to 5,000,000 g/mol, 4,000,000 g/mol, 3,000,000 g/mol, or 2,000,000 g/mol. In some embodiments, the high molecular weight polymer is a high molecular weight HPMC polymer, having a molecular weight within the above recited range. Examples of a high molecular weight HPMC polymer which can be used herein include, but are not limited to, AFFINISOL™ HPMC HME 100LV or HPMC HME 4M, each available from DuPont; METHOCEL™ K100LV (164,000 g/mol), METHOCEL™ K4M (400,000 g/mol), METHOCEL™ K15M (575,000 g/mol), each available from Colorcon, Inc.; BENECEL™ K35M Pharm (2208 substitution type; 675,000 g/mol) and BENECEL™ K100LV PH PRM (2208 substitution type; 164,000 g/mol), each available from Ashland. High molecular weight polymers or polymer blends may provide solid dispersions can be adapted for either fast release or extended-release dosage forms where it is desirable to release the 5-MeO-DMT over extended periods of time, such as for example over 10 minutes, 7 minutes, 10 minutes, 20 minutes, 30 minutes, or any range in between, or longer. For example, extended-release may refer to dosage forms in which the release of 80 wt. % of the active ingredient takes place in a range of about 5 minutes or longer, 10 minutes or longer, 15 minutes or longer, etc. following administration. While not limited to specific manufacturing techniques, solid dispersions comprising a high molecular weight polymer or polymer blend may be advantageously suited for hot melt extrusion, spray drying, or freeze drying preparation methods. For the purposes of this application a high viscosity HPMC would generally be considered to be one with a viscosity grade of 20 mPas or above. HPMC 2910 has an average content of methoxy groups of 29% and hydropropoxy groups of 10% (hence the nomenclature of 2910). Pharmacoat is a brand of low viscosity HPMC 2910, with Pharmacoat 606 (as commercially available in the UK as of 1 Jun. 2023) has a viscosity of 6 mPas. Metolose is a brand of high viscosity HPMC 2910 and methyl cellulose. Metolose 60SH50 606 (as commercially available in the UK as of 1 Jun. 2023) has a viscosity of 50 mPas Dry Blending Dry blending (giving a solid dispersion matrix) of cellulose based excipients, such as HPMC 2910, with the API at high concentrations up to approximately 95% wt:wt (excipient to 5-MeO-DMT) in the blend, beneficially slowed the dissolution release rate of the API relative to an unblended formulation.

Care is needed when making dry blends to ensure blend uniformity and monitoring of any aggregation/agglomeration may be needed. Also, the nature of the blend needs to be assessed to ensure the physical properties work well with the delivery device and with scale up, e.g. if the resultant blend is prone to static charge build up, then the blend can be difficult to load into the delivery device without losses.

The applicant also found that an intimate mix formulations of the API with excipients gave beneficial properties. Intimate mix formulation (e.g. spray drying, lyophilisation and/or hot melt extrusion with one or more suitable pharmaceutical excipients or carriers) are considered further below. These techniques are best known for generating amorphous solid dispersions with improved bioavailability and increased solubility. In the present case, with the intense Mystical Experiences associated with the API, this would not on the face of it appear beneficial. Typically such dispersions comprise API loading of around 20% wt: wt (e.g. 5-MeO-DMT to excipients) or below.

Lyophilisation Formulations

Amorphous 5-MeO-DMT salt formulations have been produced via lyophilisation processes. It is noted that in some cases these have low glass transition temperatures. Conversion to a crystalline form may therefore occur, perhaps rapidly. Solubility studies utilising a lyophilised amorphous form of 5-MeO-DMT benzoate showed an almost instantaneous dissolution rate, which would have applications where this was a desirable property.

Hot-Melt Formulations

Hot melt extrusion may be utilised to produce 5-MeO-DMT formulations according to the current invention and/or any embodiments thereof. Hot melt extrusion is the processing of polymeric materials above their glass transition temperature (Tg) in order to effect molecular level mixing of thermoplastic binders and/or polymers and active compounds.

Spray Dried Dispersions

Spray drying typically involves injecting a liquid composition of material into a chamber for contact with a drying fluid which is concurrently flowed through the chamber. The injected wet material in the form of droplets contacts the stream of drying fluid so that the liquid passes from the droplets to the drying fluid stream, producing a spray dried product that is discharged from the drying chamber, and drying fluid effluent that likewise is discharged from the drying chamber.

Advantageously, and unexpectedly, the applicant discovered that spray dried dispersions of 5-MeO-DMT gave products with lower/reduced dissolution rates. This was unexpected because spray dried dispersions are generally developed to improve the solubility of low solubility products. The expectation was that the small particles produced by spray drying would have a larger surface area, which allows them to dissolve more easily in the body.

That said, there is a limit to the amount of product that can be administered to the nasal cavity through a medical device, typically below 50 mg (approximately 0.05 ml in volume).

In the case of 5-MeO-DMT dry powder formulations, it is envisaged that single doses of up to 20 mg or above API may be needed, which may require an API loading of for example 50% wt: wt, levels which are not typically seen in spray dried solid dispersions.

Below, more specific sprayed dried formulations are considered.

5-MeO-DMT Benzoate|Spray Dried Powder Formulation

Spray dried powder formulations containing excipient(s) and the benzoate salt of 5-MeO-DMT were produced, which contained dried particles of suitable size for intranasal administration and surprisingly, a reduced dissolution rate as compared to the amorphous form of 5-MeO-DMT salts.

Respirable particles, particles which can penetrate beyond the terminal bronchioles into the gas-exchange region of the lungs are undesirable as they can, for example, trigger bronchoconstriction in asthmatics. In addition, uncontrolled recrystallisation over time within the spray dried dispersion particles may also lead to aggregation of the particles.

With this benzoate salt, the applicant has found that storage at 2-8° C., and protection from moisture, prevents recrystallisation and aggregation. In this case, it was found that a post spray drying step (conditioning the spray dried dispersion particles) at 25° C./75% RH produced a stable crystalline spray dried dispersion particle with no respirable API fines or significant aggregation.

It was also discovered that producing a spray dried dispersion with reduced amount of the benzoate salt loading (e.g. API loading to approximately 20% wt: wt) produced an amorphous dispersion with no sign of the crystalline benzoate salt.

In an embodiment, there is provided a dry powder formulation of this 5-MeO-DMT salt and one or more pharmaceutically acceptable carriers or excipients. In an embodiment, the formulation is an amorphous dry powder formulation. In an embodiment, the formulation has been produced by spray drying. In an embodiment, the formulation has been produced by lyophilisation. In an embodiment, the formulation has been produced by hot melt extrusion.

5-MeO-DMT Oxalate|Spray Dried Powder Formulation

A spray dried powder formulation of 5-MeO-DMT oxalate (50% API loading) and excipient(s) was produced and yielded partially crystalline particles (see Example 2). Without being bound by theory, it is believed that lowering the API content (as was the case with the Benzoate salt) could produce an amorphous dispersion with no sign of the crystalline salt.

In an embodiment, there is provided a dry powder formulation of this 5-MeO-DMT salt and one or more pharmaceutically acceptable carriers or excipients. In an embodiment, the formulation is an amorphous dry powder formulation. In an embodiment, the formulation has been produced by spray drying. In an embodiment, the formulation has been produced by lyophilisation. In an embodiment, the formulation has been produced by hot melt extrusion.

5-MeO-DMT Hydrobromide|Spray Dried Powder Formulation

A spray dried powder formulation of 5-MeO-DMT hydrobromide (50% API loading) and excipient(s) was produced. Surprisingly, this formulation was found to be a stable amorphous dispersion without the need for any additional drying step post spray drying. It was also state-stable when stored at above the temperature range 2-8° C.

In an embodiment, there is provided a dry powder formulation of this 5-MeO-DMT salt and one or more pharmaceutically acceptable carriers or excipients. In an embodiment, the formulation is an amorphous dry powder formulation. In an embodiment, the formulation has been produced by spray drying. In an embodiment, the formulation has been produced by lyophilisation. In an embodiment, the formulation has been produced by hot melt extrusion. In an embodiment, the formulation is non-hygroscopic.

Extended Release Formulations of the Salts of 5-MeO-DMT

Recent clinical trials undertaken by the applicant have identified the desirability of an extended release formulation of 5-MeO-DMT (or salts thereof) suitable for intranasal administration. The applicant has surprisingly discovered that the use of higher viscosity excipients, within a spray dried dispersion as described previously or subsequently, can suitably extend the release window of the API 5-MeO-DMT.

More viscous HPMCs, such as HPMC metolose 60SH50, are not typically suitable for spray drying due to the high viscosity solutions produced as feed stock. Unexpectedly, it has been found that spray drying 5-MeO-DMT with a mixture of a high viscosity HPMC and a lower viscosity HPMC (such as pharmacoat 606) produces spray dried dispersion droplets in which the dissolution of the API from the formulation is slowed.

Various ratios of high viscosity HPMC to low viscosity HPMC have been investigated and it was discovered that the dissolution rate of the API did not significantly differ between a ratio of 50:50 high:low HPMC and a ratio of 25:75 high:low HPMC. The formulations comprising a lower amount overall of high viscosity HPMC are more amenable to the spray drying process (e.g. lower viscosity feed stock).

It was noted that the products obtained with a single HPMC had yields that were higher than products obtained with mixed HPMC products in the spray drying process described above. Further investigation found that, beneficially, that the addition of a polyol to the formulation with the mixed HPMCs, improved the resultant yields (e.g. by as much as about 18% compared with a formulation lacking the polyol). Beneficially and unexpectedly, the addition of the polyol has no appreciable effect on the dissolution rate of the API in the formulation.

In an embodiment an additive such as a polyol or surfactant etc. is added to the formulation prior to spray drying. In an embodiment, the formulation comprises two (or more) different HPMCs. In an embodiment, the formulation comprises two (or more) different HPMCs where these have different viscosities. In an embodiment, the formulation comprises two (or more) different HPMCs. In an embodiment, the formulation comprises two (or more) different HPMCs where these have different viscosities, and wherein the net viscosity of the mixture is spray dryable. In an embodiment, the formulation comprises two (or more) different HPMCs where these have different viscosities, wherein the net viscosity of the mixture is spray dryable, and wherein at least one of the HPMCs alone would not be readily suitable for spray drying.

In an embodiment, there is provided an extended release dry powder formulation of 5-MeO-DMT comprising a mixture of a high viscosity HPMC and a low viscosity HPMC. In an embodiment, the extended release dry powder formulation comprises a ratio of 1:1 of the high and low HPMC. In an embodiment, the ratio is 1:2 of high to low HPMC. In an embodiment, the ratio is 1:3 of high to low HPMC.

In an embodiment, the formulation further comprises a polyol (e.g. an organic compound, e.g. 4 to 12 carbon atoms, and containing multiple hydroxyl groups (—OH)). Optionally containing 4 to 6 carbon atoms. Some of these are polyether, polyester, polycarbonate and also acrylic polyols. Polyether polyols may be further subdivided and classified as polyethylene oxide or polyethylene glycol (PEG), polypropylene glycol (PPG) and Polytetrahydrofuran or PTMEG. These have 2, 3 and 4 carbons respectively per oxygen atom in the repeat unit. Polycaprolactone polyols are also available. Polyols may be biobased and hence renewable.

In an embodiment, the polyol is selected from mannitol, xylitol, sorbitol, maltitol, erythritol, lactitol or isomalt. In an embodiment, the polyol is sorbitol. In an embodiment, the formulation comprises by weight 3% sorbitol.

In an embodiment, the extended release dry powder formulation is produced by spray drying In an embodiment, the production method comprises addition of a polyol e.g. sorbitol or mannitol or combinations of both (e.g. isomalt).

Low Crystalline Content Spray Dried Dispersions

Beneficially, the applicant has discovered that reducing the relative 5-MeO-DMT salt loading of the spray dried dispersion formulation leads to a reduction in salt crystalline content (and hence an overall increase in the amorphous content present in the dispersion). The level of crystalline content was determined using a higher than normal heating rate DSC method and the crystalline content was comparable to that of the low viscosity HPMC formulations. The increased amorphous API content in these formulations surprisingly led to a reduction in the dissolution rate of the formulation. This is contrary to the expected result, wherein amorphous solid dispersions are manufactured with the aim of enhancing the solubility and dissolution of the formulation.

In an embodiment, the dry powder formulation has a moisture content of below about 1%, about 2%, about 3%, about 4%, about 5%, about 6%, about 7%, about 8%, about 9%, about 10% by weight of the formulation.

Non-Hygroscopic 5-MeO-DMT Hydrobromide

In an embodiment, the formulation is non-hygroscopic. It has been surprisingly found that the hydrobromide salt of 5-MeO-DMT is non-hygroscopic. Hygroscopicity is the phenomenon of attracting and holding water molecules via either adsorption or absorption from the surrounding environment. Pharmaceuticals that pick up less than 0.2% moisture at 80% RH are considered non hygroscopic. Pharmaceuticals that pick up between 0.2% and 2.0% moisture at 80% RH are considered slightly hygroscopic. Pharmaceuticals that pick up between 2.0% and 15.0% moisture at 80% RH are considered moderately hygroscopic. Pharmaceuticals that pick up more than 15.0% moisture at 80% RH are considered very hygroscopic. Hygroscopic substances are difficult to handle and costly and burdensome measures must be taken in order to ensure they are not exposed to moisture during process and formulation. Exposed to moisture, hygroscopic substances can take on water and convert to a hydrous form. This presents several disadvantages. First, the hydrous forms may have the disadvantage of being less bioavailable and less dissoluble than the anhydrous forms. Second, the variation in the amount of hydrous versus anhydrous substance from batch to batch could fail to meet specifications set by drug regulatory agencies. Third, processes like milling may cause the drug substance to adhere to manufacturing equipment which may further result in processing delay, increased operator involvement, increased cost, increased maintenance and lower production yield. Fourth, in addition to problems caused by introduction of moisture during the processing of these hygroscopic substances, the potential for absorbance of moisture during storage and handling would adversely affect the dissolubility of the drug substance. Thus shelf-life of the product could be significantly decreased and/or packaging costs could be significantly increased.

Beneficially, the non-hygroscopic properties of the 5-MeO-DMT hydrobromide additionally make it a good salt form for a dry powder formulation.

Nasal Delivery Devices

In an embodiment, there is provided a nasal powder dispenser device having a reservoir containing at least one dose of powder comprising 5-MeO-DMT, or a pharmaceutically acceptable salt thereof (inclusive of any of the aspects and/or embodiments of the invention and/or formulations as described herein). Further, the embodiment may comprise one or more of: a nasal dispenser head for inserting into a user's nostril, the nasal dispenser head including a dispenser orifice; and an air expeller that, during actuation of the nasal powder dispenser device, generates a flow of compressed air so as to dispense a dose of powder into the nostril through the dispenser orifice. In an embodiment, the air expeller has an air chamber and a piston that slides in airtight manner in the air chamber so as to compress the air contained in the air chamber. In an embodiment, in the nasal powder dispenser device, a pressure of the flow of compressed air generated by the air expeller is higher than 0.7 bar; and a volume of the air chamber is greater than about 1700 mm³ (corresponding to a volume of about 12×12×12 mm).

In an embodiment, there is provided a nasal powder delivery device having a container comprising a dose of powder comprising at least particles of 5-MeO-DMT or a pharmaceutically acceptable salt thereof, a nasal delivery head, and an air discharge system generating a flow of compressed air for delivering a dose of powder into the nostril. In an embodiment, the air chamber is arranged in a skirt, and a piston sealingly slides in the air chamber to compress the air. In an embodiment, the piston is connected to an actuating member, in which, before actuation, at least one breakable bridge is provided between the skirt and the actuating member, wherein each breakable bridge is formed on the skirt and cooperates with a radial projection formed on the actuating member. In an embodiment, each radial projection has an axial extension greater than that of the respective breakable bridge and forms an inclined axial ramp on either side.

In an embodiment the device is an Aptar device (UDS—Unidose Solid) as commercially available in the UK as of 1 Jun. 2023. In an embodiment, the dry powder is administered to the subject using a dry powder device as described in U.S. Publication 2016/0296957, which is hereby incorporated by reference in its entirety.

Dry powder devices described in U.S. Publication No. 2022/0362491, International Publication No. WO 2022/123128, International Publication No. WO 2022/171969; and International Publication No. WO 2022/208014 are incorporated herein by reference.

In an embodiment, the counter ion (anion) of the 5-MeO-DMT salt is a benzoate, hydrobromide, hydrochloride, phosphate, fumarate, oxalate, tartrate, benzenesulfonate, tosylate, glycolate, ketoglutarate, malate, saccharinate or succinate salt.

In an embodiment, the formulation may contain two salts of 5-MeO-DMT, wherein the second salt of 5-MeO-DMT salt is a benzoate, hydrobromide, hydrochloride, phosphate, fumarate, oxalate, tartrate, benzenesulfonate, tosylate, glycolate, ketoglutarate, malate, saccharinate or succinate salt. The salt type can be selected by the medical practitioner or formulator to suit need and the particular circumstance of the patient being treated or the physical requirements of the formulation needed. In an embodiment one, or both salts, comprise or consist of an amorphous (non-crystalline) state. In an embodiment one, or both salts, comprise or consist of a state-stable amorphous (non-crystalline) state.

In an embodiment (one or both of) the 5-MeO-DMT salt is 5-MeO-DMT benzoate. Advantageously, the benzoate salt has shown good irritation tolerability, in particular when compared to the better known chloride salt, and has a good stability profile. In an embodiment, the 5-MeO-DMT benzoate is not crystalline. In an embodiment, the crystalline 5-MeO-DMT benzoate is characterised by one or more peaks in an X-ray powder diffraction (XRPD) diffractogram at a 2θ value of 17.5°±0.1°, 17.7°±0.1° and 21.0°±0.1° using an X-ray wavelength of 1.5406 Å.

In an embodiment (one or both of) the 5-MeO-DMT salt is 5-MeO-DMT hydrobromide, and wherein the formulation comprises substantially the same dosage amount of the active 5-MeO-DMT cation. Advantageously, the hydrobromide salt is substantially non-hygroscopic.

It should be appreciated that different salts of 5-MeO-DMT will have different formula weights. For example the hydrochloride, hydrobromide and benzoate have respectively formula weights of about 254.8 g/mol, 299.2 g/mol, 340.4 g/mol and the free base of 5-MeO-DMT 218.3 g/mol. So, this is the amount of substance that is required to give 1 mol of the active agent. So, for example for the salt, the dosage amount may be the equivalent amount of the free base delivered when the salt is taken. So 100 mg dosage amount of 5-MeO-DMT corresponds to 117 mg of the hydrochloride salt (i.e. both providing the same molar amount of the active substance). The greater mass of the salt needed is due to the larger formula weight of the hydrogen chloride salt (i.e. 218.3 g/mol for the free base as compared to 254.8 g/mol for the salt). Similarly, for a deuterated or triturated version of 5-MeO-DMT (also considered within the scope of the invention), a slight increase in mass can be expected due to the increased formula weight of these isotopic compounds. Unless stated otherwise, the mass (mg) of 5-MeO-DMT refers to the mass of benzoate salt (and so the equivalent molar amount of the 5-MeO-DMT active agent). Accordingly, with reference to the other salts mentioned herein, the appropriate mass of the other salt can be scaled accordingly using ratios of the formula weights. These masses of salts are normally rounded up or down to suit need. This rounding may be to the nearest whole, half, quarter or tenth of a milligram (mg). For example, splitting of a combined dose will typically be done to whole numbers so 3.5 and 6.5 mg (combined total of 10 mg) may be formulated to 3 and 7 mg respectively.

In an embodiment, the composition comprises the hydrochloride, phosphate, fumarate, oxalate, tartrate, benzenesulfonate, tosylate, glycolate, ketoglutarate, malate, saccharinate or succinate salt of 5-MeO-DMT. In an embodiment, the composition does not comprises a crystalline form of the hydrochloride, phosphate, fumarate, oxalate, tartrate, benzenesulfonate, tosylate, glycolate, ketoglutarate, malate, saccharinate or succinate salt of 5-MeO-DMT.

In an embodiment, the 5-MeO-DMT is administered as the free base. In an embodiment, the 5-MeO-DMT is administered as a salt. In an embodiment, the 5-MeO-DMT is not administered as a crystalline salt. In an embodiment, the 5-MeO-DMT is not administered as a polymorphic salt form. In an embodiment, the 5-MeO-DMT is not administered as a polymorph of a 5-MeO-DMT salt. In an embodiment, the 5-MeO-DMT is administered as the benzoate, fumarate, citrate, acetate, succinate, halide, fluoride, chloride, bromide, iodide, oxalate, or triflate salt. In an embodiment, the 5-MeO-DMT is administered as the benzoate salt. In an embodiment, the 5-MeO-DMT is administered as the hydrochloride salt. In an embodiment, the 5-MeO-DMT is administered as the hydrobromide salt. In an embodiment, the 5-MeO-DMT salt is administered in an amorphous form. In an embodiment, the 5-MeO-DMT salt is not administered in a crystalline form.

In an embodiment, the 5-MeO-DMT is not administered as a crystalline form of the benzoate salt. Crystalline forms of the benzoate salt are disclosed in WO2021250434 and are incorporated herein by reference. Crystalline forms of the hydrochloride salt are also disclosed in WO2021250434 and are incorporated herein by reference. In an embodiment, crystalline 5-MeO-DMT hydrochloride is characterised by peaks in an X-ray powder diffraction (XRPD) diffractogram at 2θ values of $9.2°±0.1°$, $12.2°±0.1°$, $14.1°±0.1°$, $15.0°±0.1°$, $18.5°±0.1°$, and $19.5°±0.1°$, as measured using an X-ray wavelength of 1.5406 Å.

In an embodiment, the salt anion is an aryl carboxylate. In an embodiment, the aryl carboxylate is substituted with one to three R groups. In an embodiment the one or more R groups are independently selected from: alkynyl, carbonyl, aldehyde, haloformyl, alkyl, halide, hydroxy, alkoxy, carbonate ester, carboxylate, carboxyl, carboalkoxy, methoxy, hydroperoxy, peroxy, ether, hemiacetal, hemiketal, acetal, ketal, orthoester, methylenedioxy, orthocarbonate ester, carboxylic anhydride, carboxamide, secondary, tertiary or quaternary amine, primary or secondary ketimine, primary or secondary aldimine, imide, azide, azo, cyanate, isocyanate, nitrate, nitrile, isonitrile, nitrosooxy, nitro, nitroso, oxime, pyridyl, carbamate, sulfhydryl, sulfide, disulfide, sulfinyl, sulfonyl, sulfino, sulfo, thiocyanate, isothiocyanate, carbonothioyl, carbothioic S-acid, carbothioic O-acid, thiolester, thionoester, carbodithioic acid, carbodithio, phosphino, phosphono, phosphate, borono, boronate, borino or borinate. In an embodiment the one or more R groups are independently selected from: $C_1$-$C_6$ alkyl, $C_1$-$C_6$ alkoxy, $C_1$-$C_6$ alkenyl or $C_1$-$C_6$ alkynyl, and where each of these may be optionally substituted with one to three R groups as previously described.

In an embodiment, the 5-MeO-DMT or the pharmaceutical composition comprising 5-MeO-DMT and one or more pharmaceutically acceptable carriers or excipients, is for use in a method of one or more of: treating mental disorders, in particular treatment resistant depression, major depressive disorder, persistent depressive disorder, alcohol use disorder, anxiety disorder, post-traumatic stress disorder (PTSD), body dysmorphic disorder, obsessive-compulsive disorder, eating disorder and psychoactive substance abuse.

In an embodiment, the disease or condition is: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic disorders, optionally the condition is SUNCT and/or SUNA, alcohol-related diseases and disorders, eating disorders, impulse control disorders, nicotine-related disorders, tobacco-related disorders, methamphetamine-related disorders, amphetamine-related disorders, cannabis-related disorders, cocaine-related disorders, hallucinogen use disorders, inhalant-related disorders, benzodiazepine abuse or dependence related disorders, opioid-related disorders, tobacco addiction, alcohol abuse and/or addiction.

In an embodiment, there is provided the use of a composition or formulation as described herein in a method of treatment wherein the method of treatment comprises interaction of a patient with one or more components of a prescription digital therapeutic (PDT).

In an embodiment, there is provided a prescription digital therapeutic (PDT) for use in a method of medical treatment, wherein the method comprises: administering a dose of 5-MeO-DMT, or a pharmaceutically acceptable salt thereof, to a patient in need thereof; monitoring the interaction of the patient with one or more components of the PDT via one or more electronic devices or inputs linked thereto; assessing the interaction of the patient with the one or more components of the PDT; determining the response of the patient to the administered dose of the 5-MeO-DMT based on the assessment of the interaction of the patient with the one or more components of the PDT; and recommending a dose of the 5-MeO-DMT for further administration, or a cessation of further doses of the 5-MeO-DMT.

Advantageously, 5-MeO-DMT is administered together with the PDT. In an embodiment, the method comprises the detection of relapse. In an embodiment, the method comprises recommending a dose of the 5-MeO-DMT to enhance the patient response to the treatment.

In an embodiment, the one or more components of the PDT comprise: guided meditation; breathing exercises; neuro/bio-feedback exercises; journaling; surveys/questionnaires; video and/or audio content; remote contact with one or more healthcare professionals (HCPs) and/or one or more peers who have experienced 5-MeO-DMT benzoate treatment (hereafter 'peers'); therapy tasks, such as the Values Card Sort Task; remote cognitive behavioural therapy (CBT); AI chat tools; and automated reminders and/or alerts.

A prescription digital therapeutic (PDT) is a prescription-only software that delivers evidence-based therapeutic intervention(s) to prevent, manage or treat a medical disorder or disease. Herein disclosed is the use of PDT in connection with treatment of a patient with 5-MeO-DMT (i.e. a potent psychoactive/psychedelic substance) to assist, improve and/or optimize the patient treatment outcomes, which can be altered positively (or negatively) depending on how the patient is managed.

As such, patient preparation prior to treatment with 5-MeO-DMT is believed to be important for optimal experience and outcomes. That is, the 5-MeO-DMT experience is visually and experientially all encompassing, with limited connection to the physical environment. The intensity of the experience with 5-MeO-DMT is such that conscious control or direction of the experience is not possible, therefore there is perhaps a greater need for pre-therapy preparation to enter the experience in the right sub-conscious state/mindset. Administration of 5-MeO-DMT is believed to generate a neuroplastic effect such that delivery of psychotherapy in the weeks after treatment generates a greater impact on outcomes. Long term, identifying the return of symptoms and the need for retreatment or therapy may be important for delivering sustained recovery.

The methods are designed to be delivered prior to and after administration of 5-MeO-DMT, for psychological/psychiatric conditions via a digital platform and uses actively and passively entered data to support preparation, post-treatment integration, and ongoing therapy to enhance and sustain patient response to treatment.

The methods are also useful in screening potential candidates prior to treatment with 5-MeO-DMT for likelihood and/or type of treatment response. A combination of active and passive data is used to generate a response profile that indicates whether treatment with 5-MeO-DMT will be safe and effective. Based on the identified response profile of the individual, the method may provide a clinician with a recommendation on the optimal treatment protocol (therapy, drug, dose etc), and determines any settings for automated preparation, in-experience setting and post-treatment integration. The methods support integration through automated content, therapy, and connecting individuals to therapists remotely, and to others who have also experienced 5-MeO-DMT therapy. In an embodiment, the method additionally comprises the interaction of the patient with one or more components of the PDT occurs prior to administration of the dose of the 5-MeO-DMT. In an embodiment, the method additionally comprises the interaction of the patient with one or more components of the PDT occurs prior to administration of the dose of the 5-MeO-DMT, wherein administration of the dose of the 5-MeO-DMT only occurs if the interaction of the patient with one or more components of the PDT indicates the patient is likely to respond favourably to such administration.

Favourable (or disfavourable) response may for example be determined in an appropriate manner, e.g. as suggested by one or more of:

Favourable response may for example determined in an appropriate manner, e.g. as suggested by one or more of: lower scores on symptom severity at the start of treatment could indicate good response, i.e. fewer negatively valenced words, lower scores on depression surveys; engagement with preparation: users who open the PDT/app and engage on a daily basis prior to 5-MeO-DMT administration may be more likely to respond well; lack of physical co-morbidities: e.g. user tend to respond better to CBT, and so show a similar profile with 5-MeO-DMT; social engagement/support: passive measures of social interaction (number of text messages, calls, nearby Bluetooth connections) as associated with better outcomes post 5-MeO-DMT treatment; cognitive function/flexibility: users who have faster response times, inhibition (as measured by speed and pattern of tapping on the smartphone screen) and other measures of executive function may demonstrate increased cognitive flexibility post 5-MeO-DMT and therefore the impact of 5-MeO-DMT and/or therapy is believed to be greater, leading to better outcomes In an embodiment, an interaction with AI chat tool wherein the patient responds negatively to a series of questions indicates that they are unlikely to respond favourably to 5-MeO-DMT administration. In an embodiment, lower scores on symptom severity at the start of treatment indicates good response (i.e. fewer negatively valenced words, lower scores on depression surveys). In an embodiment, higher engagement by the patient with the one or more components of the PDT indicates that they are likely to respond favourably to 5-MeO-DMT administration. In an embodiment, declining levels of engagement by the patient with the one or more components of the PDT during treatment may indicate relapse. In an embodiment, low levels of engagement by the patient with the one or more components of the PDT prior to treatment may indicate that they are unlikely to respond to favourably to such treatment. In an embodiment, a low measure of social engagement/ support prior to or during treatment may indicate that a patient is unlikely to respond favourably to treatment. In an embodiment, a low measure of social engagement/support is determined by measures of social interaction (number of text messages, calls, nearby Bluetooth™ connections). In an embodiment, the speed of a patient interaction with the one or more components of the PDT may indicate whether or not the patient is likely to respond favourably to treatment with 5-MeO-DMT and/or respond favourably to continued treatment with 5-MeO-DMT. In an embodiment, a slow speed of patient interaction may indicate the patient is less likely to respond favourably. In an embodiment, a low number of taps on a phone screen per minute during interaction with the one or more components of the PDT may indicate the patient is less likely to respond favourably. In an embodiment, a high number of taps on a phone screen per minute during interaction with the one or more components of the PDT may indicate the patient is more likely to respond favourably. In an embodiment, a fast response/speed of patient interaction may indicate the patient is more likely to respond favourably. In an embodiment, the patient interacts with one or more components of the PDT via a dedicated application (app) present, or hosted, on one or more electronic devices.

In an embodiment, the app records data regarding the interaction of the patient with one or more of the: guided meditation; breathing exercises; journaling; surveys/questionnaires; video and/or audio content; remote HCPs and/or one or more peers who have experienced 5-MeO-DMT treatment (hereafter 'peers'); therapy tasks; remote CBT; AI chat tools; and automated reminders and/or alerts and wherein the data is for use in determining the response of the patient to the administered dose of the 5-MeO-DMT, and/or for recommending a dose of the 5-MeO-DMT for further administration, or a cessation of further doses of the 5-MeO-DMT.

In an embodiment, the app records data regarding the interaction of the patient with one or more of: human electronic device interaction patterns (e.g. screen touches); patient movement (e.g. accelerometer and/or gyroscope data and/or GPS location data and/or Wi-Fi network interaction data); patient physiology (e.g. heart rate and/or respiratory rate and/or galvanic skin response and/or blood pressure and/or temperature data and/or EEG data); patient eye movement and blinking patterns; patient facial movement patterns; patient sleep patterns (e.g. frequency and/or duration and/or quality, as derived from electronic device usage patterns, actigraphy etc.); patient communication patterns (e.g. messaging data and/or voice call data and/or voice over internet protocol [VoIP] data and/or contacts communicated with data and/or duration of inbound and outbound call data and/or instant messaging data); and/or app usage data (e.g. number of app opens and/or duration of app usage and/or type of app usage).

In an embodiment, determining the response of the patient and/or recommending a dose of the 5-MeO-DMT is done remotely by, or with the input from, one or more HCPs. In an embodiment, determining the response of the patient and/or recommending a dose of the 5-MeO-DMT is done remotely by, or with the input from, one or more algorithms. In an embodiment, determining the response of the patient and/or recommending a dose of the 5-MeO-DMT is done remotely by, or with the input from, one or more HCPs and one or more algorithms. In an embodiment, determining the response of the patient includes determining whether or not the patient is currently, or in danger of, relapsing.

In an embodiment, if it is determined that there is no, or little, beneficial response of the patient, then: a treatment change is initiated to the dose of the 5-MeO-DMT; and/or a treatment change is initiated to the one or more components of the PDT. In an embodiment, the treatment change is initiated by, or with the input from, one or more algorithms. In an embodiment, the treatment change is initiated by, or with the input from, one or more HCPs. In an embodiment, the treatment change is initiated by, or with the input from, one or more HCPs and one or more algorithms.

In an embodiment, the treatment change comprises a change in one or more of: dose of the 5-MeO-DMT; frequency of administration of the 5-MeO-DMT; form of administration of the 5-MeO-DMT; and components of the PDT.

In an embodiment, the change in the one or more components of the PDT is selected from a change in one or more of: guided meditation; breathing exercises; neuro/bio-feedback exercises; journaling; surveys/questionnaires; video and/or audio content; remote contact with one or more HCPs and/or one or more peers who have experienced 5-MeO-DMT treatment (hereafter 'peers'); therapy tasks, such as the Values Card Sort Task; remote cognitive behavioural therapy (CBT); AI chat tools; and automated reminders and/or alerts.

In an embodiment, the one or more electronic devices are selected from: smart device; smartphone; smartwatch; smart glasses; smart ring; smart patch; home hub smart device (e.g. Amazon Alexa™); fitness tracker; personal computer; tablet (e.g. iPad™); and/or EEG monitor.

In an embodiment, the PDT itself initiates a change to the PDT based on the data gathered by one or more electronic devices. In an embodiment, the one or more electronic devices records and transmits data associated with the patient and/or their interactions with one or more components of the PDT to a third party, optionally the third party is one or more HCPs. In an embodiment, the data is transmitted via a secure backend service. In an embodiment, the data is encrypted prior to transmission. In an embodiment, based on the transmitted data, the third party who is optionally one or more HCPs, initiates a treatment change to the dose of the 5-MeO-DMT, and/or a treatment change to the one or more components of the PDT.

In an embodiment, the 5-MeO-DMT is administered to the patient in the presence of a HCP in a dedicated treatment room, and optionally wherein the patient is sat down.

In an embodiment, there is provided the use of a formulation as described herein comprising 5-MeO-DMT, optionally the benzoate salt, in a method of treatment, wherein the method comprises administering a formulation as described herein comprising 5-MeO-DMT, optionally the benzoate salt, to a patient in need thereof wherein the patient has, prior to administration of the 5-MeO-DMT, taken part in a virtual reality (VR) experience designed to prepare the patient for psychedelic therapy.

In an embodiment, the method of treatment further comprises additional VR experiences to complement the psychedelic therapy.

In an embodiment, there is provided the use of a formulation as described herein comprising 5-MeO-DMT, optionally the benzoate salt, in a method of treatment resistant depression treatment, wherein the method comprises administering a formulation as described herein comprising 5-MeO-DMT, optionally the benzoate salt, to a patient in need thereof wherein the patient has, prior to administration of the 5-MeO-DMT, taken part in a virtual reality (VR) experience designed to prepare the patient for psychedelic therapy.

In an embodiment, there is provided a prescription digital therapeutic (PDT) for use in a method of medical treatment, wherein the method comprises administering a dose of a formulation as described herein comprising 5-MeO-DMT, optionally the benzoate salt, to a patient in need thereof, wherein the patient has, prior to administration of the 5-MeO-DMT, taken part in a virtual reality (VR) experience designed to prepare the patient for psychedelic therapy.

In an embodiment, the method of treatment further comprises additional VR experiences to complement the PDT/psychedelic therapy.

In an embodiment, there is provided a prescription digital therapeutic (PDT) for use in a method of treatment resistant depression treatment, wherein the method comprises administering a dose of a formulation as described herein comprising 5-MeO-DMT, optionally the benzoate salt, to a patient in need thereof, wherein the patient has, prior to administration of the 5-MeO-DMT, taken part in a virtual reality (VR) experience designed to prepare the patient for psychedelic therapy.

In an embodiment, the method of treatment comprises the use of sensory deprivation.

Pharmacokinetics

The applicant has funded double-blind, randomized, Phase 1, single ascending dose studies to evaluate the safety, tolerability and pharmacokinetic profile of intranasal 5-MeO-DMT hydrochloride and intranasal 5-MeO-DMT benzoate in healthy subjects. The results of these studies have surprisingly shown that only the benzoate salt of 5-MeO-DMT exhibits dose-proportional pharmacokinetics. It is desirable that a compound for use in treatment has dose-proportional pharmacokinetics, for example, to facilitate dose and dose regimen adjustment in patients. In an embodiment, there is provided a salt of 5-MeO-DMT with dose-proportional pharmacokinetics, optionally for use in the methods disclosed herein. In an embodiment, the salt of 5-MeO-DMT with dose-proportional pharmacokinetics is the benzoate or HBr salt, optionally the benzoate salt. A double-blind, randomized, Phase 1, single ascending dose study to evaluate the safety, tolerability and pharmacokinetic profile of a liquid intranasal 5-MeO-DMT HCl (5-MeO-DMT HCl, HPMC, water for injection (WFI) and a sodium hydroxide solution to adjust pH) formulation in healthy subjects was performed. The mean (+/−SD) 5-MeO-DMT plasma log concentration-time plot is shown in FIG. 1. It can be seen that 5-MeO-DMT HCl does not display dose-proportional pharmacokinetics, with the mean concentration profiles displayed for 5 mg, 8 mg, 10 mg, 11 mg and 14 mg all being substantially similar.

A double-blind, randomized, Phase 1, single ascending dose study to evaluate the safety, tolerability and pharmacokinetic profile of intranasal 5-MeO-DMT benzoate in healthy subjects was performed. The mean (+/−SD) 5-MeO-DMT plasma linear concentration-time plot and plasma log concentration-time plot are shown in FIGS. 2 and 3, respectively. The pharmacokinetics were shown to be approximately dose linear. No dose exceeded the maximum exposure limits defined by previous preclinical work in dogs: Cmax: 421 ng/ml or AUC 220 h·ng/ml. The mean (+/−SD) 5-MeO-DMT plasma linear concentration-time plot and plasma log concentration-time plot are shown in FIGS. 9 and 10, respectively. The mean Cmax was 29 ng/ml for the 12 mg dosage. The mean Tmax was 9.5 minutes whilst the mean half-life (T1/2) was 21 minutes. Bufotenin, the O-demethylated metabolite of 5-MeO-DMT, was only detected at very low levels at the 6 mg dose level after the 16 minutes timepoint.

It will be understood that references to '5-MeO-DMT' herein mean 5-MeO-DMT free base, or a pharmaceutically acceptable salt, prodrug, hydrate, ester, co-crystal or deuterated form thereof, or a pharmaceutical composition comprising the aforementioned.

Items

1. A spray dried dry powder pharmaceutical formulation comprising 5-MeO-DMT, or pharmaceutically acceptable salt thereof, and sodium stearyl fumarate, wherein the formulation may comprise one or more pharmaceutically acceptable carriers or excipients.
2. The spray dried dry powder pharmaceutical formulation of item 1, wherein the formulation comprises 5-MeO-DMT, sodium stearyl fumarate and one or more pharmaceutically acceptable carriers or excipients.
3. The spray dried dry powder pharmaceutical formulation of item 1 or item 2, wherein the formulation comprises 50% 5-MeO-DMT by weight.
4. The spray dried dry powder pharmaceutical formulation of any one of items 1 to 3, wherein the formulation comprises methyl cellulose, optionally a high viscosity methyl cellulose.
5. The spray dried dry powder pharmaceutical formulation of any one of items 1 to 4, wherein the formulation comprises a low viscosity methyl cellulose, and a high viscosity methyl cellulose.
6. The spray dried dry powder pharmaceutical formulation of any one of items 1 to 5, wherein the formulation comprises a cellulose like/based excipient; optionally HPMC, further optionally a high viscosity HPMC.
7. The spray dried dry powder pharmaceutical formulation of item 6, wherein the formulation comprises a low viscosity HPMC and a high viscosity HPMC.
8. The spray dried dry powder pharmaceutical formulation of item 7, wherein the ratio of the low viscosity HPMC to high viscosity HPMC is in the ratio of 1:10 to 10:1, optionally 1:4 to 4:1 and further optionally 1:2 to 2:1.
9. The spray dried dry powder pharmaceutical formulation of item 7, wherein the ratio of the low viscosity HPMC to high viscosity HPMC is in the ratio of 50:50, 45:55, 40:60, 35:65, 30:70 or 25:75.
10. The spray dried dry powder pharmaceutical formulation of item 9, wherein the high viscosity HPMC has a viscosity greater or equal to about 20, 30, 40, 50 or 60 megaPascals, optionally where the HPMC is a HPMC containing about 7.0-12.0% hydroxypropyl content, about 28.0-30.0% methoxy content, and a viscosity of about 50 mPas.
11. The spray dried dry powder pharmaceutical formulation of item 9, wherein the low viscosity HPMC has a viscosity less than about 20, 15, 10, 5, 1 megaPascals, optionally where the HPMC is a HPMC containing about 7.0-12.0% hydroxypropyl content, about 28.0-30.0% methoxy content, and a viscosity of about 4.8-7.2 mPas.
12. The spray dried dry powder pharmaceutical formulation of any one of items 1 to 11, wherein the formulation comprises a polyol, optionally the polyol is mannitol, xylitol, sorbitol, maltitol, erythritol, lactitol or isomalt, further optionally the polyol is sorbitol.
13. The spray dried dry powder pharmaceutical formulation of item 12, wherein the formulation comprises about 1-10%, 2-5% or 3% polyol by weight, optionally about 3% sorbitol or mannitol or isomalt by weight.
14. The spray dried dry powder pharmaceutical formulation of any one of items 1 to 13, wherein the formulation comprises about 0.1, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9 or 2% w/w sodium stearyl fumarate.
15. The spray dried dry powder pharmaceutical formulation of any one of items 1 to 13, wherein the formulation comprises about 1, 2, 3, 4, 5, 6, 7, 8, 9 or 10% w/w sodium stearyl fumarate.
16. The spray dried dry powder pharmaceutical formulation of any one of items 1 to 15, wherein the formulation comprises 5-MeO-DMT benzoate.
17. The spray dried dry powder pharmaceutical formulation of any one of items 1 to 15, wherein the formulation comprises 5-MeO-DMT hydrochloride.
18. The spray dried dry powder pharmaceutical formulation of any one of items 1 to 15, wherein the formulation comprises 5-MeO-DMT hydrobromide.
19. The spray dried dry powder pharmaceutical formulation of any one of items 1 to 18, wherein the 5-MeO-DMT salt is amorphous.
20. The spray dried dry powder pharmaceutical formulation of any one of items 1 to 18, wherein the 5-MeO-DMT salt is crystalline.
21. The spray dried dry powder pharmaceutical formulation of any one of items 1 to 19, wherein the dry powder formulation is a free-flowing dry powder formulation.
22. An active nasal delivery device comprising the spray dried dry powder pharmaceutical formulation of any one of items 1 to 21.
23. The active nasal delivery device of item 22, wherein the device is configured to emit a powder plume comprising 5-MeO-DMT, or a pharmaceutically acceptable salt thereof, having one or more of:
    a plume geometry of:
        angle: 20 to 45 degrees;
        width: 25 to 55 mm;
    a spray pattern of:

| Distance 40 mm: | Distance 70 mm: |
|---|---|
| Dmin(mm): 15 to 25 | Dmin(mm): 15 to 40 |
| Dmax(mm): 20 to 55 | Dmax(mm): 35 to 60 |
| Area (mm$^2$): 390 to 900 | Area (mm$^2$): 800-1600 |
| Area %: 2 to 15 | Area %: 4 to 20 | a particle size distribution (at 40 mm) of:
    D10=13 to 17, D50=35 to 60, D90=650 to 700, %<10 μm=<0.1, 1, 2, 3, 4, 5, 6, 7, 8, 9 or 10%; or
a particle size distribution (at 70 mm) of:
    D10=13 to 17, D50=24 to 30, D90=540 to 610, %<10 μm=<0.1, 1, 2, 3, 4, 5, 6, 7, 8, 9 or 10%; or
a particle size distribution of:
    D10=13 to 17, D50=22 to 27, D90=35 to 56, %<9 μm=<0.1-10%; or % particles of equal to or less than 11.7 μm size of:
    0.5 to 5%.
24. The active nasal delivery device of item 22 or item 23, wherein the formulation comprises below about 5% moisture content by weight of the formulation.
25. The active nasal delivery device of any one of items 22 to 24, wherein at least 95% of the particles of the formulation are larger than 10 microns in size.
26. The active nasal delivery device of item 25, wherein the active nasal delivery device comprises a crystalline 5-MeO-DMT salt selected from:

a crystalline form of 5-MeO-DMT benzoate, characterised by one or more peaks in an XRPD diffractogram at 17.5, 17.7 and 21.0°2θ±0.1°2θ as measured using an x-ray wavelength of 1.5406 Å;

a crystalline form of 5-MeO-DMT hydrochloride, characterised by one or more peaks in an XRPD diffractogram at 9.2°±0.1°, 12.2°±0.1°, 14.1°±0.1°, 15.0°±0.1°, 18.5°±0.1°, and 19.5°±0.1°2θ as measured by x-ray powder diffraction using an x-ray wavelength of 1.5406 Å; or a crystalline form of 5-MeO-DMT hydrobromide, characterised by one or more peaks in an XRPD diffractogram at 14.6, 16.8, 20.8, 24.3, 24.9 and 27.5°2θ±0.1°2θ as measured by x-ray powder diffraction using an x-ray wavelength of 1.5406 Å.

27. The active nasal delivery device of any one of items 25 to 26, wherein the active nasal delivery device comprises: a dispenser outlet; an air expeller for generating a flow of air while the device is being actuated; and at least one reservoir that contains a single dose of formulation.

28. The active nasal delivery device of any one of items 22 to 26, wherein the active nasal delivery device comprises: a dispenser outlet; an air expeller for generating a flow of air while the device is being actuated, said air expeller including a piston that slides in an air chamber between a rest position and a dispensing position, said air chamber including a cylindrical body in which said piston slides in airtight manner; and at least one reservoir that contains a single dose of formulation, said reservoir including an air inlet that is connected to said air expeller, and a formulation outlet that is connected to said dispenser outlet, said air inlet including a formulation retainer member for retaining the formulation in the reservoir until the formulation is dispensed, and said formulation outlet being closed by a closure element that is force fitted in the formulation outlet of the reservoir; said device further including a mechanical opening system that co-operates with said closure element so as to expel said closure element mechanically from a closed position while the device is being actuated, said piston of said air expeller, when in the rest position, co-operating in non-airtight manner with said air chamber, in such a manner that said air chamber is in communication with the atmosphere in the rest position, wherein said piston includes an inner lip configured to cooperate with a cylindrical surface of a cylindrical member extending inside the cylindrical body, said cylindrical surface including fluting that co-operates in non-airtight manner with said inner lip of the piston in the rest position.

29. The active nasal delivery device of item 27 for use in a method of treating a disease or condition selected from: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic disorders, optionally the condition is SUNCT and/or SUNA, alcohol-related diseases and disorders, eating disorders, impulse control disorders, nicotine-related disorders, tobacco-related disorders, methamphetamine-related disorders, amphetamine-related disorders, cannabis-related disorders, cocaine-related disorders, hallucinogen use disorders, inhalant-related disorders, benzodiazepine abuse or dependence related disorders, opioid-related disorders, tobacco addiction, alcohol abuse and/or addiction.

30. The active nasal delivery device of item 28 for use in a method of treating a disease or condition selected from: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic disorders, optionally the condition is SUNCT and/or SUNA, alcohol-related diseases and disorders, eating disorders, impulse control disorders, nicotine-related disorders, tobacco-related disorders, methamphetamine-related disorders, amphetamine-related disorders, cannabis-related disorders, cocaine-related disorders, hallucinogen use disorders, inhalant-related disorders, benzodiazepine abuse or dependence related disorders, opioid-related disorders, tobacco addiction, alcohol abuse and/or addiction.

31. A dry blended dry powder pharmaceutical formulation comprising 5-MeO-DMT, or pharmaceutically acceptable salt thereof, and silicon dioxide, wherein the formulation may comprise one or more pharmaceutically acceptable carriers or excipients.

32. The dry blended dry powder pharmaceutical formulation of item 31, wherein the formulation comprises 5-MeO-DMT, silicon dioxide and one or more pharmaceutically acceptable carriers or excipients.

33. The dry blended dry powder pharmaceutical formulation of item 31 or item 32, wherein the formulation comprises 50% 5-MeO-DMT by weight.

34. The dry blended dry powder pharmaceutical formulation of any one of items 31 to 33, wherein the formulation comprises methyl cellulose, optionally a high viscosity methyl cellulose.

35. The dry blended dry powder pharmaceutical formulation of any one of items 31 to 34, wherein the formulation comprises a low viscosity methyl cellulose, and a high viscosity methyl cellulose.

36. The dry blended dry powder pharmaceutical formulation of any one of items 31 to 35, wherein the formulation comprises a cellulose like/based excipient; optionally HPMC, further optionally a high viscosity HPMC.

37. The dry blended dry powder pharmaceutical formulation of item 36, wherein the formulation comprises a low viscosity HPMC and a high viscosity HPMC.
38. The dry blended dry powder pharmaceutical formulation of item 37, wherein the ratio of the low viscosity HPMC to high viscosity HPMC is in the ratio of 1:10 to 10:1, optionally 1:4 to 4:1 and further optionally 1:2 to 2:1.
39. The dry blended dry powder pharmaceutical formulation of item 38, wherein the ratio of the low viscosity HPMC to high viscosity HPMC is in the ratio of 50:50, 45:55, 40:60, 35:65, 30:70 or 25:75.
40. The dry blended dry powder pharmaceutical formulation of item 39, wherein the high viscosity HPMC has a viscosity greater or equal to about 20, 30, 40, 50 or 60 megaPascals, optionally where the HPMC is a HPMC containing about 7.0-12.0% hydroxypropyl content, about 28.0-30.0% methoxy content, and a viscosity of about 50 mPas.
41. The dry blended dry powder pharmaceutical formulation of item 40, wherein the low viscosity HPMC has a viscosity less than about 20, 15, 10, 5, 1 megaPascals, optionally where the HPMC is a HPMC containing about 7.0-12.0% hydroxypropyl content, about 28.0-30.0% methoxy content, and a viscosity of about 4.8-7.2 mPas.
42. The dry blended dry powder pharmaceutical formulation of any one of items 31 to 41, wherein the formulation comprises a polyol, optionally the polyol is mannitol, xylitol, sorbitol, maltitol, erythritol, lactitol or isomalt, further optionally the polyol is sorbitol.
43. The dry blended dry powder pharmaceutical formulation of item 42, wherein the formulation comprises about 1-10%, 2-5% or 3% polyol by weight, optionally about 3% sorbitol or mannitol or isomalt by weight.
44. The dry blended dry powder pharmaceutical formulation of any one of items 31 to 43, wherein the formulation comprises about 0.1, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9 or 2% w/w silicon dioxide.
45. The dry blended dry powder pharmaceutical formulation of any one of items 31 to 44, wherein the formulation comprises about 1, 2, 3, 4, 5, 6, 7, 8, 9 or 10% w/w silicon dioxide.
46. The dry blended dry powder pharmaceutical formulation of any one of items 31 to 45, wherein the formulation comprises 5-MeO-DMT benzoate.
47. The dry blended dry powder pharmaceutical formulation of any one of items 31 to 45, wherein the formulation comprises 5-MeO-DMT hydrochloride.
48. The dry blended dry powder pharmaceutical formulation of any one of items 31 to 45, wherein the formulation comprises 5-MeO-DMT hydrobromide.
49. The dry blended dry powder pharmaceutical formulation of any one of items 31 to 48, wherein the 5-MeO-DMT salt is amorphous.
50. The dry blended dry powder pharmaceutical formulation of any one of items 31 to 48, wherein the 5-MeO-DMT salt is crystalline.
51. The dry blended dry powder pharmaceutical formulation of any one of items 31 to 50, wherein the dry powder formulation is a free-flowing dry powder formulation.
52. An active nasal delivery device comprising the dry blended dry powder pharmaceutical formulation of any one of items 31 to 51.
53. The active nasal delivery device of item 52, wherein the device is configured to emit a powder plume comprising 5-MeO-DMT, or a pharmaceutically acceptable salt thereof, having one or more of:
a plume geometry of:
angle: 20 to 45 degrees;
width: 25 to 55 mm;
a spray pattern of:

| Distance 40 mm: | Distance 70 mm: |
|---|---|
| Dmin(mm): 15 to 25 | Dmin(mm): 15 to 40 |
| Dmax(mm): 20 to 55 | Dmax(mm): 35 to 60 |
| Area (mm$^2$): 390 to 900 | Area (mm$^2$): 800-1600 |
| Area %: 2 to 15 | Area %: 4 to 20 | a particle size distribution (at 40 mm) of:
D10=13 to 17, D50=35 to 60, D90=650 to 700, %<10 μm=<0.1, 1, 2, 3, 4, 5, 6, 7, 8, 9 or 10%; or
a particle size distribution (at 70 mm) of:
D10=13 to 17, D50=24 to 30, D90=540 to 610, %<10 μm=<0.1, 1, 2, 3, 4, 5, 6, 7, 8, 9 or 10%; or
a particle size distribution of:
D10=13 to 17, D50=22 to 27, D90=35 to 56, %<9 μm=<0.1-10%; or % particles of equal to or less than 11.7 μm size of:
0.5 to 5%.
54. The active nasal delivery device of item 52 or item 53, wherein the formulation comprises below about 5% moisture content by weight of the formulation.
55. The active nasal delivery device of any one of items 52 to 54, wherein at least 95% of the particles of the formulation are larger than 10 microns in size.
56. The active nasal delivery device of item 55, wherein the active nasal delivery device comprises a crystalline 5-MeO-DMT salt selected from:
a crystalline form of 5-MeO-DMT benzoate, characterised by one or more peaks in an XRPD diffractogram at 17.5, 17.7 and 21.0°2θ±0.1°2θ as measured using an x-ray wavelength of 1.5406 Å;
a crystalline form of 5-MeO-DMT hydrochloride, characterised by one or more peaks in an XRPD diffractogram at 9.2°±0.1°, 12.2°±0.1°, 14.1°±0.1°, 15.0°±0.1°, 18.5°±0.1°, and 19.5°±0.1°2θ as measured by x-ray powder diffraction using an x-ray wavelength of 1.5406 Å; or
a crystalline form of 5-MeO-DMT hydrobromide, characterised by one or more peaks in an XRPD diffractogram at 14.6, 16.8, 20.8, 24.3, 24.9 and 27.5°2θ±0.1°2θ as measured by x-ray powder diffraction using an x-ray wavelength of 1.5406 Å.
57. The active nasal delivery device of any one of items 52 to 56, wherein the active nasal delivery device comprises: a dispenser outlet; an air expeller for generating a flow of air while the device is being actuated; and at least one reservoir that contains a single dose of formulation.
58. The active nasal delivery device of any one of items 52 to 57, wherein the active nasal delivery device comprises: a dispenser outlet; an air expeller for generating a flow of air while the device is being actuated, said air expeller including a piston that slides in an air chamber between a rest position and a dispensing position, said air chamber including a cylindrical body in which said piston slides in airtight manner; and at least one reservoir that contains a single dose of formulation, said reservoir including an air inlet that is connected to said air expeller, and a formulation outlet that is connected to said dispenser outlet, said air inlet including a formulation retainer member for retaining the formulation in the reservoir until the formulation is dispensed, and said formulation outlet being closed by a closure element that is force fitted in the formulation outlet of the reservoir; said device further including a mechanical opening system that co-operates with said closure element so as to expel said closure element mechanically from a closed position while the device is being actuated, said piston of said air expeller, when in the rest position, co-operating in non-airtight manner with said air chamber, in such a manner that said air chamber is in communication with the atmosphere in the rest position, wherein said piston includes an inner lip configured to cooperate with a cylindrical surface of a cylindrical member extending inside the cylindrical body, said cylindrical surface including fluting that co-operates in non-airtight manner with said inner lip of the piston in the rest position.

59. The active nasal delivery device of item 58 for use in a method of treating a disease or condition selected from: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic disorders, optionally the condition is SUNCT and/or SUNA, alcohol-related diseases and disorders, eating disorders, impulse control disorders, nicotine-related disorders, tobacco-related disorders, methamphetamine-related disorders, amphetamine-related disorders, cannabis-related disorders, cocaine-related disorders, hallucinogen use disorders, inhalant-related disorders, benzodiazepine abuse or dependence related disorders, opioid-related disorders, tobacco addiction, alcohol abuse and/or addiction.

60. The active nasal delivery device of item 58 for use in a method of treating a disease or condition selected from: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic disorders, optionally the condition is SUNCT and/or SUNA, alcohol-related diseases and disorders, eating disorders, impulse control disorders, nicotine-related disorders, tobacco-related disorders, methamphetamine-related disorders, amphetamine-related disorders, cannabis-related disorders, cocaine-related disorders, hallucinogen use disorders, inhalant-related disorders, benzodiazepine abuse or dependence related disorders, opioid-related disorders, tobacco addiction, alcohol abuse and/or addiction.

61. Crystalline 5-MeO-DMT HCl characterised by one or more peaks in an X-ray powder diffraction (XRPD) diffractogram at 2θ values of $11.1°±0.1°$, $13.4°±0.1°$ or $16.9°±0.1°$ using an X-ray wavelength of 1.5406 Å.

62. The crystalline 5-MeO-DMT HCl of item 61 wherein the crystalline HCl is characterised by one or more peaks in an X-ray powder diffraction (XRPD) diffractogram at 2θ values of $8.7°±0.1°$, $11.1°±0.1°$, $13.4°±0.1°$ or $16.9°±0.1°$ using an X-ray wavelength of 1.5406 Å.

63. The crystalline 5-MeO-DMT HCl of item 61 wherein the crystalline HCl is characterised by one or more peaks in an X-ray powder diffraction (XRPD) diffractogram at 2θ values of $8.7°±0.1°$, $11.1°±0.1°$, $13.4°±0.1°$ or $16.9°±0.1°$ using an X-ray wavelength of 1.5406 Å.

64. The crystalline 5-MeO-DMT HCl of item 61 wherein the crystalline HCl is characterised by one or more peaks in an X-ray powder diffraction (XRPD) diffractogram at 2θ values of $8.7°±0.1°$, $11.1°±0.1°$, $13.4°±0.1°$, $14.6°±0.1°$ or $16.9°±0.1°$ using an X-ray wavelength of 1.5406 Å.

65. The crystalline 5-MeO-DMT HCl of item 61 wherein the crystalline HCl is characterised by one or more peaks in an X-ray powder diffraction (XRPD) diffractogram at 2θ values of $8.7°±0.1°$, $11.1°±0.1°$, $13.4°±0.1°$, $14.6°±0.1°$, $16.9°±0.1°$ or $20.7°±0.1°$ using an X-ray wavelength of 1.5406 Å.

66. The crystalline 5-MeO-DMT HCl of item 61 wherein the crystalline HCl is characterised by one or more peaks in an X-ray powder diffraction (XRPD) diffractogram at 2θ values of $8.7°±0.1°$, $10.1°±0.1°$, $11.1°±0.1°$, $13.4°±0.1°$ or $16.9°±0.1°$ using an X-ray wavelength of 1.5406 Å.

67. A pharmaceutical formulation comprising 5-MeO-DMT HCl Form IV, wherein the formulation is characterised by one or more peaks in an X-ray powder diffraction (XRPD) diffractogram at 2θ values of $8.7°±0.1°$, $10.1°±0.1°$, $11.1°±0.1°$, $13.4°±0.1°$ or $16.9°±0.1°$ using an X-ray wavelength of 1.5406 Å.

Definitions

As used herein, the term "active nasal delivery device" refers to a nasal delivery device configured to actively deliver a formulation following actuation by a subject/patient or third party. This contrasts with a passive nasal delivery device wherein delivery of a formulation relies on inhalation by the subject/patient to draw the formulation out of the device.

As used herein, the term "free flowing" refers to the ability of the plurality of solid particles to move in unbroken continuity, similar to a fluid (e.g., the individual solid particles within a plurality of solid units do not significantly adhere or stick to one another), to permit insufflation into a nasal cavity. The 'free flowing' ability of a plurality of solid particles may be measured by one or more standard methods such as: visual observations, Carr's Index and/or Hausner Factor.

As used herein, "stable" refers to the ability of the therapeutic agent (e.g., a 5-MeO-DMT) to maintain its therapeutic efficacy (e.g., all or the majority of its intended biological activity and/or physiochemical integrity) over extended periods of time. Stable formulations exhibit physical integrity and biological activity and a reduced susceptibility to chemical transformation (e.g., oxidation) prior to administration into a patient. Stable drug formulations have a shelf life at about 5° C. and/or at about 25° C. of equal to or greater than 3, 6, 12, 18, or 24 months.

As used herein, "state-stable" refers to the ability of the therapeutic agent (e.g., amorphous 5-MeO-DMT) to substantially maintain its amorphous state over an extended period of time. For example, a state-stable amorphous solid maintains at least 75%, 85%, 90%, or 95% (w/w) of its amorphous form (i.e., resisting crystallization) under storage conditions of between 2° C. and 25° C. and a relative humidity of 60% RH or below for a period of 1, 3, 6, or 12 months The term "extended-release" refers to a drug formulation that provides for gradual release of a drug over an extended period of time, e.g., 2-20 minutes or more, compared to an immediate release formulation of the same drug, such that the active agent (e.g., a 5-MeO-DMT, or a pharmaceutically acceptable salt thereof) formulated in a unit dosage form has a dissolution release profile in which at least 10-80% (e.g., 10-60%, 10-40%, 10-20%, 20-80%, 40-80%, or 60-80%) of the agent is released within the 20 minutes of testing. Preferably, although not necessarily, extended release results in substantially constant blood levels of a drug over an extended time period that are within the therapeutic range for the disease being treated. Preferably an extended release formulation of a 5-MeO-DMT yields plasma 5-MeO-DMT levels that fall within a concentration range that is between, for example, 5-45 ng/ml, 5-40 ng/mL, 5-35 ng/ml, 5-30 ng/ml, 5-25 ng/ml, 5-20 ng/ml, 10-50 ng/ml, 15-50 ng/ml, 20-50 ng/ml, 25-50 ng/ml, 30-50 ng/ml, 35-50 ng/ml, 40-50 ng/ml, 10-40 ng/ml, or 10-30 ng/ml.

By "immediate release" is meant a mode of releasing the active agent (e.g., a 5-MeO-DMT, or a pharmaceutically acceptable salt thereof) formulated in a unit dosage form that has a dissolution release profile in which at least 80%, 85%, 90%, 95%, or 99% of the agent is released within the first two minutes of testing.

As used herein, the term "residence time" refers to a time period during which a compound, such 5-MeO-DMT, is present in nasal cavity, for example along the nasal cilia and mucus layer. The residence time of the compound (e.g., 5-MeO-DMT) may be formulated to have an extended residence time of at least 10 minutes, 15 minutes, 20 minutes, 25 minutes, 30 minutes or greater compared to an immediate release formulation which has a residence time of fewer than 10 minutes, 8 minutes, 6 minutes, 5 minutes, or 2 minutes.

As used herein, the term "treating" refers to administering the dry powder formulation for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease (e.g., depression and/or alcohol use disorder) to ameliorate the disease and improve the patient's condition. The term "treating" also includes treating a patient to delay progression of a disease or its symptoms. Thus, in the claims and embodiments, treating is the administration to a patient either for therapeutic or prophylactic purposes.

As used herein, the term "amount sufficient to" refers to a quantity of the dry formulation sufficient to, when administered to the subject, including a mammal, for example a human, effect beneficial or desired results, such as clinical results. For example, in the context of treating depression, described herein, these terms refer to an amount of the composition sufficient to achieve a treatment response as compared to the response obtained without administration of the composition. The quantity of a given composition described herein that will correspond to such an amount may vary depending upon various factors, such as the given agent, the pharmaceutical formulation, the route of administration, the type of disease or disorder, the identity of the subject (e.g., age, sex, weight) or host being treated, and the like. An "amount sufficient to," or the like, of a composition of the present disclosure, also include an amount that results in a beneficial or desired result in a subject as compared to a control (e.g., a decrease in the score on the Montgomery-Asberg Depression Rating Scale).

As used herein, the term "spray pattern" refers to the image formed by the interaction of a spray plume and a light sheet that are perpendicular to each other. The person skilled in the art will appreciate how to evaluate the spray pattern of a formulation in light of their own common general knowledge and/or the disclosure contained herein.

As used herein, the term "plume geometry" refers to the image formed by the interaction of a spray plume and a light sheet that are parallel to each other. The person skilled in the art will appreciate how to evaluate the plume geometry of a formulation in light of their own common general knowledge and/or the disclosure contained herein.

As used herein, the term "dry blended" refers to a free-flowing dry powder formulation produced utilising a dry blending process.

EXAMPLES

Example 1: Spray Drying of 5-MeO-DMT Hydrobromide Salt with HPMC

Spray drying 5-MeO-DMT hydrobromide and HPMC (Pharmacoat 606) in water produced a 50% wt: wt API to excipient spray dried dispersion (SDD). The spray drying parameters were as below:

| Feed Solution | |
|---|---|
| Sample Reference | 30130-01-01 |
| HPMC (as Pharmacoat 606) | 1.01 g |
| 5-MeO-DMT hydrobromide | 1.05 g |
| Water (deionized) | 40.12 g |
| Spray Drying Parameters | |
| Instrument | Procept |
| Nozzle | 2 fluid nozzle |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Gas Pressure (bar) | 1.2 |
| Yield | |
| Mass of SDD Produced (g) | 1.54 |
| Yield (%) | 75 |

Figure 1:
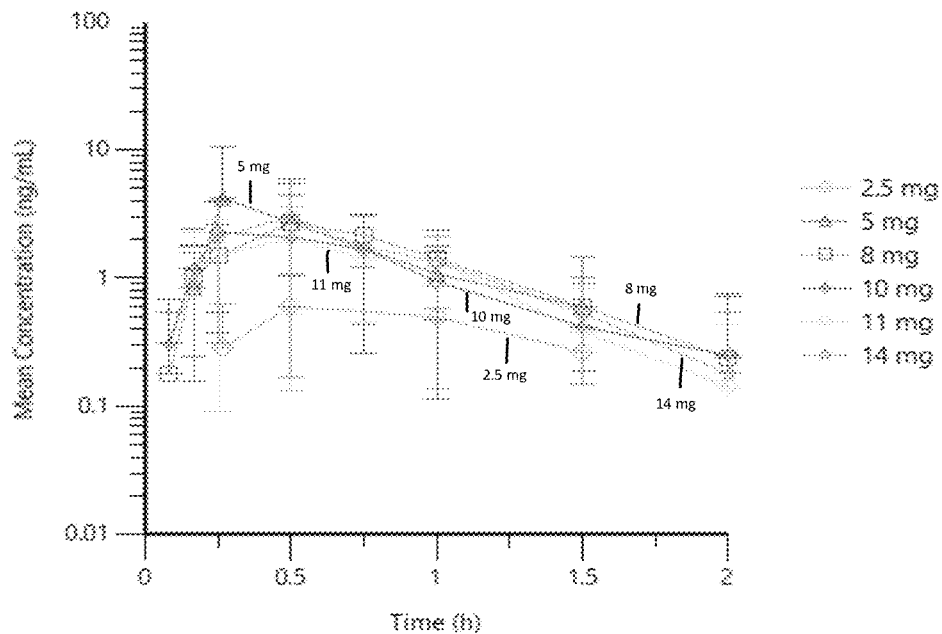
FIG. 1 shows the mean (+/−SD) 5-MeO-DMT HCl plasma log concentration-time plot.
Figure 2:
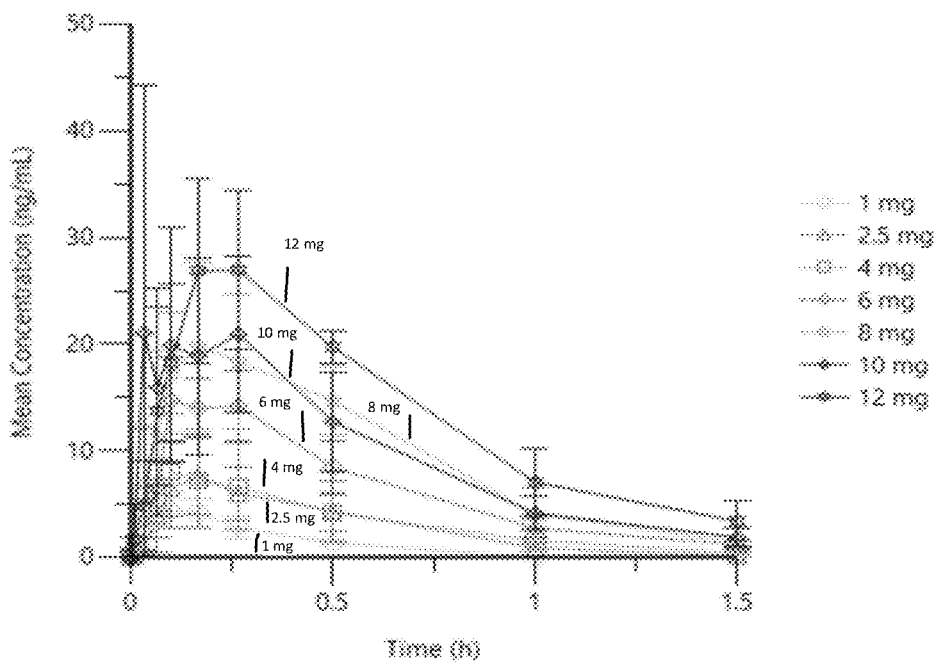
FIG. 2 shows the mean (+/−SD) 5-MeO-DMT benzoate plasma linear concentration-time plot.
Figure 3:
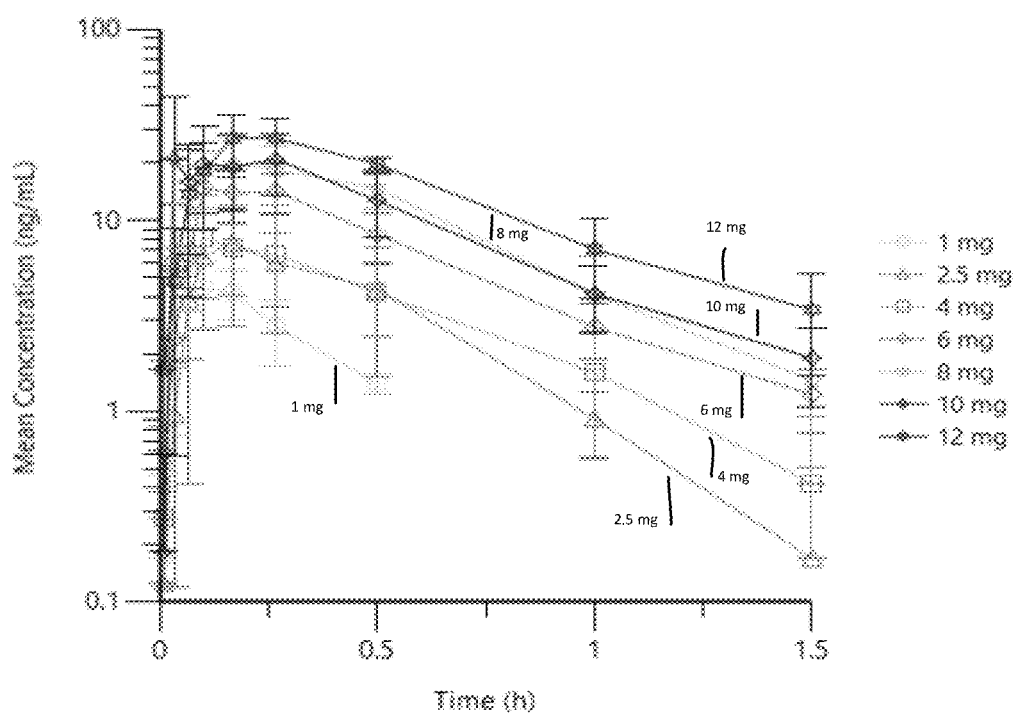
FIG. 3 shows the mean (+/−SD) 5-MeO-DMT benzoate plasma log concentration-time plot.
Figure 4:
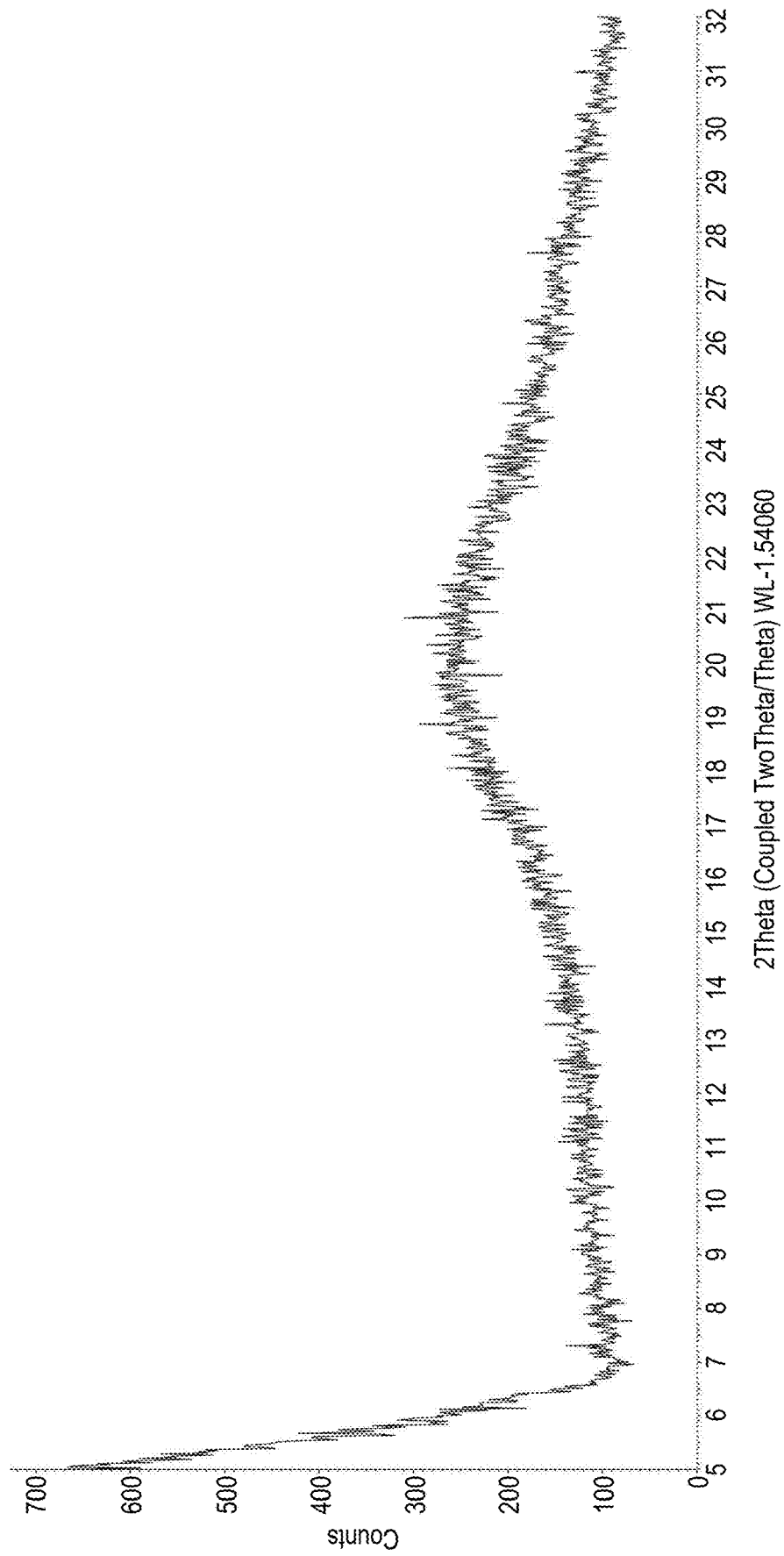
FIG. 4 shows an XRPD for the spray dried dispersion (SDD) of Example 1.
Figure 5:
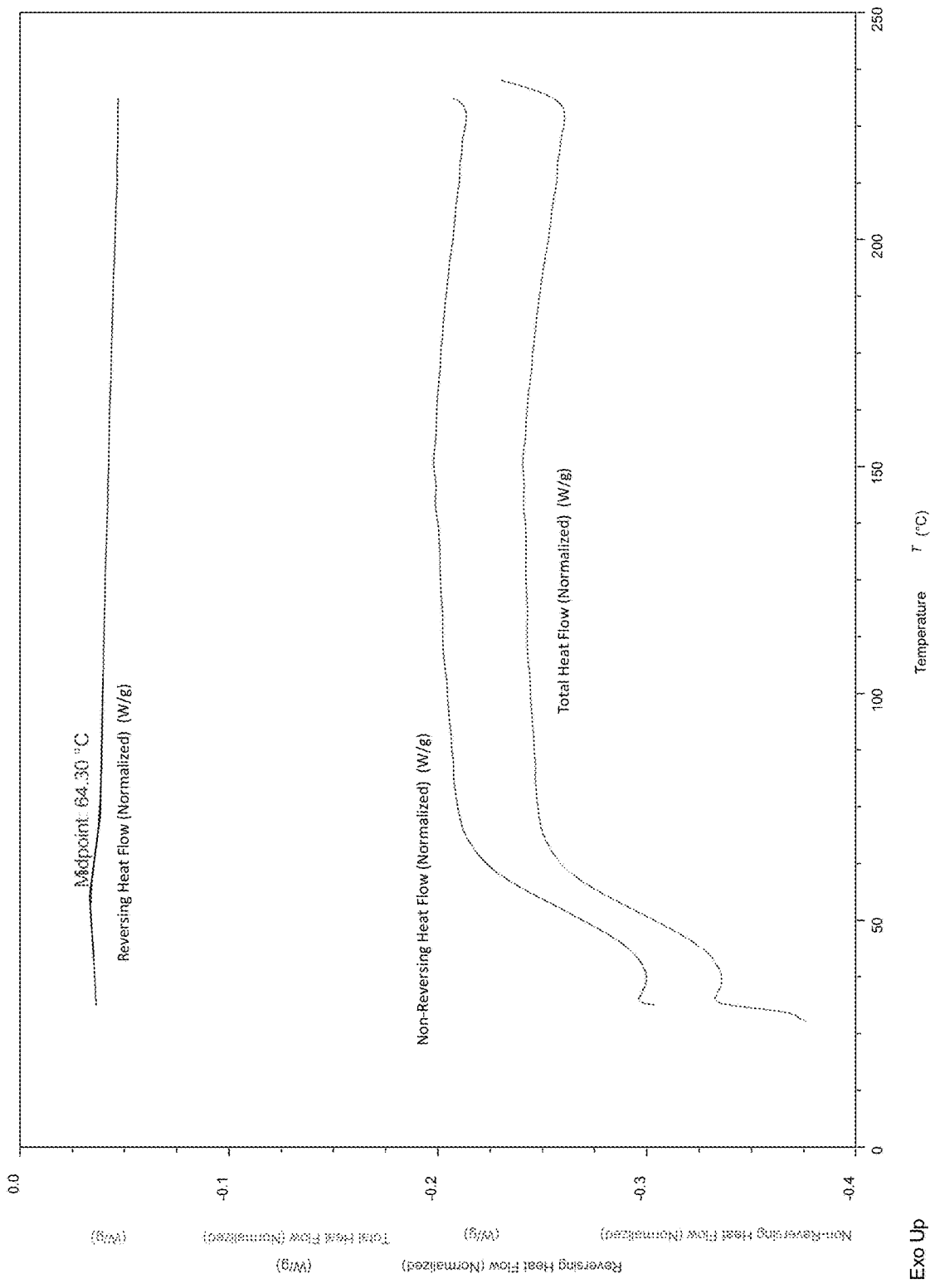
FIG. 5 shows a DSC thermogram for the SDD of Example 1.

The SDD produced was amorphous, as shown by X-ray powder diffractogram (XRPD) analysis (FIG. 4), and the absence of an enthalpy of melting when the SDD was examined by differential scanning calorimetry (DSC) (FIG. 5).

Example 2: Spray Drying of 5-MeO-DMT Oxalate Salt with HPMC

Spray drying 5-MeO-DMT oxalate and HPMC (Pharmacoat 606) in water produced a 50% wt: wt API to excipient SDD. The spray drying parameters were as below:

| Feed Solution | |
|---|---|
| Sample Reference | 31030-02-01 |
| HPMC (as Pharmacoat 606) | 1.02 g |
| 5-MeO-DMT Oxalate | 1.01 g |
| Water (deionized) | 40.01 g |

| Spray Drying Parameters | |
|---|---|
| Instrument | Procept |
| Nozzle | 2 fluid nozzle |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Gas Pressure (bar) | 1.2 |
| Yield | |
| Mass of SDD Produced (g) | 1.32 |
| Yield (%) | 65 |

Figure 6:
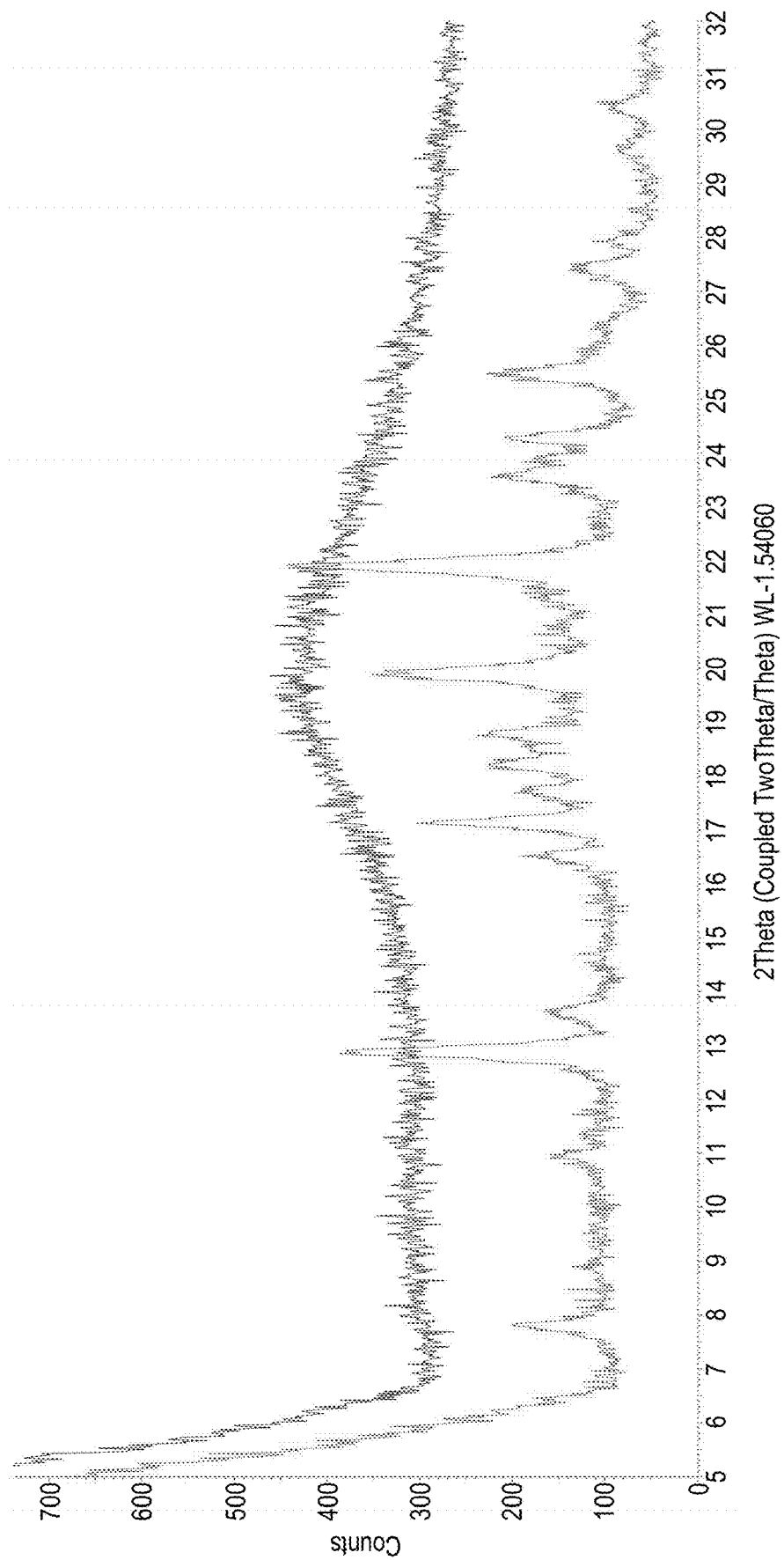
FIG. 6 shows an XRPD for the SDD of Example 2, pre and post dynamic vapour sorption (DVS).
Figure 7:
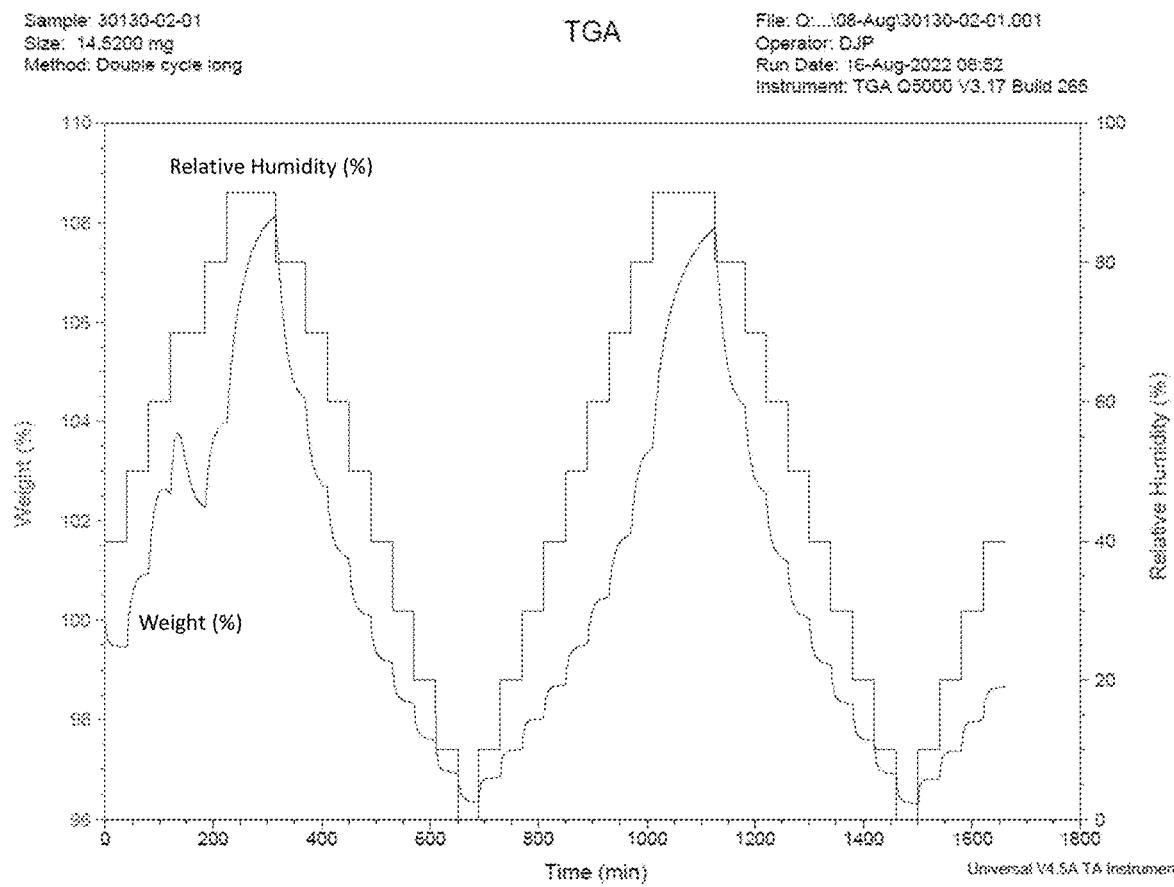
FIG. 7 shows a DVS isotherm for the SDD of Example 2.
Figure 8:
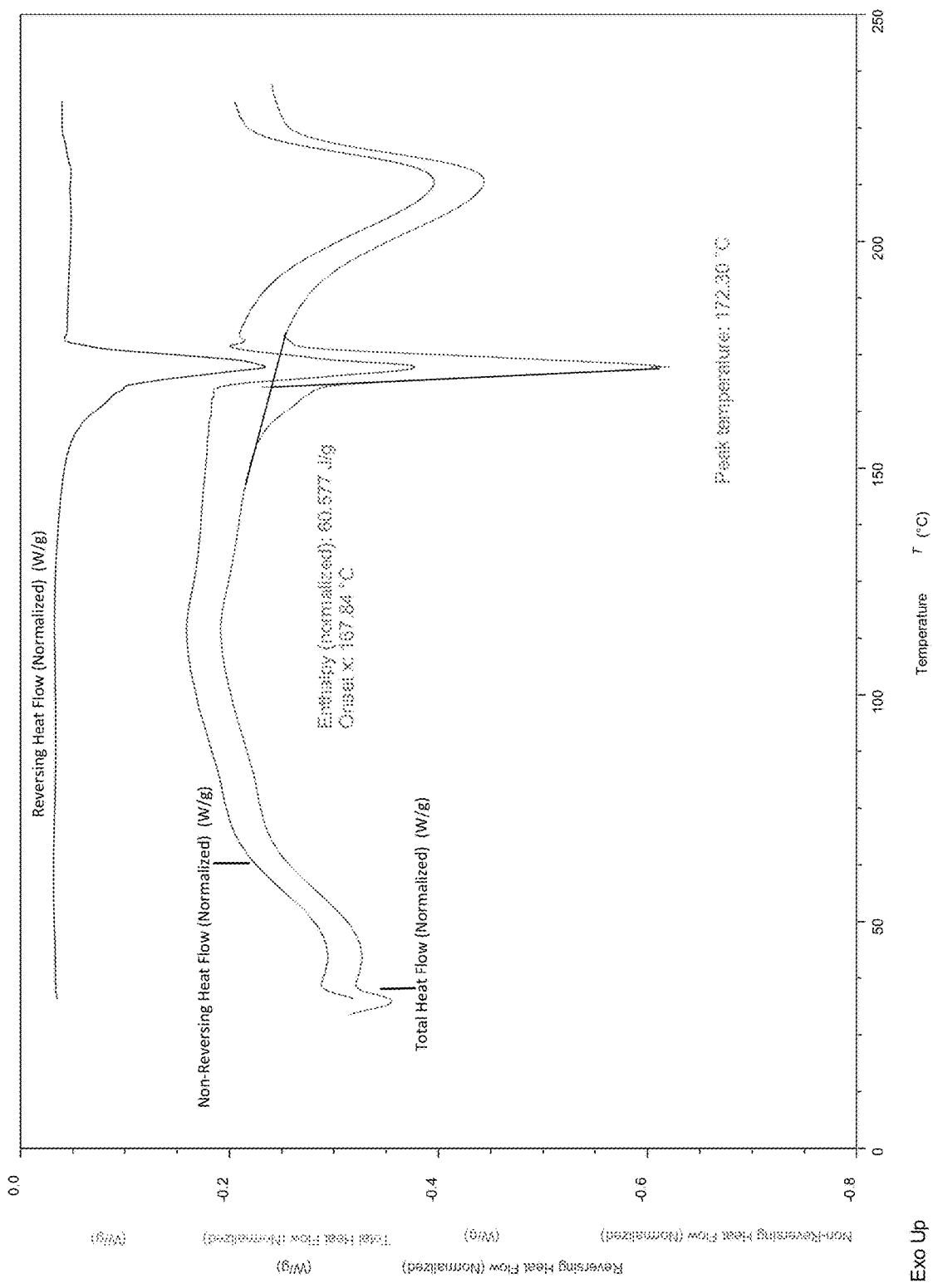
FIG. 8 shows a DSC thermogram for the SDD of Example 2.

The SDD produced was a physically state-unstable amorphous SDD that underwent recrystallization at a relative humidity of above ~60%, as shown by dynamic vapour sorption (DVS) analysis. The XRPD analysis of the SDD pre and post DVS are shown in FIG. 6, the SDD is amorphous pre DVS and partially crystalline post DVS. The DVS isotherm is shown in FIG. 7 and the DSC thermogram is shown in FIG. 8.

Example 3: Spray Drying of 5-MeO-DMT Hydrobromide Salt with PVP

Spray drying 5-MeO-DMT hydrobromide and polyvinylpyrrolidone (PVP) in water produced a 50% wt: wt API to excipient SDD. The spray drying parameters were as below:

| Feed Solution | |
|---|---|
| Sample Reference | 31030-05-01 |
| PVP K30 | 0.253 g |
| 5-MeO-DMT Hydrobromide | 0.250 g |
| Water (deionized) | 10.221 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Yield | |
| Mass of SDD Produced (g) | 0.36 |
| Yield (%) | 65 |

Figure 9:
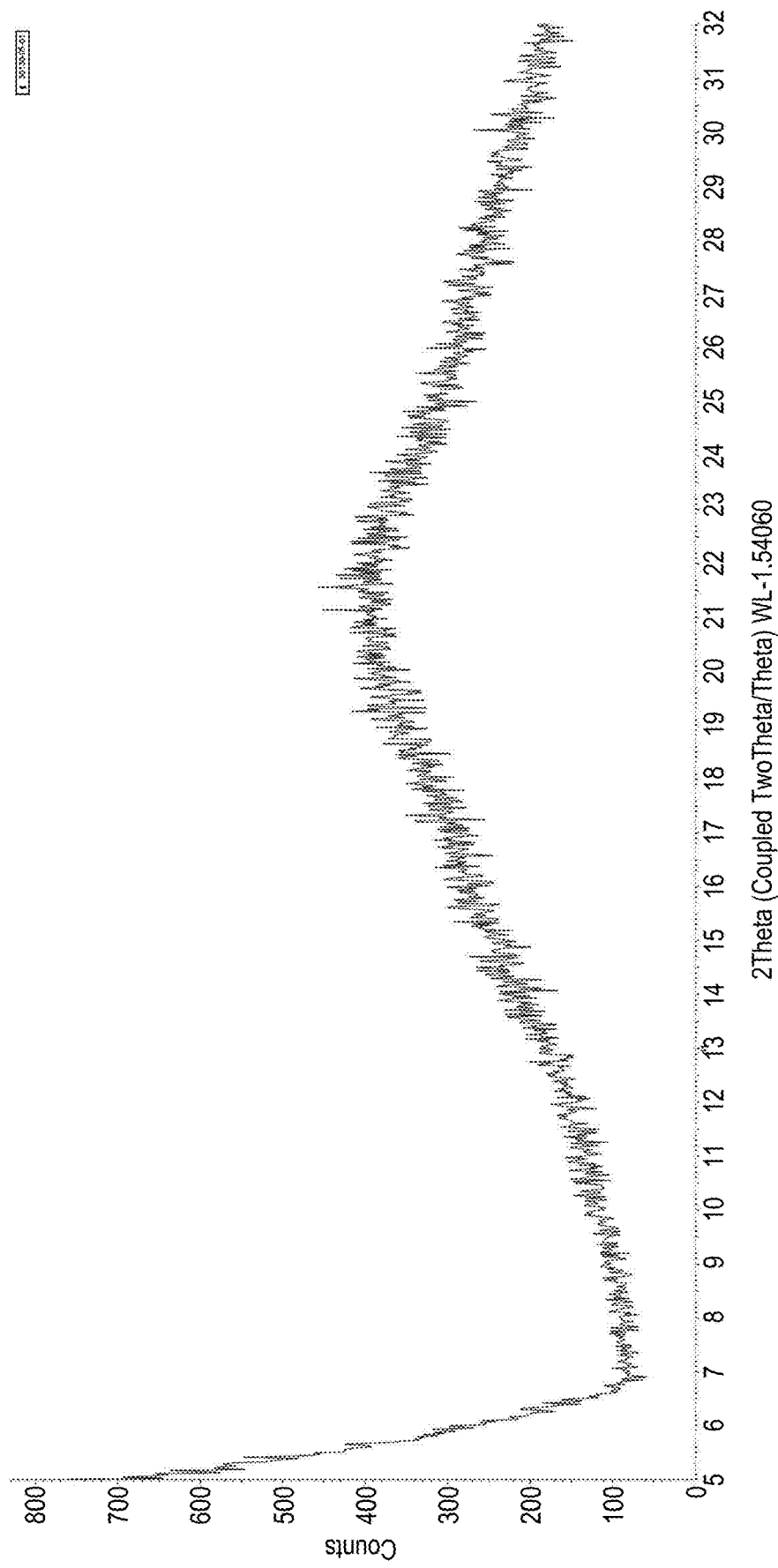
FIG. 9 shows an XRPD for the SDD of Example 3.
Figure 10:
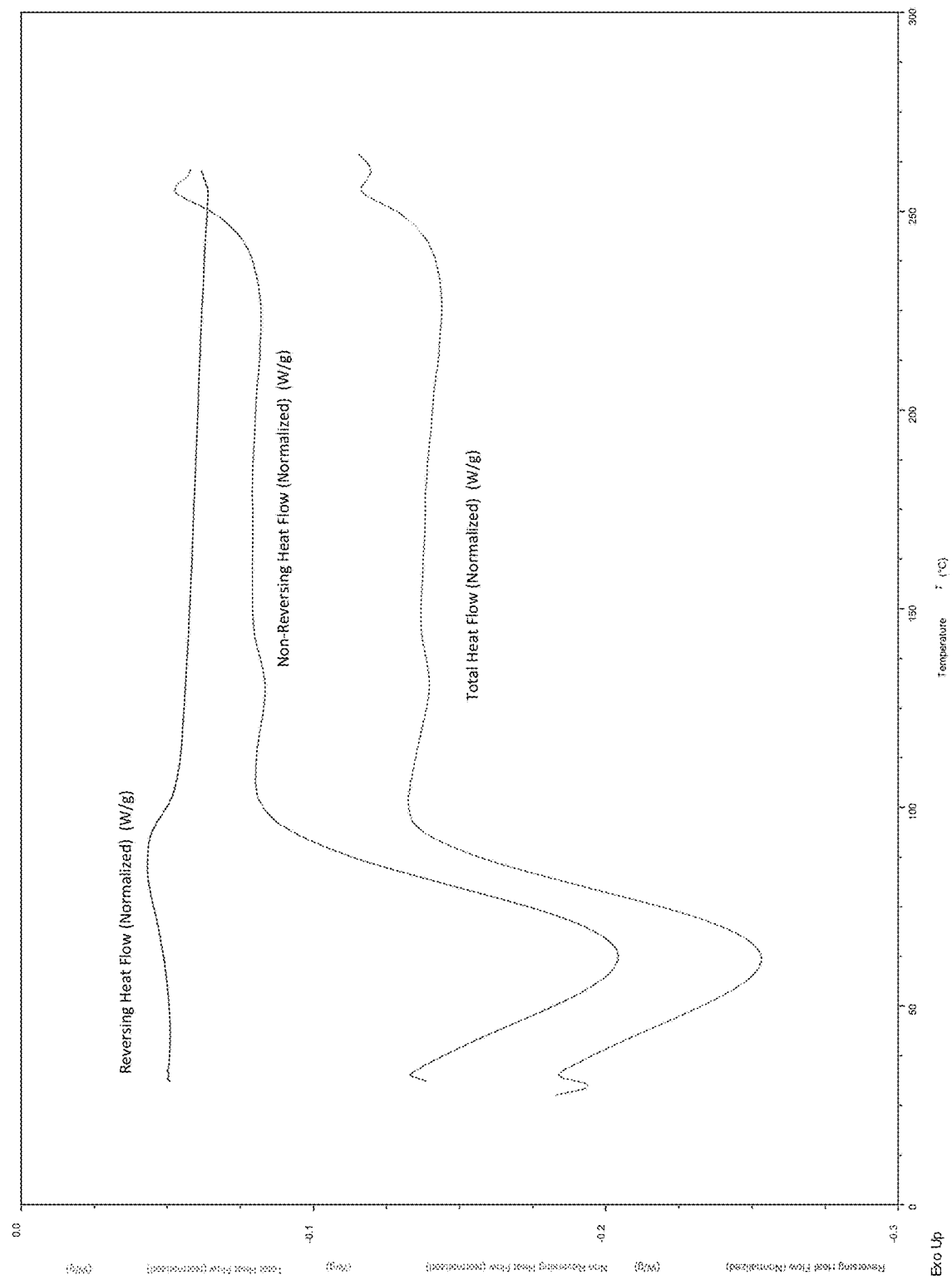
FIG. 10 shows a DSC thermogram for the SDD of Example 3.

The SDD produced was amorphous, as shown by XRPD analysis (FIG. 9), and the absence of an enthalpy of melting when the SDD was examined by DSC (FIG. 10).

Example 4: Spray Drying of 5-MEO-DMT Benzoate Salt with Trehalose

Spray drying 5-MeO-DMT benzoate and trehalose in water produced a 50% wt: wt API to excipient SDD. The spray drying parameters were as below:

| Feed Solution | |
|---|---|
| Sample Reference | 31030-07-01 |
| Trehalose | 0.253 g |
| 5MeO DMT Benzoate | 0.249 g |
| Water (de ionized) | 10.001 g |

| Spray Drying Parameters | |
|---|---|
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Yield | |
| Mass of SDD Produced (g) | 0.222 |
| Yield (%) | 44 |

Figure 11:
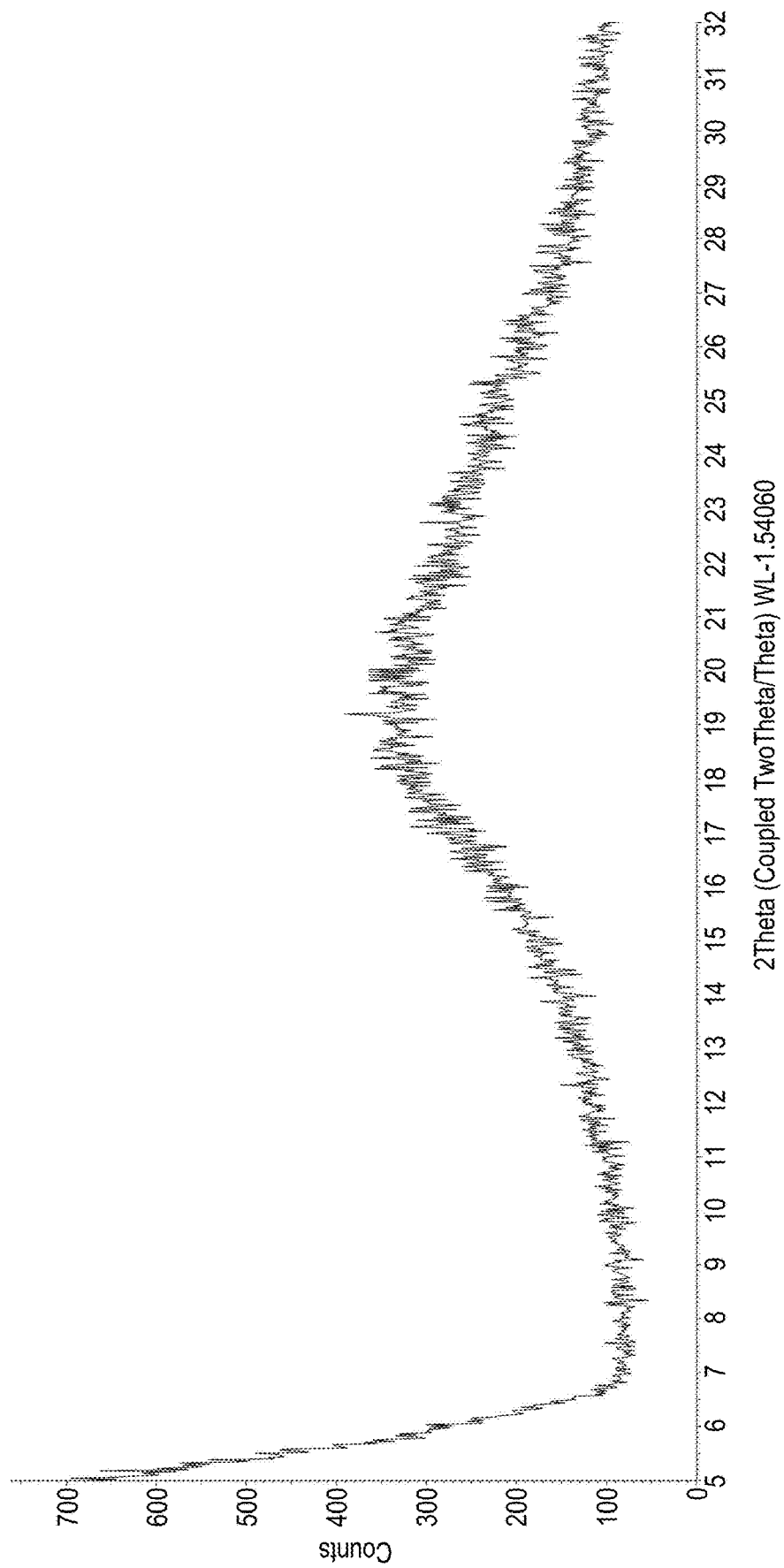
FIG. 11 shows an XRPD for the SDD of Example 4.
Figure 12:
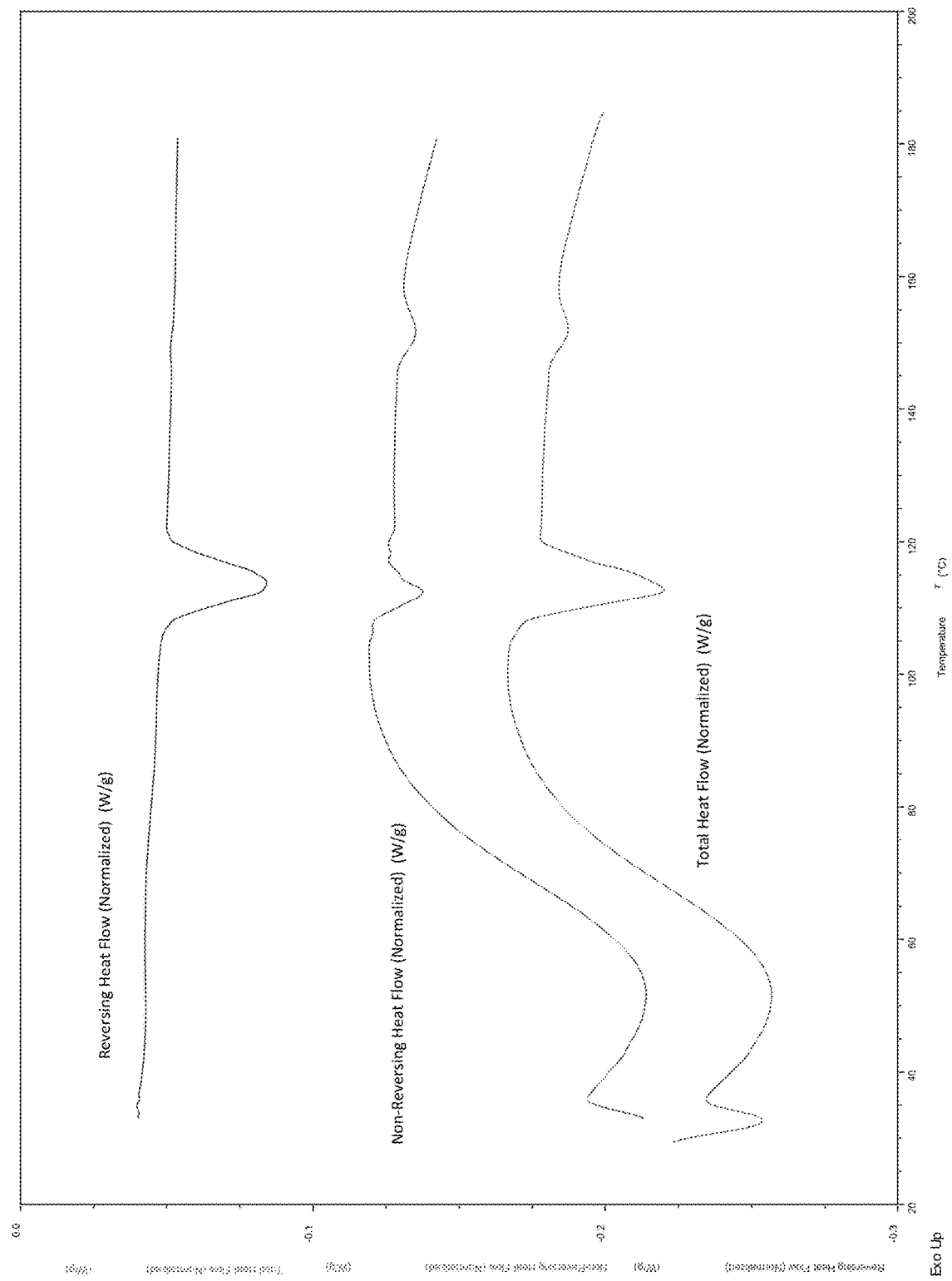
FIG. 12 shows a DSC thermogram for the SDD of Example 4.

The SDD produced was predominantly amorphous by XRPD (FIG. 11), however, there was evidence of partially crystalline material in the XRPD and an enthalpy of melting observed in the DSC (FIG. 12) indicating possible physical instability of the SDD.

Example 5: Spray Drying of 5-MeO-DMT Benzoate Salt with HPMC Mixtures

Spray drying of 5-MeO-DMT benzoate with a mixture of HPMC 2910 in water produced a 50% wt: wt API to excipient SDD. The spray drying parameters were as below:

| Feed Solution | |
|---|---|
| Sample Reference | 30130-08-01 |
| Pharmacoat 606 | 1.19 g |
| Metolose 60SH50 | 1.19 g |
| 5-MeO-DMT Benzoate | 2.38 g |
| Water (deionized) | 95.24 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Yield | |
| Yield (%) | 34.7 |

The process for producing the feed solution was as follows: the required mass of water was weighed into a 50 mL vial. The required mass of HPMC (Pharmacoat 606) and metolose were added to the water whilst stirring and allowed to fully dissolve. Once dissolved the required mass of API was transferred into the solution and allowed to dissolve. Once dissolved the feed solution was spray dried immediately.

Figure 13:
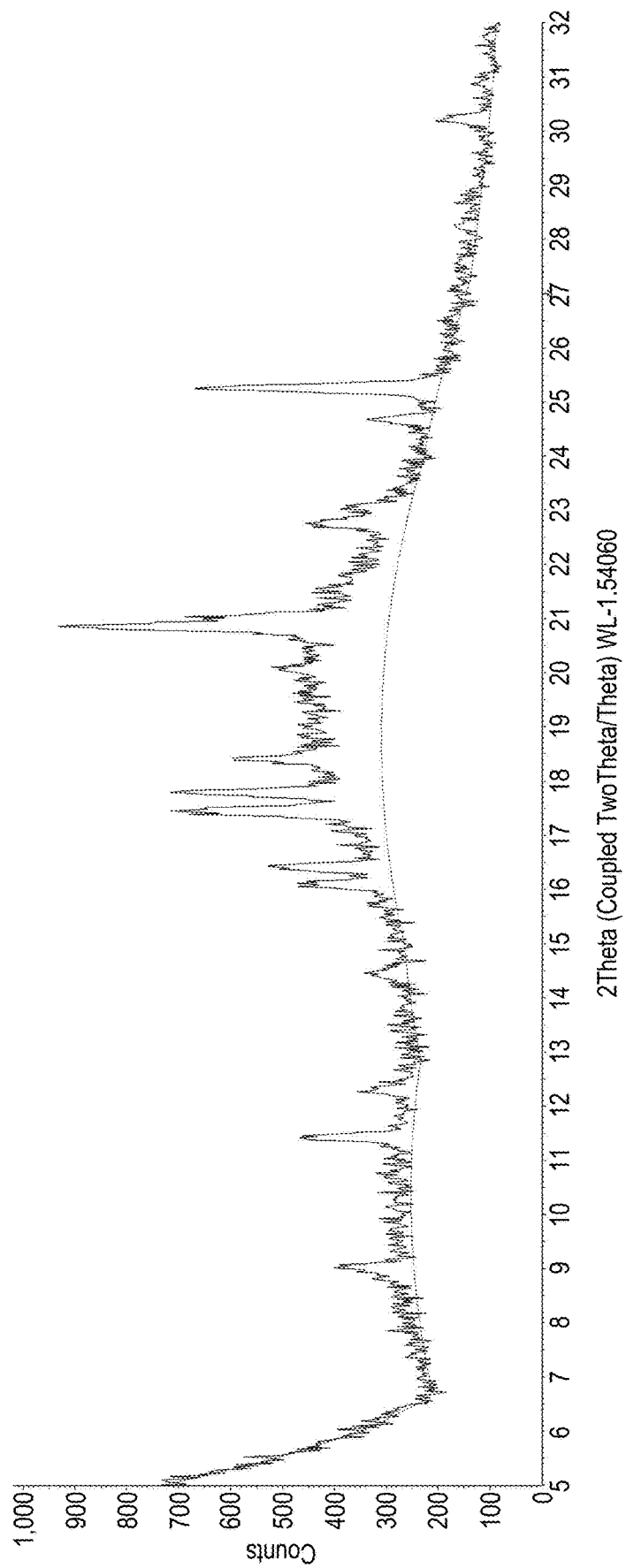
FIG. 13 shows an XRPD for the SDD of Example 5.

The SDD produced was partially crystalline (FIG. 13) and furthermore, at 25% loading of metolose, the yield was quite low.

Example 6: Spray Drying of 5-MeO-DMT Benzoate Salt with HPMC Mixtures

Spray drying of 5-MeO-DMT benzoate with a mixture of HPMC 2910 in water produced a 50% wt: wt API to excipient SDD. The spray drying parameters were as below:

| Feed Solution | |
|---|---|
| Sample Reference | 30130-08-02 |
| Pharmacoat 606 | 1.785 g |
| Metolose 60SH50 | 0.595 g |
| 5-MeO-DMT Benzoate | 2.38 g |
| Water (deionized) | 95.24 g |
| Spray Drying Parameters | |
| Instrument | Procept |
| Nozzle | Ultrasonic |
| Inlet Flow (m³/min) | 0.7 |
| Inlet Temperature (C) | 125 |
| Cyclone Gas Pressure (bar) | 0.5 |
| Pump Speed (RPM) | 60 (2 g per minute) |
| Nozzle Power % | 98% |
| Yield | |
| Yield (%) | 62.7 |

Figure 14:
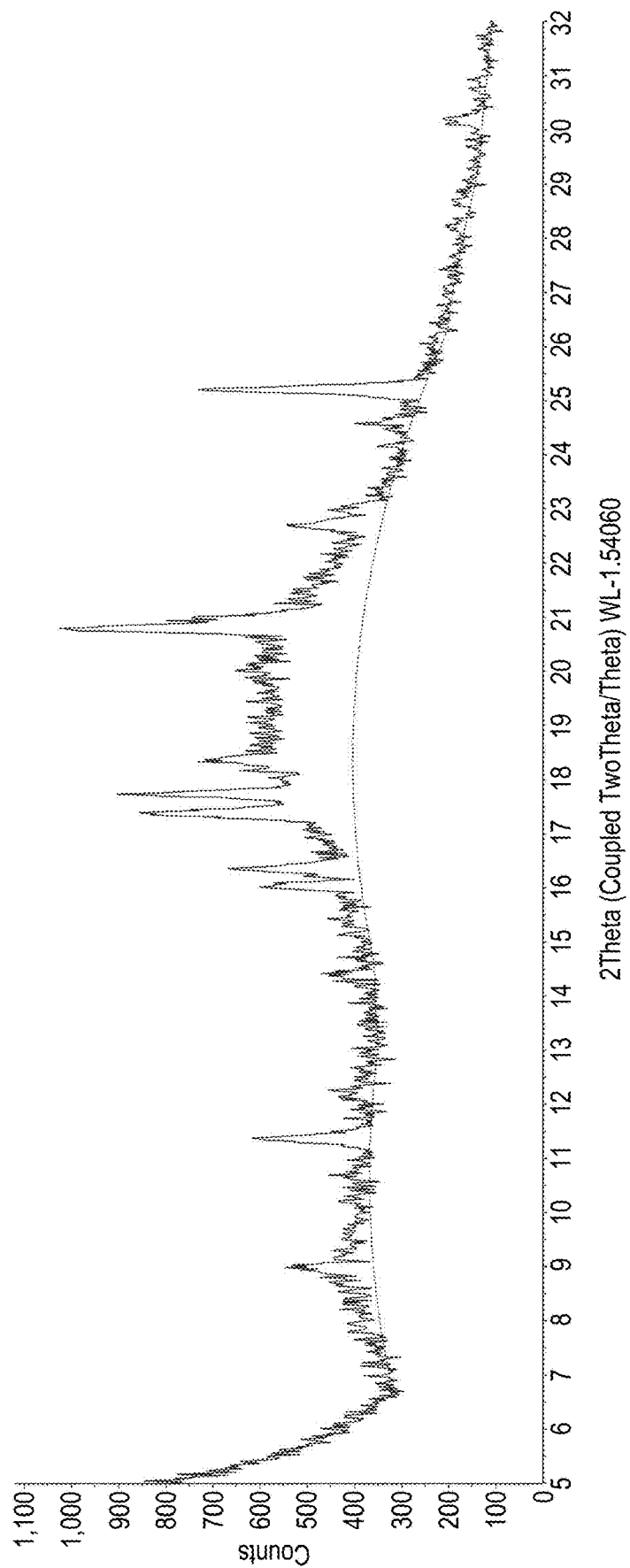
FIG. 14 shows an XRPD for the SDD of Example 6.

The process for producing the feed solution was as described in Example 5. The SDD produced was partially crystalline (FIG. 14), however, surprisingly the use of 12.5% total loading of metolose led to a significant improvement in yield over the SDD produced in Example 5 (25% metolose).

Figure 15:
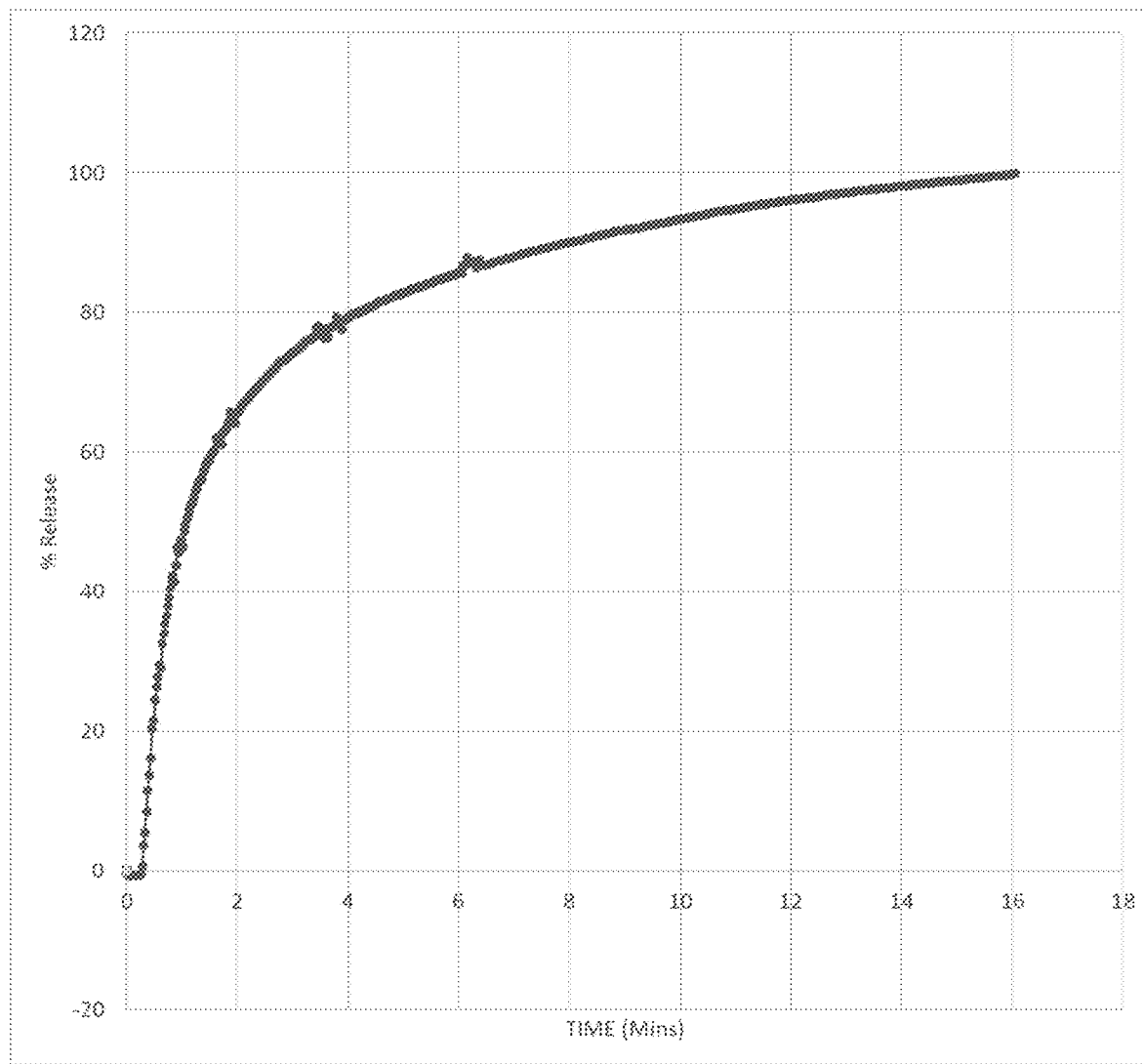
FIG. 15 shows the dissolution profile of the SDD of Example 6.

The dissolution profile for the SDD produced can be seen in FIG. 15, this shows that ~80% release has occurred by ~4 minutes.

Example 7: Spray Drying of 5-MeO-DMT Benzoate Salt with HPMCAS

Spray drying of 5-MeO-DMT benzoate with hydroxypropyl methylcellulose acetate succinate (HPMCAS) M produced a 50% wt: wt API to excipient SDD. HPMCAS is produced in three substitution grades: L, M and H. The spray drying parameters were as below:

| Feed Solution | |
|---|---|
| Sample Reference | 30120-08-03 |
| HPMCAS M | 2.38 g |
| 5-MeO-DMT Benzoate | 2.38 g |
| Water (deionized) | 47.62 g |
| Acetone | 47.62 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 96% |
| Yield | |
| Yield (%) | 44.7 |

The process for producing the feed solution was as follows: the required mass of acetone was weighed into a 50 mL vial. The required mass of HPMC-AS was added to the acetone whilst stirring and allowed to fully dissolve. Once dissolved the required mass of water was added to the solution followed by API and the vial was then stirred until the API dissolved. Once dissolved the feed solution was spray dried immediately.

Figure 16:
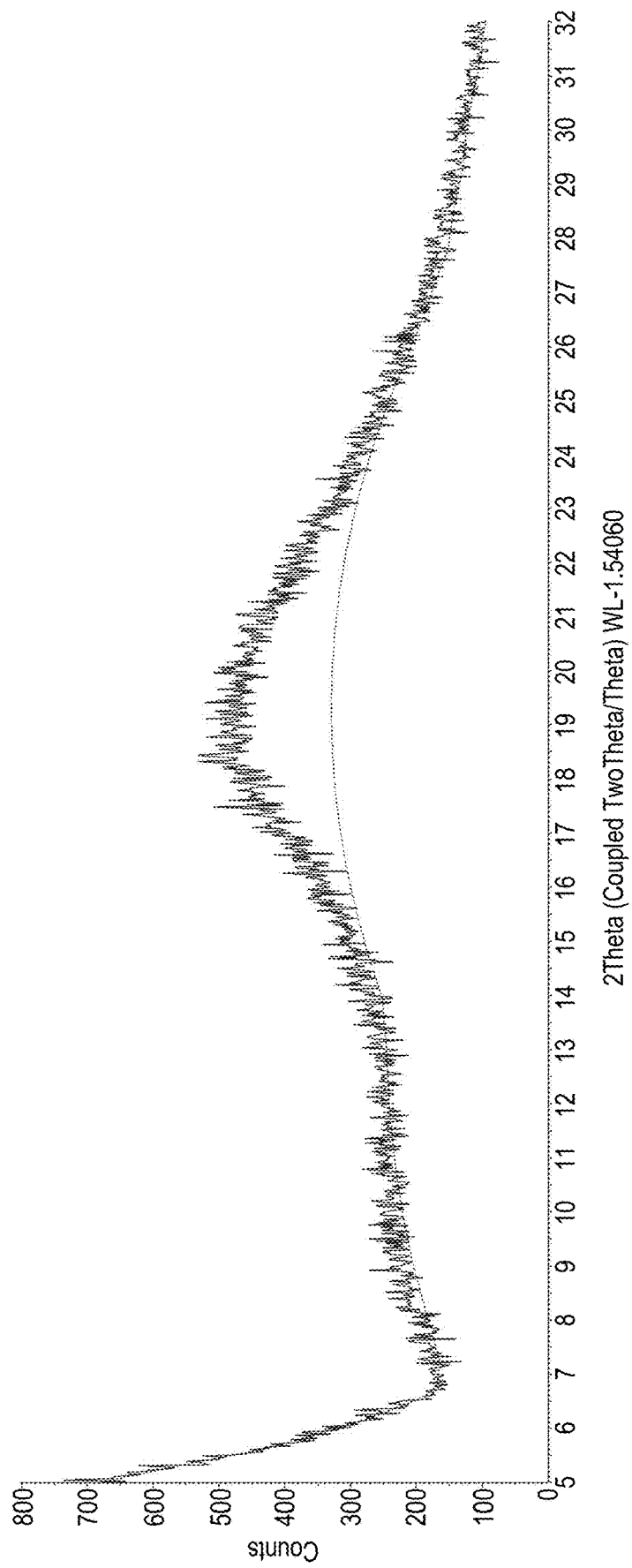
FIG. 16 shows an XRPD for the SDD of Example 7.

The SDD produced was state-stable and amorphous (FIG. 16).

Example 8: Spray Drying of 5-MeO-DMT Benzoate Salt with HPMCAS/Metolose

Spray drying of 5-MeO-DMT benzoate with HPMCAS M and Metolose 60SH50 in water produced a 50% wt: wt API to excipient SDD. The spray drying parameters were as below:

| Feed Solution | |
|---|---|
| HPMCAS M | 1.19 g |
| Metolose 60SH50 | 1.19 g |
| 5-MeO-DMT Benzoate | 2.38 g |
| Water (deionized) | 47.62 g |
| Acetone | 47.62 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Nozzle Power % | 96% |
| Yield | |
| Yield (%) | 29.2 |

The process for producing the feed solution was as follows: the required mass of acetone was weighed into a 50 mL vial. The required mass of HPMC-AS was added to the acetone whilst stirring and allowed to fully dissolve. Once dissolved the required mass of water was added to the solution followed by HPMC, the vial was stirred over night to dissolve. Once dissolved the API was added and stirred, once dissolved the feed solution was spray dried immediately.

Figure 17:
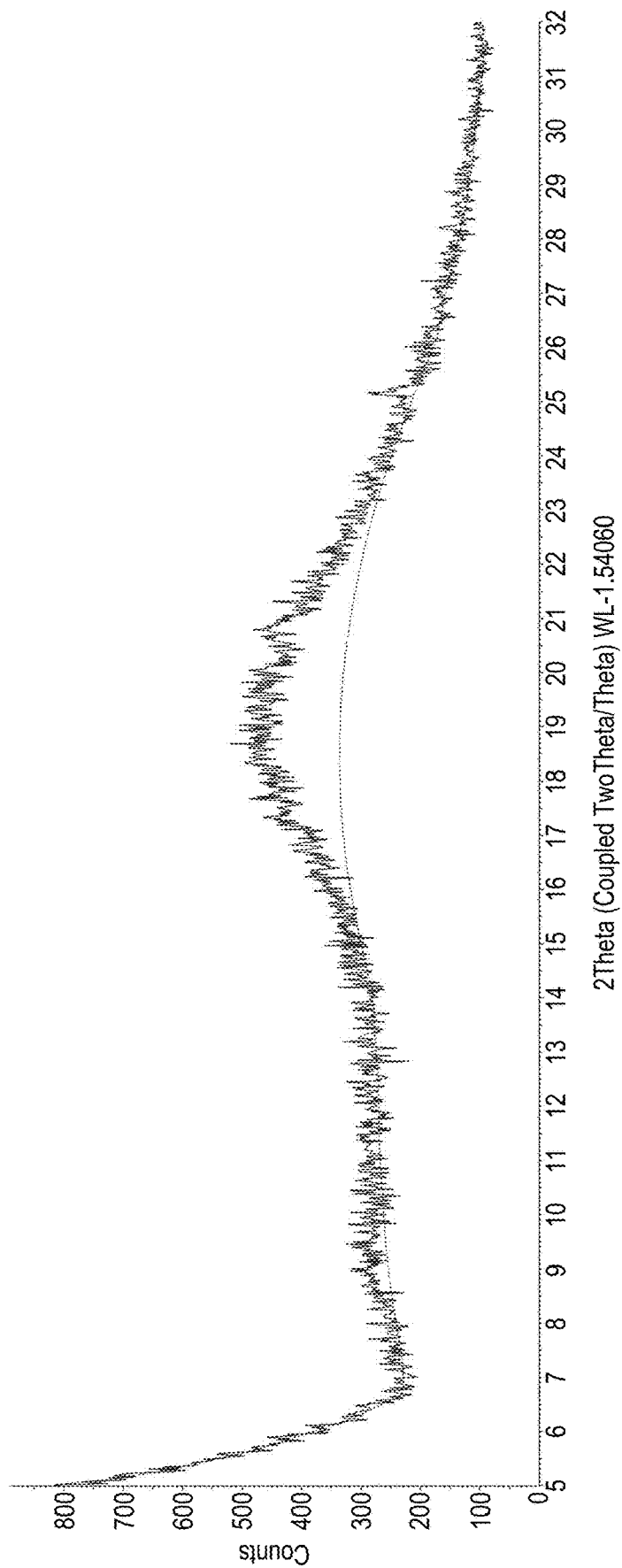
FIG. 17 shows an XRPD for the SDD of Example 8.

The SDD produced was predominantly amorphous (FIG. 17), however, there was some difficulty in spray drying viscous solutions containing HPMC-AS.

Example 9: Spray Drying of 5-MeO-DMT Benzoate Salt with HPMCAS/Metolose

Spray drying of 5-MeO-DMT benzoate with HPMCAS M and Metolose 60SH50 in water produced a 50% wt: wt API to excipient SDD. The spray drying parameters were as below:

| Feed Solution | |
|---|---|
| HPMCAS M | 1.785 g |
| Metolose 60SH50 | 1.595 g |
| 5-MeO-DMT benzoate | 2.38 g |
| Water (deionized) | 47.62 gg |
| Acetone | 47.62 g |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Nozzle Power % | 96% |
| Yield | |
| Yield (%) | 27.2 |

The process for producing the feed solution was as follows: the required mass of acetone was weighed into a 50 mL vial. The required mass of HPMC-AS was added to the acetone whilst stirring and allowed to fully dissolve. Once dissolved the required mass of water was added to the solution followed by HPMC, the vial was stirred over night to dissolve. Once dissolved the API was added and stirred, once dissolved the feed solution was spray dried immediately.

Figure 18:
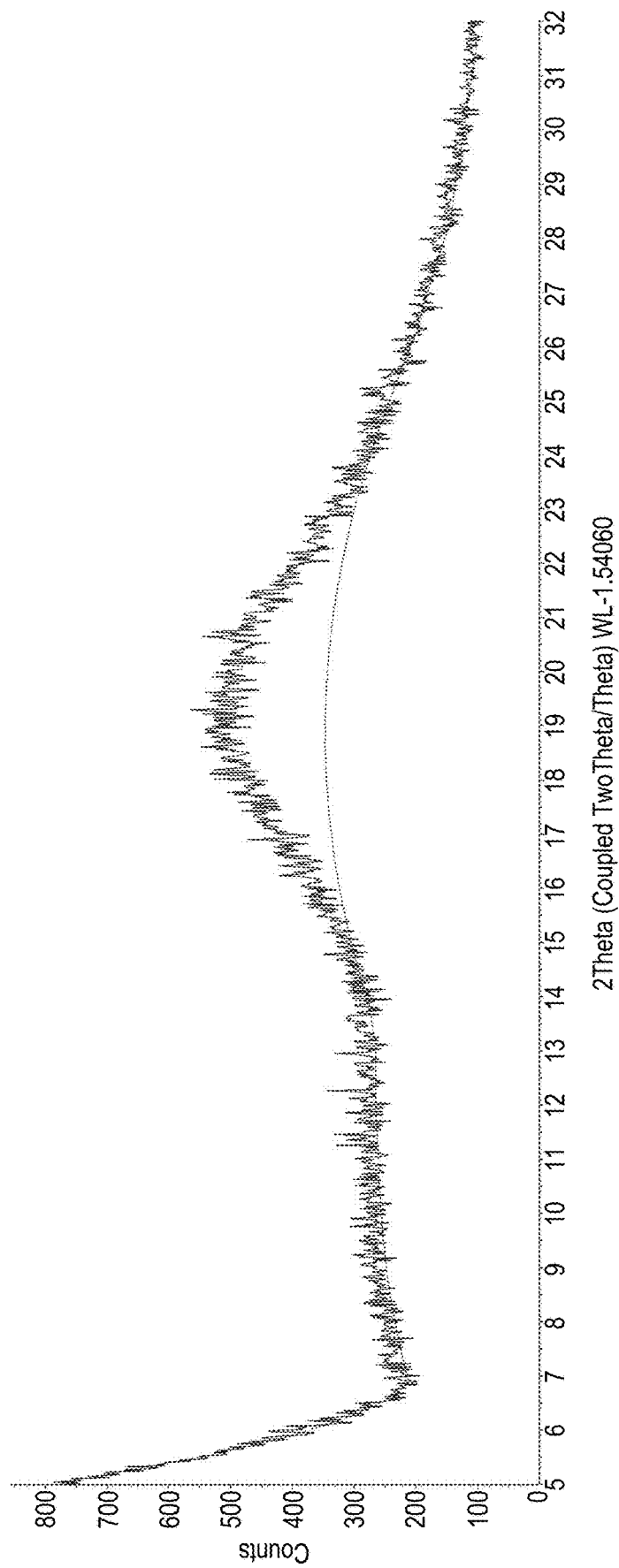
FIG. 18 shows an XRPD for the SDD of Example 9.

The SDD produced was predominantly amorphous (FIG. 18), however, there was some difficulty in spray drying viscous solutions containing HPMC-AS.

Example 10: Spray Drying of 5-MeO-DMT Benzoate Salt with HPMC Mixtures

Spray drying of 5-MeO-DMT benzoate with a mixture of HPMC 2910 in water produced a 10% wt: wt API to excipient SDD. The spray drying parameters were as below:

| SDD Composition | |
| --- | --- |
| Sample Reference | 3815-02-01 |
| Pharmacoat 606 | 67.5% |
| Metolose 60SH50 | 22.5% |
| 5-MeO-DMT Benzoate | 10% |
| Spray Drying Parameters | |
| Instrument | Procept |
| Nozzle | Ultrasonic |
| Inlet Flow ($m^3$/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 58% |

The process for spray drying the feed solution was as follows: the required mass of water was weighed into a 50 mL vial. The required mass of HPMC and Metolose were added to the water whilst stirring and allowed to fully dissolve. Once dissolved the required mass of API was transferred into the solution and allowed to dissolve. Once dissolved the feed solution was spray dried immediately.

Figure 19:
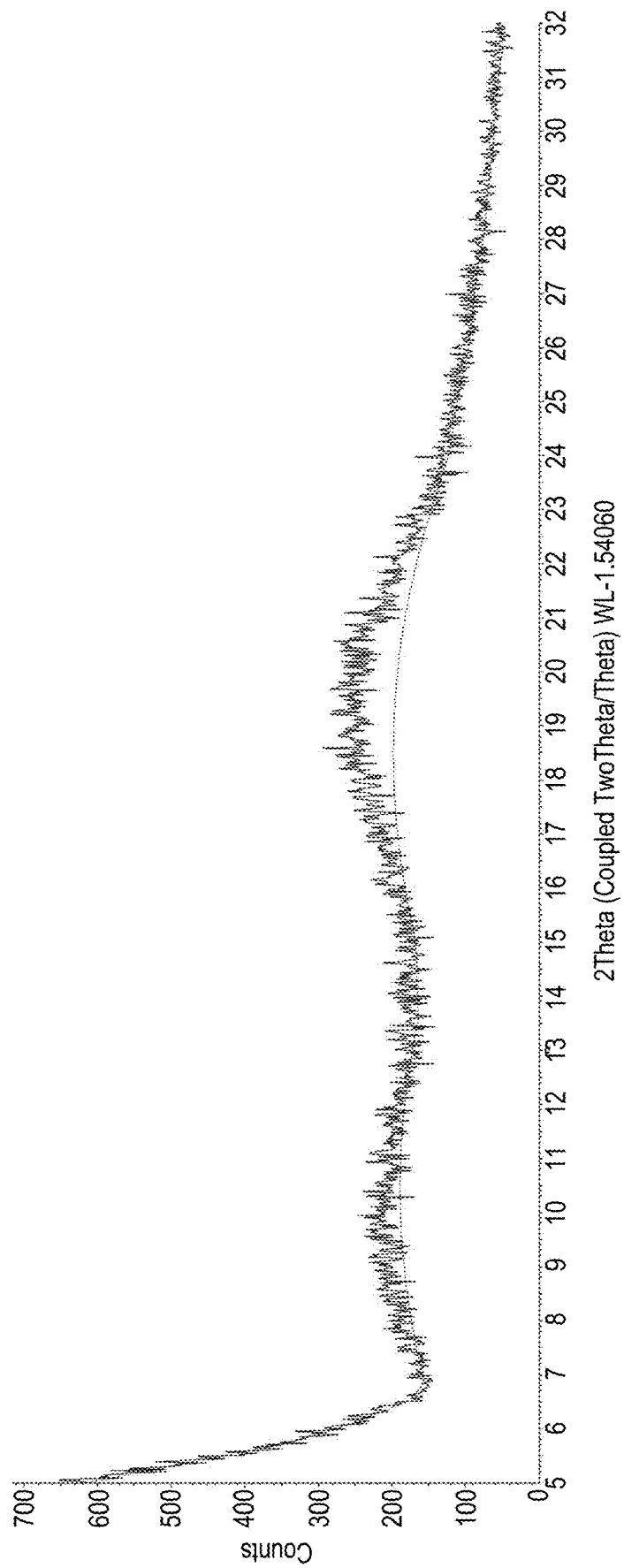
FIG. 19 shows an XRPD for the SDD of Example 10.
Figure 20:
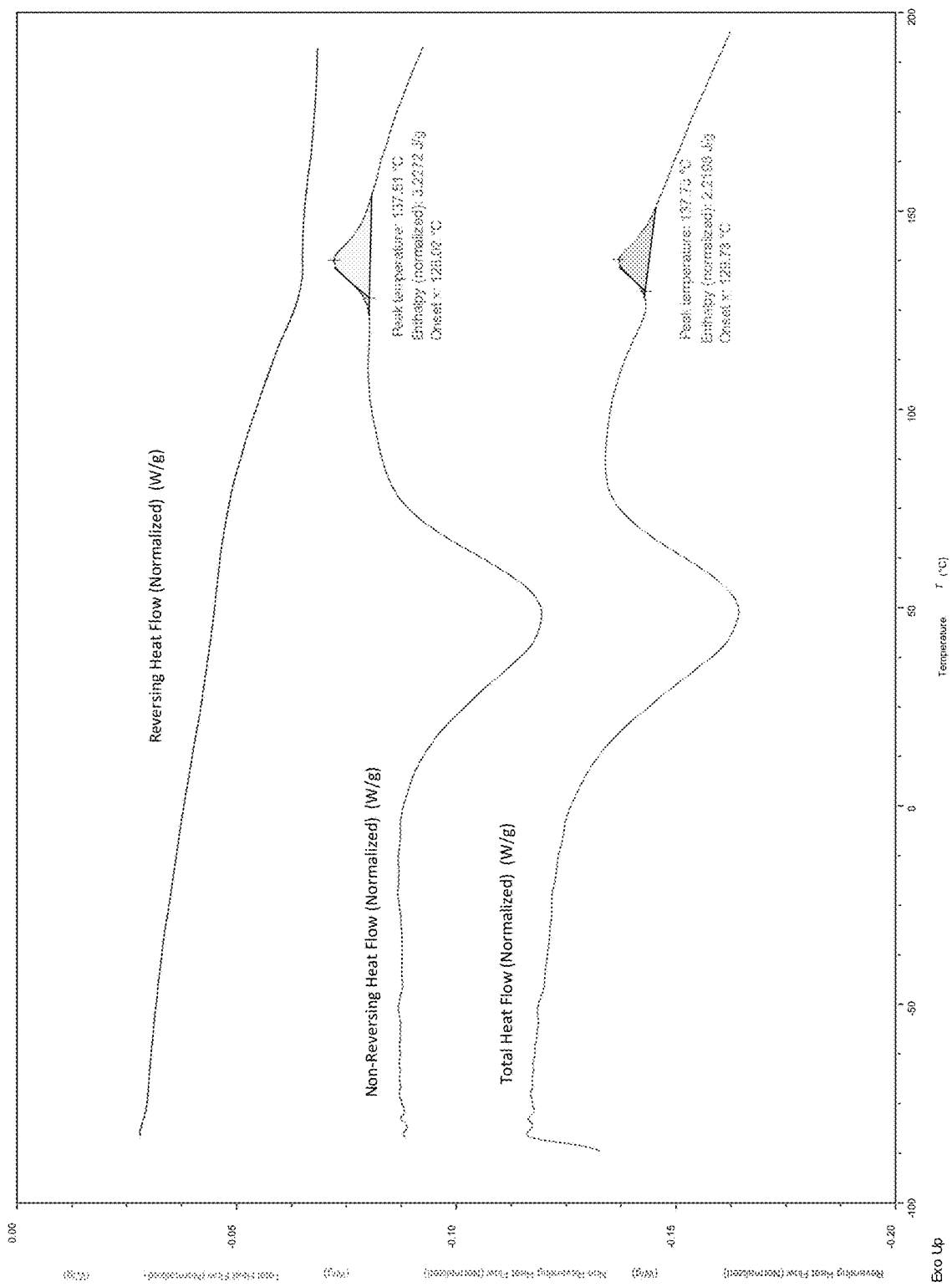
FIG. 20 shows a DSC thermogram for the SDD of Example 10.
Figure 21:
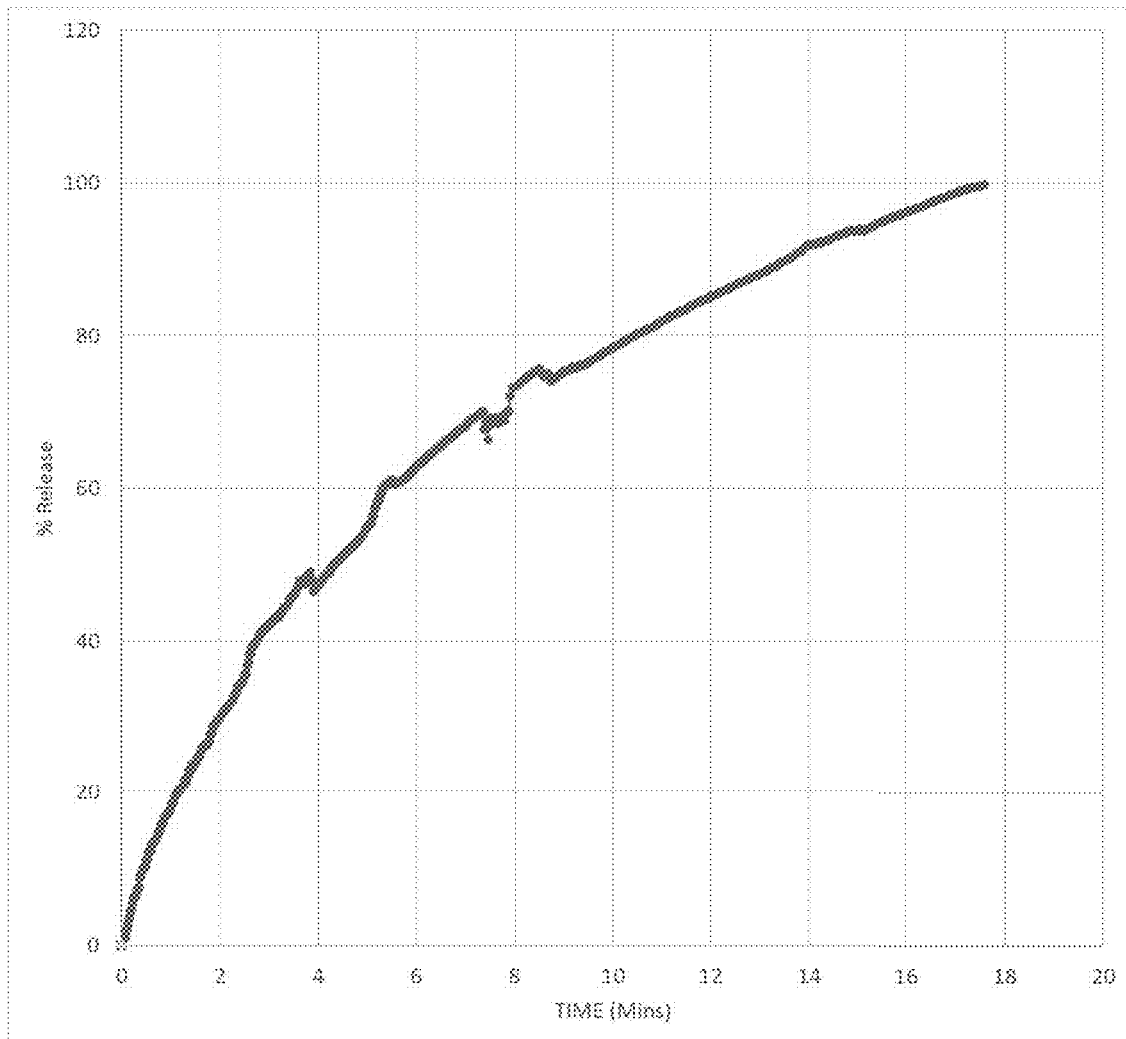
FIG. 21 shows the dissolution profile for the SDD of Example 10.

The SDD produced was stable and amorphous by XRPD (FIG. 19) and DSC (FIG. 20). The dissolution profile of the SDD (FIG. 21) shows that ~80% release has occurred by ~10 minutes, compared with the ~4 minutes for the SDD of Example 6.

Example 11: Spray Drying of 5-MeO-DMT Benzoate Salt with HPMC Mixtures

Spray drying of 5-MeO-DMT benzoate with a mixture of HPMC 2910 in water produced a 30% wt: wt API to excipient SDD. The spray drying parameters were as below:

| SDD Composition | |
| --- | --- |
| Sample Reference | 3815-02-01 |
| Pharmacoat 606 | 67.5% |
| Metolose 60SH50 | 22.5% |
| 5-MeO-MT Benzoate | 10% |
| Spray Drying Parameters | |
| Instrument | Procept |
| Nozzle | Ultrasonic |
| Inlet Flow ($m^3$/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 58% |

The process for spray drying the feed solution was as follows: the required mass of water was weighed into a 50 mL vial. The required mass of HPMC and metolose were added to the water whilst stirring and allowed to fully dissolve. Once dissolved the required mass of API was transferred into the solution and allowed to dissolve. Once dissolved the feed solution was spray dried immediately.

Figure 22:
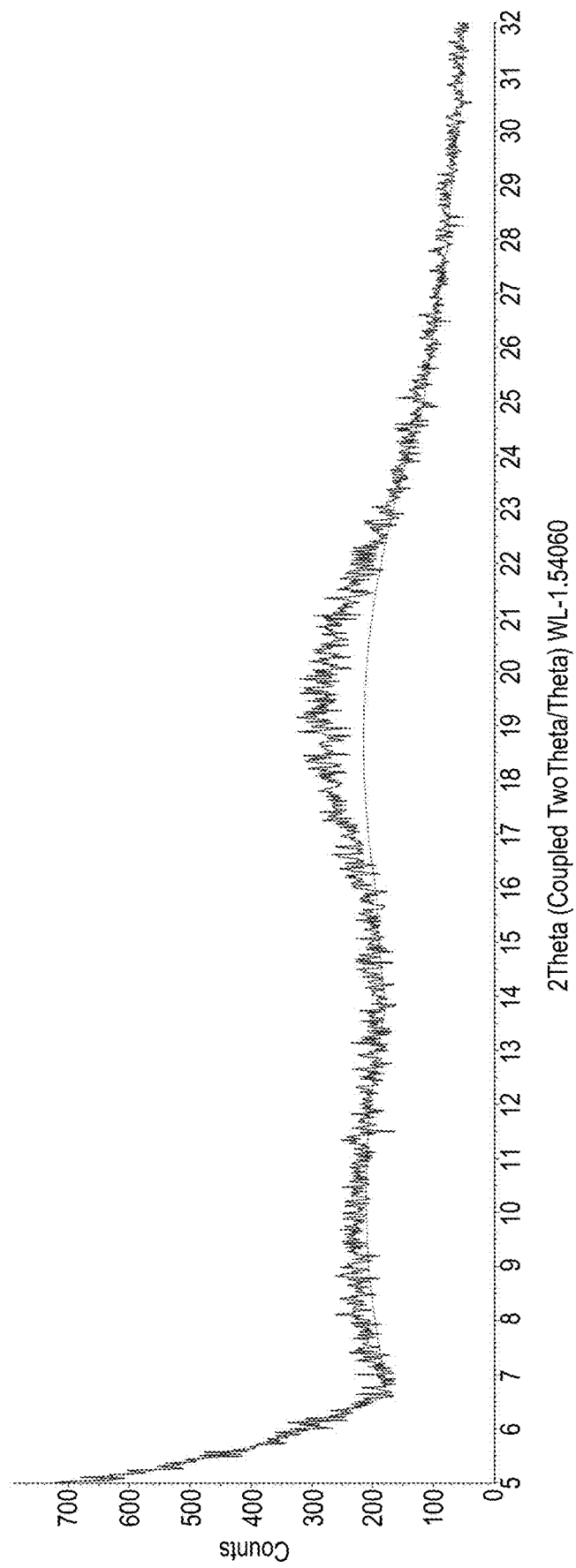
FIG. 22 shows an XRPD for the SDD of Example 11.
Figure 23:
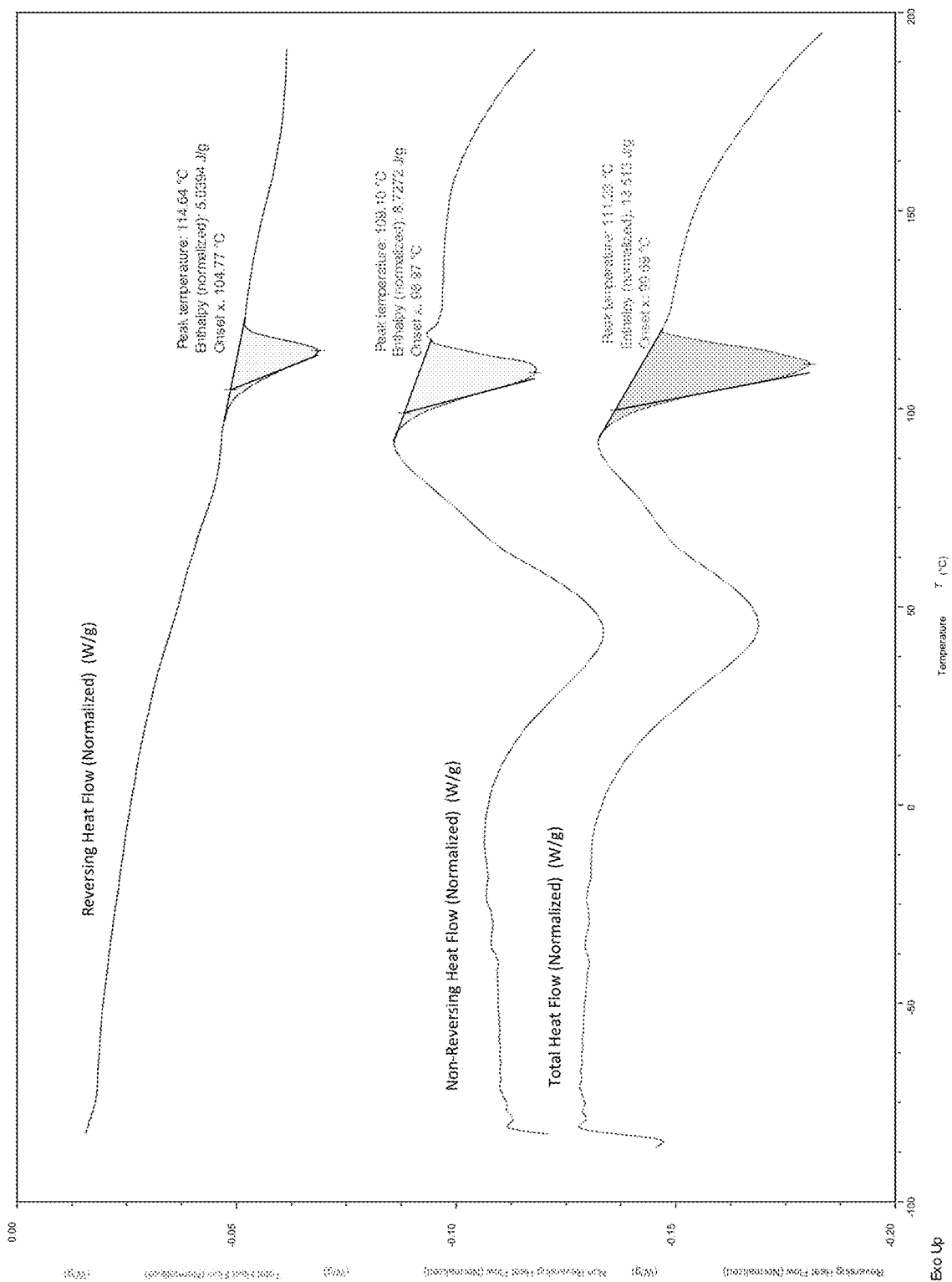
FIG. 23 shows a DSC thermogram for the SDD of Example 11.
Figure 24:
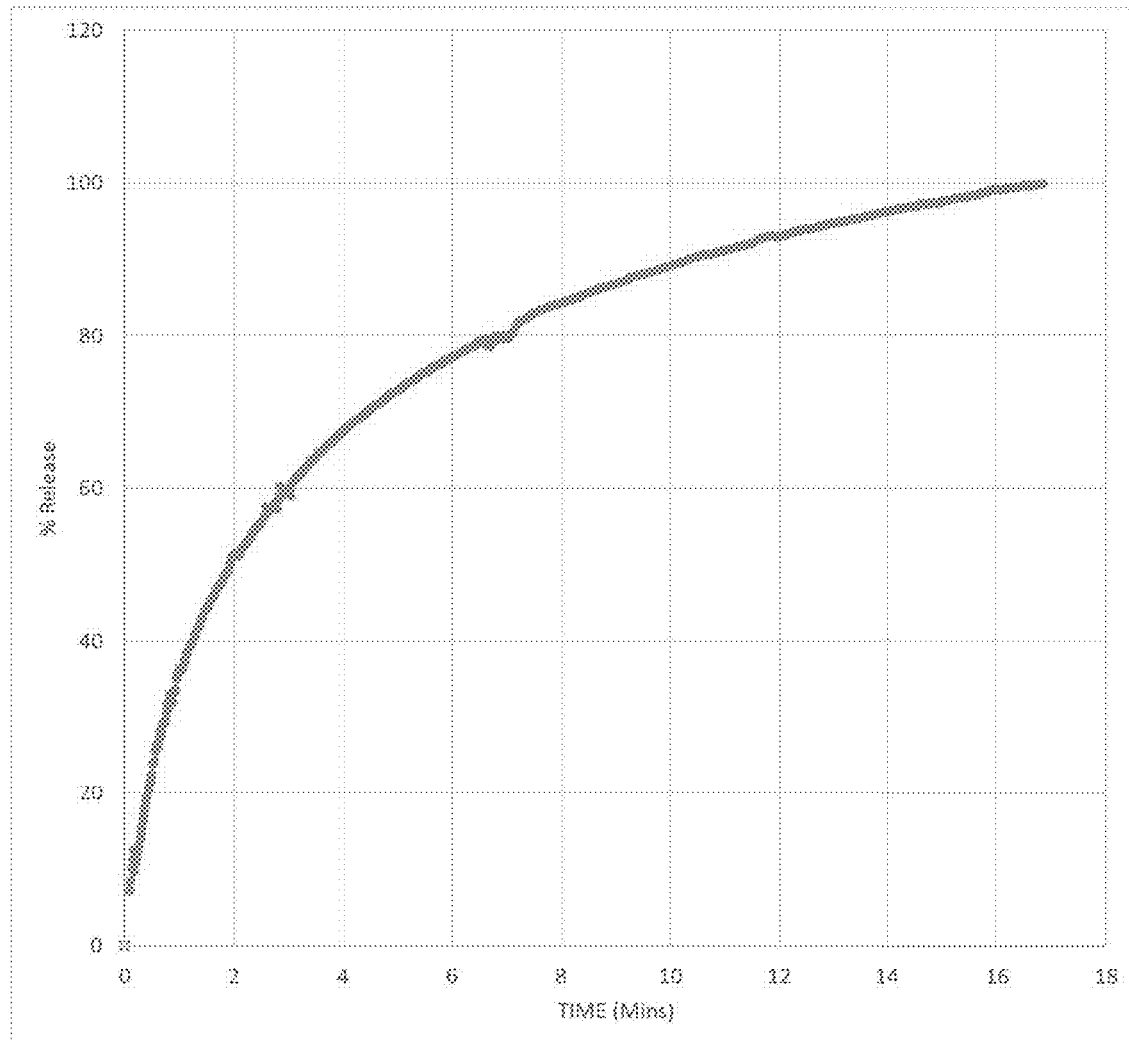
FIG. 24 shows the dissolution profile for the SDD of Example 11.

The SDD produced was stable and amorphous by XRPD (FIG. 22) and DSC (FIG. 23). The dissolution profile of the SDD (FIG. 24) shows that ~80% release has occurred by ~6.5 minutes, compared with ~4 minutes for the SDD of Example 6 and ~10 minutes for the SDD of Example 10.

Example 12: Spray Drying of 5-MeO-DMT Benzoate Salt with HPMC Mixtures

Spray drying of 5-MeO-DMT benzoate salt with a mixture of HPMC 2910 in water produced a 50% wt: wt API to excipient SDD. The spray drying parameters were as below:

| SDD Composition | |
| --- | --- |
| Sample Reference | 3815-02-02 |
| Pharmacoat 606 | 52.5% |
| Metolose 60SH50 | 17.5% |
| 5-MeO-DMT Benzoate | 30% |
| Spray Drying Parameters | |
| Instrument | Procept |
| Nozzle | Ultrasonic |
| Inlet Flow ($m^3$/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 60% |

The spray drying process was as follows: the required mass of water was weighed into a 50 mL vial. The required mass of HPMC and metolose were added to the water whilst stirring and allowed to fully dissolve. Once dissolved the required mass of API was transferred into the solution and allowed to dissolve. Once dissolved the feed solution was spray dried immediately.

Figure 25:
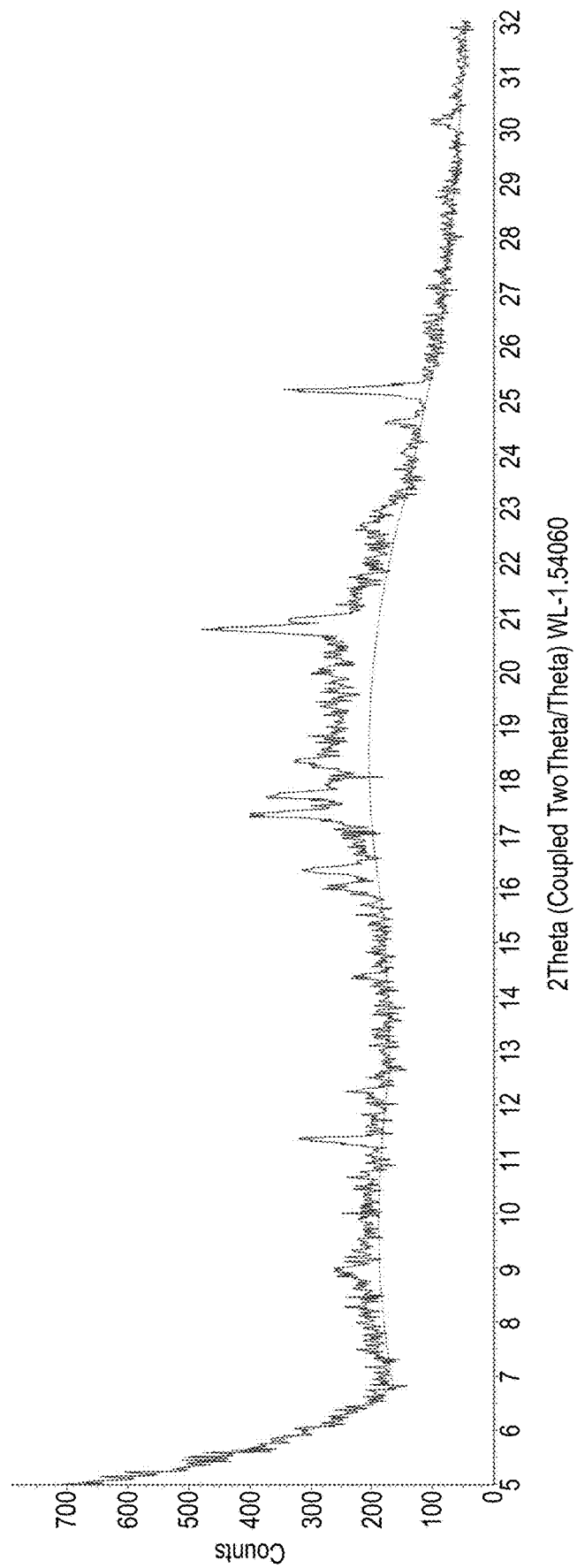
FIG. 25 shows an XRPD for the SDD of Example 12.
Figure 26:
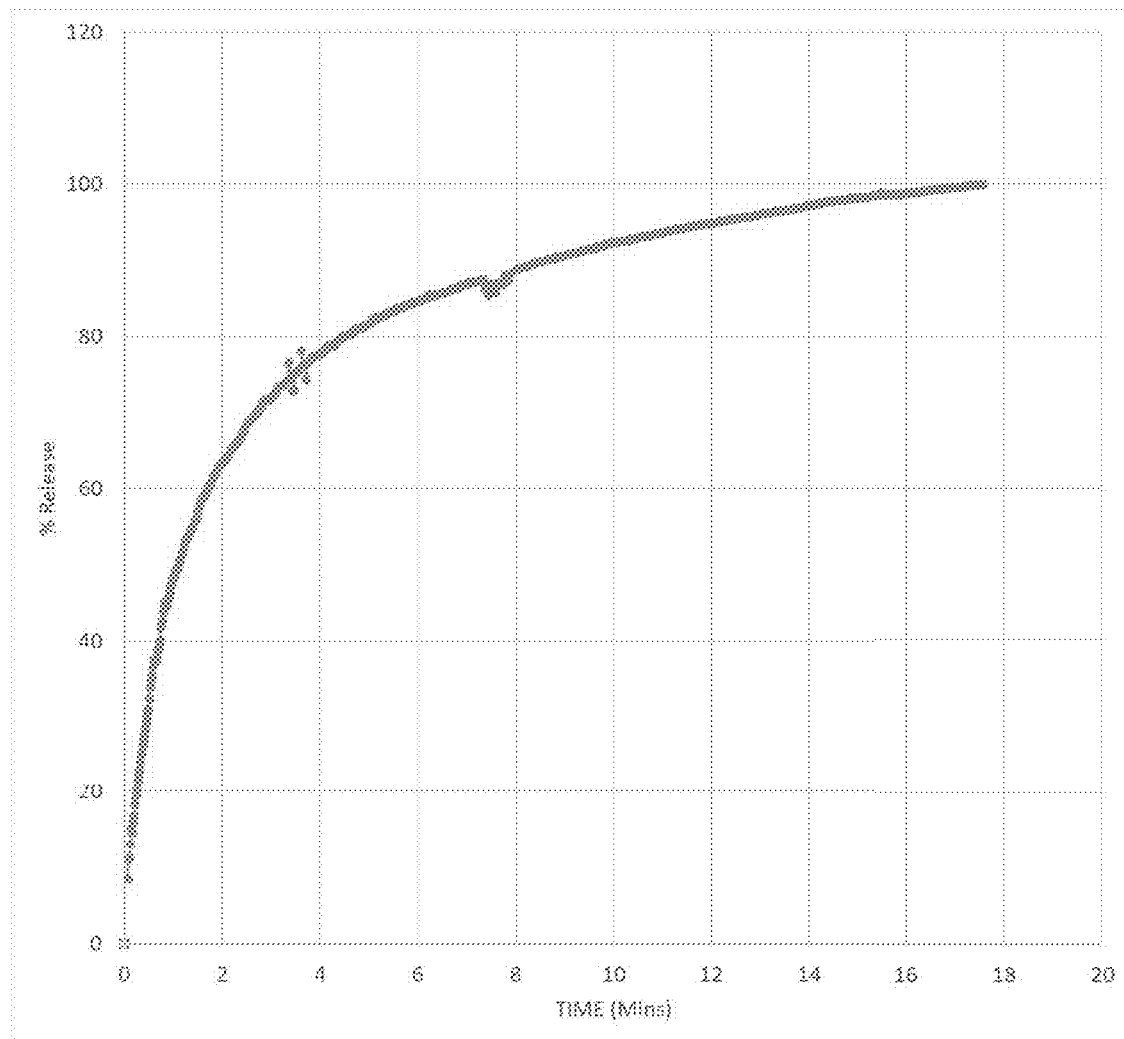
FIG. 26 shows the dissolution profile for the SDD of Example 12.

The SDD produced was partially crystalline (FIG. 25) with a dissolution profile (FIG. 26) that shows that ~80% release has occurred by ~4.5 minutes, compared with ~4 minutes for the SDD of Example 6, ~10 minutes for the SDD of Example 10 and ~6.5 minutes for the SDD of Example 11.

Figure 27:
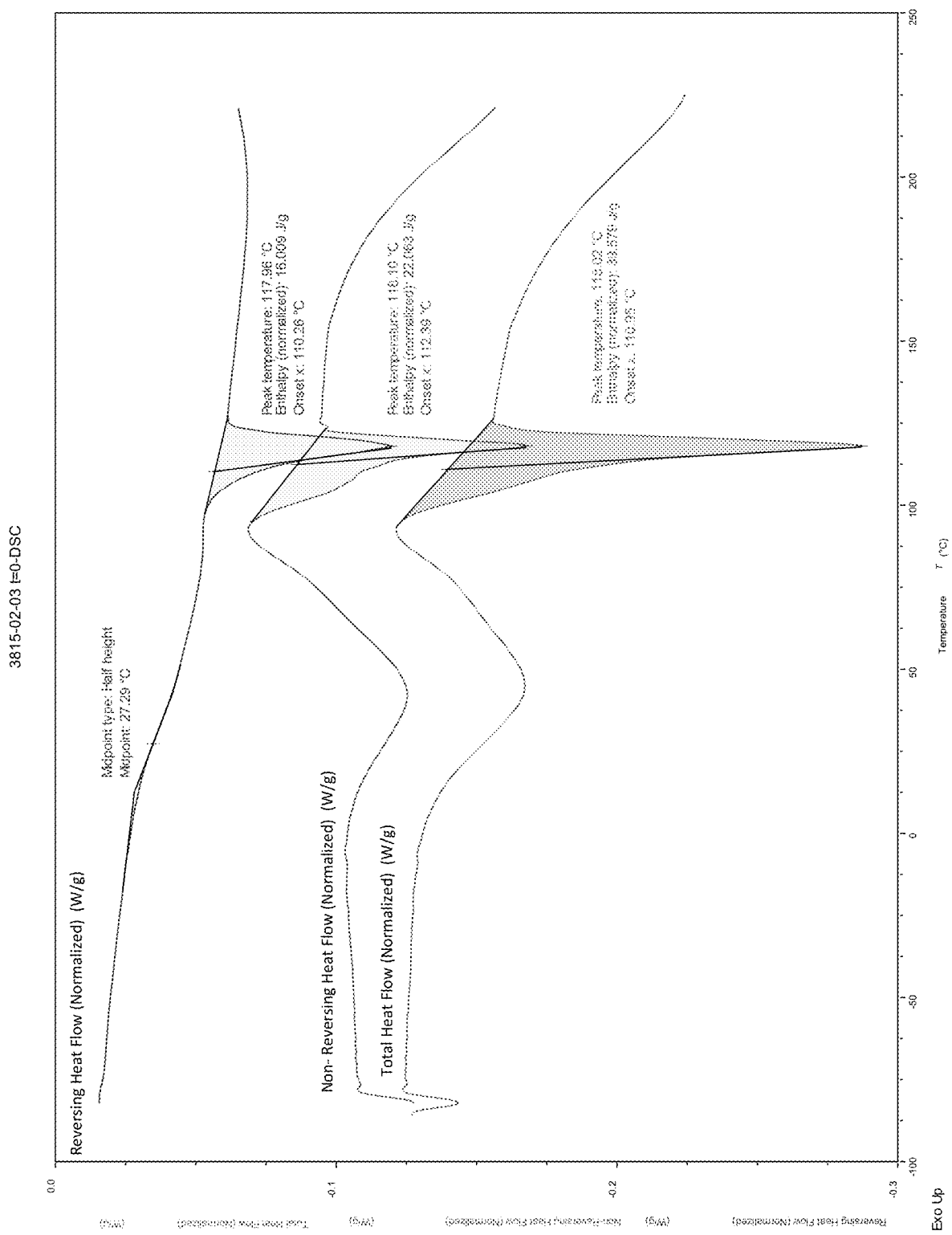
FIG. 27 shows a DSC thermogram for the SDD of Example 12.

The DSC thermogram for the SDD (FIG. 27) shows a small peak at ~140° C. indicating the presence of crystalline API. Such a peak is not seen in the equivalent HBr or HCl salt formulations.

Example 13: Spray Drying of 5-MeO-DMT Benzoate Salt with HPMC Mixtures

Spray drying of 5-MeO-DMT benzoate salt with a mixture of HPMC 2910 and sorbitol in water produced a 10% wt: wt API to excipient SDD. The spray drying parameters were as below:

| SDD Composition | |
| --- | --- |
| Sample Reference | 3815-02-04 |
| Pharmacoat 606 | 65.25% |
| Metolose 60SH50 | 21.75% |
| Sorbitol M | 3% |
| 5-MeO-MT Benzoate | 10% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | |
| Yield | |
| Yield (%) | 61% |

The spray drying process was as follows: the required mass of water was weighed into a 50 mL vial. The required mass of HPMC and metolose were added to the water whilst stirring and allowed to fully dissolve. Once dissolved the required mass of API and sorbitol were transferred into the solution and allowed to dissolve. Once dissolved the feed solution was spray dried immediately.

Figure 28:
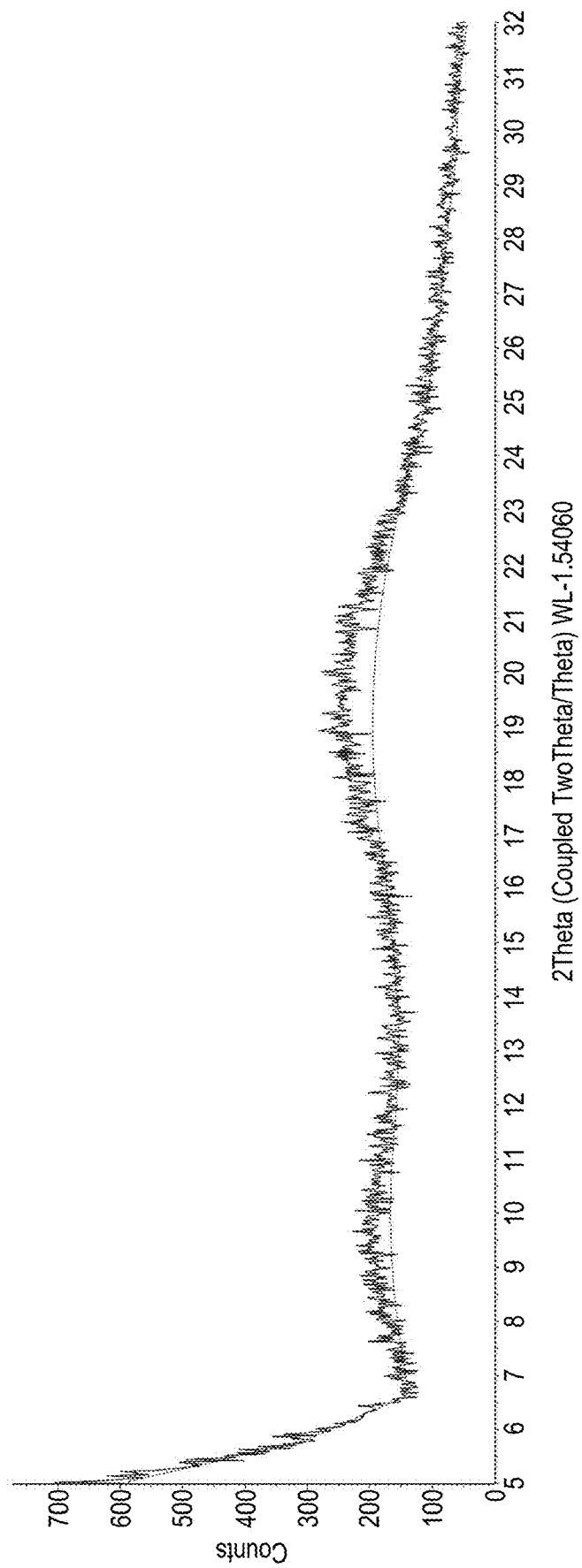
FIG. 28 shows an XRPD for the SDD of Example 13.
Figure 29:
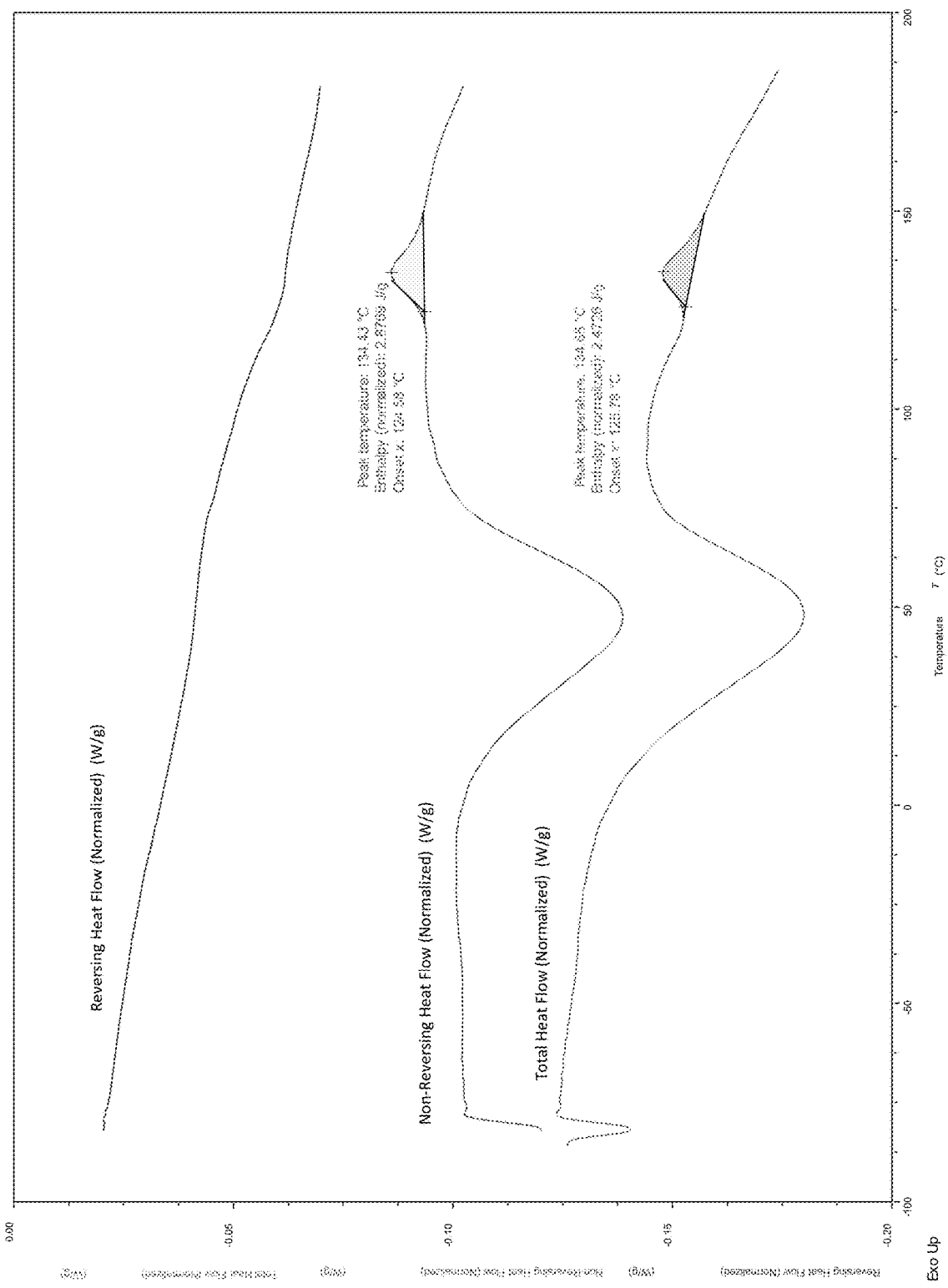
FIG. 29 shows a DSC thermogram for the SDD of Example 13.
Figure 30:
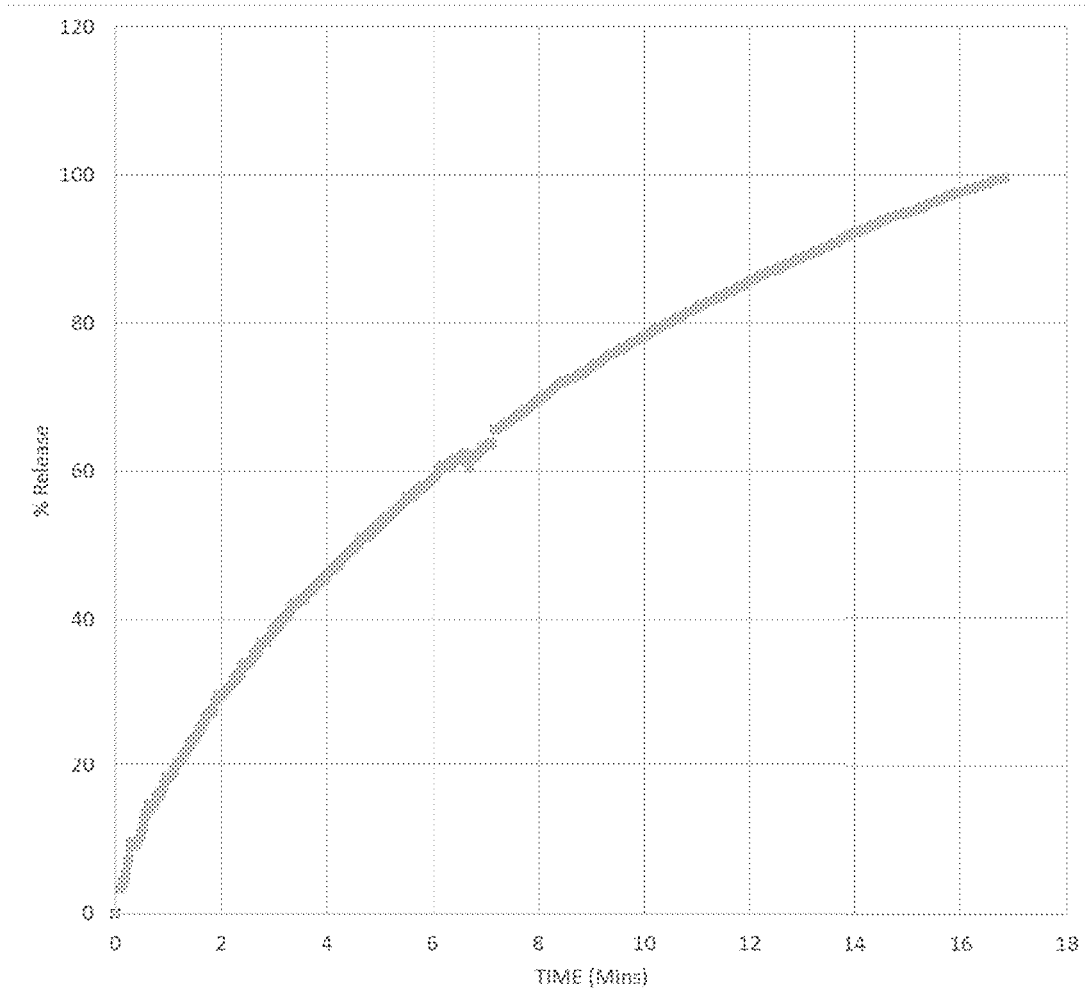
FIG. 30 shows the dissolution profile for the SDD of Example 13.

The SDD produced was stable and amorphous, as shown in FIGS. 28 and 29, and the yield had improved over that which was observed for the SDD of Example 12. The dissolution profile (FIG. 30) shows that ~80% release has occurred by ~10 minutes compared with ~4 minutes for the SDD of Example 6, ~10 minutes for the SDD of Example 10, ~6.5 minutes for the SDD of Example 11 and ~4.5 minutes for Example 12.

Example 14: Spray Drying of 5-MeO-DMT Benzoate Salt with HPMC Mixtures

Spray drying of 5-MeO-DMT benzoate salt with a mixture of HPMC 2910 and sorbitol in water produced a 30% wt: wt API to excipient SDD. The spray drying parameters were as below:

| SDD Composition | |
| --- | --- |
| Sample Reference | 3815-02-05 |
| Pharmacoat 606 | 50.25% |
| Metolose 60SH50 | 16.75% |
| Sorbitol M | 3% |
| 5-MeO-DMT Benzoate | 30% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 3.1 |
| Yield | |
| Yield (%) | 78% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

Figure 31:
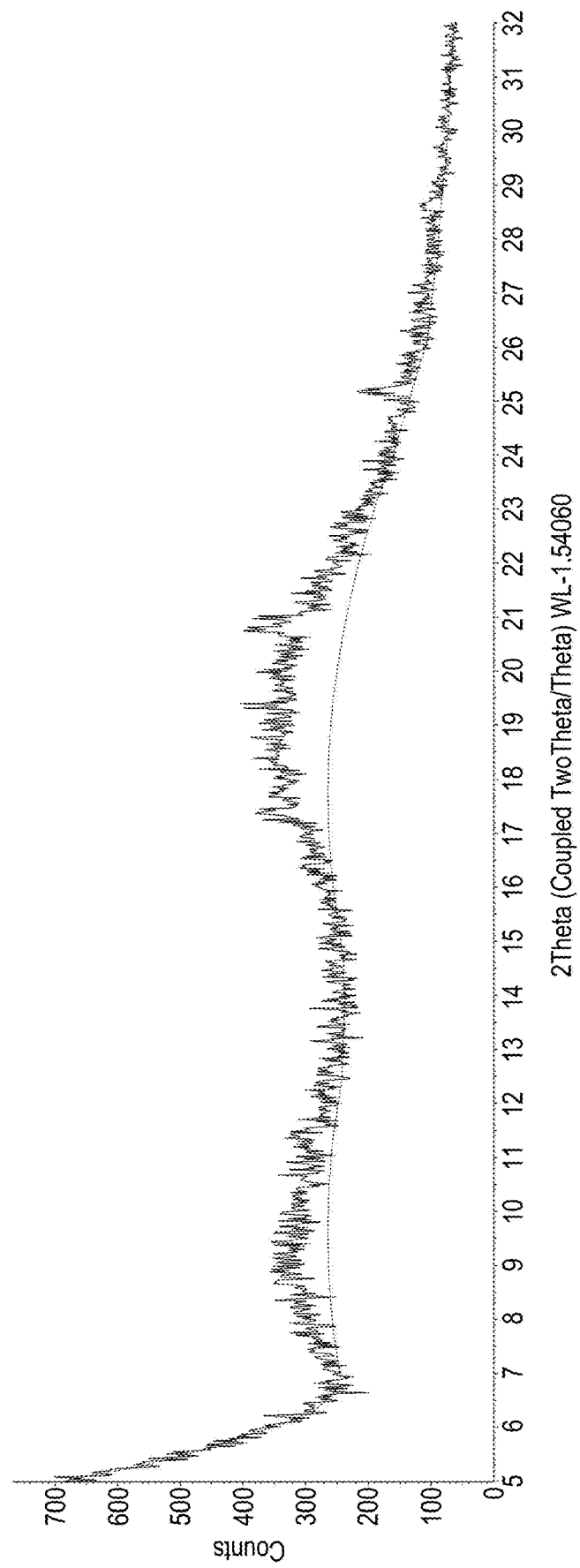
FIG. 31 shows an XRPD of the SDD of Example 14.
Figure 32:
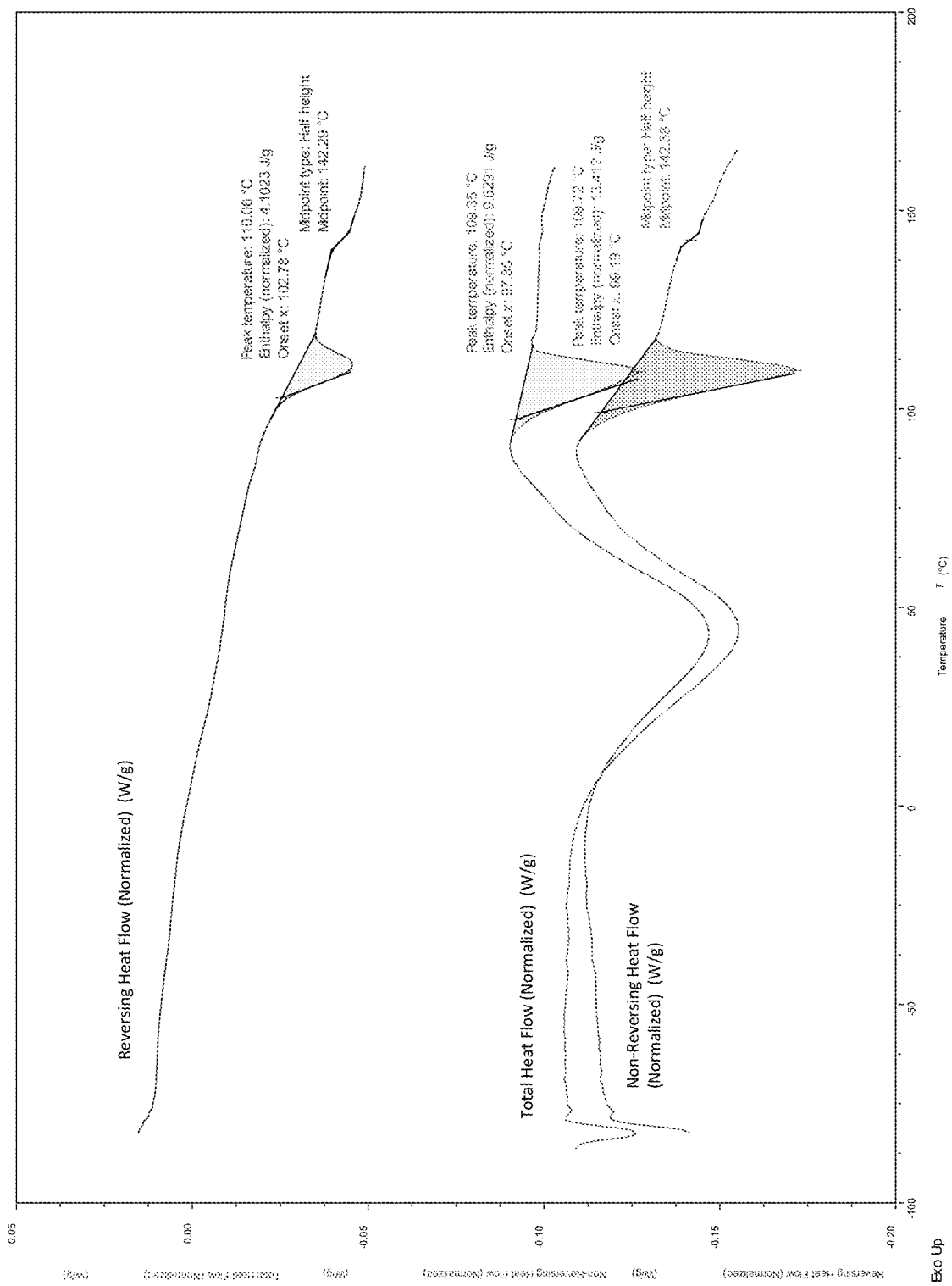
FIG. 32 shows a DSC thermogram for the SDD of Example 14.

The SDD produced was amorphous (FIG. 31) and similar to that produced in Example 12, however, the yield was significantly improved, 52% vs 78%. The DSC thermogram shown in FIG. 32.

Figure 33:
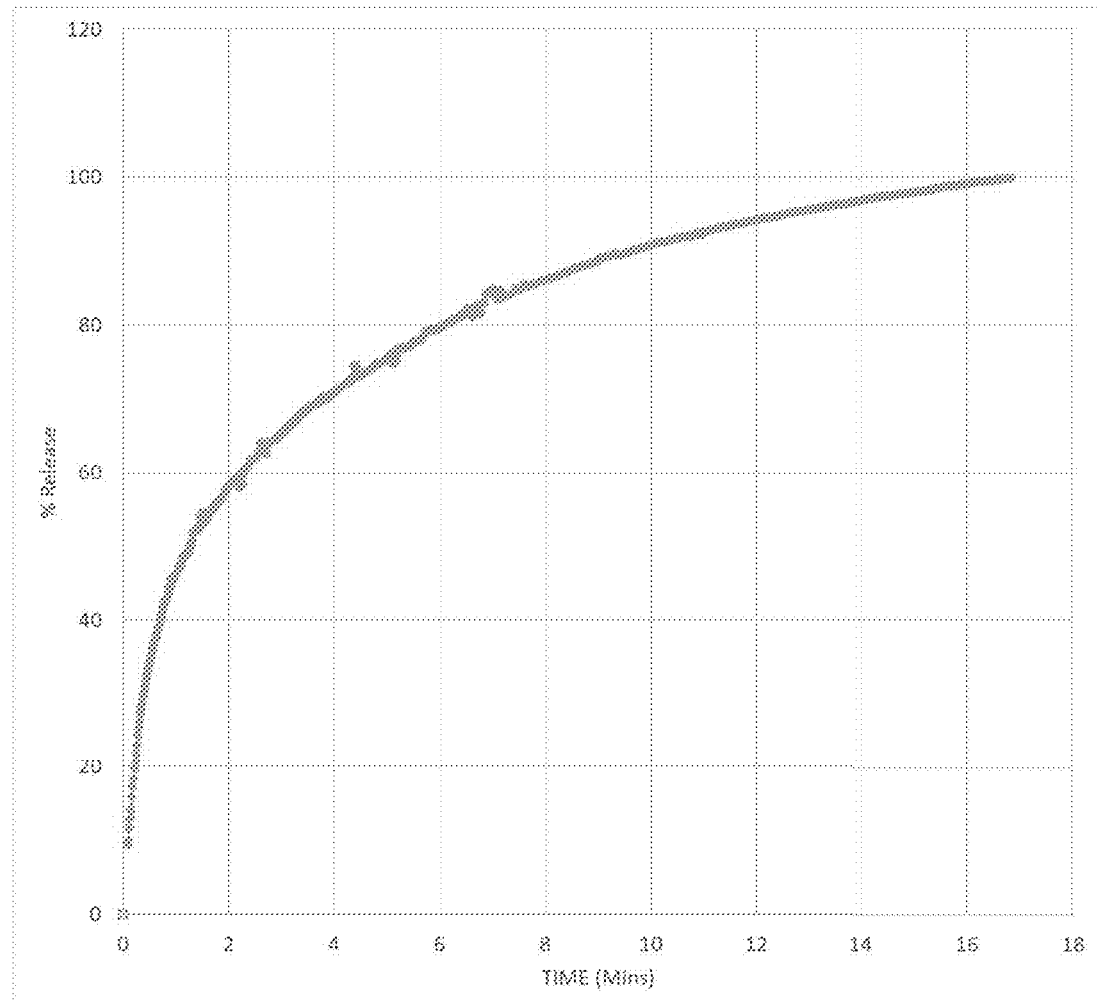
FIG. 33 shows the dissolution profile for the SDD of Example 14.

The dissolution profile, shown in FIG. 33, shows that for the SDD of Example 14 ~80% release has occurred by ~6 minutes, compared with ~4 minutes for the SDD of Example 6, ~10 minutes for the SDD of Example 10, ~6.5 minutes for the SDD of Example 11, ~4.5 minutes for Example 12 and ~10 minutes for the SDD of Example 13.

The inclusion of sorbitol results in an improved yield with no impact on the dissolution rate or stability.

Example 15: Spray Drying of 5-MeO-DMT Benzoate Salt with HPMC Mixtures

Spray drying of 5-MeO-DMT benzoate salt with a mixture of HPMC 2910 and sorbitol in water produced a 50% wt: wt API to excipient SDD. The spray drying parameters were as below:

| SDD Composition | |
| --- | --- |
| Sample Reference | 3815-02-06 |
| Pharmacoat 606 | 35.25% |
| Metolose 60SH50 | 11.75% |
| Sorbitol M | 3% |
| 5-MeO-MT Benzoate | 50% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 4.8 |
| Yield | |
| Yield (%) | 70% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

Figure 34:
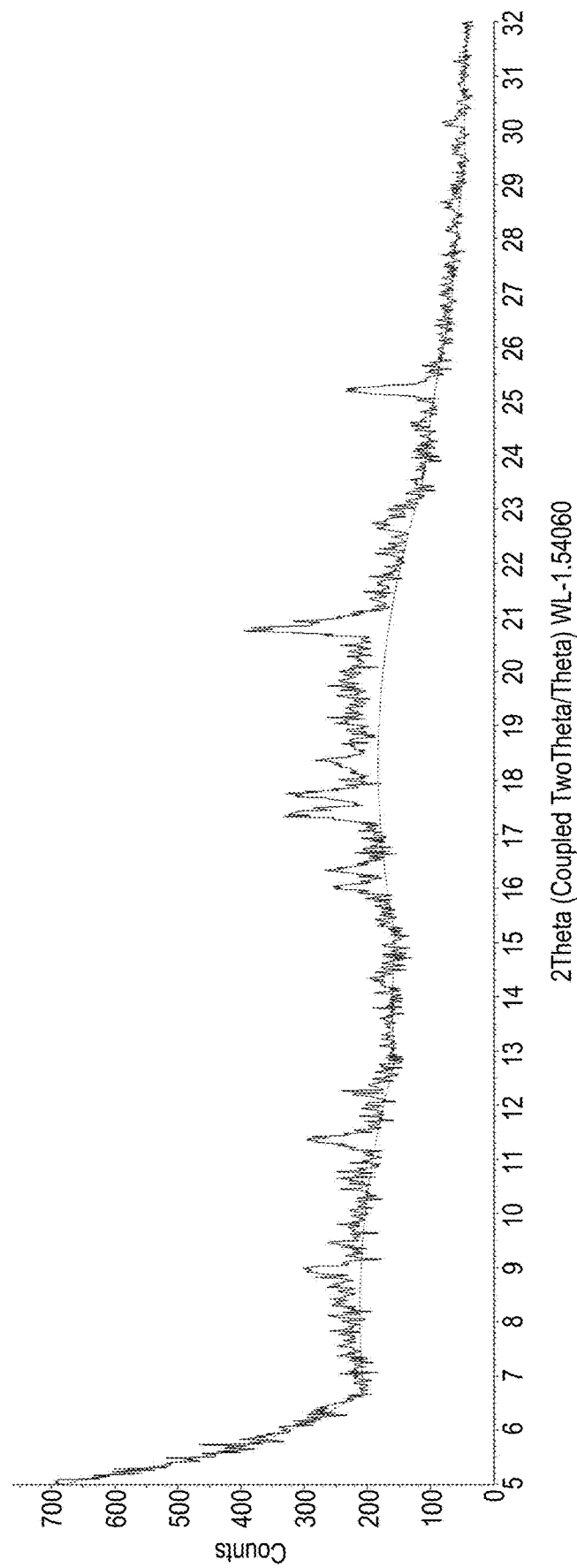
FIG. 34 shows an XRPD of the SDD of Example 15.
Figure 35:
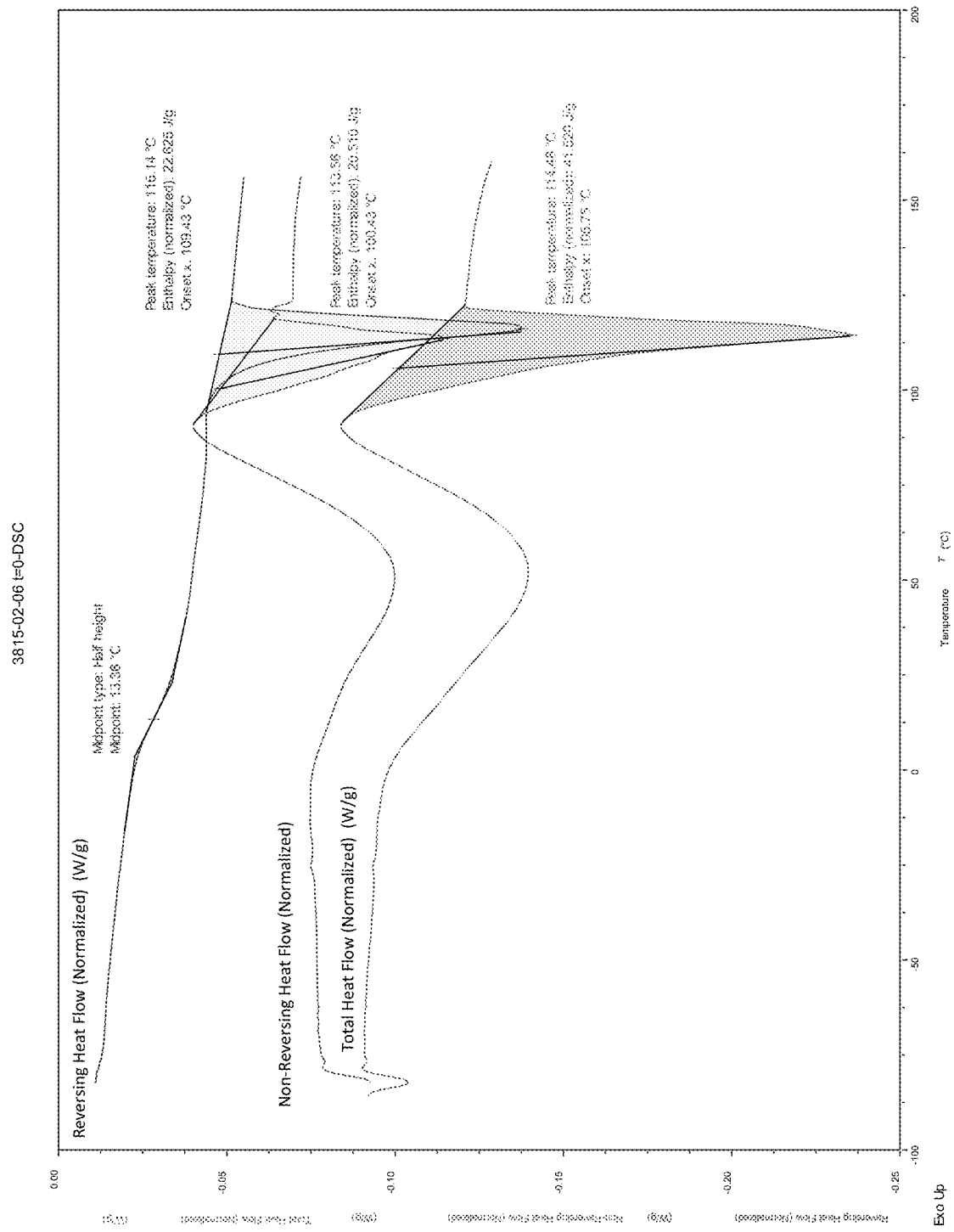
FIG. 35 shows a DSC thermogram for the SDD of Example 15.
Figure 36:
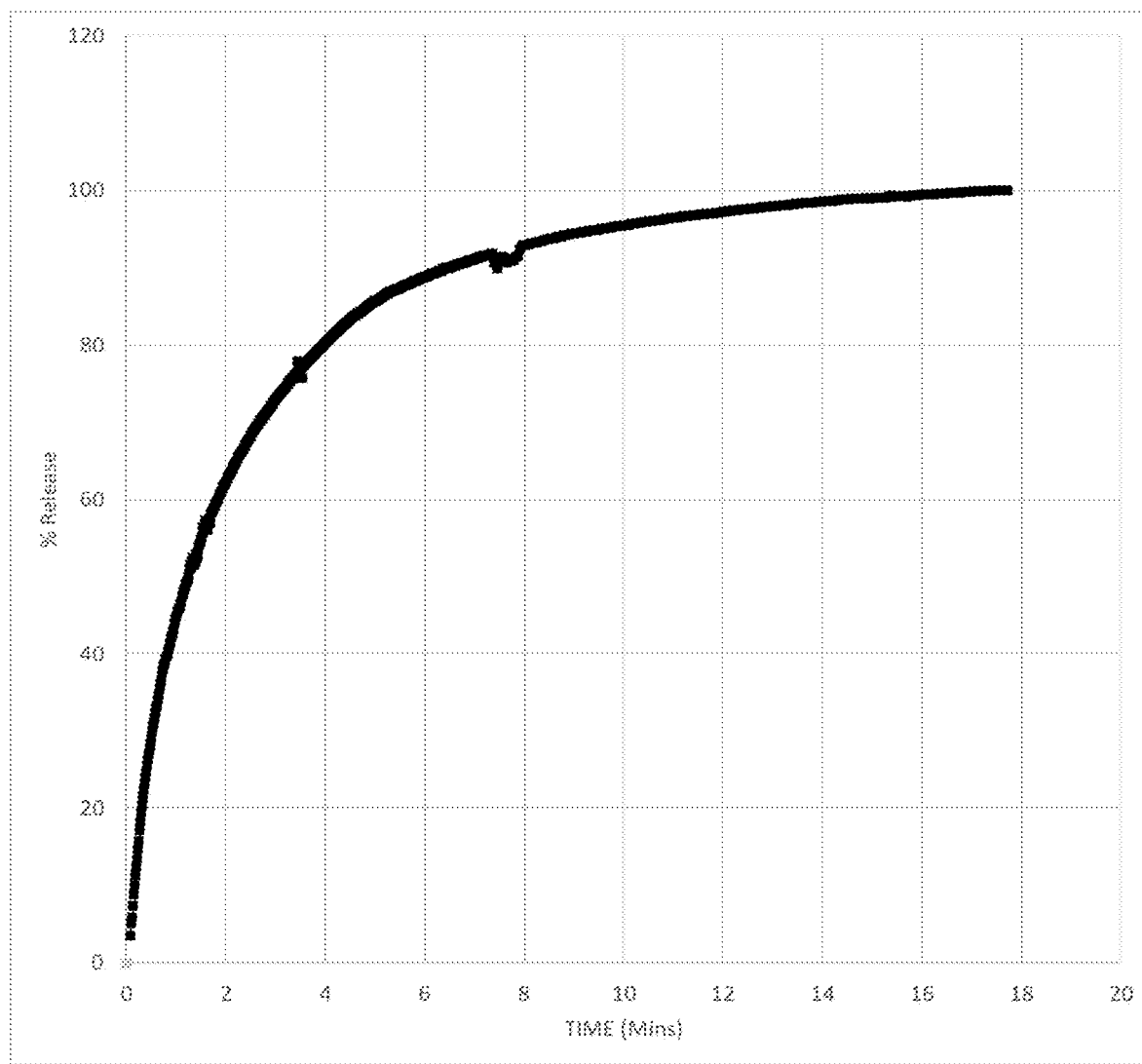
FIG. 36 shows the dissolution profile for the SDD of Example 15.

The SDD produced was partially crystalline (FIG. 34) and the DSC thermogram and dissolution profile of this SDD can be seen in FIGS. 35 and 36. The dissolution profile, shown in FIG. 33, shows that for the SDD of Example 15 ~80% release has occurred by ~4 minutes, compared with ~4 minutes for the SDD of Example 6, ~10 minutes for the SDD of Example 10, ~6.5 minutes for the SDD of Example 11, ~4.5 minutes for Example 12, ~10 minutes for the SDD of Example 13 and ~6 minutes for the SDD of Example 14.

Example 16: Spray Drying of 5-MeO-DMT Hydrobromide Salt with HPMC Mixtures

Spray drying of 5-MeO-DMT hydrobromide salt with a mixture of HPMC 2910 and sorbitol in water produced a 50% wt: wt API to excipient SDD. The spray drying parameters were as below:

| SDD Composition | |
| --- | --- |
| Sample Reference | 3815-37-01 |
| Pharmacoat 606 | 35.25% |
| Metolose 60SH50 | 11.75% |
| Sorbitol M | 3% |
| 5-MeO-DMT hydrobromide | 50% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 4.8 |
| Yield | |
| Yield (%) | 81.75% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

The SDD produced was stable and amorphous, unlike that of Example 15, with a dissolution profile similar to that of Example 15. Additionally, the yield for this SDD was higher than that of the SDD of Example 15.

Example 17: Spray Drying of 5-MeO-DMT Hydrochloride Salt with HPMC Mixtures

Spray drying of 5-MeO-DMT hydrochloride salt with a mixture of HPMC 2910 and sorbitol in water produced a 50% wt: wt API to excipient SDD. The spray drying parameters were as below:

| SDD Composition | |
| --- | --- |
| Sample Reference | 3815-37-02 |
| Pharmacoat 606 | 35.25% |
| Metolose 60SH50 | 11.75% |
| Sorbitol M | 3% |
| 5-MeO-MT hydrochloride | 50% |
| Spray Drying Parameters | |
| Instrument | Procept |
| Nozzle | Ultrasonic |
| Inlet Flow (m³/min) | 0.7 |
| Inlet Temperature (° C.) | 125 |
| Cyclone Gas Pressure (bar) | 0.5 |
| Pump Speed (RPM) | 60 (2 g per minute) |
| Nozzle Power % | 98% |
| Feed Sock % solids | 4.8 |
| Yield | |
| Yield (%) | 78.4% |

The spray drying process was as follows: the required mass of water was weighed into a 50 mL vial. The required mass of HPMC and metolose were added to the water whilst stirring and allowed to fully dissolve. Once dissolved the required mass of API and sorbitol was transferred into the solution and allowed to dissolve. Once dissolved the feed solution was spray dried immediately.

The SDD produced was stable and amorphous, unlike the SDD produced in Example 15. The dissolution profile was similar to the SDD of Example 15.

Example 18: Lyophilisation of HBr Salt with PVP

Lyophilisation of Hydrobromide salt with PVP in water to produce a 50% wt: wt API lyophilized dispersion.

| Feed Solution | | | |
| --- | --- | --- | --- |
| Sample Reference | | | |
| PVP | | 250 mg | |
| 5-MeO-DMT HBr | | 250 mg | |
| Water (de ionized) | | 10 ml | |
| Lyophilsation Profile | | | |
| Temp | Ramp | Hold | Vacuum |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 37:
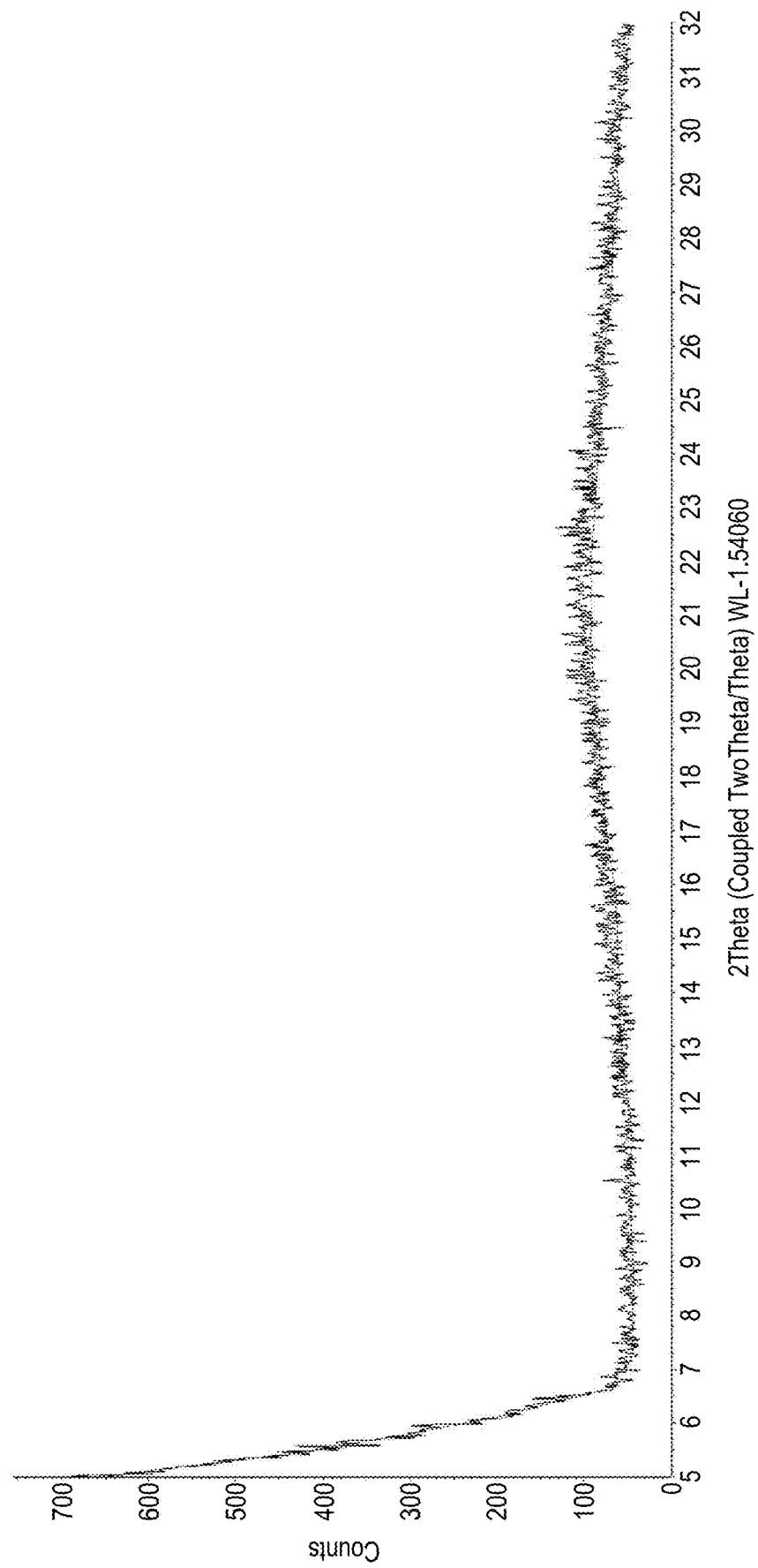
FIG. 37 shows an XRPD of the lyophilized dispersion of Example 18.
Figure 38:
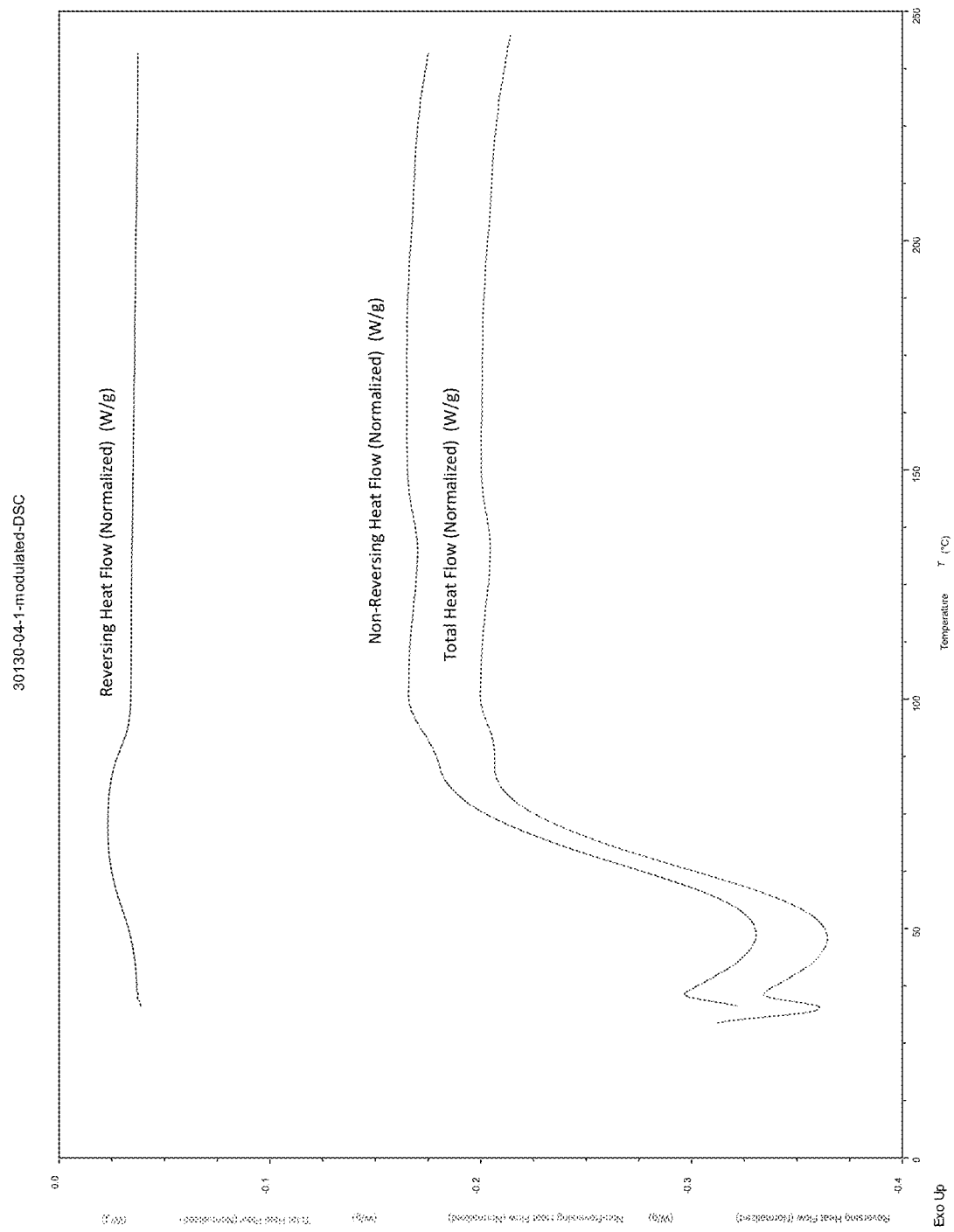
FIG. 38 shows a DSC thermogram for the lyophilized dispersion of Example 18.

Demonstrates that the HBr at 50% loading in PVP will produce an amorphous lyophilized product. FIG. 37 shows an XRPD of the lyophilized dispersion of Example 18. FIG. 38 shows a DSC thermogram for the lyophilized dispersion of Example 18.

Example 19: Lyophilisation of HBr Salt with Lactose Monohydrate

Lyophilisation of Hydrobromide salt with lactose monohydrate in water to produce a 50% wt: wt API lyophilized dispersion.

| Feed Solution | | | |
| --- | --- | --- | --- |
| Sample Reference | | 30130-04-3 | |
| Lactose monohydrate | | 250 mg | |
| 5-MeO-DMT HBr | | 250 mg | |
| Water (de ionized) | | 10 ml | |
| Lyophilisation Profile | | | |
| Temp | Ramp | Hold | Vacuum |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 39:
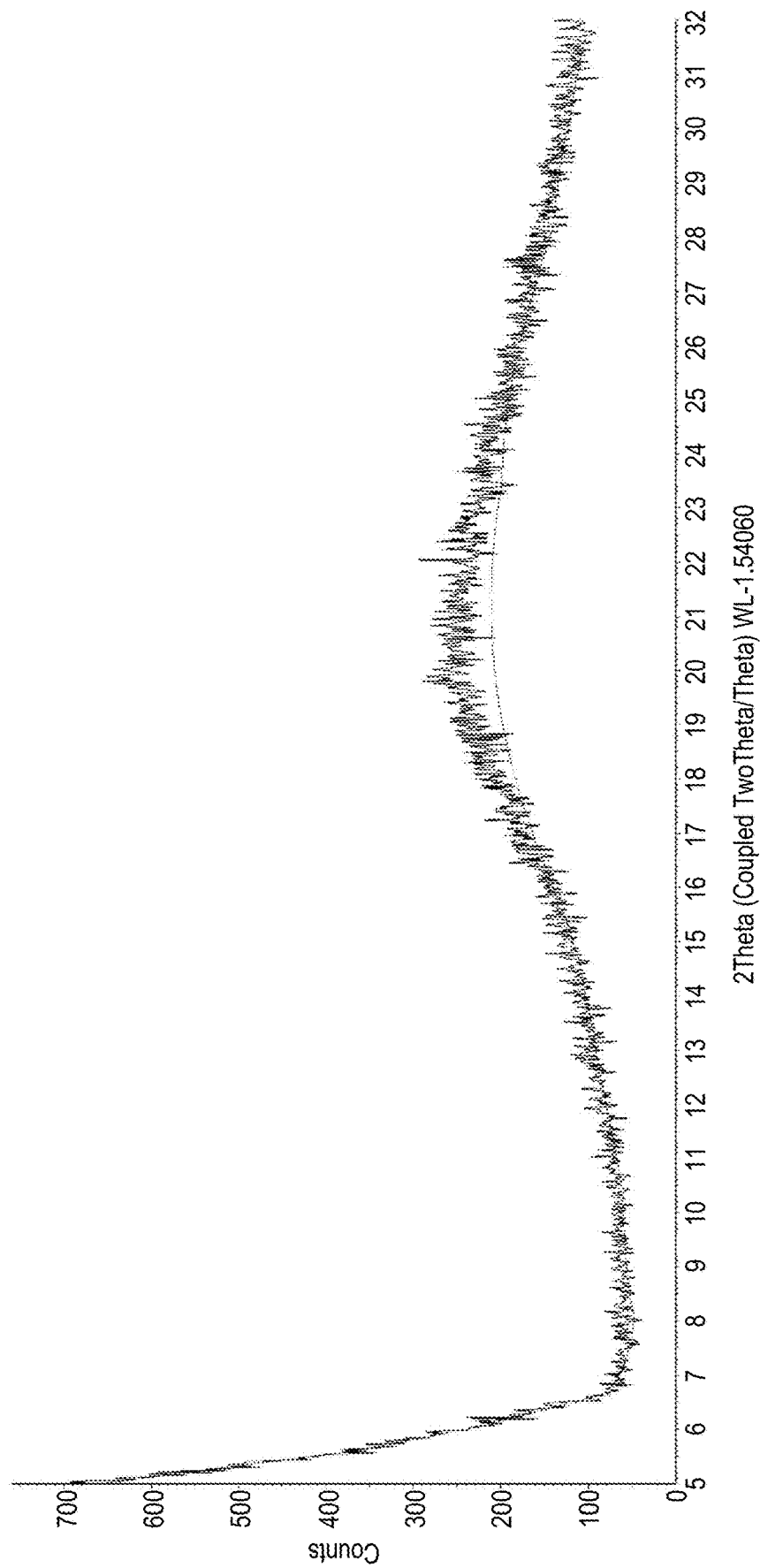
FIG. 39 shows an XRPD of the lyophilized dispersion of Example 19.
Figure 40:
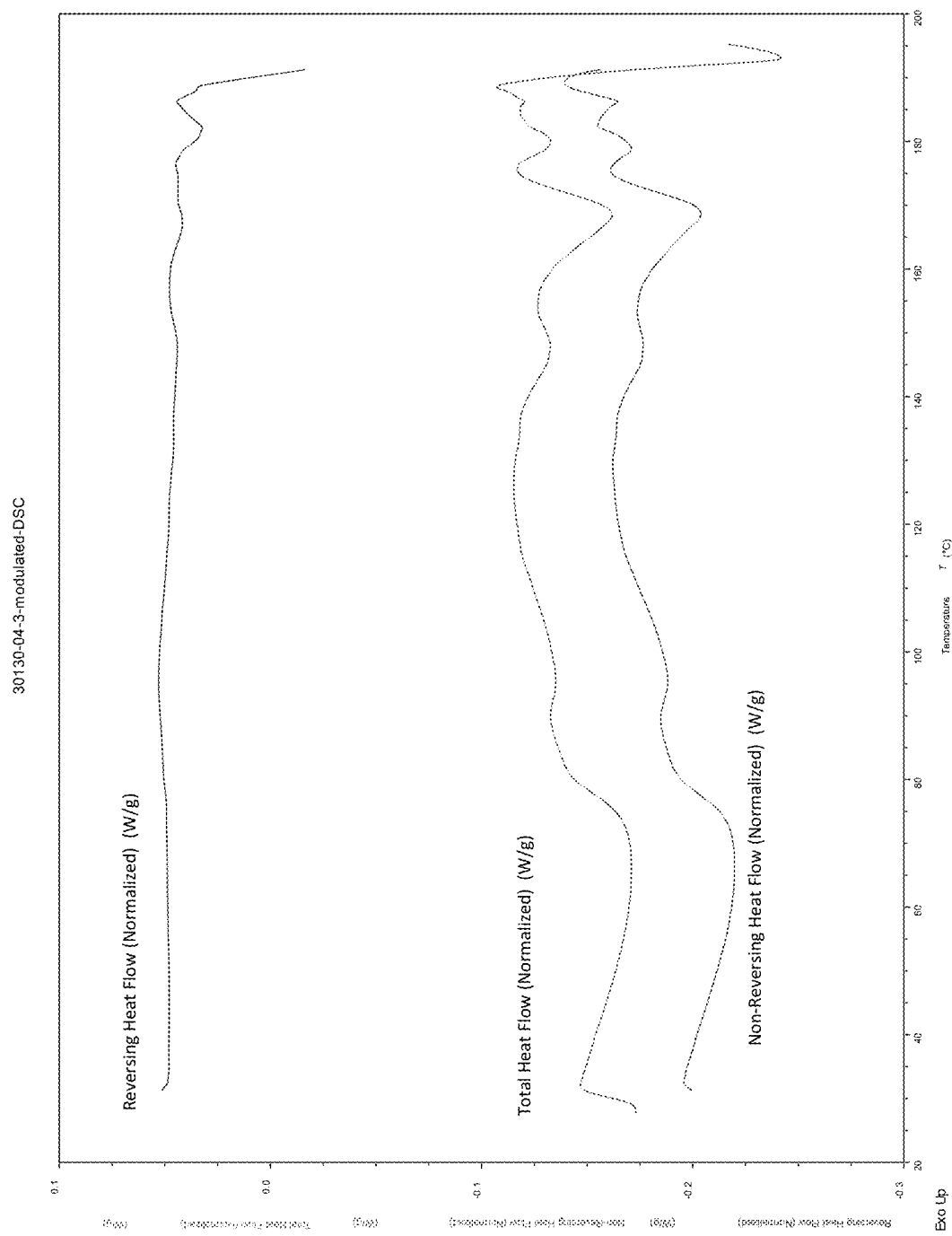
FIG. 40 shows a DSC thermogram for the lyophilized dispersion of Example 19.

Demonstrates that the HBr at 50% loading in lactose monohydrate will produce an amorphous lyophilized product. FIG. 39 shows an XRPD of the lyophilized dispersion of Example 19. FIG. 40 shows a DSC thermogram for the lyophilized dispersion of Example 19.

Example 20: Lyophilisation of HBr Salt with Trehalose

Lyophilisation of Hydrobromide salt with lactose trehalose in water to produce a 50% wt: wt API lyophilized dispersion.

| Feed Solution | |
| --- | --- |
| Sample Reference | 30130-04-4 |
| trehalose | 250 mg |
| 5-MeO-MT HBr | 250 mg |
| Water (de ionized) | 10 ml |

| Lyophilisation Profile | | | |
| --- | --- | --- | --- |
| Temp | Ramp | Hold | Vacuum |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 41:
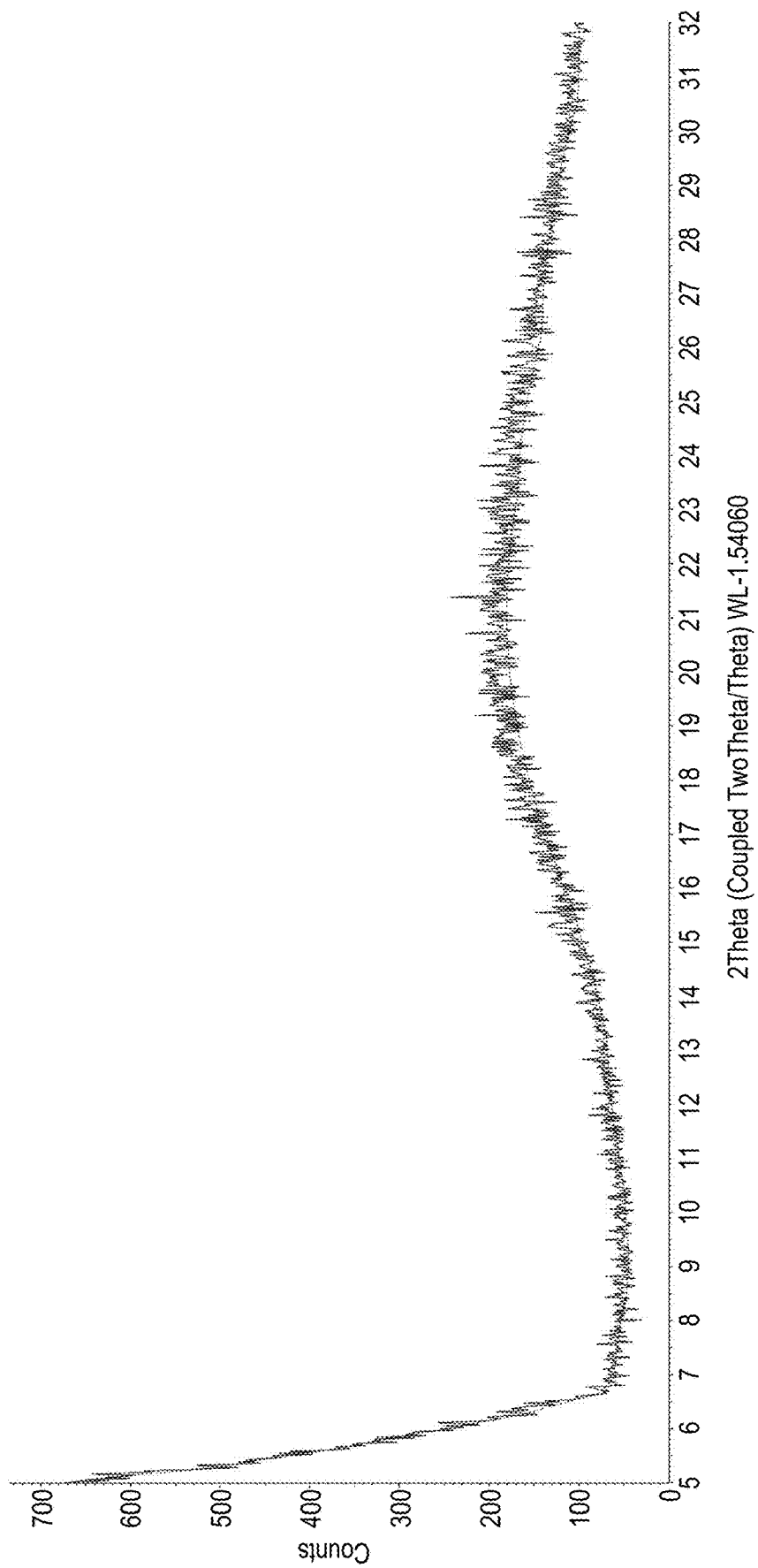
FIG. 41 shows an XRPD of the lyophilized dispersion of Example 20.
Figure 42:
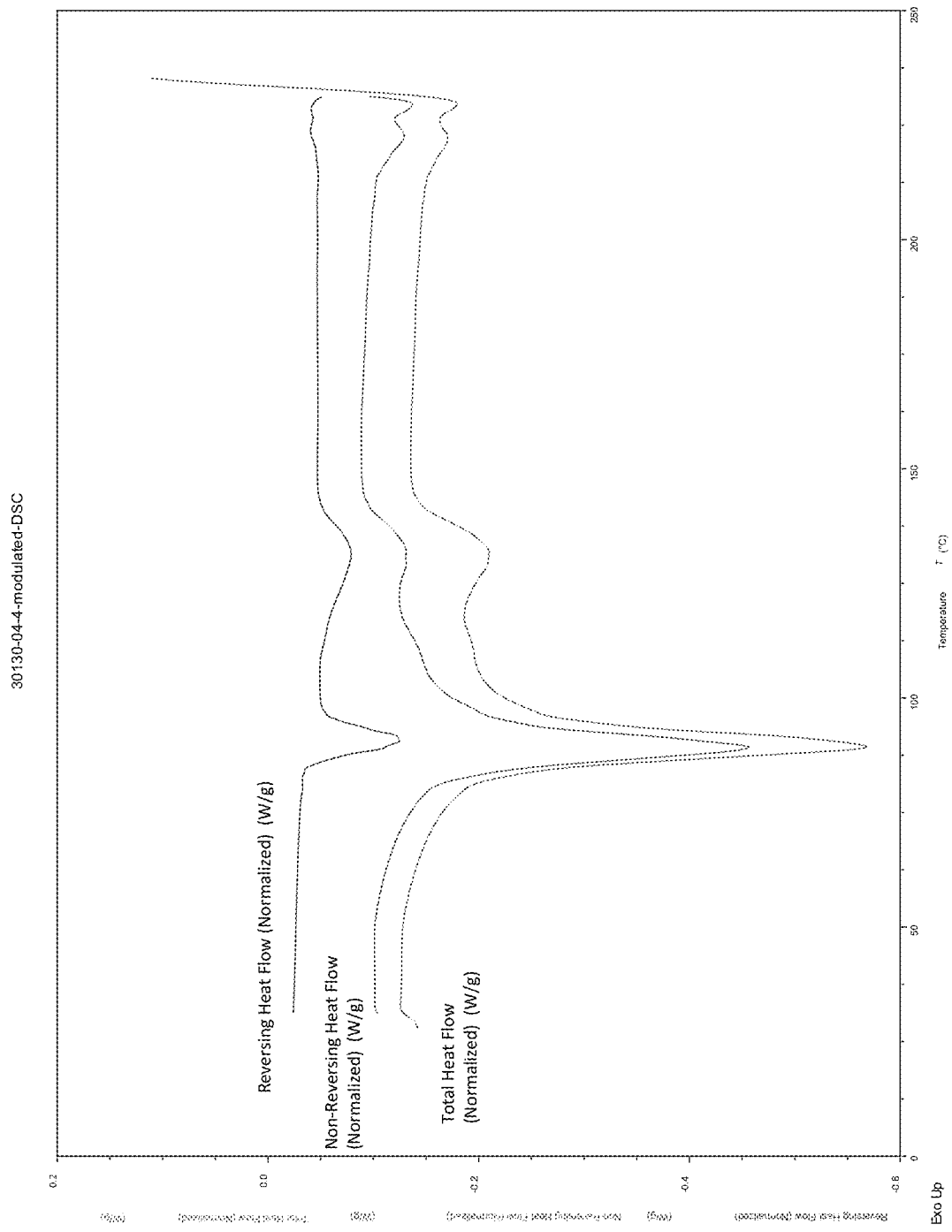
FIG. 42 shows a DSC thermogram for the lyophilized dispersion of Example 20.

Demonstrates that the HBr at 50% loading in trehalose will produce an amorphous lyophilized product. FIG. 41 shows an XRPD of the lyophilized dispersion of Example 20. FIG. 42 shows a DSC thermogram for the lyophilized dispersion of Example 20.

Example 21: Lyophilisation of Oxalate Salt with Trehalose

Lyophilisation of Oxalate salt with lactose trehalose in water to produce a 50% wt: wt API lyophilized dispersion.

| Feed Solution | |
| --- | --- |
| Sample Reference | 30130-04-5 |
| Trehalose | 250 mg |
| 5-MeO-MT oxalate | 250 mg |
| Water (de ionized) | 10 ml |

| Lyophilisation Profile | | | |
| --- | --- | --- | --- |
| Temp | Ramp | Hold | Vacuum |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 43:
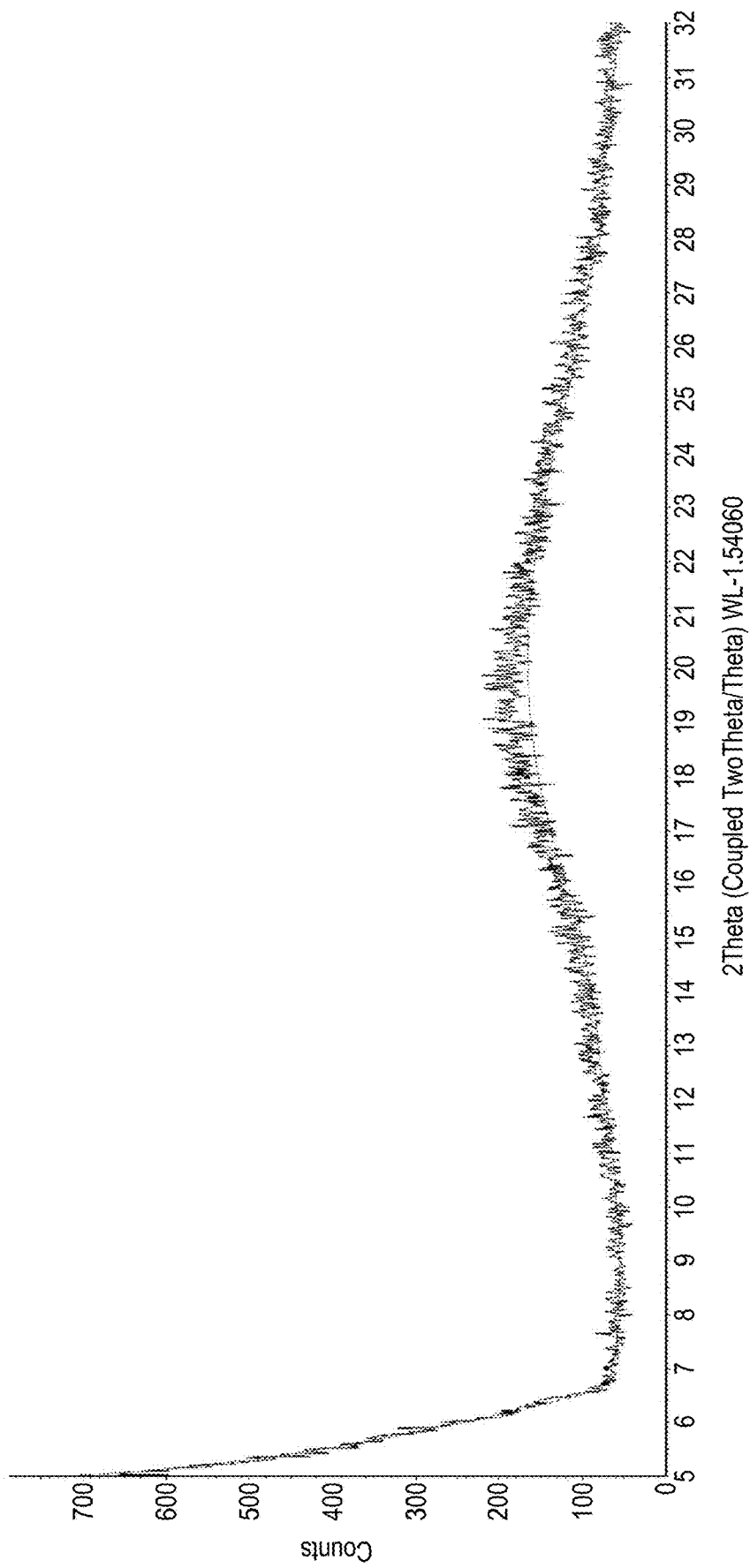
FIG. 43 shows an XRPD of the lyophilized dispersion of Example 21.
Figure 44:
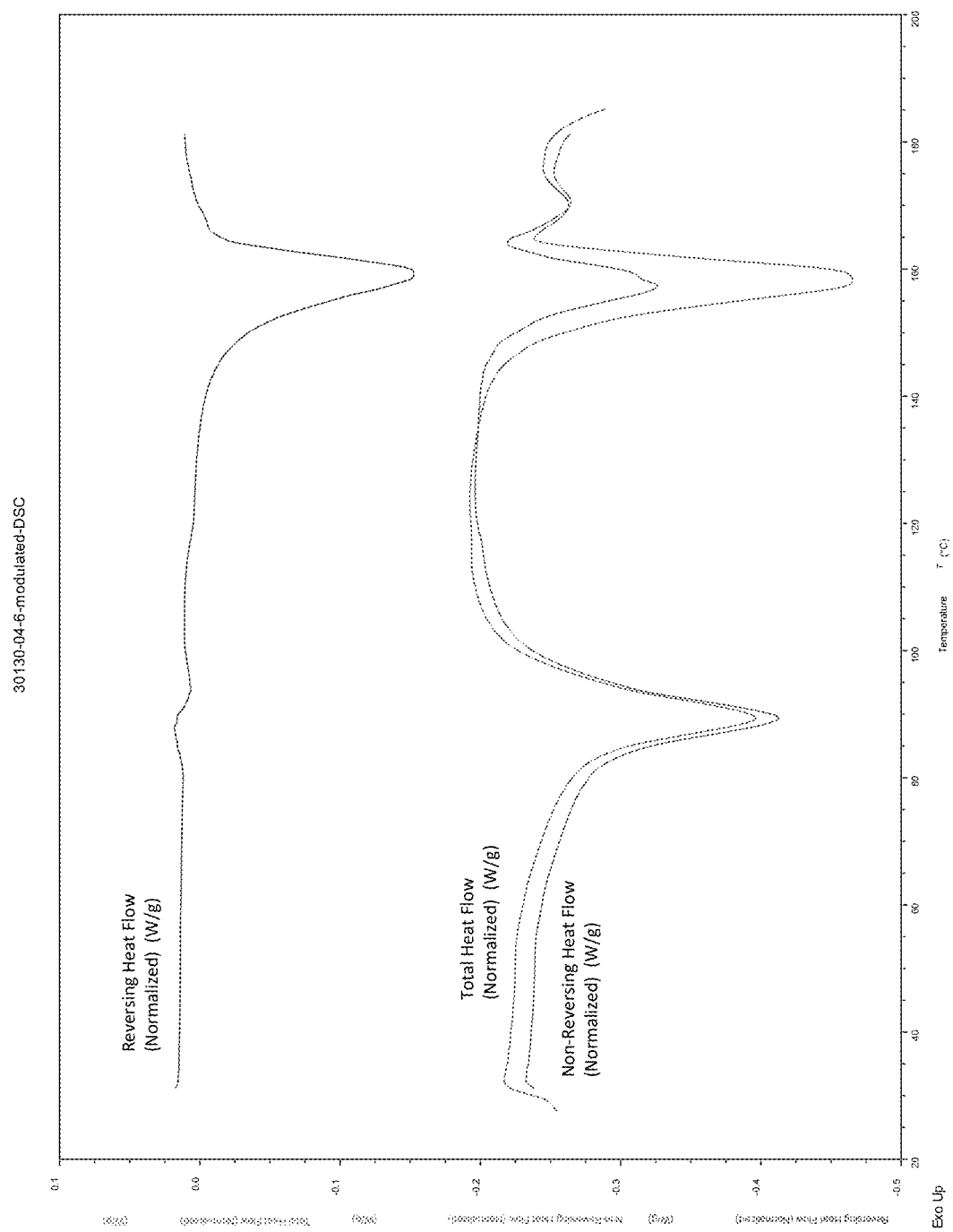
FIG. 44 shows a DSC thermogram for the lyophilized dispersion of Example 21.

Demonstrates that the Oxalate at 50% loading in trehalose will produce an amorphous lyophilized product. FIG. 43 shows an XRPD of the lyophilized dispersion of Example 21. FIG. 44 shows a DSC thermogram for the lyophilized dispersion of Example 21.

Example 22: Lyophilisation of HBr Salt with Mannitol and Trehalose

Lyophilisation of HBr salt with mannitol/trehalose in water to produce a 50% wt: wt API lyophilized dispersion.

| Feed Solution | |
| --- | --- |
| Sample Reference | 3815-24-02 |
| Mannitol | 150 mg |
| Trehalose | 50 mg |
| 5-MeO-MT HBr | 200 mg |
| Water (de ionized) | 10 ml |

| Lyophilisation Profile | | | |
| --- | --- | --- | --- |
| Temp | Ramp | Hold | Vacuum |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 45:
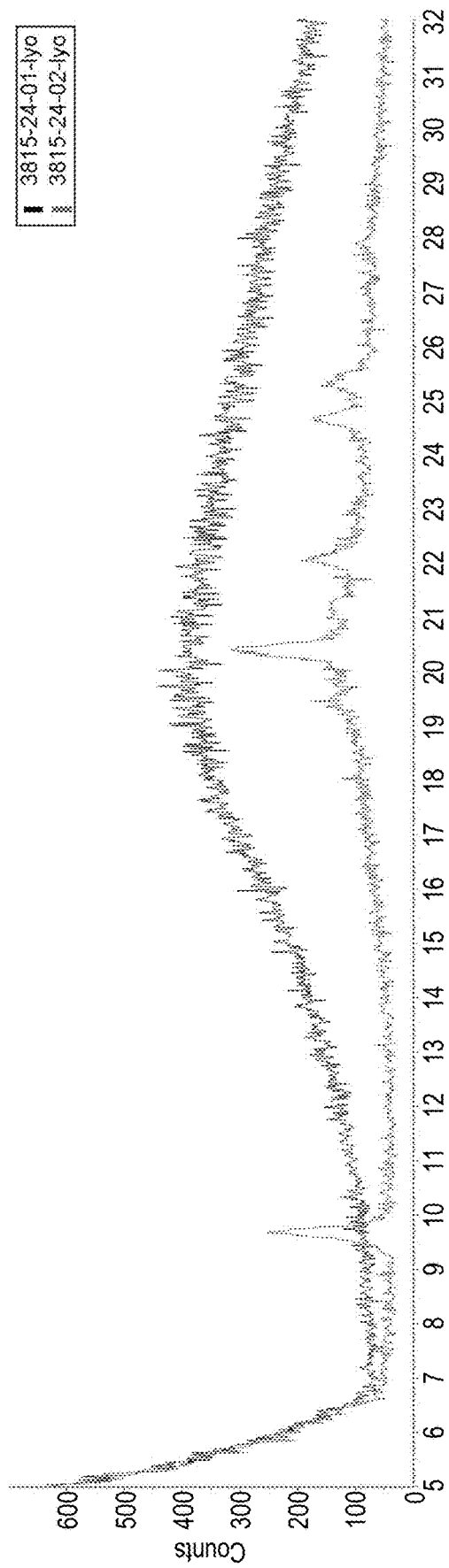
FIG. 45 shows an XRPD of the lyophilized dispersion of Example 22.
Figure 46:
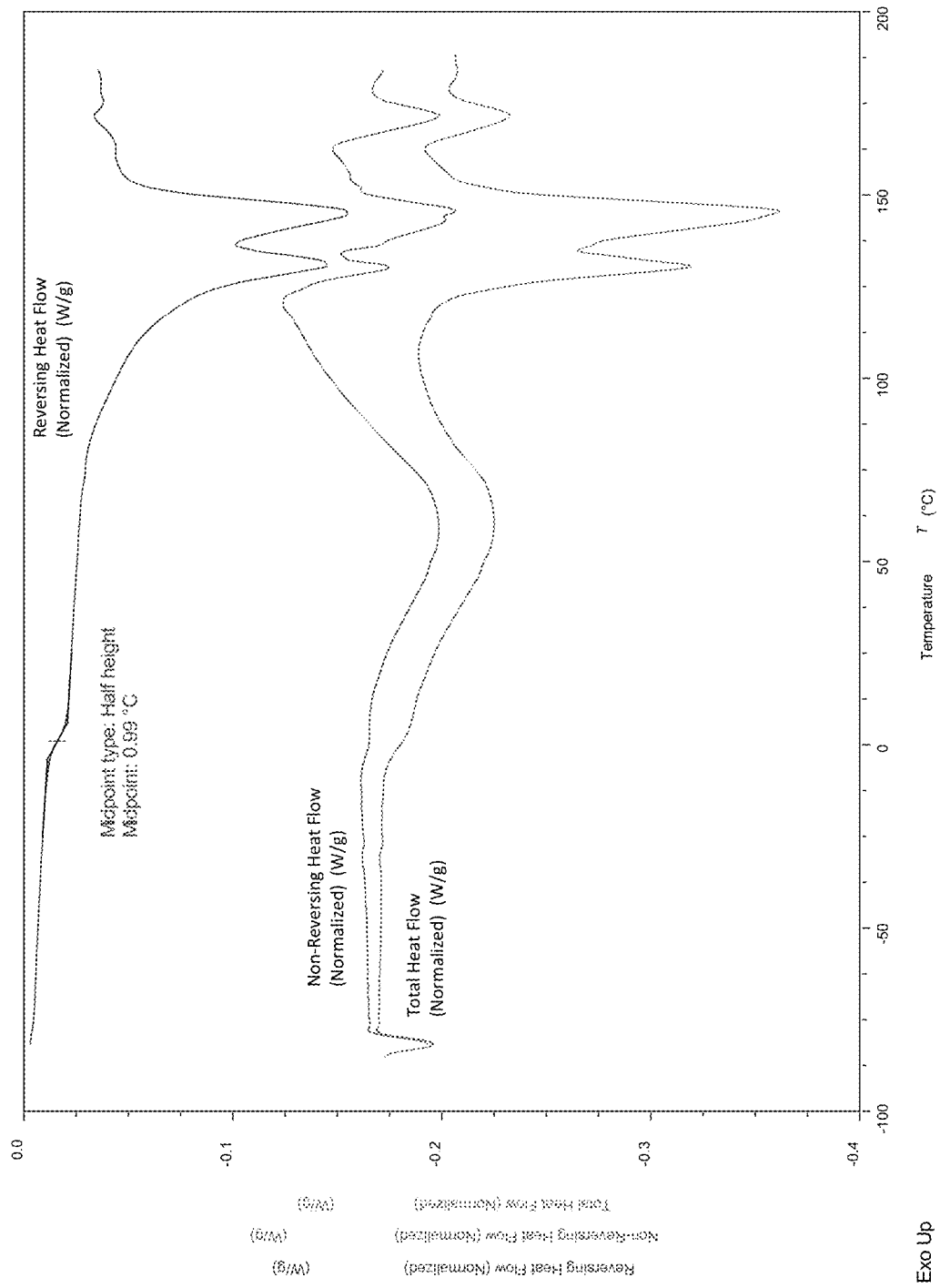
FIG. 46 shows a DSC thermogram for the lyophilized dispersion of Example 22.

Demonstrates that the HBr at 50% loading in mannitol/trehalose does not produce an amorphous lyophilized product. FIG. 45 shows an XRPD of the lyophilized dispersion of Example 22. FIG. 46 shows a DSC thermogram for the lyophilized dispersion of Example 22.

Example 23: Lyophilisation of HBr Salt with Mannitol and Trehalose

Lyophilisation of HBr salt with mannitol/trehalose in water to produce a 50% wt: wt API lyophilized dispersion.

| Feed Solution | |
| --- | --- |
| Sample Reference | 3815-24-02 |
| Mannitol | 150 mg |
| Trehalose | 50 mg |
| 5MeO DMT HBr | 200 mg |
| Water (de ionized) | 10 ml |

| Lyophilisation Profile | | | |
| --- | --- | --- | --- |
| Temp | Ramp | Hold | Vacuum |
| +20° C. | | 10 mins | |
| −50° C. | 140 mins | 240 mins | |
| −50° C. | — | 10 mins | 500 |
| −30° C. | 40 mins | 900 mins | 500 |
| −30° C. | — | 8100 mins | 500 |
| +20° C. | 100 mins | 900 mins | 100 |
| +20 | — | 500 mins | 100 |

Figure 47:
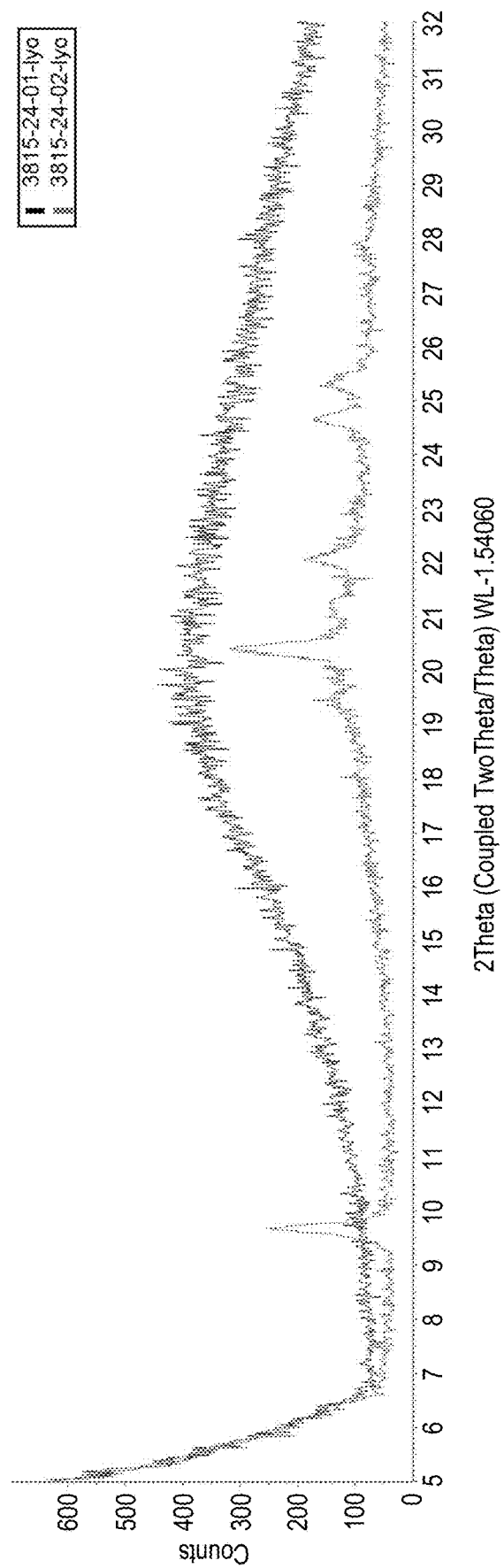
FIG. 47 shows an XRPD of the lyophilized dispersion of Example 23.
Figure 48:
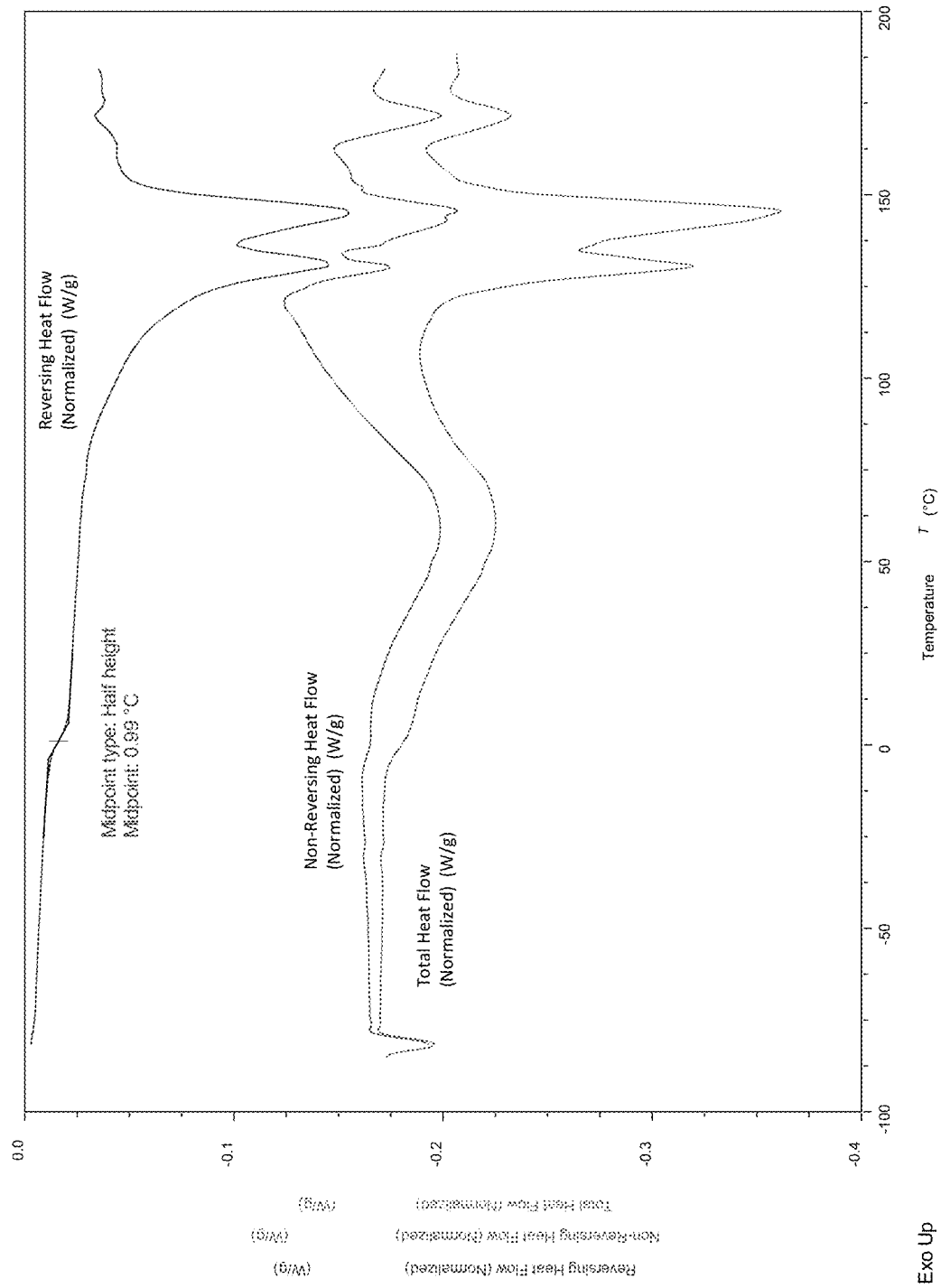
FIG. 48 shows a DSC thermogram for the lyophilized dispersion of Example 23.

Demonstrates that the HBr at 50% loading in mannitol/trehalose does not produce an amorphous lyophilized product. FIG. 47 shows an XRPD of the lyophilized dispersion of Example 23. FIG. 48 shows a DSC thermogram for the lyophilized dispersion of Example 23.

Example 24: Stable Amorphous Formulations of 5-MeO-DMT HBr and HCl

The formulations of 5-MeO-DMT HBr and HCl as described in Examples 16 and 17 were stored for 1 month at (i) 25° C./60% RH or (ii) 2-8° C. The formulations comprised 50% by weight of either 5-MeO-DMT HBr or HCl, a 3:1 ratio of HPMC 606:Metolose 60SH 50 and 3% sorbitol.

Figure 49:
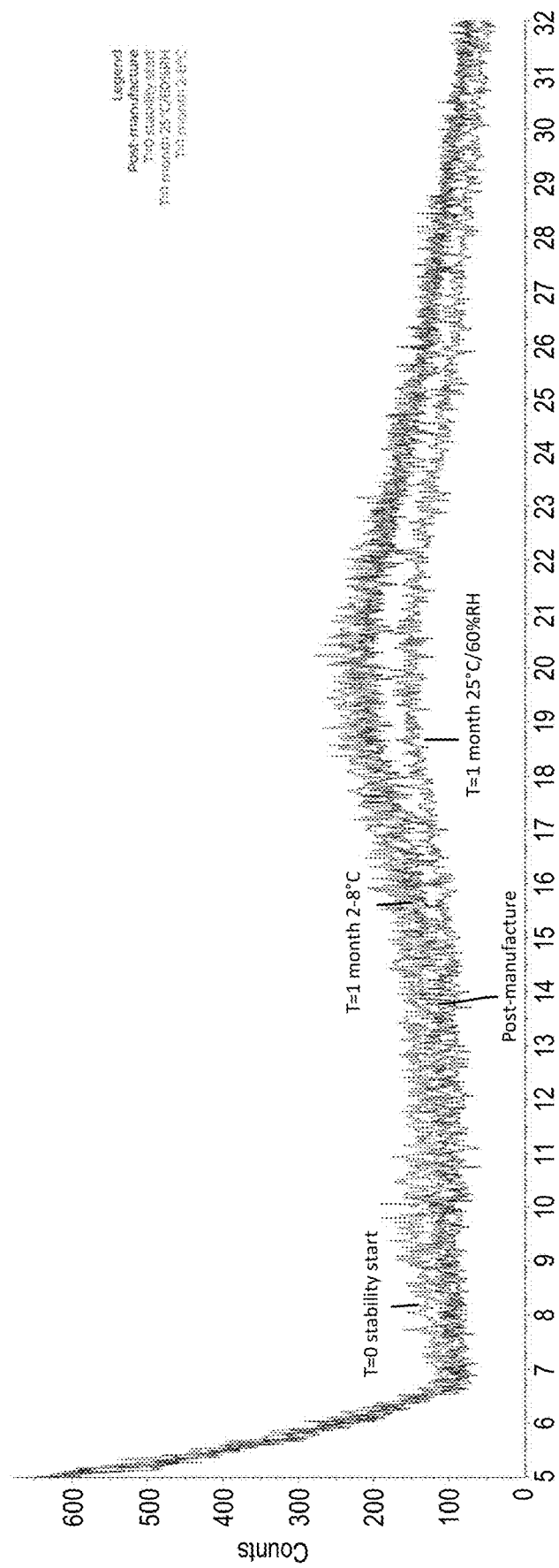
FIG. 49 shows an XRPD diffractogram for the HBr formulation of Example 16 at T=0, T=1 month post storage at 25° C./60% RH and T=1 month post storage at 2-8° C.

A formulation of 5-MeO-DMT HBr stored for 1 month at (i) 25° C./60% RH or (ii) 2-8° C. remained amorphous. FIG. 49 shows an XRPD diffractogram for the HBr formulation of Example 16 at T=0, T=1 month post storage at 25° C./60% RH and T=1 month post storage at 2-8° C. The XRPD showed that the formulation remained amorphous. Analysis by TGA, mDSC, HPLC and scanning electron microscope (SEM) imaging further confirmed that the formulation remained amorphous.

Figure 50:
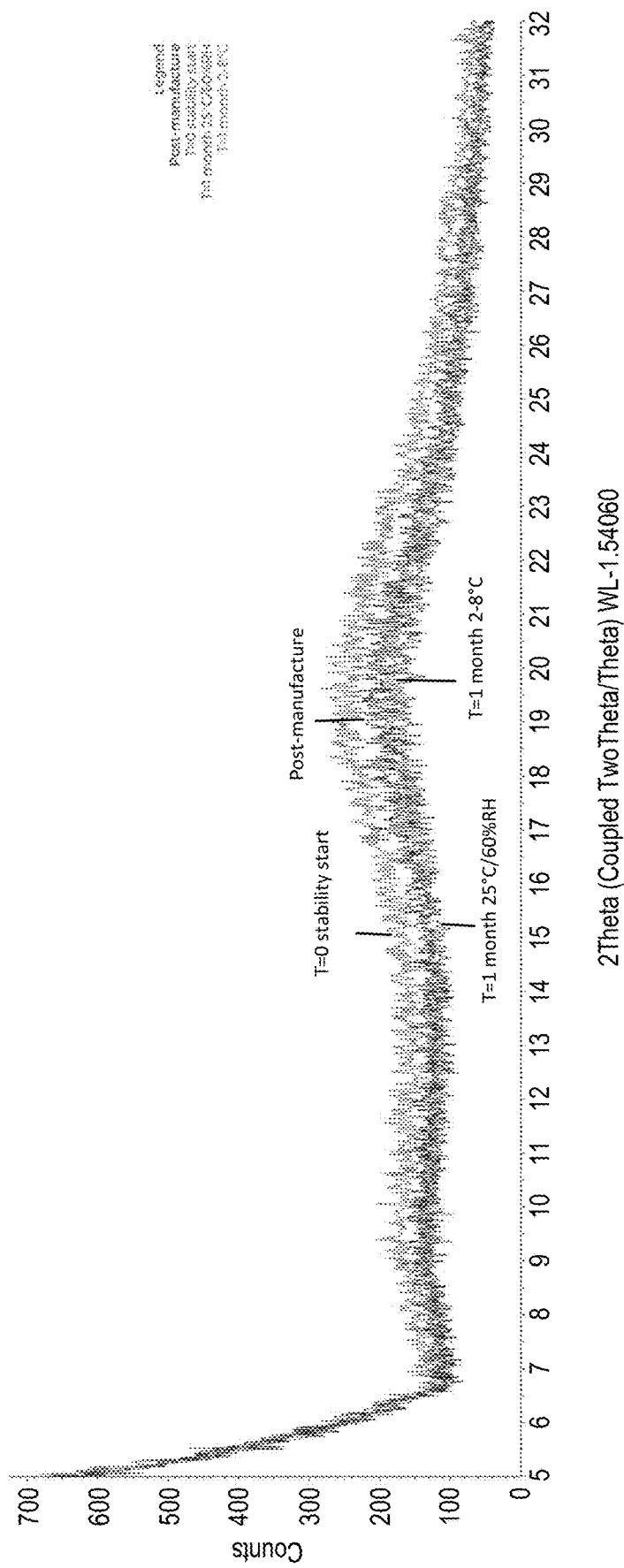
FIG. 50 shows an XRPD diffractogram for the HCl formulation of Example 17 at T=0, T=1 month post storage at 25° C./60% RH and T=1 month post storage at 2-8° C.

A formulation of 5-MeO-DMT HCl stored for 1 month at (i) 25° C./60% RH or (ii) 2-8° C. remained amorphous. FIG. 50 shows an XRPD diffractogram for the HCl formulation of Example 17 at T=0, T=1 month post storage at 25° C./60% RH and T=1 month post storage at 2-8° C. The XRPD showed that the formulation remained amorphous. Analysis by TGA, mDSC, HPLC and scanning electron microscope (SEM) imaging further confirmed that the formulation remained amorphous. There is therefore provided, in an embodiment, a state-stable amorphous formulation of 5-MeO-DMT suitable for storage at, at least, 25° C./60% RH for at least 1, 2, 3, 4, 5, 6, 7, 8, 9, 10, 11 or 12 months, wherein the formulation comprises 5-MeO-DMT HBr or 5-MeO-DMT HCl.

In an embodiment, there is provided a stable amorphous formulation of 5-MeO-DMT. In an embodiment, there is provided a state-stable amorphous formulation of 5-MeO-DMT. In an embodiment, there is provided a stable amorphous formulation of 5-MeO-DMT suitable for storage at, at least, 25° C./60% RH for at least 1, 2, 3, 4, 5, 6, 7, 8, 9, 10, 11, 12 or 24 months. In an embodiment, there is provided an amorphous 5-MeO-DMT HBr formulation. In an embodiment, there is provided a method for producing a stable amorphous formulation of 5-MeO-DMT, as described herein. In an embodiment, there is provided a method for producing a state-stable formulation of 5-MeO-DMT, as described herein.

Example 25: Method for the Determination of Dissolution Rate

The dissolution rate of SDD was determined using a method comprising the use of a UV-fibre optic-based dissolution apparatus (one such suitable device is the Rainbow® Dynamic Dissolution Monitor by Pion Inc) and simulated nasal fluid. The simulated nasal fluid comprises 7.45 g/L NaCl, 1.29 g/L KCl, 0.32 g/L $CaCl_2)\times 2H_2O$ and deionised water.

The dissolution apparatus was set up with a 2 mm probe to measure the dissolution rate. 10 mg of the SDD (5 mg API) was transferred into 5 mL of simulated nasal fluid, heated to a constant temperature of 37° C. and stirred at 150 RPM using a crossed stirrer bar. Measurements were taken at 3s intervals for 130 intervals followed by 60 measurements taken at 10s intervals for a total time of 16 minutes and 30s. Detection of dissolution is by UV absorbance.

In an embodiment, there is provided a method of determining the dissolution rate of a SDD. In an embodiment, the SDD is a 5-MeO-DMT SDD. In an embodiment, said 5-MeO-DMT SDD may be as described previously or subsequently herein.

In an embodiment, a 0.5, 1, 1.5, 2, 2.5, 3, 3.5, 4, 4.5 or 5 mm probe may be used. In an embodiment, 1, 2, 3, 4, 5, 6, 7, 8, 9, 10, 11, 12, 13, 14, 15, 16, 17, 18, 19 or 20 mg of the SDD may be used. In an embodiment, 1 to 100 mg of the SDD may be used. In an embodiment, 1-100 mL of simulated nasal fluid is used. In an embodiment, 1, 2, 3, 4, 5, 6, 7, 8, 9, 10, 11, 12, 13, 14, 15, 16, 17, 18, 19 or 20 mL of nasal fluid is used. In an embodiment, the constant temperature used is 37° C.±/−1, 2, 3, 4 or 5° C. In an embodiment, the solution is stirred at 50, 60, 70, 80, 90, 100, 110, 120, 130, 140, 150, 160, 170, 180 190 or 200 RPM. In an embodiment, the solution is stirred at 50-200 RPM. In an embodiment, measurements are taken at 1, 2, 3, 4, 5, 6, 7, 8, 9 or 10s intervals for 50, 60, 70, 80, 90, 100, 110, 120, 130, 140, 150, 160, 170, 180 190 or 200 intervals followed by 50, 60, 70, 80, 90, 100, 110, 120, 130, 140, 150, 160, 170, 180 190 or 200 measurements taken at 1, 2, 3, 4, 5, 6, 7, 8, 9 or 10s intervals.

Example 26: Method for the Determination of Crystalline Content

A method has been developed for the determination of the crystalline content of psychedelic formulations. Differential scanning calorimetry (DSC) is a thermoanalytical technique in which the difference in the amount of heat required to increase the temperature of a sample and reference is measured as a function of temperature. Both the sample and reference are maintained at nearly the same temperature throughout the experiment. Differential scanning calorimetry can be used to measure a number of characteristic properties of a sample. Using this technique it is possible to observe fusion and crystallization events as well as glass transition temperatures Tg.

The inventors have discovered that a heating rate of 10° C. per minute is not optimised for the determination of crystalline content in psychedelic formulations. The enthalpy obtained from the melt of crystalline 5-MeO-DMT in a formulation was reduced with increased heating rate indicating that a DSC heating rate of 10° C. per minute is not suitable.

Surprisingly, heating rates of above 10° C. per minute is required in order to evaluate the crystalline content of psychedelic formulations. The optimal heating rate has been discovered to be between 10° and 200° C. per minute, between 110 and 190° C. per minute, between 12° and 180° C. per minute, between 13° and 170° C. per minute or between 14° and 160° C. per minute. In an embodiment, the optimal heating rate for the determination of crystalline content of a psychedelic formulation by DSC is 150° C. per minute. In an embodiment, there is provided a method of determining the crystalline content of a 5-MeO-DMT formulation by DSC is 150° C. per minute. In an embodiment, there is provided a method of determining the crystalline content of a spray dried 5-MeO-DMT formulation by DSC is 150° C. per minute.

Example 27: Further Stability Testing of Amorphous Formulations of 5-MeO-DMT HBr and HCl The formulations of 5-MeO-DMT HBr and HCl as described in Examples 16 and 17 were stored for 2 months at (i) 25° C./60% RH or (ii) 2-8° C. The formulations comprised 50% by weight of either 5-MeO-DMT HBr or HCl, a 3:1 ratio of HPMC606:Metolose 60SH 50 and 3% sorbitol.

Figure 51:
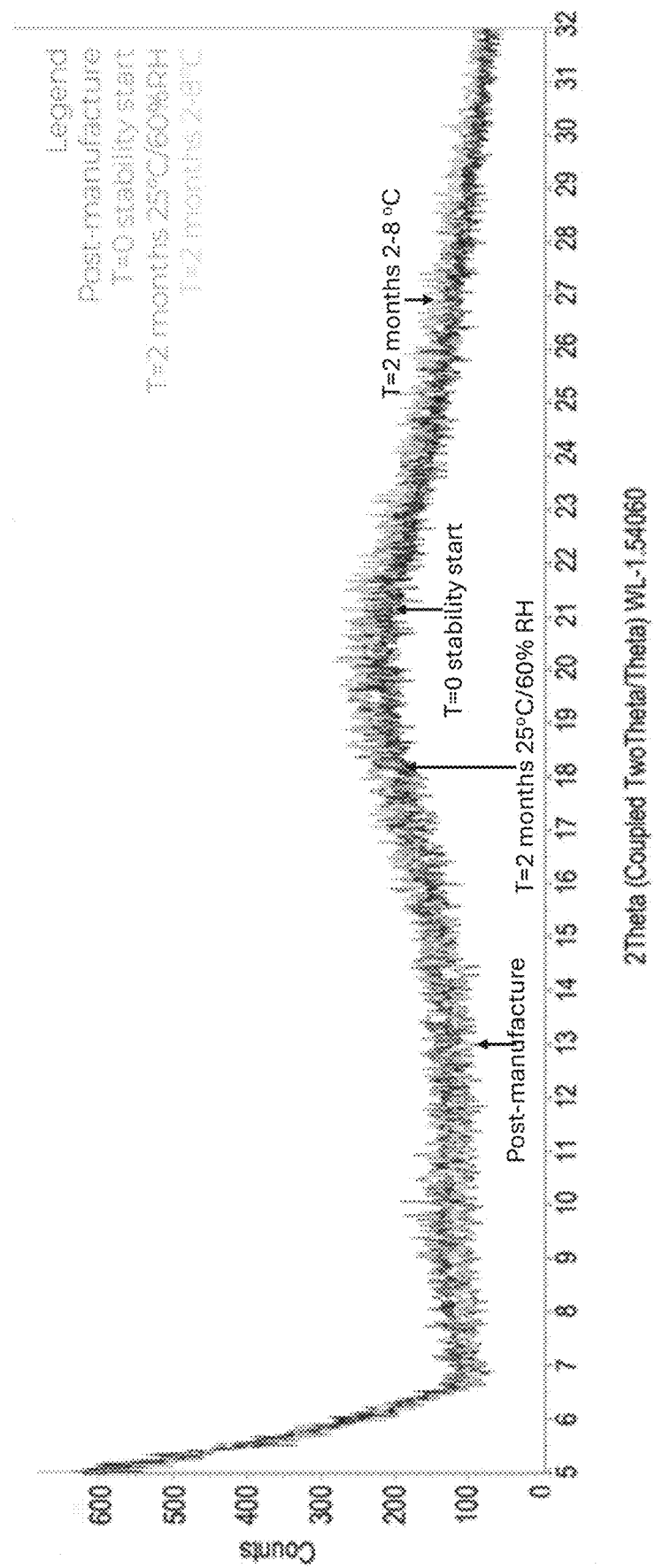
FIG. 51 shows an XRPD diffractogram for the HBr formulation of Example 16 at T=0, T=2 months post storage at 25° C./60% RH and T=2 months post storage at 2-8° C.

A formulation of 5-MeO-DMT HBr stored for 2 months at (i) 25° C./60% RH or (ii) 2-8° C. remained amorphous. FIG. 51 shows an XRPD diffractogram for the HBr formulation of Example 16 at T=0, T=2 months post storage at 25° C./60% RH and T=2 months post storage at 2-8° C. The XRPD showed that the formulation remained amorphous. Analysis by TGA, mDSC, HPLC and scanning electron microscope (SEM) imaging further confirmed that the formulation remained amorphous.

Figure 52:
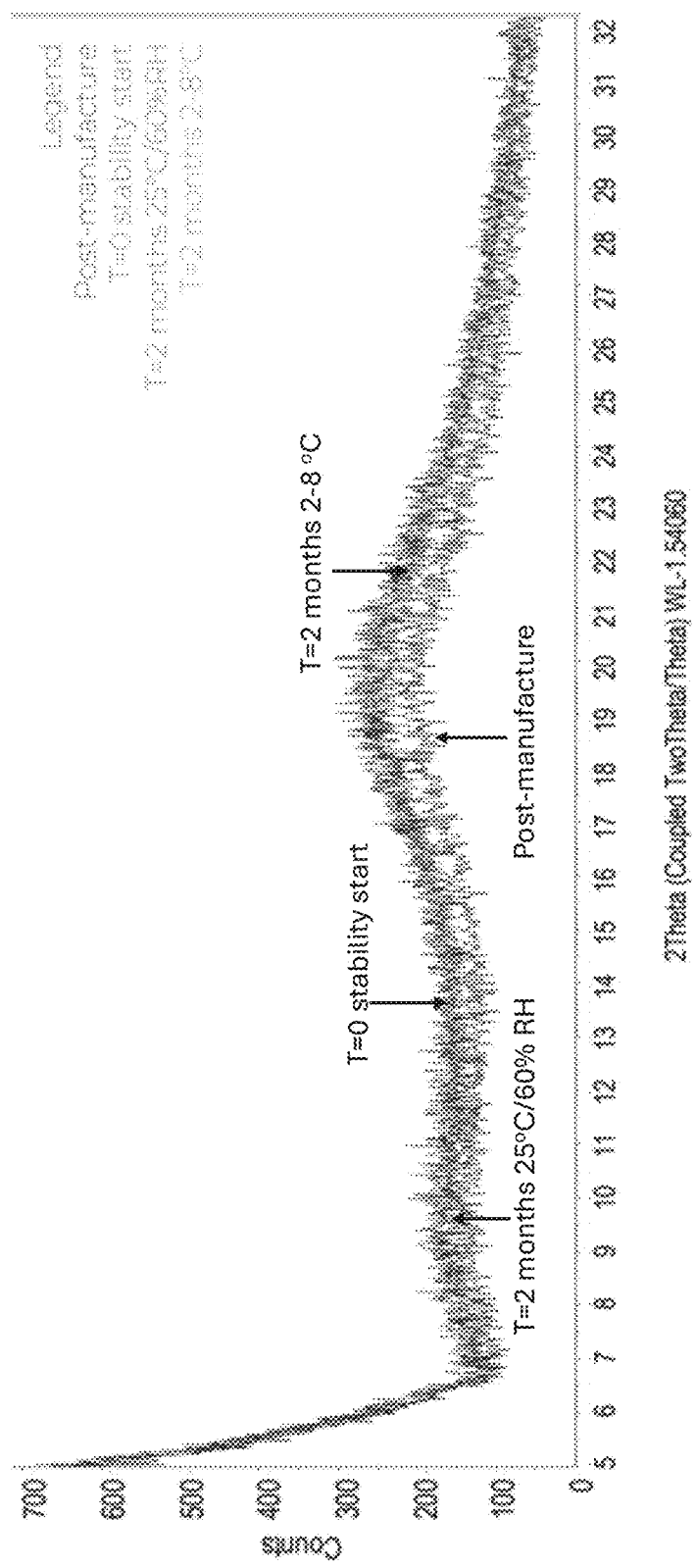
FIG. 52 shows an XRPD diffractogram for the HCl formulation of Example 17 at T=0, T=2 months post storage at 25° C./60% RH and T=2 months post storage at 2-8° C.

A formulation of 5-MeO-DMT HCl stored for 2 months at (i) 25° C./60% RH or (ii) 2-8° C. remained amorphous. FIG. 52 shows an XRPD diffractogram for the HCl formulation of Example 17 at T=0, T=2 months post storage at 25° C./60% RH and T=2 months post storage at 2-8° C. The XRPD showed that the formulation remained amorphous. Analysis by TGA, mDSC, HPLC and scanning electron microscope (SEM) imaging further confirmed that the formulation remained amorphous.

Example 27a: Further Stability Testing of a Formulation of 5-MeO-DMT HCl

The 5-MeO-DMT HCl formulations of Example 27 were investigated following storage at 6 months. The formulation stored at 2-8° C. remained amorphous whilst the formulation stored at 25° C./60% RH exhibited recrystallisation (28.8% crystallinity) into a new crystalline form of 5-MeO-DMT HCl.

Figure 58:
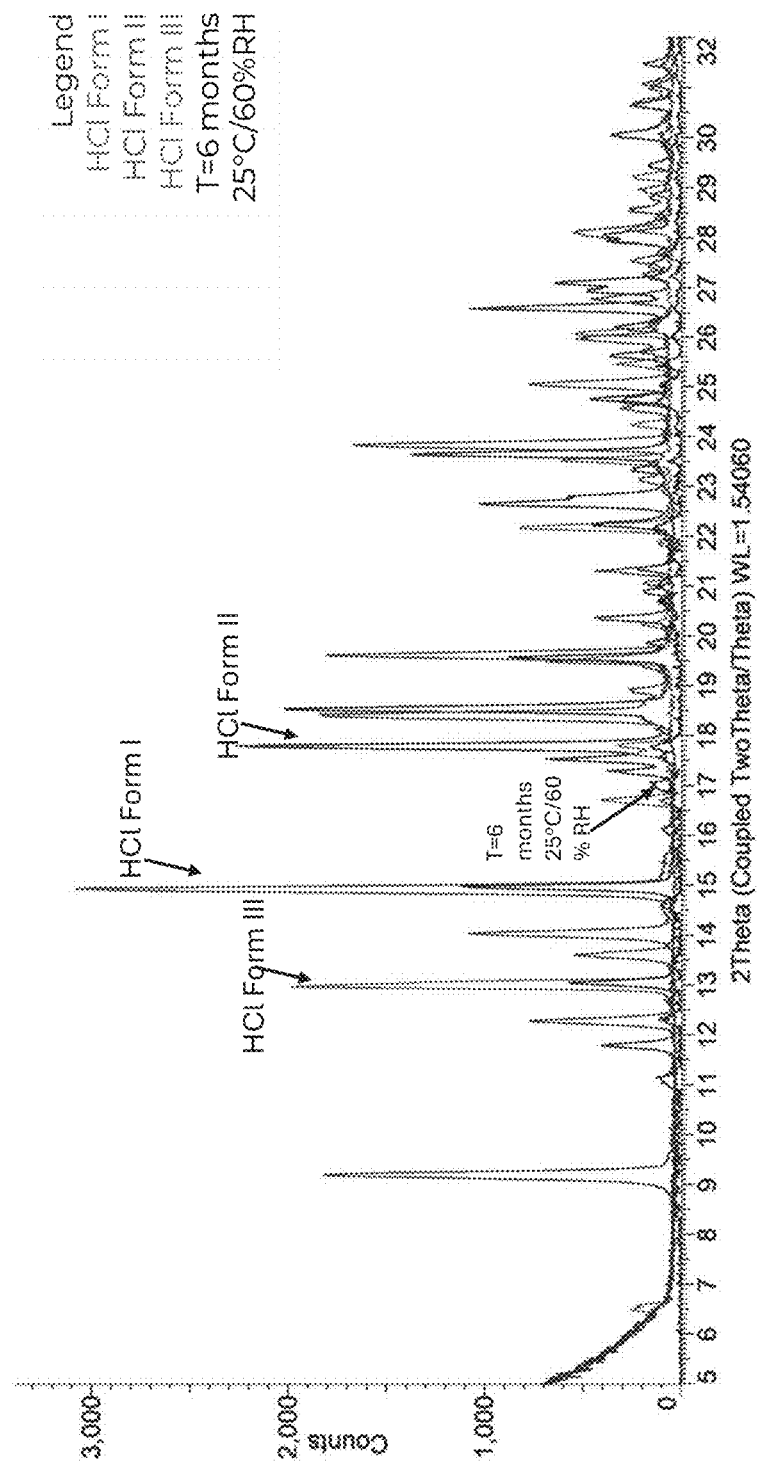
FIG. 58 shows an XRPD diffractogram overlay of the three previously known crystalline forms of 5-MeO-DMT HCl (Forms I-III) and the XRPD diffractogram pattern exhibited by the 5-MeO-DMT HCl formulation of Example 27 following storage at 25° C./60% RH for 6 months.

Three crystalline forms of 5-MeO-DMT HCl have previously been characterised, see for example U.S. Pat. No. 11,518,743. FIG. 58 shows an XRPD diffractogram overlay of the three previously known crystalline forms of 5-MeO-DMT HCl (Forms I-III) and the XRPD diffractogram pattern exhibited by the 5-MeO-DMT HCl formulation of Example 27 following storage at 25° C./60% RH for 6 months.

The Tables below show the XRPD diffractogram patterns of Forms I-III and that of the new Form, and their respective relative intensities:

| HCl Form I | | | HCl Form II | | | HCl Form III | | |
|---|---|---|---|---|---|---|---|---|
| Angle | d Value | Rel. Intensity | Angle | d Value | Rel. Intensity | Angle | d Value | Rel. Intensity |
| 9.191° | 9.614 | 0.57 | 11.786° | 7.502 | 0.17 | 6.509° | 13.568 | 0.06 |
| 12.275° | 7.205 | 0.25 | 12.650° | 6.992 | 0.01 | 12.341° | 7.166 | 0.04 |
| 13.601° | 6.505 | 0.17 | 13.042° | 6.783 | 0.25 | 12.979° | 6.815 | 1.00 |
| 14.030° | 6.307 | 0.35 | 13.789° | 6.417 | 0.02 | 14.420° | 6.137 | 0.04 |
| 14.925° | 5.931 | 1.00 | 14.968° | 5.914 | 0.49 | 16.706° | 5.303 | 0.21 |
| 15.513° | 5.708 | 0.01 | 16.120° | 5.494 | 0.02 | 17.643° | 5.023 | 0.10 |
| 18.403° | 4.817 | 0.59 | 17.283° | 5.127 | 0.14 | 17.805° | 4.978 | 0.16 |
| 18.896° | 4.693 | 0.06 | 17.529° | 5.055 | 0.29 | 19.519° | 4.544 | 0.25 |
| 19.613° | 4.523 | 0.60 | 17.791° | 4.982 | 1.00 | 20.226° | 4.387 | 0.09 |
| 21.305° | 4.167 | 0.14 | 18.363° | 4.828 | 0.05 | 21.056° | 4.216 | 0.08 |
| 22.899° | 3.881 | 0.02 | 18.530° | 4.784 | 0.91 | 21.882° | 4.059 | 0.03 |
| 23.133° | 3.842 | 0.06 | 19.571° | 4.532 | 0.37 | 22.175° | 4.006 | 0.44 |
| 23.436° | 3.793 | 0.04 | 19.858° | 4.467 | 0.05 | 23.525° | 3.779 | 0.34 |
| 23.826° | 3.732 | 0.54 | 20.354° | 4.360 | 0.18 | 24.239° | 3.669 | 0.11 |
| 24.565° | 3.621 | 0.08 | 20.883° | 4.250 | 0.06 | 25.454° | 3.497 | 0.18 |
| 25.048° | 3.552 | 0.24 | 21.344° | 4.160 | 0.08 | 26.101° | 3.411 | 0.19 |
| 25.716° | 3.461 | 0.04 | 22.244° | 3.993 | 0.17 | 27.201° | 3.276 | 0.06 |
| 25.974° | 3.428 | 0.13 | 22.715° | 3.912 | 0.38 | 28.161° | 3.166 | 0.14 |
| 26.226° | 3.395 | 0.04 | 23.321° | 3.811 | 0.09 | 28.408° | 3.139 | 0.05 |
| 26.783° | 3.326 | 0.13 | 23.645° | 3.760 | 0.66 | 29.220° | 3.054 | 0.12 |
| 27.271° | 3.268 | 0.04 | 24.751° | 3.594 | 0.21 | 29.841° | 2.992 | 0.03 |
| 27.547° | 3.235 | 0.06 | 25.620° | 3.474 | 0.15 | 30.361° | 2.942 | 0.03 |
| 28.110° | 3.172 | 0.16 | 26.224° | 3.396 | 0.12 | 30.876° | 2.894 | 0.02 |
| 28.955° | 3.081 | 0.05 | 26.593° | 3.349 | 0.51 | | | |
| 30.045° | 2.972 | 0.02 | 26.947° | 3.306 | 0.21 | | | |
| 30.670° | 2.913 | 0.06 | 27.103° | 3.287 | 0.30 | | | |
| 31.009° | 2.882 | 0.03 | 27.442° | 3.248 | 0.04 | | | |
| 31.431° | 2.844 | 0.03 | 27.706° | 3.217 | 0.02 | | | |
| | | | 28.051° | 3.178 | 0.16 | | | |
| | | | 28.541° | 3.125 | 0.11 | | | |
| | | | 28.813° | 3.096 | 0.05 | | | |
| | | | 29.442° | 3.031 | 0.05 | | | |
| | | | 30.057° | 2.971 | 0.15 | | | |
| | | | 30.648° | 2.915 | 0.10 | | | |
| | | | 31.078° | 2.875 | 0.08 | | | |
| | | | 31.474° | 2.840 | 0.08 | | | |

| Form IV | | | | | |
|---|---|---|---|---|---|
| Angle | d Value | Rel. Intensity | Close to | Form | Difference |
| 8.726° | 10.126 | 0.06 | 9.191 | I | −0.465 |
| 11.122° | 7.949 | 0.34 | 11.786 | II | −0.664 |
| 12.266° | 7.210 | 0.27 | 12.275 | I | −0.009 |
| 12.993° | 6.808 | 0.15 | 12.979 | III | 0.014 |
| 13.393° | 6.606 | 0.21 | 13.601 | I | −0.208 |
| 14.617° | 6.055 | 0.27 | 14.42 | III | 0.197 |
| 16.694° | 5.306 | 0.33 | 16.706 | III | −0.012 |
| 16.989° | 5.215 | 0.45 | 17.283 | II | −0.294 |
| 17.510° | 5.061 | 0.23 | 17.529 | II | −0.019 |
| 17.777° | 4.985 | 0.50 | 17.791 | II | −0.014 |
| 20.225° | 4.387 | 0.11 | 20.226 | III | −0.001 |
| 20.699° | 4.288 | 0.32 | 20.883 | II | −0.184 |
| 21.025° | 4.222 | 0.38 | 21.056 | III | −0.031 |
| 21.604° | 4.110 | 0.14 | 21.344 | II | 0.260 |
| 22.140° | 4.012 | 0.44 | 22.175 | III | −0.035 |
| 22.983° | 3.867 | 0.16 | 22.899 | I | 0.084 |
| 23.514° | 3.780 | 0.26 | 23.525 | III | −0.011 |
| 24.171° | 3.679 | 0.14 | 24.239 | III | −0.068 |
| 24.711° | 3.600 | 1.00 | 24.751 | II | −0.040 |
| 25.034° | 3.554 | 0.32 | 25.048 | I | −0.014 |
| 25.432° | 3.500 | 0.31 | 25.454 | III | −0.022 |

Form IV

| Angle | d Value | Rel. Intensity | Close to | Form | Difference |
|---|---|---|---|---|---|
| 26.017° | 3.422 | 0.17 | 25.974 | I | 0.043 |
| 26.576° | 3.351 | 0.11 | 26.593 | II | −0.017 |
| 26.851° | 3.318 | 0.12 | 26.783 | I | 0.068 |
| 27.239° | 3.271 | 0.19 | 27.271 | I | −0.032 |
| 27.674° | 3.221 | 0.26 | 27.706 | II | −0.032 |
| 28.310° | 3.150 | 0.07 | 28.408 | III | −0.098 |
| 29.206° | 3.055 | 0.13 | 29.22 | III | −0.014 |
| 29.941° | 2.982 | 0.11 | 29.841 | III | 0.100 |
| 30.377° | 2.940 | 0.04 | 30.361 | III | 0.016 |
| 30.824° | 2.899 | 0.07 | 30.876 | III | −0.052 |
| 31.281° | 2.857 | 0.09 | 31.431 | I | −0.150 |
| 31.505° | 2.837 | 0.14 | 31.474 | II | 0.031 |

In an embodiment, there is provided crystalline 5-MeO-DMT HCl characterised by one or more of the peaks in the Table above characteristic of Form IV.

In an embodiment, there is provided crystalline 5-MeO-DMT HCl characterised by one or more peaks in an X-ray powder diffraction (XRPD) diffractogram at 2θ values of 11.1°±0.1°, 13.4°±0.1° or 16.9°±0.1° using an X-ray wavelength of 1.5406 Å.

In an embodiment, there is provided crystalline 5-MeO-DMT HCl characterised by one or more peaks in an X-ray powder diffraction (XRPD) diffractogram at 2θ values of 8.7°±0.1°, 11.1°±0.1°, 13.4°±0.1° or 16.9°±0.1° using an X-ray wavelength of 1.5406 Å.

In an embodiment, there is provided crystalline 5-MeO-DMT HCl characterised by one or more peaks in an X-ray powder diffraction (XRPD) diffractogram at 2θ values of 8.7°±0.1°, 11.1°±0.1°, 13.4°±0.1° or 16.9°±0.1° using an X-ray wavelength of 1.5406 Å.

In an embodiment, there is provided crystalline 5-MeO-DMT HCl characterised by one or more peaks in an X-ray powder diffraction (XRPD) diffractogram at 2θ values of 8.7°±0.1°, 11.1°±0.1°, 13.4°±0.1°, 14.6°±0.1° or 16.9°±0.1° using an X-ray wavelength of 1.5406 Å.

In an embodiment, there is provided crystalline 5-MeO-DMT HCl characterised by one or more peaks in an X-ray powder diffraction (XRPD) diffractogram at 2θ values of 8.7°±0.1°, 11.1°±0.1°, 13.4°±0.1°, 14.6°±0.1°, 16.9°±0.1° or 20.7°±0.1° using an X-ray wavelength of 1.5406 Å.

In an embodiment, there is provided crystalline 5-MeO-DMT HCl characterised by one or more peaks in an X-ray powder diffraction (XRPD) diffractogram at 2θ values of 8.7°±0.1°, 10.1°±0.1°, 11.1°±0.1°, 13.4°±0.1° or 16.9°±0.1° using an X-ray wavelength of 1.5406 Å.

The skilled person will appreciate that the peak values may be ±0.1°, ±0.2° or ±0.3°.

In an embodiment, there is provided a pharmaceutical formulation comprising 5-MeO-DMT HCl Form IV, wherein the formulation is characterised by one or more of the peaks in the Table above characteristic of Form IV.

In an embodiment, there is provided a pharmaceutical formulation comprising 5-MeO-DMT HCl Form IV, wherein the formulation is characterised by one or more peaks in an X-ray powder diffraction (XRPD) diffractogram at 2θ values of 8.7°±0.1°, 10.1°±0.1°, 11.1°±0.1°, 13.4°±0.1° or 16.9°±0.1° using an X-ray wavelength of 1.5406 Å.

In an embodiment, there is provided a pharmaceutical formulation and/or nasal delivery device as described herein, comprising crystalline 5-MeO-DMT HCl Form IV.

In an embodiment, there is provided the use of 5-MeO-DMT HCl Form IV, or a pharmaceutical formulation or nasal delivery device comprising Form IV, in a method of treatment as described herein.

Example 28: Nasal Deposition Profile Analysis

The nasal cavity is recognised as a promising systemic drug delivery route due to the highly vascularised capillary bed within the nasal mucosa. There is therefore a need for formulations or compositions as described herein with an optimised particle size distribution which show turbinate deposition. There is also a need for delivery devices which can selectively deliver a formulation or composition as described herein to the nasal turbinates.

Materials 5-methoxy-N,N-dimethyltryptamine (5-MeO-DMT) Benzoate (as described in Example 15) was provided by Beckley Psytech, Hydroxypropyl methylcellulose (HPMC) ((Pharmacoat 606-substitution 2910, viscosity 6 cP) ShinEtsu Chemical, Japan), HPLC grade 99% ethanol, HPLC grade 99% methanol, HPLC grade water, Glycerol and Brij-35 (Fisher Scientific, United Kingdom). Ultrapure water 18.2 MΩ (Veolia Elga LabWater system, in house) Active devices (UDSp, Aptar Pharma, France).

Preparation of 5-MeO-DMT Spray Dried Dispersion (5-MeO-DMT SDD)

Feed solution was prepared at 50% w/w 5-MeO-DMT Benzoate loading (32.1% 5-MeO-DMT). Both polymers were dissolved in water under ambient stirring overnight. D-sorbitol and 5-MeO-DMT Benzoate were added to solution and dissolved under ambient stirring, producing a clear lightly straw-coloured solution. Feed solution was spray dried using the ProCepT 4M8-Trix Spray Dryer fitted with a 25 kHz Ultrasonic nozzle (ProCepT, Belgium), according to the spay drying parameters outlined in the Table below. Formulation was filled and assembled into UDSp devices at 37.4±1.9 mg fill weight, under reduced humidity, when required for analysis.

Target Spray Drying Parameters for 5-MeO-DMT Feed Solution

| Inlet temperature (° C.) | Outlet temperature (° C.) | Nozzle air (bar) | Cooling air (bar) | Drying airflow (m³/min) | Liquid feed rate (g/min) |
|---|---|---|---|---|---|
| 105 | 80-85 | 2.00 | 0.5 | 0.70 | 2.0 |

Particle Size Analysis by Laser Diffraction

Particle Size Distribution (PSD) was determined using a Sympatec HELOS H4459 particle size analyser equipped with an R5 lens (Sympatec GmbH, Germany) in triplicate. Bulk powder was analysed using the RODOS dry powder dispersion unit at 3 bar dispersal pressure and powder from active devices (ExDevice) were manually actuated into the laser diffractor with the tip of the device positioned 3 cm from the mid-point of the laser.

Methodology—Summary

The Alberta Idealised Nasal Inlet (AINI) and Stage 1 collection cup of the Next Generation Impactor (NGI) was coated with solution containing 12 g Brij-35, 20 g glycerol and 80 mL ethanol. Once dried, AINI and NGI was assembled with the addition of a pre-separator with 15 mL 50:50 (v/v) methanol:water diluent in the reservoir. The UDSp loaded with 37.4 mg formulation was positioned at either 30, 45 or 60° to the horizontal and inserted 1 cm into the nasal orifice of the AINI. A 7.5 L/min airflow was applied for 15 seconds upon actuation of the UDSp, delivering 1.875 L of air. After actuation, the configuration was disassembled and 15 mL diluent used to dissolve material on the UDSp's exterior, deposited in the AINI and the NGI collection cup, with the addition of a secondary dilution. Analysis was performed in triplicate and analysed by HPLC, with Two-way ANOVA statistical analysis.

Methodology—Detailed

Nasal deposition was measured using the Alberta Idealised Nasal Inlet (AINI) with the Copley Next Generation Impactor (NGI) from an Aptar Unidose Powder Nasal spray system (UDSp)

A) Coating of AINI and NGI Collection Cups 12 g Brij-35, 20 g glycerol and 80 mL ethanol were mixed until dissolved to form a coating solution. Bottom of AINI was sealed and 20 mL coating solution was added through the vestibule while the AINI was inverted. The AINI was slowly rotated horizontally 360° clockwise and anticlockwise then rotated vertically 360° clockwise and anticlockwise. Excess coating solution was drained and the AINI was placed on its left side, back and right side for 15 minutes each. AINI was positioned upright for 30 minutes to allow any further excess coating solution to drain and for the coat to dry.

2 mL of coating solution was pipetted onto NGI Stage 1 collection cup and rocked for 5 minutes using the NGI rocker in order to coat. Excess solution was drained and the cup was allowed to dry.

B) NGI Assembly

NGI was assembled with the coated Stage 1 collection cup and uncoated collection cups for states 2-7 and micro-orifice collector. The pre-separator and throat piece were attached and a leak test was performed using the critical flow controller and high-capacity pump. The flowmeter was attached to the throat piece and the flowrate set to 7.5 L/min.

The throat piece was removed and 15 mL 50:50% v/v HPLC grade water:HPLC grade methanol (diluent) was added to the pre-separator insert cup. The AINI was then installed on the pre-separator.

C) Actuation

The UDSp containing 5-MeO-DMT was weighed to obtain a pre-actuation mass. The UDSp was then clamped into position such that the tip of the UDSp was inserted 1 cm into the vestibule of the AINI. The angle of insertion was set using an electronic protractor. The UDSp was actuated using 7.5 L/min flowrate for 15 seconds.

D) HPLC Sample Collection

UDSp was then removed and weighed to obtain a post-actuation mass. The exterior of the UDSp was washed with 15 mL diluent in a glass dish and the washings were collected for HPLC analysis.

AINI was disassembled and each component was thoroughly washed in separate glass dishes with 15 mL diluent. These washings were then collected for HPLC analysis.

The pre-separator was removed from the NGI, the top and bottom were then covered and the pre-separator was inverted to wash the interior with the previously added 15 mL diluent. These washings were then collected for HPLC analysis.

15 mL diluent was added to the Stage 1 collection cup and the cup was rocked for 10 minutes using the NGI rocker to wash. These washings were then collected for HPLC analysis.

E) HPLC

HPLC was carried out on the samples to quantify 5-MeO-DMT content. Where necessary samples were diluted to stay within the linearity of the quantification method.

In an embodiment, there is provided the use of the above described method, or similar, in a method of nasal deposition analysis of one or more of the formulations or compositions as described herein.

In an embodiment, there is provided the use of the above described method, or similar, in a method of nasal deposition analysis of one or more of the 5-MeO-DMT formulations or compositions as described herein.

In an embodiment, there is provided the use of the above described method, or similar, in a method of nasal deposition analysis of one or more psychedelic dry powder formulations or compositions.

In an embodiment, there is provided the use of the above described method, or similar, in a method of nasal deposition analysis of a psychedelic dry powder formulation or composition.

In an embodiment, there is provided the use of the above described coating, or similar, in a method of psychedelic formulation or composition nasal deposition analysis. In an embodiment, there is provided the use of the above described coating, or similar, in a method of nasal deposition analysis of a psychedelic dry powder formulation or composition. In an embodiment, there is provided the use of the above described coating, or similar, in a method of nasal deposition analysis of one or more psychedelic dry powder formulations or compositions.

Results

Figure 53:
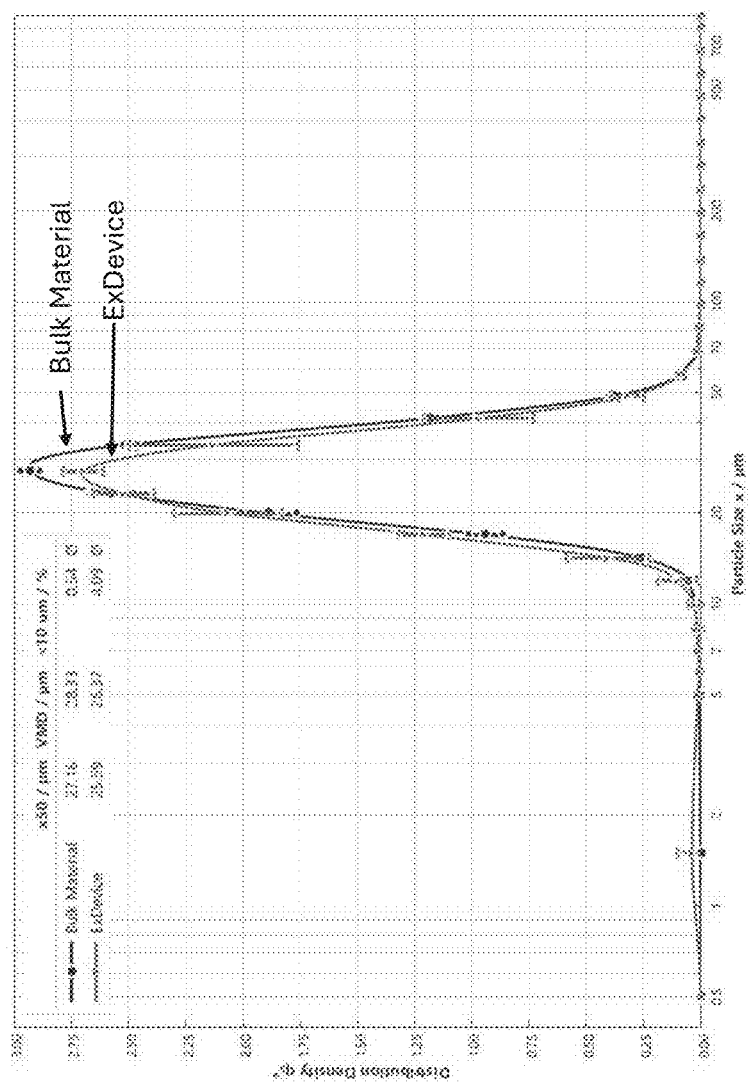
FIG. 53 shows the particle size distribution of a 5-MeO-DMT SDD as Bulk Material (Red) and ExDevice (Green).

Pharmacopeia guidelines states that a nasal powder should demonstrate that deposition of the products is localised within the nasal cavity, and the current method requires that most of the particles are larger than 10 μm as determined by laser diffraction. Analysis was performed on the 5-MeO-DMT SDD with the Sympatec, and the particle size distribution shown in FIG. 53. Using the ultrasonic nozzle an optimised nasal powder was achieved in which the mean particle diameter was close to the diameter recommended while maintaining minimal particles below 10 μm, passing acceptance criteria requested by EMA.

The AINI was used to assess the deposition profile of the 5-MeO-DMT SDD formulation with the method outlined above. The AINI consists of four components for the nasal cavity—the vestibule (nostril), turbinates, olfactory and nasopharynx-which is assembled and attached to a pre-separator. The pre-separator is incorporated to capture any deposition that would falsely land on Stage 1 due to particle bounce in the internal surfaces of the AINI.

Figure 54:
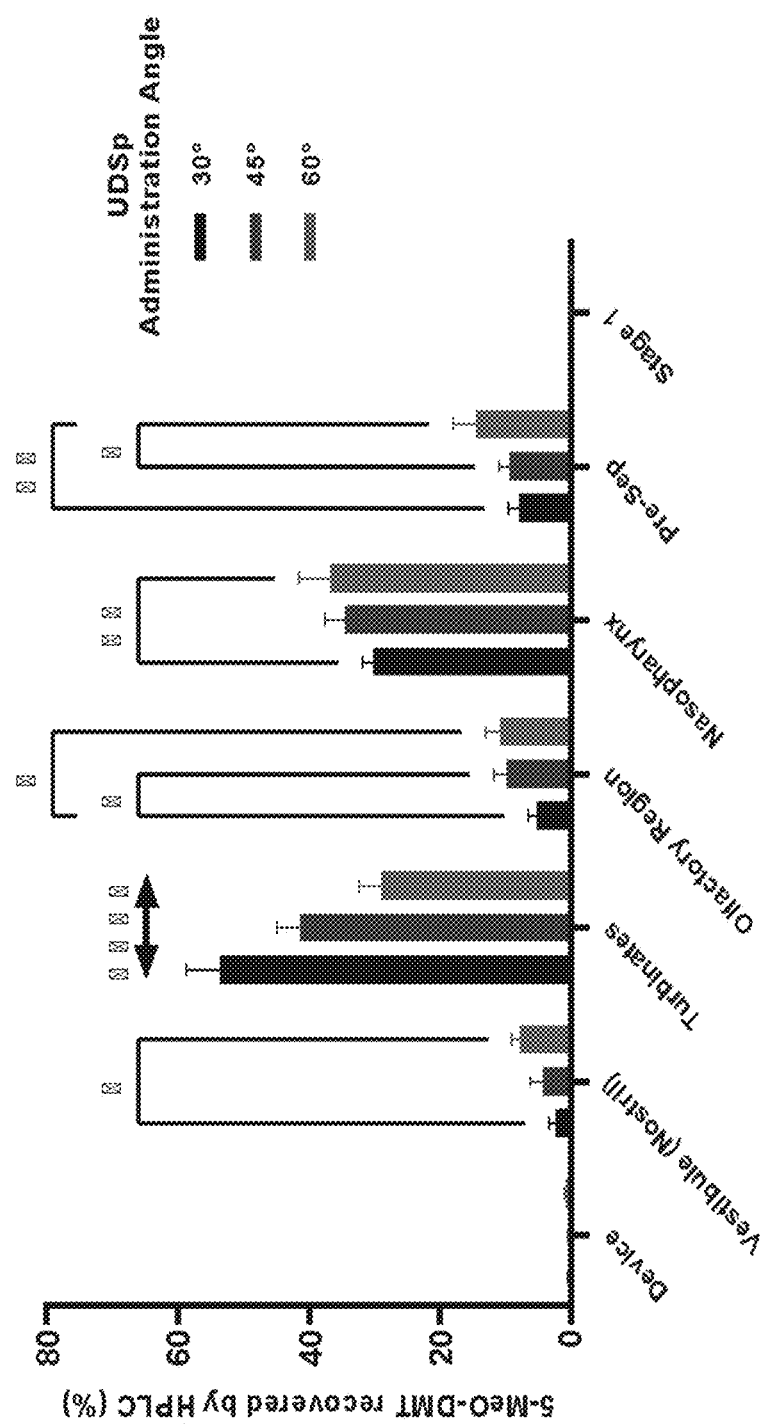
FIG. 54 shows the nasal deposition profile for a 5-MeO-DMT SDD delivered via an active delivery nasal delivery device.

Minimal deposition was seen in the vestibule compared to commercially available nasal sprays. Minimal deposition was also seen in the lung analogue. The majority of the formulation was found in the turbinates and the olfactory region showed deposition from 5-11%-which is advantageous as it is theorised that a minimum of 0.01-1% of the oral dose is effective for nose-to-brain absorption. The results of the AINI can be seen in FIG. 54.

There is therefore provided an advantageous method for the delivery of a 5-MeO-DMT SDD.

Figure 55:
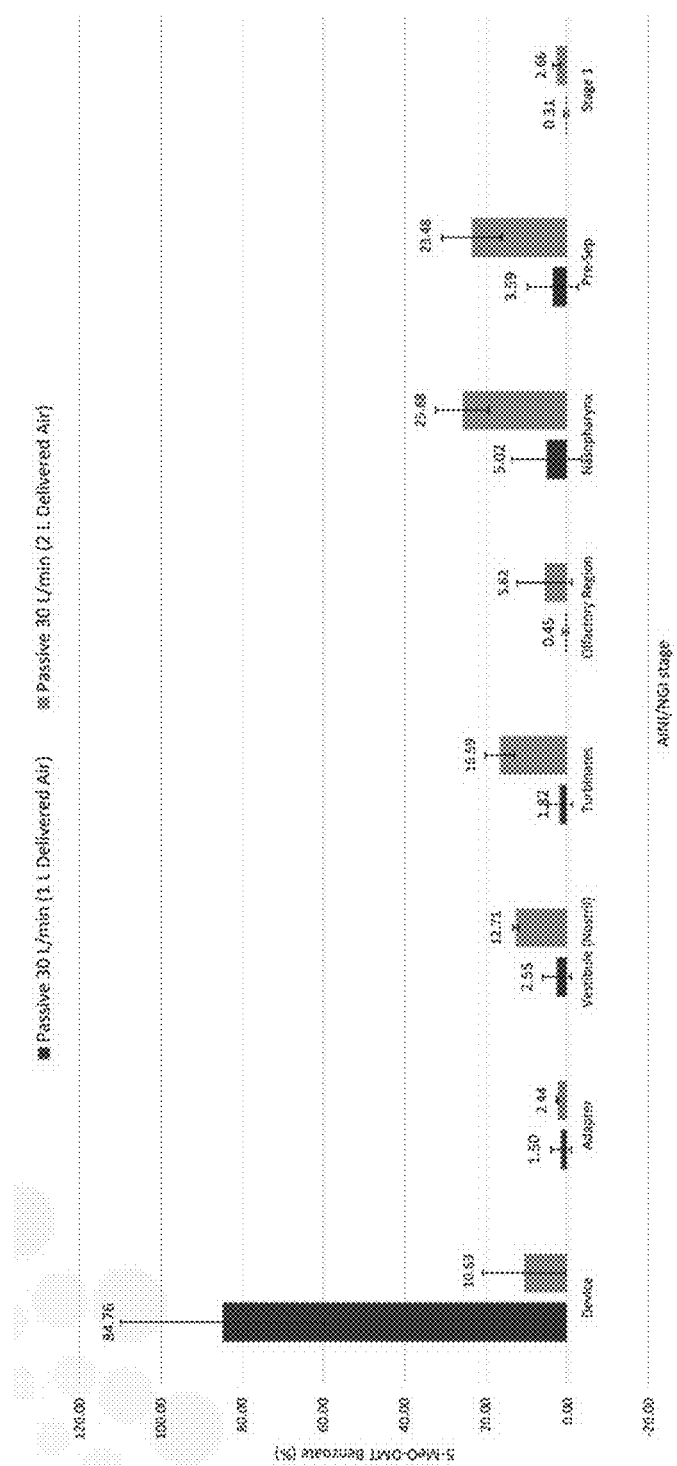
FIG. 55 shows the nasal deposition profile for a 5-MeO-DMT SDD delivered via a passive delivery nasal delivery device.

The same 5-MeO-DMT SDD (as per Example 15) was filled into the passive nasal delivery device at a loading suitable to deliver 12 mg 5MeO DMT free base equivalent. The passive device was positioned into an adapter and drawn through the AINI/NGI with a flow rate of 30 L/min to deliver either 1 L or 2 L of air respectively. The nasal deposition profile produced can be seen in FIG. 55. It can be readily seen that very little drug product was deposited in the desired locations of the turbinates and olfactory region.

There is therefore provided an advantageous method for the delivery of a 5-MeO-DMT SDD wherein said SDD is delivered by an active nasal delivery device.

In an embodiment, there is provided the use of a formulation or composition as described herein in a method of treating a patient in need thereof, wherein the formulation or composition is administered intranasally via an active delivery nasal device, as described herein, and wherein more than 30%, 40%, 50%, 60%, 70%, 80% or 90% of the formulation or composition is deposited to the turbinates and/or olfactory region of the nasal cavity.

In an embodiment, the method of treating a patient in need thereof is a method of treating one or more of the conditions or diseases described herein.

In an embodiment, there is provided the use of a formulation or composition as described herein in a method of treating a patient in need thereof, wherein the formulation or composition is administered intranasally via an active delivery nasal device and wherein less than 30%, 25%, 20%, 15%, 10%, 5%, 4%, 3%, 2% or 1% is deposited in the lungs.

In an embodiment, there is provided a nasal delivery device for delivering a formulation or composition as described herein to an olfactory region of a nasal cavity, the device comprising a formulation or composition as described herein. In an embodiment, the device is an active nasal delivery device wherein a plunger style actuator, or similar, is depressed to administer a dose. In an embodiment, the nasal delivery device is not a breath actuated delivery device. In an embodiment, the device comprises a dose volume up to 140 mm$^3$.

In an embodiment, the nasal delivery device may be as described in any one of WO21005308; WO22123128; WO22171969; and WO22208014 (the contents of which are incorporated by reference).

In an embodiment, there is provided a dispenser device, optionally for dispensing a formulation or composition as described herein, the dispenser device comprising: a formulation or composition as described herein; a dispenser outlet (10); an air expeller (20) for generating a flow of air while the device is being actuated, said air expeller (20) including a piston (21) that slides in an air chamber (22) between a rest position and a dispensing position, said air chamber (22) including a cylindrical body (222) in which said piston (21) slides in airtight manner; and at least one reservoir (30) that contains a single dose of composition, said reservoir (30) including an air inlet (31) that is connected to said air expeller (20), and a composition outlet (32) that is connected to said dispenser outlet (10), said air inlet (31) including a composition retainer member (40) for retaining the composition in the reservoir (30) until the composition is dispensed, and said composition outlet (32) being closed by a closure element (50) that is force fitted in the composition outlet (32) of the reservoir (30); said device further including a mechanical opening system (61, 62) that co-operates with said closure element (50) so as to expel it mechanically from its closed position while the device is being actuated, said mechanical opening system comprising a rod assembly (61, 62), a first rod portion (61) being part of said air expeller (20) and sliding in said air chamber (22) during actuation of the device, and a second rod portion (62) pushed by said first rod portion (61) during actuation of the device, said rod assembly (61, 62) cooperating at the end of the actuation stroke with said closure element (50) to expel it mechanically from its closed portion, said piston (21) of said air expeller (20), when in its rest position, co-operating in non-airtight manner with said air chamber (22), in such a manner that said air chamber (22) is in communication with the atmosphere in the rest position, said piston (21) including an inner lip (215) that slides in airtight manner on said cylindrical surface (614) during actuation of the device, and that co-operates in non-airtight manner with fluting (615) formed on said cylindrical surface (614) in the rest position to put the air chamber (22) in communication with the atmosphere in the rest position, said piston 21) co-operating in airtight manner with said cylindrical body (222) in any positions, and co-operating in non-airtight manner with said cylindrical surface (614) only in the rest position.

In an embodiment, there is provided a dispenser device, optionally for dispensing a formulation or composition as described herein, the dispenser device comprising: a formulation or composition as described herein; a dispenser outlet; an air expeller for generating a flow of air while the device is being actuated, said air expeller including a piston that slides in an air chamber between a rest position and a dispensing position, said air chamber including a cylindrical body in which said piston slides in airtight manner; and at least one reservoir that contains a single dose of composition, said reservoir including an air inlet that is connected to said air expeller, and a composition outlet that is connected to said dispenser outlet, said air inlet including a composition retainer member for retaining the composition in the reservoir until the composition is dispensed, and said composition outlet being closed by a closure element that is force fitted in the composition outlet of the reservoir; said device further including a mechanical opening system that co-operates with said closure element so as to expel said closure element mechanically from a closed position while the device is being actuated, said piston of said air expeller, when in the rest position, co-operating in non-airtight manner with said air chamber, in such a manner that said air chamber is in communication with the atmosphere in the rest position, wherein said piston includes an inner lip configured to cooperate with a cylindrical surface of a cylindrical member extending inside the cylindrical body, said cylindrical surface including fluting that co-operates in non-airtight manner with said inner lip of the piston in the rest position.

In an embodiment, said piston comprises one or more markings which are visible only when the piston is in the rest position and not visible when the piston is in the dispensing position. In an embodiment, a method comprising the use of the dispenser device comprises the actuation of the piston from the rest position to the dispensing position such that the one or more markings are no longer visible. In an embodiment, successful actuation of the dispensing device occurs when the one or more markings are no longer visible. In an embodiment, the one or more markings may be: one or more coloured lines, one or more coloured shapes, one or more words or written text or one or more physical features.

In an embodiment, there is provided an active nasal delivery device as described herein comprising one or more markings, said markings being visible when the active nasal delivery device is in the resting state and not visible following successful actuation of said active nasal delivery device. In an embodiment, the absence from view of said markings represents successful actuation of the active nasal delivery device. In an embodiment, the one or more markings may be as described herein.

A method of intranasally delivering a powder pharmaceutical formulation comprising a psychedelic and one or more pharmaceutically acceptable carriers or excipients, to a patient, wherein 30% or more, 40% or more, 50% or more, 60% or more, 70% or more, 80% or more, 90% or more, 91% or more, 92% or more, 93% or more, 94% or more, 95% or more, 96% or more, 97% or more, 98% or more or 99% or more of the formulation reaches the turbinates and olfactory region, wherein the psychedelic is 5-MeO-DMT, or a pharmaceutically acceptable salt thereof, and the formulation is delivered via a nasal powder dispenser device which may comprise one or more of:

a nasal dispenser head for inserting into a patient's nostril, the nasal dispenser head including a dispenser orifice; and an air expeller that, during actuation of the nasal powder dispenser device, generates a flow of compressed air so as to dispense a dose of the powder pharmaceutical formulation into the nostril through the dispenser orifice.

In an embodiment, there is provided an intranasal delivery system, optionally comprising an active nasal delivery device as described herein, comprising:

a dry powder formulation comprising a plurality of powder particles of 5-MeO-DMT, or a pharmaceutically acceptable salt thereof; and an active nasal delivery device, optionally as described herein, configured to deliver the particles to the turbinates and olfactory region of the nasal cavity of a subject at a single actuation;

wherein the system is operably configured to emit a powder plume comprising 5-MeO-DMT, or a pharmaceutically acceptable salt thereof, having one or more of:

a plume geometry of:
        angle: 20 to 45 degrees;
        width: 25 to 55 mm;
    a spray pattern of:

| Distance 40 mm: | Distance 70 mm: |
|---|---|
| Dmin(mm): 15 to 25 | Dmin(mm): 15 to 40 |
| Dmax(mm): 20 to 55 | Dmax(mm): 35 to 60 |
| Area (mm$^2$): 390 to 900 | Area (mm$^2$): 800-1600 |
| Area %: 2 to 15 | Area %: 4 to 20 | a particle size distribution (at 40 mm) of:
        D10=13 to 17, D50=35 to 60, D90=650 to 700, %<10 μm=<0.1, 1, 2, 3, 4, 5, 6, 7, 8, 9 or 10%; or
    a particle size distribution (at 70 mm) of:
        D10=13 to 17, D50=24 to 30, D90=540 to 610, %<10 μm=<0.1, 1, 2, 3, 4, 5, 6, 7, 8, 9 or 10%; or
    a particle size distribution of:
        D10=13 to 17, D50=22 to 27, D90=35 to 56, %<9 μm=<0.1-10%; or
    % particles of equal to or less than 11.7 μm size of:
        0.5 to 5%.

In an embodiment, there is provided an intranasal delivery system, optionally comprising an active nasal delivery device as described herein, comprising:

a dry powder formulation comprising a plurality of powder particles of 5-MeO-DMT, or a pharmaceutically acceptable salt thereof; and an active nasal delivery device, optionally as described herein, configured to deliver the particles to the turbinates and olfactory region of the nasal cavity of a subject at a single actuation;

wherein the system is operably configured to emit a powder plume comprising 5-MeO-DMT, or a pharmaceutically acceptable salt thereof, having one or more of:

a plume geometry of:
        angle: 20 to 45 degrees;
        width: 25 to 55 mm;
    a spray pattern of:

| Distance 40 mm: | Distance 70 mm: |
|---|---|
| Dmin(mm): 15 to 25 | Dmin(mm): 25 to 40 |
| Dmax(mm): 35 to 55 | Dmax(mm): 45 to 60 |
| Area (mm$^2$): 600 to 850 | Area (mm$^2$): 1100 to 1700 |
| Area %: 1 to 5 | Area %: 4 to 8 | a particle size distribution (at 40 mm) of:
        D10=13 to 17, D50=35 to 60, D90=650 to 700, %<10 μm=<0.1, 1, 2, 3, 4, 5, 6, 7, 8, 9 or 10%; or
    a particle size distribution (at 70 mm) of:
        D10=13 to 17, D50=24 to 30, D90=540 to 610, %<10 μm=<0.1, 1, 2, 3, 4, 5, 6, 7, 8, 9 or 10%; or
    % particles of equal to or less than 11.7 μm size of:
        0.5 to 5%.

In an embodiment, there is provided an intranasal delivery system, optionally comprising an active nasal delivery device as described herein, comprising:

a dry powder formulation comprising a plurality of powder particles of 5-MeO-DMT, or a pharmaceutically acceptable salt thereof; and an active nasal delivery device, optionally as described herein, configured to deliver the particles to the turbinates and olfactory region of the nasal cavity of a subject at a single actuation;

wherein the system is operably configured to emit a powder plume comprising 5-MeO-DMT, or a pharmaceutically acceptable salt thereof, having one or more of:

a plume geometry of:
        angle: 20 to 35 degrees;
        width: 25 to 45 mm;
    a spray pattern of:

| Distance 40 mm: | Distance 70 mm: |
|---|---|
| Dmin(mm): 15 to 25 | Dmin(mm): 15 to 40 |
| Dmax(mm): 20 to 35 | Dmax(mm): 35 to 50 |
| Area (mm$^2$): 390 to 460 | Area (mm$^2$): 800-1200 |
| Area %: 5 to 15 | Area %: 7 to 20 | a particle size distribution of:
        D10=13 to 17, D50=22 to 27, D90=35 to 56, %<9 μm=<0.1-10%; or % particles of equal to or less than 11.7 μm size of:
    0.5 to 5%.

In an embodiment, there is provided an intranasal delivery system, optionally comprising an active nasal delivery device as described herein, comprising:

a dry powder formulation comprising a plurality of powder particles of 5-MeO-DMT, or a pharmaceutically acceptable salt thereof; and an active nasal delivery device, optionally as described herein, configured to deliver the particles to the turbinates and olfactory region of the nasal cavity of a subject at a single actuation;

wherein the system is operably configured to emit a powder plume comprising 5-MeO-DMT, or a pharmaceutically acceptable salt thereof, having one or more of:

a plume geometry of:
    angle: 27 or 40 degrees;
    width: 33 or 50 mm;
a spray pattern of:

| Distance 40 mm: | Distance 70 mm: |
|---|---|
| Dmin(mm): 21 or 22 | Dmin(mm): 33 or 34 |
| Dmax(mm): 41 or 47 | Dmax(mm): 52 or 54 |
| Area (mm$^2$): 640 or 827 | Area (mm$^2$): 1230 or 1545 |
| Area %: 3 or 4 | Area %: 5 or 7 | a particle size distribution (at 40 mm) of:
    D10=15 or 16, D50=38 or 54, D90=684 or 685, %<10 μm=<0.1, 1, 2, 3, 4, 5, 6, 7, 8, 9 or 10%; or
a particle size distribution (at 70 mm) of:
    D10=15 or 16, D50=27 or 28, D90=558 or 596, %<10 μm=<0.1, 1, 2, 3, 4, 5, 6, 7, 8, 9 or 10%; or
a particle size distribution of:
    D10=13 to 17, D50=22 to 27, D90=35 to 56, %<9 μm=<0.1-10%; or
% particles of equal to or less than 11.7 μm size of: 0.5 to 5%.

In an embodiment, the powder plume of 5-MeO-DMT, or a pharmaceutically acceptable salt thereof, has a plume geometry of: angle: 22 to 35 degrees; width: 27 to 55 mm; or plume geometry of: angle: 22 to 33 degrees; width: 27 to 42 mm; or a plume geometry of: angle: 25 to 30 degrees; width: 29 to 39 mm; or a plume geometry of: angle: 26 to 28 degrees; width: 32 to 35 mm; or a plume geometry of: angle: 27.5 degrees; width: 34.33 mm; or a plume geometry of: angle: 24.4 degrees; width: 30.30 mm; or a plume geometry of: angle: 24.8 degrees; width: 30.76 mm; or a plume geometry of: angle: 27.4 degrees; width: 34.13 mm; or a plume geometry of: angle: 30.5 degrees; width: 38.29 mm; or a plume geometry of: angle: 39.2 degrees; width: 50.35 mm; or a plume geometry of: angle: 33.43 degrees; width: 52.25 mm; or a plume geometry of: angle: 28 degrees; width: 34 mm; or a plume geometry of: angle: 24 degrees; width: 30 mm; or a plume geometry of: angle: 25 degrees; width: 31 mm; or a plume geometry of: angle: 27 degrees; width: 34 mm; a plume geometry of: angle: 31 degrees; width: 38 mm or a plume geometry of: angle: 20, 21, 22, 23, 24, 25, 26, 27, 28, 29, 30, 31, 32, 33, 34, 35, 36, 37, 38, 39, 40, 41, 42, 43, 44, 45 or 46 degrees; width: 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 or 56 mm.

In an embodiment, the powder plume of 5-MeO-DMT, or a pharmaceutically acceptable salt thereof, has a spray pattern of:

| Distance 40 mm: | Distance 70 mm: |
|---|---|
| Dmin(mm): 18 to 22 | Dmin(mm): 20 to 30 |
| Dmax(mm): 25 to 30 | Dmax(mm): 40 to 45 |

| Distance 40 mm: | Distance 70 mm: |
|---|---|
| Area (mm$^2$): 400 to 450 | Area (mm$^2$): 900-1100 |
| Area %: 7 to 13 | Area %: 9 to 15 | or

| Distance 40 mm: | Distance 70 mm: |
|---|---|
| Dmin(mm): 19 to 21 | Dmin(mm): 24 to 28 |
| Dmax(mm): 27 to 29 | Dmax(mm): 42 to 44 |
| Area (mm$^2$): 425 to 435 | Area (mm$^2$): 950-1050 |
| Area %: 8 to 11 | Area %: 12 to 14 |

In an embodiment, the powder plume of 5-MeO-DMT, or a pharmaceutically acceptable salt thereof, has a spray pattern of:

| Distance 40 mm: | Distance 70 mm: |
|---|---|
| Dmin(mm): 21.45 or 22.10 | Dmin(mm): 33.43 or 33.43 |
| Dmax(mm): 40.66 or 47.23 | Dmax(mm): 52.25 or 53.50 |
| Area (mm$^2$): 639.6 or 827.1 | Area (mm$^2$): 1229.6 or 1544.9 |
| Area %: 2.7 or 3.5 | Area %: 5.3 or 6.6 | or

| Distance 40 mm: | Distance 70 mm: |
|---|---|
| Dmin(mm): 20 or 18 | Dmin(mm): 21 or 29 or 31 |
| Dmax(mm): 28 or 24 or 27 | Dmax(mm): 44 or 39 or 43 |
| Area (mm$^2$): 431 or 424 or 406 or 449 | Area (mm$^2$): 1049 or 919 or 1039 or 1029 |
| Area %: 8 | Area %: 9 or 10 | or

| Distance 40 mm: | Distance 70 mm: |
|---|---|
| Dmin(mm): 18 to 20 | Dmin(mm): 20 to 32 |
| Dmax(mm): 24 to 28 | Dmax(mm): 39 to 45 |
| Area (mm$^2$): 405 to 450 | Area (mm$^2$): 915 to 1050 |
| Area %: 7 to 9 | Area %: 9 to 11 |

In an embodiment, the particle size distribution of the powder plume of 5-MeO-DMT, or a pharmaceutically acceptable salt thereof, is:
    D10-15.54 or 15.05 or 15.89 or 15.31, D50-26.8 or 28.21 or 38.27 or 53.92, D90-558.4 or 595.9 or 683.8 or 385.3, %<10 μm-5.45 or 3.01 or 3.90 or 3.79; or
    D10=10.4 or 10.7, D50=21.0 or 22.8, D90-38.4 or 14.9, %<10 μm-8.65% or 8.35%; or (Spray pattern at Distance 40 mm: Dmin(mm): 20.43 or 20.17 or 17.79 or 20.09; Dmax(mm): 27.59 or 24.32 or 29.68 or 27.46; Area (mm$^2$): 431.0 or 423.7 or 405.6 or 449.0; Area %: 8.1 or 7.8 or 7.5 or 8.3. Distance 70 mm: Dmin(mm): 20.84 or 29.23 or 30.67 or 31.10; Dmax(mm): 43.69 or 38.83 or 42.82 or 43.31; Area (mm$^2$): 1048.5 or 919.4 or 1038.8 or 1029.2; Area %: 10.3 or 10.1 or 9.0 or 10.1)

D10=13, 14, 15, 16 or 17, D50=22, 23, 24, 25, 26 or 27, D90=35, 36, 37, 38, 39, 40, 41, 42, 43, 44, 45, 46, 47, 48, 49, 50, 51, 52, 53, 54, 55 or 56, %<9 μm=<0.1, 1, 2, 3, 4, 5, 6, 7, 8, 9 or 10%.

In an embodiment, the % particles of equal to or less than 11.7 μm size of the powder plume of 5-MeO-DMT, or a pharmaceutically acceptable salt thereof, is: 0.5 to 5%, 0.6 to 4%, 0.7 to 3%, 0.8 to 2%, 0.9 to 1%.

In an embodiment, the active nasal delivery has an actuation force of between 30 and 60N. In an embodiment, the actuation force is between 40 and 50N. In an embodiment, the actuation force is 41, 42, 43, 44, 45, 46, 47, 48 or 49N. In an embodiment, the actuation force is 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80N. In an embodiment, the actuation force is 36N. In an embodiment, the actuation force is 37N. In an embodiment, the actuation force is 38N. In an embodiment, the actuation force is 39N. In an embodiment, the actuation force is 36N.

In an embodiment, the dry powder formulation comprising a plurality of powder particles of 5-MeO-DMT, or a pharmaceutically acceptable salt thereof, comprises a crystalline form of 5-MeO-DMT, or a pharmaceutically acceptable salt thereof, as described herein.

In an embodiment, the dry powder formulation comprising a plurality of powder particles of 5-MeO-DMT, or a pharmaceutically acceptable salt thereof, has a moisture content of <5%, <4%, <3%, <2%, or <1%. In an embodiment, the moisture content is <2%, <1.9%, <1.8%, <1.7%, <1.6%, <1.5%, <1.4%, <1.3%, <1.2% or <1.1%.

In an embodiment, the dry powder formulation comprising a plurality of powder particles of 5-MeO-DMT, or a pharmaceutically acceptable salt thereof, has <5%, <4%, <3%, <2%, <1%, <0.9%, <0.8%, <0.7%, <0.6%, <0.5%, <0.4%, <0.3%, <0.2%, <0.1%, <0.09%, <0.08%, <0.07%, <0.06%, <0.05%, <0.04%, <0.03%, <0.02% or <0.01% by weight of a hydroxyl impurity.

In an embodiment, the dry powder formulation comprising a plurality of powder particles of 5-MeO-DMT, or a pharmaceutically acceptable salt thereof, has <5%, <4%, <3%, <2%, <1%, <0.9%, <0.8%, <0.7%, <0.6%, <0.5%, <0.4%, <0.3%, <0.2%, <0.1%, <0.09%, <0.08%, <0.07%, <0.06%, <0.05%, <0.04%, <0.03%, <0.02% or <0.01% of by weight of any one impurity.

In an embodiment, the dry powder formulation comprising a plurality of powder particles of 5-MeO-DMT, or a pharmaceutically acceptable salt thereof, has <5%, <4%, <3%, <2%, <1%, <0.9%, <0.8%, <0.7%, <0.6%, <0.5%, <0.4%, <0.3%, <0.2%, <0.1%, <0.09%, <0.08%, <0.07%, <0.06%, <0.05%, <0.04%, <0.03%, <0.02% or <0.01% of by weight of any impurity.

In an embodiment, the impurity profile is determined by RP-HPLC. In an embodiment, the % particles of equal to or less than 11.7 μm size of the powder plume is determined by Next Generation Impactor and HPLC. In an embodiment, the moisture content is determined by Karl Fisher coulometric titration.

In an embodiment, the plume geometry is analysed using the Proveris SprayVIEW apparatus (or equivalent) in conjunction with the Proveris automated actuation device. In an embodiment, Analysis is performed at one distance (7.0 cm). In an embodiment, the settings are as follows: Orifice tip distance (cm): 7.0, Frame rate (Hz): 500, Number of images 250, Lens aperture 2.0, Camera position from horizontal (cm): 27.0, Camera height (cm): 8.0, Laser position (cm): 5.2, Laser depth (cm): 5.3, Laser height (cm): 13.2, Actuator position (cm): 7.0, Plume orientation: 0 deg, Palette: Gradient, Arm 1/Arm 2 (%): 20-30%, Evacuation time (ms): 1000, Setting time (ms): 1000.

In an embodiment, the spray pattern is determined using the Proveris SprayVIEW apparatus (or equivalent) in conjunction with the Proveris automated actuation device. In an embodiment, analysis is performed at two distances (4.0 cm and 7.0 cm). In an embodiment, the settings are as above for the 7.0 cm distance and as follows for the 4.0 cm distance (where different from the settings used for 7.0 cm): Orifice tip distance (cm): 4.0, Camera position from horizontal (cm): 8.0 and Camera height (cm): 22.

In an embodiment, the particle size distribution is determined by laser diffraction using a Malvern Mastersizer (or equivalent). In an embodiment, the settings are as follows: Instrument: Malvern Mastersizer 3000 with Malvern software (or equivalent), Sampling handling Unit: Hydro MV dispersion unit, Material Refractive Index: 1.590, Absorption Refractive Index: 0.001, Dispersant Refractive Index: 1.391 (2,2,4-trimethylpentane), Obscuration Limits: 10-20%, Sonification time: Externally sonicated for 120 secs during sample preparation prior to addition to Hydro MV, Stirrer Speed: 3000 rpm, Measurement time: 30 secs, Background time: 30 secs, Dispersant: 2,2,4-trimethylpentante (RI=1.391) and Lecithin 0.05% w/w, degassed and equilibrated to ambient temperature.

In an embodiment, the aerodynamic particle size distribution (DISP) is determined by a method based on USP <601>, using the Proveris Sprayview and a Copley Next Generation Impactor (NGI) or equivalent, complying with USP/Ph. Eur. In an embodiment, standard solutions are prepared based on the label claim for the drug product (xmg per 100 ml diluent) where x=label claim. In an embodiment, the settings are as follows: Actuation acceleration: 5000 mm/s/s, Actuation velocity: 70 mm/s, Symmetric: Yes, Initial delay: 0 ms, Hold time: 100 ms, Final delay: 0 ms, Stroke length: 14 mm, One shot is fired into the NGI. Weigh the device prior to (W1) and after firing (W2) to calculate shot weight (W3). W1-W2=shot weight (W3), Add 5 ml of test solvent to each NGI cup then place on NGI gentle rocker for 5 minutes. Quantitatively wash the expansion chamber, bungs, inlet cone, all cups and the Proveris collar with diluent into the correct flask size and make to volume. Assay is determined via HPLC.

In an embodiment, the particle size distribution (PSD) is determined by laser diffraction. In an embodiment, the analysis is performed using Sympatec instrumentation with R5 lens and a dispersal pressure of 3 bar. The intranasal delivery system/device is held in a clamp stand and positioned central with the extractor and so the tip of the device is 3 cm from the mid-point of the laser. After referencing, the device is manually/hand actuated so the powder passes through the laser beam, which takes a reading. Readings are performed with an R5 lens, in triplicate and then an average calculated.

Example 29: Further 5-MeO-DMT Formulations

A spray dried formulation of 50% 5-MeO-DMT benzoate with 34.5% HPMC 606, 3% isomalt and 12.5% methyl cellulose (MC) SM-100 grade was produced.

The isomalt used was an agglomerated spherical isomalt (galenIQ 721) with the following properties: Solubility: 42 g/100 g solution at 20° C. water and Bulk density: 0.40 g/cm$^3$.

| SDD Composition | |
| --- | --- |
| Sample Reference | 3815-46-08 |
| Pharmacoat 606 | 34.5% |
| MC SM-100 | 12.5% |
| Isomalt | 3% |
| 5-MeO-DMT benzoate | 50% |
| Spray Drying Parameters | |
| Instrument | Procept |
| Nozzle | Twin-fluid nozzle |
| Inlet Flow (m³/min) | 0.7 |
| Inlet Temperature (° C.) | 130 |
| Cyclone Gas Pressure (bar) | 1.2-1.5 |
| Pump Speed (RPM) | 100 (~1.6-2 g per minute) |
| Feed Stock % solids | 10 |
| Yield | |
| Yield (%) | 44.519% |

Figure 56:
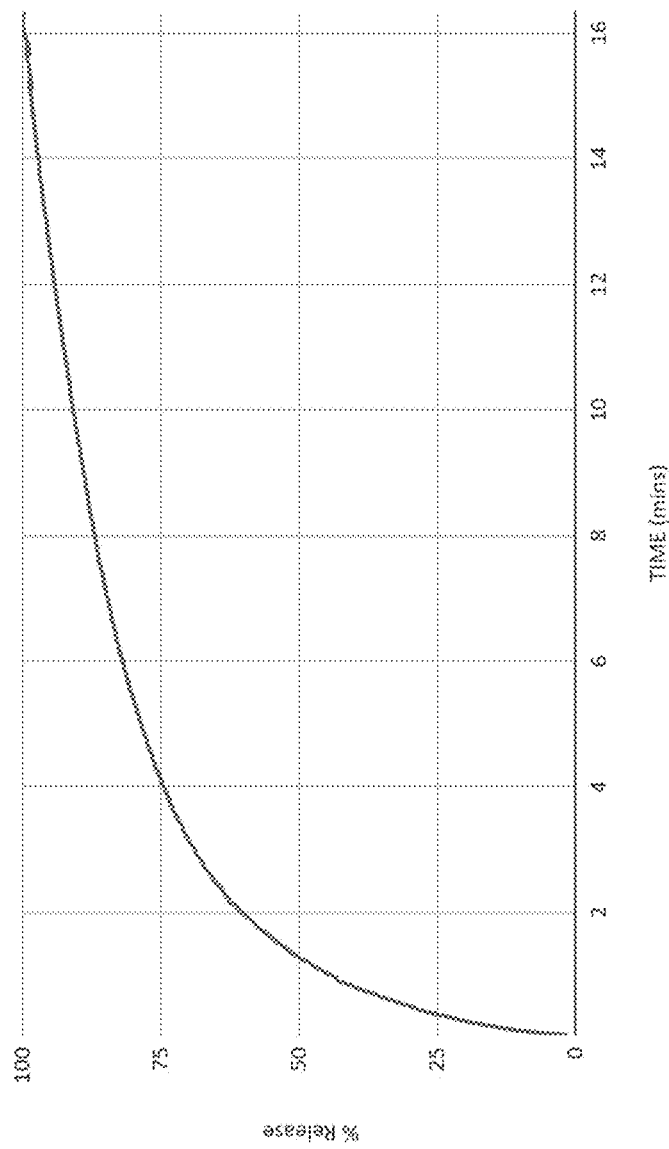
FIG. 56 shows the dissolution profile of a 5-MeO-DMT formulation comprising HPMC, isomalt and methyl cellulose.

The dissolution profile, shown in FIG. 56, shows that for this SDD ~80% release has occurred by ~6 minutes. In an embodiment, there is therefore provided a 5-MeO-DMT formulation comprising HPMC, isomalt and methyl cellulose. In an embodiment, there is therefore provided an extended release formulation of 5-MeO-DMT.

A spray dried formulation of 50% 5-MeO-DMT benzoate with 3% sorbitol and 47% MC SM-25 was produced.

| SDD Composition | |
| --- | --- |
| Sample Reference | 3815-46-09 |
| MC SM-25 | 47% |
| Sorbitol | 3% |
| 5-MeO-DMT benzoate | 50% |
| Spray Drying Parameters | |
| Instrument | Procept |
| Nozzle | Twin-fluid nozzle |
| Inlet Flow (m³/min) | 0.7 |

-continued

| | |
| --- | --- |
| Inlet Temperature (° C.) | 130 |
| Cyclone Gas Pressure (bar) | 2 |
| Pump Speed (RPM) | 100 -> 400 to achieve ~0.8 g/min feed rate. |
| Feed Stock % solids | 10 |
| Yield | |
| Yield (%) | 36.017% |

Figure 57:
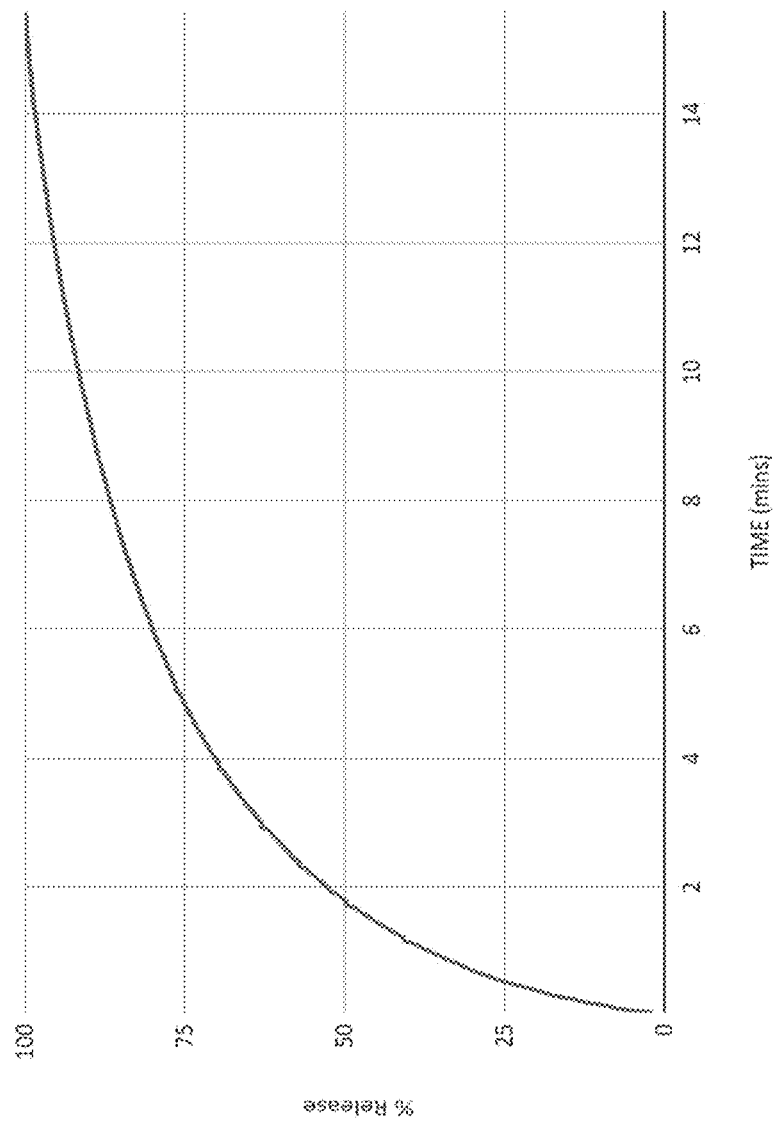
FIG. 57 shows the dissolution profile of a 5-MeO-DMT formulation comprising sorbitol and methyl cellulose.

The dissolution profile, shown in FIG. 57, shows that for this SDD ~80% release has occurred by ~6 minutes. In an embodiment, there is therefore provided a 5-MeO-DMT formulation comprising methyl cellulose and sorbitol. In an embodiment, there is therefore provided an extended release formulation of 5-MeO-DMT.

Example 30:5-MeO-DMT Buccal Formulations

Buccal formulations of 5-MeO-DMT have been developed and are characterised below:

| | Composition of formulations (% w/w) | | | | | |
| --- | --- | --- | --- | --- | --- | --- |
| Component | S01 | S12 | S26 | S27 | S28 | S29 |
| 5-MeO-DMT benzoate | 3.14 | 3.14 | 3.14 | 1.57 | 3.14 | 6.27 |
| 5-MeO-DMT (corrected for salt) | 2.01 | 2.01 | 2.01 | 1.01 | 2.01 | 4.02 |
| Ethanol | 30.00 | 30.00 | 60.00 | 30.00 | 30.00 | 35.00 |
| Water | — | 0.99 | — | — | — | — |
| Propylene glycol | 2.00 | 2.00 | 2.00 | 2.00 | 2.00 | 5.00 |
| Eudragit RS100 | — | 2.00 | — | — | — | — |
| Eudragit E100 | 2.00 | — | 2.00 | 2.00 | — | 2.00 |
| HFA 134a | 62.86 | 61.87 | 32.86 | 64.43 | 64.86 | 51.73 |
| Total | 100.00 | 100.00 | 100.00 | 100.00 | 100.00 | 100.00 |

The formulations were evaluated in an in vitro nasal epithelium permeation experiment using ovine nasal epithelium. The mean cumulative amount of 5-MeO-DMT (μg/mL, % applied dose) delivered to the receptor solution at 1 h and peak flux (μg/min), following application of the 6 formulations to reconstructed oral tissues is shown below:

| | Cumulative (μg/mL) | | | Peak Flux (ug/min) | | | % Dosed (cumulative) | | |
| --- | --- | --- | --- | --- | --- | --- | --- | --- | --- |
| Formulation | N | Mean | Std Dev | N | Mean | Std Dev | N | Mean | Std Dev |
| S01 | 4 | 33.95 | 8.69 | 4 | 1.61 | 0.41 | 4 | 24.89% | 6.37% |
| S12 | 5 | 51.51 | 11.38 | 5 | 1.60 | 0.64 | 5 | 86.57% | 19.13% |
| S26 | 5 | 24.63 | 3.04 | 5 | 1.10 | 0.41 | 5 | 20.19% | 2.49% |
| S27 | 5 | 19.93 | 4.25 | 5 | 0.93 | 0.14 | 5 | 32.39% | 6.91% |
| S28 | 5 | 25.82 | 2.57 | 5 | 1.20 | 0.32 | 5 | 19.03% | 1.89% |
| S29 | 4 | 83.59 | 7.43 | 4 | 2.86 | 0.23 | 4 | 43.50% | 3.87% |

The formulation S29 delivered the most (p<0.05; ~ 1.6-fold more) 5-MeO-DMT to the receptor solution after 1 hour compared to formulation S12. Formulation S12 delivered more (p<0.05; ~ 1.5-fold) 5-MeO-DMT to the receptor solution compared to all other formulations.

Regarding the peak flux, formulation S29 also had the greatest (p<0.05; ~ 1.8-fold) peak flux between the tested formulations. However, considering percent applied dose, formulation S12 delivered more 5-MeO-DMT to the receptor solution as a cumulative percentage (p<0.05; 2-fold) and a peak flux percentage (p<0.05; 1.8-fold). It should be noted that S29 contains nearly double (4.02% w/w) API compared to S01, S12, S26, and S28 (2.01% w/w).

In an embodiment, there is therefore provided a buccal formulation of 5-MeO-DMT or a pharmaceutically acceptable salt thereof, as described herein. In an embodiment, the buccal formulation comprises an alcohol. In an embodiment, the buccal formulation comprises ethanol. In an embodiment, the buccal formulation comprises a copolymer of poly(ethylacrylate, methyl-methacrylate, and chloro trimethyl-ammonioethyl methacrylate). In an embodiment, the buccal formulation comprises Eudragit. In an embodiment, the buccal formulation comprises Eudragit RS100. In an embodiment, the buccal formulation comprises Eudragit E100. In an embodiment, the buccal formulation comprises propylene glycol. In an embodiment, the buccal formulation comprises a hydroglurocarbon. In an embodiment, the buccal formulation comprises 1,1,1,2-tetrafluoroethane. In an embodiment, the buccal formulation comprises between 1% to 30%, 1% to 25%, 1% to 20%, 1% to 15%, 1% to 10%, 1% to 9%, 1% to 8%, 1% to 7%, 1% to 6%, 1% to 5%, 1% to 4%, 1% to 3%, 1% to 2% API. In an embodiment, the buccal formulation comprises one or more pharmaceutically acceptable carriers or excipients, wherein each carrier or excipient are individually present as between 1% to 50%, 1% to 40%, 1% to 30%, 1% to 25%, 1% to 20%, 1% to 15%, 1% to 10%, 1% to 9%, 1% to 8%, 1% to 7%, 1% to 6%, 1% to 5%, 1% to 4%, 1% to 3%, 1% to 2% w/w of the total buccal formulation.

Example 31: Vaporisable Formulations of 5-MeO-DMT

The inhalation route of administration allows for high bioavailability and low variability in bioavailability between patients and between re-administrations in the same patient, and it therefore allows for a high rate and a high reproducibility of peak experiences. A 5-MeO-DMT aerosol may be generated by volatilization of the drug by way of a vaporiser device. Such a device may comprise a hot air generator and a detachable valve balloon from which the aerosol may be inhaled by the patient. The hot air generator may generate temperatures adjustable between about 40° C. to about 210° C., with an airflow rate of about 12 litres per minute. The central part of the device may be a dosing capsule to which relevant doses of 5-MeO-DMT in an alcohol solution may be applied and which may then be applied into the filling chamber of the device, where it may be heated via the hot air. The dosing capsules may contain a small disc made of tightly packed stainless-steel wire mesh (called the drip pad or liquid pad). The bottom and the lid of the dosing capsules may have holes, allowing airflow through the dosing capsules.

To prepare for the administration, a patient may be asked to initially perform 1-2 deep inhalations with full exhalations, ending this sequence with a deep exhalation. Then, with the mouthpiece firmly held against the lips, the full and complete volume of the inhalation balloon may be inhaled in one inhalation, holding the breath for 10 (±2.5) seconds, followed by a normal exhalation. After completing the inhalation procedure, the patient may be instructed to lie down.

The thermal decomposition properties of a range of salt forms of 5-MeO-DMT has been investigated and is summarised in the report below:

| Salt | TGA Guidance |
| --- | --- |
| Phosphate | Decomp around 200° C. |
| Fumarate | Decomp around 200° C. |
| Oxalate | Melts 176° C., full mass loss |
| Tartrate | Melt ~140° C., decomp ~200° C. |
| Benzenesulfonate | Melt 76° C., gross dcomp starts 280° C. |
| Tosylate | Melt 110° C, gross dcomp starts 280° C |
| Hydrobromide | Melt 149° C., gross dcomp starts 220° C. |
| Glycolate | Melt 95° C., gross dcomp starts 170° C. |
| Ketoglutarate | Melt 85° C., gross dcomp starts 170° C. |
| Saccharinate | Melt 80° C., gross dcomp starts 180° C. |
| Malate | Melt 100° C, gross dcomp starts 250° C. |
| Benzoate | Melt ~123° C., dcomp starts ~220° C., full mass loss |

The benzoate and oxalate salts were the only salt forms which underwent full mass loss and within a reasonable temperature range. There is therefore provided an advantageous salt form of 5-MeO-DMT for vaporisation wherein said form is the benzoate or oxalate salt form. In an embodiment, the 5-MeO-DMT salt is in a crystalline form.

In an embodiment, there is provided a vaporisable formulation or composition of 5-MeO-DMT benzoate. In an embodiment, there is provided a method of treatment comprising administration of a formulation of composition of 5-MeO-DMT benzoate by vaporisation. In an embodiment, there is provided a formulation or composition comprising 5-MeO-DMT benzoate and an alcohol. In an embodiment, the alcohol is ethanol. In an embodiment, there is provided a 5-MeO-DMT benzoate aerosol.

In an embodiment, there is provided a vaporisable formulation or composition of 5-MeO-DMT oxalate. In an embodiment, there is provided a method of treatment comprising administration of a formulation of composition of 5-MeO-DMT oxalate by vaporisation. In an embodiment, there is provided a formulation or composition comprising 5-MeO-DMT oxalate and an alcohol. In an embodiment, the alcohol is ethanol. In an embodiment, there is provided a 5-MeO-DMT oxalate aerosol. The formulation may be as described herein. The formulation may be used as described herein.

Example 32: Further Dry Blended 5-MeO-DMT Formulations

Work has been undertaken to produce new and improved dry blended 5-MeO-DMT formulations with advantageous characteristics.

All dry blended formulations comprised 1:1 5-MeO-DMT benzoate to HPMC 606.

The dry blended formulations were produced as follows:
A dry blend for this experiment was prepared in bulk of 3.5 g of the Benzoate salt and 3.5 g of HPMC 606.
This was initially mixed for 5 minutes at 32 rpm on a Turbula T2C blender.
~500 mg of this powder was then weighed out to 10 vials (with any remaining amount split equally between the two control plain powder vials).
A required amount of each of the chosen agents (5.05 mg for 500 mg in the case of 1% w/w loading and 26.32 mg for 500 mg for 5% w/w) was weighed out and added to an appropriate vial.
All vials were then put onto secondary blending (including the plain powder control vials) for 5 min at 32 rpm on Turbula.
The dry blended formulations are set out below:

| Formulation | Production Method | Additional Excipients | Storage |
| --- | --- | --- | --- |
| 1 | Dry blend | No | Fridge |
| 2 | Dry blend | No | 25° C./60%RH |

| Form-ulation | Production Method | Additional Excipients | Storage |
|---|---|---|---|
| 3 | Dry blend | 1% w/w silicon dioxide (SD) | Fridge |
| 4 | Dry blend | 1% w/w silicon dioxide (SD) | 25° C./60%RH |
| 5 | Dry blend | 5% w/w microcrystalline cellulose (MCC) | Fridge |
| 6 | Dry blend | 5% w/w microcrystalline cellulose (MCC) | 25° C./60%RH |
| 7 | Dry blend | 1% w/w calcium silicate (CS) | Fridge |
| 8 | Dry blend | 1% w/w calcium silicate (CS) | 25° C./60%RH |
| 9 | Dry blend | 1% w/w sodium stearyl fumarate (SSF) | Fridge |
| 10 | Dry blend | 1% w/w sodium stearyl fumarate (SSF) | 25° C./60%RH |

The following observations were made regarding the properties of the dry blended 5-MeO-DMT formulations at T=0:

Plain Powder controls—Some layering of the two components was observed prior to secondary blending. The powder flowed, but not readily, with a tendency to stick slightly to the bottom of the container. An off-white powder with visible crystals of the drug.

1% w/w Silicone Dioxide—Some lumps of the Silicone were observed at the surface of the powder. Flowability was improved greatly.

5% w/w MCC—Moderately improved flowability was observed, however some powder was noticed to stick around the edges at the bottom of the vial. It is possible this is MCC.

1% w/w Calcium Silicate—well improved flowability with no noticeable lumps of the agent visible.

1% w/w SSF—some improvement to flowability, although similarly to MCC, some powder was observed to stick around the edges at the bottom of the vial. No SSF could be observed.

The following observations were made regarding the properties of the dry blended 5-MeO-DMT formulations at T=1 week:

Plain Powder controls
1—Fridge—Flowable powder with visible white and off-white layers.
2—Less layers, initially only the top part flowed, with the bottom caked. As the vial was turned gently, all of the powder began to flow.

1% w/w Silicone Dioxide
3—Fridge—Flowable powder.
4—Flowable powder with some lumps of Silica observed.

5% w/w MCC
5—Fridge—Flowable powder that coated the glass walls of the vial.
6—Flowable powder that coated the glass walls of the vial. Some light caking was observed on the edges at the bottom.

1% w/w Calcium Silicate
7—Fridge—Very light caking observed, powder flowed almost as soon as the vial was turned to its side.
8—As above.

1% w/w SSF
9—Fridge—The worst of all samples, a light caking present that broke almost as soon as the vial was turned. Some caking remained on the edges at the bottom of the vial.
10—Powder with good flowability.

The following observations were made regarding the properties of the dry blended 5-MeO-DMT formulations at T=2 weeks:

Plain Powder controls
1—Fridge—Flowed after turning the vial.
2—Flowed upon tapping the vial, observed initially to have formed a cake.

1% w/w Silicone Dioxide
3—Fridge—Flowed very well readily.
4—Flowed very well.

5% w/w MCC
5—Fridge—Flowed after turning the vial. Poorer flow observed compared to the Silica sample.
6—Caked, but the cake broke after the vial was tipped to the side. Some powder remained caked in the edges at the bottom.

1% w/w Calcium Silicate
7—Fridge—Flowed very well, readily.
8—Flowed well.

1% w/w SSF
9—Fridge—Flowed after turning, some caking was present similar to that present in the MCC sample.
10—Observed to have caked slightly, but that cake breaks as soon as the vial was tipped.

The following observations were made regarding the properties of the dry blended 5-MeO-DMT formulations at T=3 weeks:

Plain Powder controls
1—Fridge—Flowed after turning the vial. The cake that was initially present broke gradually upon turning.
2—As above, however the cake formed seemed harder and more difficult to break.

1% w/w Silicone Dioxide
3—Fridge—Any cake formed broke as soon as the vial was turned. Flowed very well, readily.
4—As above.

5% w/w MCC
5—Fridge—Although any cake formed broke almost as soon as the vial was turned, the observed flow was poorer to that observed in the Silica sample. Some powder was observed to stick to the bottom edge of the vial.
6—As above.

1% w/w Calcium Silicate
7—Fridge—Flowed well as soon as the vial was turned. Powder was observed to statically stick to the walls of the vial as the turning motion was continued.
8—As above.

1% w/w SSF
9—Fridge—Initially caked, broke after turning for a while. Some powder was observed to stick in the edges at the bottom of the vial. Flowed, but rather poorly by comparison to other samples.
10—As above, however, the cake was observed to break slightly quicker/easier. Less sticking was observed at the bottom of the vial when compared with sample 9.

The following observations were made regarding the properties of the dry blended 5-MeO-DMT formulations at T=4 weeks:

Plain Powder controls
1—Fridge—Flows after turning the vial. Cake breaks gradually upon turning. No significant change from the previous timepoint.

2—As above, however the cake formed seems harder and slightly more difficult to break. No significant change from the previous timepoint.

1% w/w Silicone Dioxide
- 3—Fridge—Any cake formed breaks as the vial is turned. Flows well, however some powder was observed to deposit on the walls of the vial.
- 4—As above, but less powder was sticking to the walls of the vial.

5% w/w MCC
- 5—Fridge—Although any cake formed breaks almost as soon as the vial is turned, the observed flow is poorer to that observed in the Silica sample. Some powder was observed to stick to the bottom edge of the vial. No change observed from the previous timepoint.
- 6—Caked more than the sample stored in the fridge. The caking is slightly more significant than that observed in the previous timepoint.

1% w/w Calcium Silicate
- 7—Fridge—Flows well as soon as the vial is turned. Powder was observed to statically stick to the walls of the vial as the turning motion was continued. Some drug aggregates were found in this sample similar to those observed in the sample stored in the stability chamber at the previous timepoint.
- 8—As above; additionally, a flat sheet of a drug aggregate that was observed in the previous timepoint was found here again.

1% w/w SSF
- 9—Fridge—Initially caked, breaks after tapping the vial. Clear segregation and sticking present at the bottom of the vial, possibly due to a large difference in the particle size of the main components of the blend and SSF. Flows, but rather poorly by comparison to other samples.
- 10—As above, however, the cake was observed to break slightly quicker/easier. Less sticking was observed at the bottom of the vial when compared with sample 9.

It is desirable that a dry powder formulation possess good flow characteristics that reduce the effects of excessive agglomeration, have minimal adhesion to surfaces during processing/filling and upon storage within the container/administration device and minimal caking.

It has advantageously been discovered that a dry blend formulation comprising silicone dioxide possessed the most desirable flow properties compared to a range of other excipients tested.

There is therefore provided a pharmaceutical formulation comprising both 5-MeO-DMT, or a pharmaceutically acceptable salt thereof, and silicon dioxide. The formulation may be a dry blended formulation. The formulation may comprise one or more pharmaceutically acceptable carriers or excipients. The formulation may be as described herein. The formulation may be used as described herein. In an embodiment, the formulation is a free-flowing powder formulation.

Example 33: Further Spray Dried 5-MeO-DMT Formulations

Work has been undertaken to produce new and improved spray dried 5-MeO-DMT formulations with advantageous characteristics.

All spray dried formulations comprised 50% 5-MeO-DMT benzoate with 3:1 ratio of HPMC606:Metolose 60SH50 and 3% sorbitol. The spray dried formulations were produced as follows:

The feedstock for the SD was initially prepared at 10% solid content with the following % formula
- 50% Benzoate salt of DMT
- 35.25% HPMC 606
- 11.75% Metolose 60SH50
- 3% Sorbitol.

During the process ~56 mL of water was added to dilute the stock to ~6.25% solid content, which was much more efficient to pump and atomise.

Final parameters were as follows:
- Atomising gas pressure: 1 bar
- Pump speed: 150 rpm, equal to ~2 g/min feed rate
- Inlet temperature: 125° C.

Split the prepared SDD (Spray Dried Dispersion) into individual vials per test by weighing it directly into scintillation vials. The powder should be split into equal amounts for an accurate comparison of the action of the anticaking agents. Every type should be split into two vials for two different storage conditions of 2-8° C. and 25° C./60% RH. E.g. if 4 anticaking agents are tested, there should be a total of 10 vials, 2*4+2 controls for each storage condition.

Weigh the required amount of the anticaking agent on a weighing boat based on the calculation of the required final concentration of the mix. That is:
- If 5% w/w of the agent is required and 500 mg of the blend are present in the vial, 500 mg becomes 95% of the final mix. Therefore, if $0.95x=500$ mg, $0.05x=$ (500 mg*0.05)/0.95=26.32 mg
- If the excipient is observed to stick to the weighing boat, same re-weighing exercise as described in the dry blend procedure should be performed to calculate material losses.

Put all vials on blending on a Turbula T2C blender for 5 min at 32 rpm. This should include controls with no agent added.

Seal the vials with parafilm and set on storage on the appropriate storage condition.

The spray dried formulations are set out below:

| Formulation | Production Method | Additional Excipients | Storage |
|---|---|---|---|
| 1 | Spray dried | No | Fridge |
| 2 | Spray dried | No | 25° C./60%RH |
| 3 | Spray dried | 1% w/w silicon dioxide (SD) | Fridge |
| 4 | Spray dried | 1% w/w silicon dioxide (SD) | 25° C./60%RH |
| 5 | Spray dried | 5% w/w microcrystalline cellulose (MCC) | Fridge |
| 6 | Spray dried | 5% w/w microcrystalline cellulose (MCC) | 25° C./60%RH |
| 7 | Spray dried | 1% w/w calcium silicate (CS) | Fridge |
| 8 | Spray dried | 1% w/w calcium silicate (CS) | 25° C./60%RH |
| 9 | Spray dried | 1% w/w sodium stearyl fumarate (SSF) | Fridge |
| 10 | Spray dried | 1% w/w sodium stearyl fumarate (SSF) | 25° C./60%RH |

The following observations were made regarding the properties of the spray dried 5-MeO-DMT formulations at T=0:

Plain Powder controls—white powder of low density. Hardly flows, needs to be agitated to facilitate it.

1% w/w Silicone Dioxide—White powder of low density. Flows when the vial is turned to its side.

5% w/w MCC—White powder of low density. Flows after an initial impact to break a cake. Flow improved compared to that of a plain powder.

1% w/w Calcium Silicate—Similar observations to those of the MCC samples, however the flow observed is poorer.

1% w/w SSF—Flows upon turning the vial, but sticks a bit if the motion is continued. Flows readily upon impact.

The following observations were made regarding the properties of the spray dried 5-MeO-DMT formulations at T=1 week:

Plain Powder controls
  1—Fridge—the powder flows only after tapping and shaking the vial, however it is a poor flow.
  2—Powder sticks to the sides of the vial and cakes. Some agitation (tapping) is required to encourage any flow, however it tends to stick and flow in clumps.

1% w/w Silicone Dioxide
  3—Fridge—flows after turning the vial, but with some aggregates present. Much improved compared to SDD alone.
  4—powder still sticks, but less agitation is required for flow. More overall movement is present.

5% w/w MCC

5—Fridge—Flows after some light shaking, but still clumps a bit after that. Powder sticks still to the walls of the vial.

6—Similarly to the Silica sample, powder needs to be encouraged to flow with some tapping. Seems slightly better than the Silica sample.

1% w/w Calcium Silicate

7—Fridge—tapping and shaking is required to encourage the flow. Still sticks afterwards, both to the walls of the vial and to itself.

8—A lot of powder sticking to the walls of the vial was observed. Powder flows after some tapping, but with plenty of aggregates present.

1% w/w SSF

9—Fridge—Flows reasonably well after some light shaking, small amounts still stick to the glass.

10—Best flow across all vials, but similarly, tapping is required to facilitate it.

The following observations were made regarding the properties of the spray dried 5-MeO-DMT formulations at T=2 weeks:

Plain Powder controls

1—Fridge—Powder caked, flow cannot be facilitated by turning the vial. Material does begin to flow after some tapping, however it is a poor flow, in clumps.

2—As above.

1% w/w Silicone Dioxide

3—Fridge—Powder initially caked, but breaks after tapping. Flows, however poorly. Can be considered a slight improvement compared to the control.

4—As above, but the powder was observed to be slightly more clumpy.

5% w/w MCC

5—Fridge—Tapping was required to break the cake and facilitate the flow. Some powder remained stuck to the walls of the vial despite continuous turning and tapping.

6—As above.

1% w/w Calcium Silicate

7—Fridge—Any cake formed breaks as the vial is turned. Some powder remained stuck to the walls of the vial. Most of that (but not all) can be detached with tapping.

8—As above.

1% w/w SSF

9—Fridge—The cake breaks almost as soon as the vial is turned. Best flow out of all the samples tested.

10—Formed a cake, but as the vial is turned to the side, this breaks easily and begins to flow well.

The following observations were made regarding the properties of the spray dried 5-MeO-DMT formulations at T=3 weeks:

Plain Powder controls

1—Fridge—Powder flows after tapping the vial, although rather poorly. Large aggregates formed on the walls of the vial that cannot be easily removed with tapping.

2—As above, however poorer flow was observed and more sticking to the walls of the vial.

1% w/w Silicone Dioxide

3—Fridge—Powder initially caked, but breaks after tapping. Flows, although poorly. Can be considered a slight improvement compared to the control, but not a significant one.

4—As above, but the powder was observed to flow ever so slightly better.

5% w/w MCC

5—Fridge—More tapping by comparison to previous samples was required to break the cake and facilitate the flow. Some powder remained stuck to the walls of the vial despite continuous turning and tapping, this cannot be easily detached.

6—As above, however, a slightly better flow was observed.

1% w/w Calcium Silicate

7—Fridge—Tapping and shaking is required to break the formed cake. A lot of powder remained stuck to the walls of the vial can be detached with tapping.

8—As above.

1% w/w SSF

9—Fridge—The cake breaks after some turning and tapping. Best flow out of all the samples tested. Some powder was observed to stick to the walls of the vial, however considerably less when compared to other samples.

10—Caked slightly more than the sample 9, other than that similar observations.

A spray dried 5-MeO-DMT formulation comprising 1% magnesium stearate was prepared and the following observations were made regarding the properties of the formulation at T=4 weeks:

Fridge—The powder flows after tapping the vial, but gradually aggregates back as the vial is turned, sticking to the glass walls of the vial. Some powder remains stuck to the sides and the bottom of the vial. This cannot be removed with continuous tapping.

25/60—Powder flows after tapping, however aggregates back, with patches growing on turning the vial. A round agglomerate was present in the vial before any motion was started. Some powder sticks to the bottom of the vial; this cannot be removed with continuous tapping.

Note: This sample was prepared by taking an aliquot of SDD control as stored in the fridge, adding an appropriate amount of Magnesium Stearate and blending, same as in the case of all other samples.

The following observations were made regarding the properties of the spray dried 5-MeO-DMT formulation comprising SSF at T=8 weeks:

9—Fridge—Powder begins to flow almost as soon as the vial is turned. Slight aggregation was observed on the wall of the vial as the motion continued, but the patch doesn't grow.

10-Powder flows after turning the vial and some light tapping. Continues to flow well. Some powder was observed to stick around the bottom of the vial when it is being turned on its side. This patch grows, but only to a point, then stops. This aggregate can be easily detached with a single tap.

It is desirable that a dry powder formulation possess good flow characteristics that reduce the effects of excessive agglomeration, have minimal adhesion to surfaces during processing/filling and upon storage within the container/administration device and minimal caking.

It has advantageously been discovered that a spray dried formulation comprising sodium stearyl fumarate possessed the most desirable flow properties compared to a range of other excipients tested.

There is therefore provided a pharmaceutical formulation comprising both 5-MeO-DMT, or a pharmaceutically acceptable salt thereof, and sodium stearyl fumarate. The formulation may comprise one or more pharmaceutically acceptable carriers or excipients. The formulation may be a spray dried formulation. The formulation may be as described herein. The formulation may be used as described herein. In an embodiment, the formulation is a free-flowing powder formulation.

The invention claimed is:

1. A dry blended free-flowing dry powder pharmaceutical formulation comprising 5-methoxy-N,N-dimethyltryptamine (5-MeO-DMT), or a pharmaceutically acceptable salt thereof, and silicon dioxide.

2. The dry blended free-flowing dry powder pharmaceutical formulation of claim 1, wherein the formulation comprises from 40% to 60% 5-MeO-DMT by weight.

3. The dry blended free-flowing dry powder pharmaceutical formulation of claim 1, wherein the formulation comprises methyl cellulose.

4. The dry blended free-flowing dry powder pharmaceutical formulation of claim 1, wherein the formulation comprises a low viscosity methyl cellulose and a high viscosity methyl cellulose.

5. The dry blended free-flowing dry powder pharmaceutical formulation of claim 1, wherein the formulation comprises a cellulose like or based excipient.

6. The dry blended free-flowing dry powder pharmaceutical formulation of claim 4, wherein the formulation comprises a low viscosity hydroxypropyl methyl cellulose (HPMC) and a high viscosity HPMC.

7. The dry blended free-flowing dry powder pharmaceutical formulation of claim 6, wherein the ratio of the low viscosity HPMC to high viscosity HPMC is in the ratio of 1:10 to 10:1.

8. The dry blended free-flowing dry powder pharmaceutical formulation of claim 6, wherein the ratio of the low viscosity HPMC to high viscosity HPMC is in the ratio of between 50:50 and 25:75.

9. The dry blended free-flowing dry powder pharmaceutical formulation of claim 8, wherein the high viscosity HPMC has a viscosity characterized as greater or equal to about 20 millipascal-second (mPa•s) where the HPMC is a HPMC comprising about 7.0-12.0% hydroxypropyl content, about 28.0-30.0% methoxy content, and a viscosity of about 50 mPa•s.

10. The dry blended free-flowing dry powder pharmaceutical formulation of claim 8, wherein the low viscosity HPMC has a viscosity characterized as less than about 20 millipascal-second (mPa•s) where the HPMC is a HPMC comprising about 7.0-12.0% hydroxypropyl content, about 28.0-30.0% methoxy content, and a viscosity of about 4.8-7.2 mPa•s.

11. The dry blended free-flowing dry powder pharmaceutical formulation of claim 1, wherein the formulation comprises a polyol.

12. The dry blended free-flowing dry powder pharmaceutical formulation of claim 11, wherein the formulation comprises about 1-10% polyol by weight.

13. The dry blended free-flowing dry powder pharmaceutical formulation of claim 12, wherein the formulation comprises about 3% sorbitol, mannitol, or isomalt by weight.

14. The dry blended free-flowing dry powder pharmaceutical formulation of claim 12, wherein the formulation comprises about 3% sorbitol by weight.

15. The dry blended free-flowing dry powder pharmaceutical formulation of claim 1, wherein the formulation comprises from about 1% w/w to about 10% w/w silicon dioxide.

16. The dry blended free-flowing dry powder pharmaceutical formulation of claim 15, wherein the formulation comprises 5-MeO-DMT benzoate.

17. The dry blended free-flowing dry powder pharmaceutical formulation of claim 15, wherein the formulation comprises 5-MeO-DMT hydrochloride.

18. The dry blended free-flowing dry powder pharmaceutical formulation of claim 15, wherein the formulation comprises 5-MeO-DMT hydrobromide.

19. The dry blended free-flowing dry powder pharmaceutical formulation of claim 15, wherein the 5-MeO-DMT salt is amorphous.

20. The dry blended free-flowing dry powder pharmaceutical formulation of claim 15, wherein the 5-MeO-DMT salt is crystalline.

* * * * *